US006348586B1

(12) United States Patent
Chang et al.

(10) Patent No.: US 6,348,586 B1
(45) Date of Patent: Feb. 19, 2002

(54) UNIQUE ASSOCIATED KAPOSI'S SARCOMA VIRUS SEQUENCES AND USES THEREOF

(75) Inventors: Yuan Chang, Irvington, NY (US); Roy A. Bohenzky, Mountain View, CA (US); James J. Russo; Isidore S. Edelman, both of New York, NY (US); Patrick S. Moore, Irvington, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/230,371

(22) PCT Filed: Jul. 22, 1997

(86) PCT No.: PCT/US97/13346

§ 371 Date: Nov. 17, 1999

§ 102(e) Date: Nov. 17, 1999

(87) PCT Pub. No.: WO98/04576

PCT Pub. Date: Feb. 5, 1998

Related U.S. Application Data

(63) Continuation-in-part of application No. 08/757,669, filed on Nov. 29, 1996, now Pat. No. 6,183,751, which is a continuation-in-part of application No. 08/748,640, filed on Nov. 13, 1996, now Pat. No. 5,854,398, which is a continuation-in-part of application No. 08/747,887, filed on Nov. 13, 1996, now Pat. No. 5,853,734, which is a continuation-in-part of application No. 08/728,323, filed on Oct. 10, 1996, now Pat. No. 5,948,676, which is a continuation-in-part of application No. 08/708,678, filed on Sep. 5, 1996, now Pat. No. 5,859,225, which is a continuation-in-part of application No. 08/729,615, filed on Jul. 25, 1996, now abandoned, which is a continuation-in-part of application No. 08/687,253, filed on Jul. 25, 1996, now Pat. No. 5,854,418, which is a continuation-in-part of application No. 08/686,350, filed on Jul. 25, 1996, now Pat. No. 5,831,064, which is a continuation-in-part of application No. 08/686,349, filed on Jul. 25, 1996, now Pat. No. 5,861,500, which is a continuation-in-part of application No. 08/686,243, filed on Jul. 25, 1996, now Pat. No. 5,863,787.

(51) Int. Cl.[7] .................... A61K 39/245; C07H 21/04; C07K 14/03; C12N 7/00

(52) U.S. Cl. .............................. 536/23.72; 424/231.1; 424/186.1; 424/229.1; 435/325; 435/320.1; 435/235.1; 435/6; 514/44; 536/23.1; 536/24.1; 536/24.32; 536/24.33; 530/350

(58) Field of Search .......................... 424/231.1, 186.1, 424/229.1; 435/325, 320.1, 235.1, 6; 514/44; 536/23.1, 23.72, 24.1, 24.32, 24.33; 530/350

(56) References Cited

U.S. PATENT DOCUMENTS 5,801,042 A 9/1998 Chang et al.
5,830,759 A 11/1998 Chang et al.
5,861,240 A 1/1999 Ganem
6,093,550 A 7/2000 Chang et al.
6,150,093 A 11/2000 Chang et al.
6,183,751 B1 2/2001 Chang et al.

FOREIGN PATENT DOCUMENTS

WO WO9606159 2/1996
WO WO9615779 5/1996
WO WO9712042 4/1997
WO WO9724057 7/1997
WO WO9727208 7/1997
WO WO9803657 1/1998
WO WO9804284 2/1998
WO WO9804576 2/1998
WO WO9811132 3/1998
WO WO9815289 4/1998

OTHER PUBLICATIONS

Muzny et al. Gen Embl Database. Accession No. AC023681, Submitted Feb. 17, 2000.*

Chang et al. Science, vol. 266. Dec. 16, 1994, p 1865–1869.*

Baer et al (1983) DNA sequence and experssion of the B95–8 Epstein–Barr virus genome, *Nature* 310, 207–211.

Mosca et al (1987) Herpes simplex virus type–1 can reactivate transcription of latent human immunodeficiency virus, *Nature* 325, 67–70.

Delli Bovi et al (1987) Isolation of a rearranged human transforming gene following transfection of kaposi sarcoma DNA, *Proc Natl Acad Sci USA* 84, 5660–5664.

Gallo (1993) Aspects of the molecular pathogenesis of AIDS, *J Cellular Biochem* 17E, 5.

Gallo (1994) New approaches for interfering with human immunodeficiency virus replication and for Kaposi's sarcoma, *J Cellular Biochem* 18B, 108.

Chang et al (1994) Identification of herpesvirus–like DNA sequences in AIDS–associated Kaposi's sarcoma, *Science* 265, 1865–1869.

Cesarman et al (1995) Kaposi's sarcoma–associated herpesvirus–like DNA sequences are present in AIDS–related body cavity based lymphomas, *The FASEB Journal* 9, A973, abstract 5650.

Gompels et al (1988) Conservation of glycoprotein H (gH) in herpesviruses: nucleotide sequence of the gH gene from herpesvirus saimiri, *J Gen Virol* 69, 2819–2829.

(List continued on next page.)

*Primary Examiner*—Phuong T. Bui
(74) *Attorney, Agent, or Firm*—John P. White; Cooper & Durham LLP

(57) ABSTRACT

This invention provides an isolated nucleic acid molecule which encodes Kaposi's Sarcoma-Associated Herpesvirus (KSHV) polypeptides. This invention provides an isolated polypeptide molecule of KSHV. This invention provides an antibody specific to the polypeptide. Antisense and triplex oligonucleotide molecules are also provided. This invention provides a vaccine for Kaposi's Sarcoma (KS). This invention provides methods of vaccination, prophylaxis, diagnosis and treatment of a subject with KS and of detecting expression of a DNA virus associated with Kaposi's sarcoma in a cell.

14 Claims, 15 Drawing Sheets

OTHER PUBLICATIONS

Gompels et al (1991) Characterization and sequence analyses of antibody–selected antigenic variants of herpes simplex virus show a conformationally complex epitope on glycoprotein H, *J Virol* 65, 2393–2401.

Baer et al (1984) DNA sequence and expression of the B95–8 Epstein–Barr virus genome, *Nature* 310, 207–211.

Mosca et al (1987) Herpes simplex virus type–1 can reactive transcription of latent human immunodeficiency virus, *Nature* 325, 67–70.

Delli Bovi et al (1987) Isolation of a rearranged human transforming gene following transfection of kaposi sarcoma DNA, *Proc Natl Acad Sci USA* 84, 5660–5664.

Gallo (1993) Aspectf of the molecular pathogenesis of AIDS, *J Cellular Biochem* 17E, 5.

Gallo (1994) New approaches for interfering with human immunodeficiency virus replication and for Kaposi's sarcoma, *J Cellular Biochem* 18B, 108.

Chang et al (1994) Identification of herpesvirus–like DNA sequences in AIDS–associated Kaposi's sarcoma, *Science* 265, 1865–1869.

Cesarman et al (1995) Kaposi's Sarcoma–associated herpesvirus–like DNA sequences are present in AIDS–related body cavity based lymphomas, *The FASEB Journal* 9, A973, abstract 5650.

Gompels et al (1988) Conservation of glycoprotein H (gH) in herpesviruses: nucleotide sequence of the gH gene from herpesvirus saimiri, *J Gen Virol* 69, 2819–2929.

Gompels et al (1991) Characterization and sequence analysis of antibody–selected antigenic variants of herpes simplex virus show a conformationally complex epitope on glycoprotein H, *J Virol* 65, 2393–2401.

Forrester et al (1992) Construction and properties of a mutant of herpes simplex virus type 1 with glycoprotein H coding sequence deleted, *J Virol* 66, 341–348.

Roop et al (1993) A mutant herpes simplex virus type 1 unable to express glycoprotein L cannot enter cells, and its particles lack glycoprotein H, *J Virol* 67, 2285–2297.

Scott et al (1993) Identification and sequence analysis of the homologues of the herpes simplex virus type 1 glycoprotein H in Marek's disease virus and the herpesvirus of turkeys, *J Gen Virol* 74, 1185–1190.

Liu et al (1993) Human herpesvirus–6 glycoprotein H and L homologs are components of the gp100 complex and the gH external domain is the target for neutralizing monoclonal antibodies, *Virology* 197, 12–22.

Tewari et al (1994) Characterization of immune responses to baculovirus–expressed equine herpesvirus type 1 glycoproteins D and H in a murine model, *J Gen Virol* 75, 1735–1741.

McGowan et al (1994) Expression and characterisation of equine herpesvirus 1 glycoprotein H using a recombinant baculovirus, *Arch Virol* 137, 389–395.

Pulford et al (1994) Expression of the Epstein–Barr virus envelope fusion glycoprotein gp85 gene by a recombinant baculovirus, *J Gen Virol* 75, 3241–3248.

Farrell et al (1994) Vaccine potential of a herpes simplex virus type 1 mutant with an essential glycoprotein deleted, *J Virol* 68, 927–932.

Baranowski et al (1995) Synthesis and processing of bovine herpesvirus–1 glycoprotein H, *Virology* 206, 651–654.

Ambroziak and Blackbourn (1995) Herpes–like sequences in HIV–infected and uninfected Kaposi's sarcoma, *Science* 268, 582–583.

Bassett et al (1995) Cancer in the African population of Harare, Zimbabwe, 1990–1992, *Int J Canc* 63, 29–36.

Benelli et al (1996) Isolation of spindle–shaped cell populations from primary cultures of Kaposi's sarcoma of different stage, *Cancer Lett* 100, 125–132.

Boshoff et al (1995) Kaposi's sarcoma–associated herpesvirus infects endothelial and spindle cells, *Nat Med* 1, 1274–1278.

Brady et al (1995) Altered cytokine expression in T lymphocytes from human immunodeficiency virus tat–transgenic mice, *J Virol* 69, 7622–7629.

Braun et al (1995) Identification of target genes for the Ewing's sarcoma EWS/FLI fusion protein by representational difference analysis, *Mol Cell Biol* 15, 4623–4630.

Broder and Karp (1995) Progress against cancer, *J Cancer Res* 121, 633–647.

Cesarman et al (1995) Kaposi's sarcoma–associated herpesvirus–like DNA sequences are present in AIDS–related body cavity based lymphomas, *Faseb* 9, A973.

Cesarman et al (1995) Kaposi's sarcoma–associated herpesvirus–like DNA sequence in AIDS–related body–cavity–based lymphomas, *New Eng J Med* 332, 1186–1191.

Cesarman (1995) Periobital edema in Kaposi's sarcoma, *New Eng J Med* 333, 799.

Cesarman et al (1995) In vitro establishment and characterization of two acquired immunodeficiency syndrome–related lymphoma cell lines (BC–1 and BC–2) containing Kaposi's sarcoma–associated herpesvirus–like (KSHV) DNA sequences, *Blood* 86, 2708–2714.

Chang (1995) Letter to the editor, *Science* 267, 1079.

Chang et al (1995) Letter to the editor, *Annals Oncol* 6, 744–745.

Chang et al (1994) Identification of herpesvirus–like DNA sequences in AIDS–associated Kaposi's sarcoma, *Science* 266, 1865–1869.

Chee et al (1990) Human cytomegalovirus encodes three G protein–coupled receptor homologue, *Nature* 344, 774–777.

Cohen (1994) Is a new virus the cause of KS?, *Science* 266, 1803–1804.

Cohen (1995) Controversy: is KS really caused by new herpesvirus, *Science* 268, 1847–1848.

Coleman et al (1995) Generalized endemic Kaposi's sarcoma, *Clin Exp* 20, 471–473.

Collandre et al (1995) Kaposi's sarcoma and new herpesvirus, *Lancet* 345, 1043.

Costagliola et al (1995) Can antiviral agents decrease the occurence of Kaposi's sarcoma?, *Lancet* 346, 578.

Delellis et al (1995) Herpesvirus–like DNA sequences in non–AIDS Kaposi's sarcoma, *J Infect Dis* 172, 1605–1607.

Drew and Brindley (1995) Female–specific sequences isolated from *Schistoma mansoni* by representational difference analysis, *Mol Biochem Parasitology* 71, 173–181.

Dupin (1995) Letter to the editor, *New Eng J Med* 333, 798.

Duvic (1995) Human immunodeficiency virus and the skin: selected controversies, *J Inves Derm* 105, S117–120S.

Ekman (1995) Herpes virus like (KSHV) DNA in various forms of Kaposi's sarcoma (KS) and malignant lymphoma (ML), *National Canc Inst* 11, S74.

Farid (1995) Letter to the editor, *New Eng J Med* 332, 1647.

Gallo (1995) Human retroviruses in the second decade: a personal perspective, *Nat Med* 1, 753–759.

Geddes et al (1995) Birthplace and classic Kaposi's sarcoma in Italy, *J Nat Canc Inst* 87, 1015–1017.

Glassman and Hale (1995) Cutaneous cryptococcosis and Kaposi's sarcoma occurring in the same lesions in a patient with the acquired immunodeficiency syndrome, *Clin Exp Derm* 20, 480–486.

Gluckman et al (1995) KS–associated herpesvirus–like DNA sequences after allogeneic bone–marrow transplantation *Lancet* 346, 1558–1559.

Gooding (1992) Virus proteins that counteract host immune defense, *Cell* 71, 5–7.

Griffiths (1995) Progress in the clinical management of herpesvirus infections, *Antiviral Chemistry Chemotherapy* 6, 191–209.

Grau et al (1995) Association of *Mycoplasma penetrans* with human immunodeficiency virus infection, *J Infec Dis* 172, 672–681.

Horuk (1994) Molecular properties of the chemokine receptor family, *Trends Pharmacol Sci* 15, 159–165.

Howard et al (1995) Association of human herpes virus with pulmonary Kaposi's sarcoma, *Lancet* 346, 712.

Hermans and Clumeck (1995) Kaposi's sarcoma in patients infected with human immunodeficiency virus (HIV): an overview, *Cell Mol Biol*, 357–364.

Ioachim (1995) Kaposi's sarcoma and KSHV, *Lancet* 346, 1360.

Jahan et al (1989) Analysis of human KS biopsies and cloned cell lines for cytomegalovirus, HIV–1, and other selected DNA virus sequences, *Aids Research Human Retro* 5, 225–231.

Jones et al (1995) AIDS–associated Kaposi's sarcoma, *Science* 267, 1078–1079.

Jung and Desrosiers (1995) Association of the viral oncoprotein STP–C488 with cellular *ras, Mol Cell Biol* 15, 6506–6512.

Jung et al (1995) Downregulation of lck–mediated signal transduction by tip of *Herpesvirus saimiri, J Virol 69*, 7814–7822.

Kaplan et al (1995) USPHS/IDSA guidelines for the prevention of opportunistic infections in persons infected with human immunodeficiency virus: introduction, *Clin Inf Dis* 21, S1–S111.

Karcher and Alkan (1995) Herpes–like DNA sequences, AIDS–related tumors, and Castlemen's disease, *New Eng J Med* 333, 797–798.

Karp and Broder (1995) Molecular foundations of cancer: new targets for intervention, *Nat Med* 1, 309–320.

Kempf et al (1995) Human herpesvirus type 6 and cytomegalovirus in AIDS–associated Kaposi's sarcoma, *Human Pathol* 26, 914–919.

Klauke et al (1995) Sex hormones as a cofactor in the pathgenesis of epidemic Kaposi's sarcoma, *AIDS* 9, 1295–1296.

Lebbe et al (1995) Kaposi's sarcoma and a new herpesvirus, *Lancet* 345, 1180.

Levy (1995) A new human herpesvirus: KSHV or HHV8?, *Lancet* 346, 786.

Levine (1995) Viral–associated neoplasms in humans: additional clues, *J Nat Canc Inst* 87, 947–949.

Lin et al (1995) Is Kaposi' sarcoma–associated herpesvirus detectable in semen of HIV–infected homosexual men? *Lancet* 346, 1601–o1602.

Lisitsyin (1995) Representational difference analysis: finding the differences between genomes, *Trends Genetics* 11, 303–307.

Murphy (1994) The molecular biology of leukocyte chemoattractant receptors, *Annu Rev Immunol* 12, 593–633.

Macasaet et al (1995) Kaposi's sarcoma presenting as a vulvar mass, *Obstet Gyn* 86, 695–697.

Mallery et al (1995) Cultured AIDS–related Kaposi's sarcoma (AIDS–KS) cells demonstrate impaired bioenergetic adaption to oxidant challenge: implication for oxidant stress in AIDS–KS pathogenesis, *J Cell Biol* 59, 317–328.

Marmor et al (1995) Evidence for an effect of human leukocyte antigens on susceptibility to Kaposi's sarcoma related to charge and peptide–binding properties of class I molecules, *Aids* 9, 1194–1195).

McGrath et al (1995) Identification of a clonal form of HIV in early Kaposi's sarcoma: evidence for a novel model of oncogenesis, "sequential neoplasia" *J Acq Immun Def* 8, 379–385.

Memar and Tyring (1995) Cutaneous viral infections, *J Am Acad Derm* 33, 279–287.

Memar et al (1995) Human herpesvirus–8: detection of novel herpesvirus–like DNA sequences in Kaposi's sarcoma and other lesions, *J Mol Med* 73, 603–609.

Moore et al (1995) Bacillary angiomatosis in patients with AIDS: multiorgan imaging findings 1, *Radiology* 197, 67–72.

Moore and Chang (1995) Detection of Herpesvirus–like DNA sequences in Kaposi's sarcoma in patients with and those without HIV infection, *New Eng J Med* 332, 1181–1185.

Morris et al (1995) Viral infection and cancer, *Lancet* 346, 754–758.

Maier et al (1996) Over–expression of hepatocyte growth factor in human Kaposi's sarcoma, *Int J Cancer* 65, 168–172.

Nador et al (1995) Herpes–like DNA sequences in a body––cavity–based lymphoma in an HIV–negative patient, *New Eng J Med* 333, 943.

Newton et al (1995) Cancer and HIV infection in Rwanda, *Lancet* 345, 1378–1379.

Noel (1995) Kaposi's sarcoma and KSHV, *Lancet* 346, 1359.

Pastore et al (1995) Distribution of Kaposi's sarcoma herpesvirus sequences among lymphoid mailgnancies in Italy and Spain, *Br J Haem* 91, 918–920.

Rady et al (1995) Herpesvirus–like DNA sequences in non–kaposi's sarcoma skin lesions of transplant patients, *Lancet* 345, 1339–1340.

Rady et al (1995) Herpesvirus–like DNA sequences in classic Kaposi's sarcomas, *J Med Virol* 47, 179–183.

Relman (1995) Has trench fever returned, *New Eng J Med* 332, 463–464.

Roizman (1995) New viral footprints in Kaposi's sarcoma, *New Eng J Med* 332, 1227–1228.

Roulston et al (1995) Regulation of human immunodeficiency virus type 1 and cytokine gene expression in myeloid cells by NF–kB/Rel transcription factors, *Microbiol Res* 59, 481–505.

Rubin (1995) Letter to the editor, *Science* 267, 157–158.

Saiag et al (1995) Local treatments of AIDS associated Kaposi's sarcoma, *Ann Der Ven* 122, 551–557.

Schalling et al (1995) A role for a new herpes virus (KSHV) in different forms of Kaposi's sarcoma, *Nat Med* 1, 707–708.

Schulz and Weiss (1995) A finger on the culprit, *Nature* 373, 17.

Schutte et al (1995) Identification by representational difference analysis of a homozygous deletion in pancreatic carcinoma that lies within the BRCA2 region, *Proc Natl Acad Sci USA* 92, 5950–5954.

Serraino et al (1995) HIV transmission and Kaposi's sarcoma among European women, *Aids* 9, 971–973.

Soulier et al (1995) Kaposi's sarcoma–associated herpesvirus–like DNA sequence in multicentric Castleman's disease, *Blood* 86, 1276–1280.

Stewart et al (1995) Herpesvirus infections in persons infected with human immunodeficiency virus, *Clin Inf Dis* 21, S114–S120.

Su et al (1996) Detection and sequence analysis of a new herpesvirus–like agent in AIDS and non–AIDS Kaposi's sarcoma in Taiwan, *J Formosan Med* 95, 13–18.

Telford et al (1995) The DNA sequence of equine herpesvirus 2, *J Mol Biol* 249, 520–528.

Wang et al (1995) Acquired immunodeficiency syndrome–related Kaposi's sarcoma, *Mayo Clin Proc* 70, 869–879.

Whitby et al (1995) Detection of Kaposi's sarcoma associated herpesvirus in pheripheral blood of HIV–infected individuals and progression to Kaposi's, *Lancet* 346, 799–802.

Winston and Klotman (1996) Are we missing an epidemic of HIV–associated nephropathy? *Am Soc Nephrol* 7, 1–7.

Ziegler and Katongole–Mbidde (1996) Kaposi's sarcoma in childhood: an analysis of 100 cases from Uganda and relationship to HIV infection, *Int J Canc* 65, 200–203.

Ansari et al (1996) Primary blood cavity–based AIDS–related lymphomas, *Am J Clin Pathol* 105, 221–229.

Armenian et al (1996) Risk factors for non–Hodgkins's lymphomas in acquired immunodeficiency syndrome (AIDS), *Am J Epidemol* 143, 374–379.

Arvanitakis et al (1996) Human herpesvirus KSHV encodes a constitutively active G–protein–coupled receptor linked to cell proliferation, *Nature* 385, 347–350.

Biggar and Melbye (1996) Marital status in relation to Kaposi's sarcoma, non–Hodgkin's lymphoma, and anal cancer in the pre–AIDS era, *J Acq Immun Def Syn Hum Retrovirol* 11, 178–182.

Bigoni et al (1996) Human herpesvirus 8 is present in the lymphoid system of healthy persons and can reactivate in the course of AIDS, *J Infect Dis* 173, 542–549.

Corey (1996) Commentary: lack of detection of HSV DNA in PBMCs and lymph nodes of HIV–infected persons, *J Med Virol* 48, 47.

DiAlberti et al (1996) Kaposi's sarcoma herpesvirus in oral Kaposi's sarcoma, *Oral Oncol* 328, 68–69.

Foreman et al (1996) Cultured Kaposi's sarcoma tumor cells fail to stimulate T cell proliferation, *Clin Immunol Immunopathol* 78, 172–179.

Gyulai et al (1996) Herpesvirus–like DNA sequence in angiosarcoma in a patient without HIV infection, *N Eng J Med* 334, 540–541.

Heredia et al (1996) Detection of herpesvirus type 8 (HIV–8) sequences in patients with Kaposi's sarcoma in Spain, *J Acq Immun Def Syn Hum Retroviral* 11, 310–311.

Jaffe (1996) Primary body cavity–based AIDS–related lymphomas, evolution of a new disease entity, *Am J Clin Pathol* 105, 141–143.

Jin et al (1996) Detection of Kaposi's sarcoma–associated herpesvirus–like DNA sequence in vascular lesions, a reliable diagnostic marker for Kaposi's sarcoma, *Am J Clin Pathol* 105, 360–363.

Kemény et al (1996) Herpesvirus–like nucleic acid sequences in patients with western European sporadic Kaposi's sarcoma, *J Invest Derm* 106, 381.

Kiaris et al (1996) Detection of herpesvirus–like DNA sequences in Mediterranean Kaposi's sarcoma, *Oncol Rep* 3, 355–356.

Renne et al (1996) Lytic growth of Kaposi's sarcoma–associated herpesvirus (human herpesvirus 8) in culture, *Nat Med* 2, 342–346.

Rettig et al (1996) Kaposi's sarcoma–associated herpesvirus infection of bone marrow dendritic cells from multiple myeloma patients, *Science* 276, 1851–1854.

Sable and Mandel (1996) The role of molecular techniques in the understanding of emerging infections, *Molec Med Today* 2, 120–128.

Sosa et al (1996) Herpesvirus–like DNA in AIDS Kaposi's sarcoma in Argentina, *J Acq Immun Def Syn Hum Retrovirol* 11, 308.

Tompkins (1996) Bartonella species infections, including cat–scratch disease, trench fever, and bacillary angiomatosis: what molecular techniques have revealed, *Western J Med* 164, 39–41.

Tur (1996) Treatment of Kaposi's sarcoma, *Arch Dermatol* 132, 327–331.

Tyring (1996) HHV8 and skin cancers in immunosuppressed patients, *Lancet* 347, 338–339.

Weiss (1996) Human herpesvirus 8 in lymphoma and Kaposi's sarcoma: now the virus can be propagated, *Nat Med* 2, 277–278.

Zalla (1996) Kaposi's sarcoma: An update, *Dermatol Surg* 22, 274–287.

Giraldo et al. (1972) Herpes–type virus particles in tissue culture of Kaposi's sarcoma from different geographic regions, *Journal of the National Cancer Institute* 49, 1509–1513.

Giraldo et al. (1984) Kaposi's sarcoma: a natural model of interrelationships between viruses, immunologic responses, genetics and oncogenesis, *Antibiotics and Chemotherapeutics* 32, 1–11.

Iochim et al. (1992) Cytomegalovirus, angiomatosis, and Kaposi's sarcoma: new observations of a debated relationship, *Modern Pathology* 5, 169–178.

Jahan et al. (1989) Analysis of human KS biopsies and cloned cell lines for cytomegalovirus, HIV–1, and other selected DNA virus sequences, *AIDS Research and Human Retroviruses* 5, 225–231.

Walter et al. (1984) Kaposi's sarcoma: presence of herpes–type virus particles in a tumor specimen, *Human Pathology* 15, 1145–1146.

Dupin et al. (1995) Herpesvirus–like DNA sequences in patients with Mediterranean Kaposi's sarcoma, *The Lancet* 345, 761–762.

Huang et al. (1995) Human herpesvirus–like nucleic acid in various forms of Kaposi's sarcoma, *The Lancet* 345, 759–761.

Su et al. (1995) Herpesvirus–like DNA sequence in Kaposi's sarcoma from AIDS and non–AIDS patients in Taiwan, *The Lancet* 345, 722–723.

McGrath et al. (1995) Identification of a clonal form of HIV in early Kaposi's sarcoma: evidence for a novel model of oncogenesis, "sequential neoplasia" *J Acq Immun Def Hum Retroviral* 8, 379–385.

Relman (1995) Has trench fever returned?, *New Eng J Med* 332, 463–464.

Schulz and Weiss (1995) A finger on the culprit, *Nature* 373, 17–18.

Gewirtz (1994) Suppression of megakaryocytopoises by macrophage inflammatory proteins, U.S. Patent No. 5,306, 709, issued Apr. 26, 1994.

Fahey, III et al. (1992) Method and agents for promoting wound healing, U.S. Patent No. 5,145,676, issued Sep. 8, 1992.

Miles et al. (1995) Method to treat Kaposi's sarcoma, U.S. Patent No. 5,470,824, issued Nov. 28, 1995.

Cocchi et al. (1995) Identification of Rantes, MIP–1α, and MIP–1β as the major HIV–suppressive factors produced by $CD8^{+T\ cells,}$ *Science* 270, 1811–1815.

Franceschi and Serraino (1995) Letters to the Editor: Kaposi's sarcoma and KSHV, *The Lancet* 346, 1360–1361.

Gaidano et al. (1995) Molecular pathogenesis of non–Hodgkin lymphoma: a clinical perspective, *Haematologica* 80, 454–472.

Gelman (1995) Pathogenesis of AIDS–related Kaposi's sarcoma, *Oncology Reports* 2, 321–324.

Morgello (1995) Pathogenesis and classification of primary central nervous system lymphoma: an update, Brain Pathology 5, 383–393.

Murphy (1994) The nolecular biology of leukocyte chemoattractant receptors, *Annu Rev Immunol* 12, 593–633.

Oppenheim et al. (1991) Properties of the novel proinflammatory supergene "intercrine" cytokine family, *Ann Rev Immunol* 9, 617–648.

Carbone et al (Sep. 1, 1996) Kaposi's sarcoma–associated herpesvirus DNA sequences in AIDS–related and AIDS–unrelated lymphomatous effusions, *Br J Haematol* 94, 533–543.

Cesarman et al (Jul. 1996) Kaposi's sarcoma–associated herpesvirus in non–AIDS related lymphomas occurring in body cavities, *Am J Pathol* 149, 53–57.

Chang et al. (Jan. 22, 1996) Kaposi's sarcoma–associated herpesvirus and Kaposi's sarcoma in Africa, *Arch Intern Med* 156, 202–204.

Corbellino et al. (May 20, 1996) Restricted tissue distribution of extralesional Kaposi's sarcoma–associated herpesvirus–like DNA sequences in AIDS patients with Kaposi's sarcoma, *AIDS Res Hum Retroviruses* 12, 651–657.

Decker et al. (Jul. 1, 1996) The Kaposi sarcoma–associated herpesvirus (KSHV) is present as an intact latent genome in KS tissue but replicates in the peripheral blood mononuclear cells of KS patients, *J Exp Med* 184, 283–288.

Dictor et al. (Jun. 1996) Human herpesvirus 8 (Kaposi's sarcoma–associated herpesvirus) DNA in Kaposi's sarcoma lesions, AIDS Kaposi's sarcoma cell lines, endothelial Kaposi's sarcoma simulators, and the skin of immunosuppressed patients, *Am J Pathol* 148, 2009–2016.

Enwonwu (Jul. 1996) Pathogenesis of oral Kaposi's sarcoma in HIV–infection: relevance of endogenous glucocorticoid excess in blood and saliva, (*Eur J Cancer B*) *Oral Oncol* 32B, 271–274.

Gaidano et al. (Jul. 1996) Establishment of AIDS–related lymphoma cell lines from lymphomatous effusions, *Leukemia* 10, 1237–1240.

Humphrey et al. (Jul. 1, 1996) Kaposi's sarcoma (KS)–associated herpesvirus–like DNA sequence in peripheral blood mononuclear cells: association with KS and persistence in patients receiving anti–herpesvirus drugs, *Blood* 88, 297–301.

Luppi et al. (May 16, 1996) Frequency and distribution of herpesvirus–like DNA sequences (KSHV) in different stages of classic Kaposi's sarcoma and in normal tissues from an Italian population, *Int J Cancer* 66, 427–431.

Mesri et al. (May 1, 1996) Human herpesvirus–8/ Kaposi's sarcoma–associated herpesvirus is a new transmissible virus that infects B cells, *J Exp Med* 183, 2385–2390.

Miller et al. (May 16, 1996) Antibodies to butyrate–inducible antigens of Kaposi's sarcoma–associated herpesvirus in patients with HIV–1 infection, *N Eng J Med* 334, 1292–1297.

Monini et al. (May 2, 1996) Kaposi's sarcoma–associated herpesvirus DNA sequence in prostate tissue and human semen, *N Engl J Med* 334, 1168–1172.

Nador et al. (Jul. 15, 1996) Primary effusion lymphoma: a distinct clinicopathologic entity associated with the Kaposi's sarcoma–associated herpes virus, *Blood* 88, 645–656.

Offermann et al. (Sep. 1996) Antioxidant–sensitive regulation of inflammatory–response genes in Kaposi's sarcoma cells, *J Aquir Immune Defic Syndr Hum Retrovirol* 13, 1–11.

O'Neill et al. (Apr. 1996) Herpes virus–like sequences are specifically found in Kaposi sarcoma lesions, *J Clin Pathol* 49, 306–308.

Otsuki et al. (Aug. 1996) Detection of HHV–8/KSHV DNA sequences in AIDS–associated extranodal lymphoid malignancies, *Leukemia* 10, 1358–1362.

Rüdlinger (Feb. 1996) Das enigma Kaposi–sarkom, *Der Hautarzt* 47, 91–95.

Said et al. (Jun. 15, 1996) Kaposi's sarcoma–associated herpesvirus (KSHV or HHV8) in primary effusion lymphoma: ultrastructural demonstration of herpesvirus in lymphoma cells, *Blood* 87, 4937–4943.

Su et al. (Jan. 1996) Detection and sequence analysis of a new herpesvirus–like agent in AIDS and non–AIDS Kaposi's sarcoma in Taiwan, *J Formos Med Assoc* 95, 13–18.

Tomita et al. (Mar. 28, 1996) Absence of Kaposi's sarcoma–associated herpesvirus–like DNA sequences (KSHV) in angiosarcomas developing in body–cavity and other sites, *Int J Cancer* 66, 141–142.

Zhong et al. (Jun. 25, 1996) Restricted expression of Kaposi sarcoma–associated herpesvirus (human herpesvirus 8) genes in Kaposi sarcoma, *Proc Natl Acad Sci USA* 93, 6641–6646.

Ziegler et al. (Jan. 17, 1996) Kaposi's sarcoma in childhood: an analysis of 100 cases from Uganda and relationship to HIV infection, *Int J Cancer* 65, 200–203.

Blackbourn, David et al (1996) The Infectious Nature of the Novel Herpesvirus–like DNA Sequence Detected in Kaposi's Sarcoma, Int. Conf. AIDS vol. 11, No. 2, p. 215, abstract No. Th.A.273.

Bennet, J et al (1996) Characterization of the DNA Polymerase and Glycoprotein B Genes in Kaposi's Sarcoma–Associated and Related Herpesviruses: Int. Conf. AIDS vol. 11, No. 2, p. 7, abstract No. We.A.161.

Ostrand, K. (1996) Simian Homologues of Human Herpesvirus–8 (or KSHV) in Retroperitoneal Fibromatosis in Macques Int. Conf. AIDS vol. 11, No. 2, p. 7, abstract No. Th.A.275.

Zhong et al. (Jun. 1, 1996) Restricted Expression of Kaposi Sarcoma–Associated Herpesvirus (Human herpesvirus 8) Genes in Kaposi Sarcoma, *Proc Natl Acad Sci USA* 93, 6641–6646 (Exhibit 17).

Russo JJ et al (Dec. 10, 1996) Nucleotide Sequence of the Kaposi Sarcoma–Associated Herpesvirus (HV8) *Proc. Natl Acad Sci USA* 93, 25, 14862–14867 (Exhibit 18).

Simpson GR et al (Oct. 26, 1996) Prevalence of Kaposi's Sarcoma Associated Herpesvirus Infection Measured By Antibodies to recombinant Capsid Protein and Latent Immunofluorescence Antigen, *Lancet The* 348, 9035, 1133–1138 (Exhibit 19).

Neipel F et al (Jan. 1, 1997) Human Herpesvirus 8 Encodes A Homolog of Interleukin–6 *Journal of Virology* 71,1, 839–842 (Exhibit 20).

Russo JJ et al: Nucleotide Sequence of the Kaposi Sarcoma–Associated Herpesvirus (HHV8) *Proc Natl Acad Sci USA* 93, No. 25, (Dec. 10, 1996) 14862–14867 (Exhibit 21).

Takeishi et al: Nucleotide Sequences of a functional cDNA for Human Thymidylate Synthase *Nucleic Acid Research* 13, 1985, 2035–2043, figure 2 (Exhibit 22).

Parravicini et al. In Situ Detection of Human Herpesvirus–8 DNA sequences in AIDS–Associated Kaposi's sarcoma. Abstracts of 3rd Conf. Retro. And Opportun. Infect. Jan. 28–Feb. 1, 1996, p. 55, see Abstract (Exhibit 23).

Moore et al. Primary Characterization of a Herpesvirus agent associated with Kaposi's Sarcoma. *J Virol* Jan. 1996 70, No. 1, 549–558, see entire article (Exhibit 24).

* cited by examiner

Figure 1:
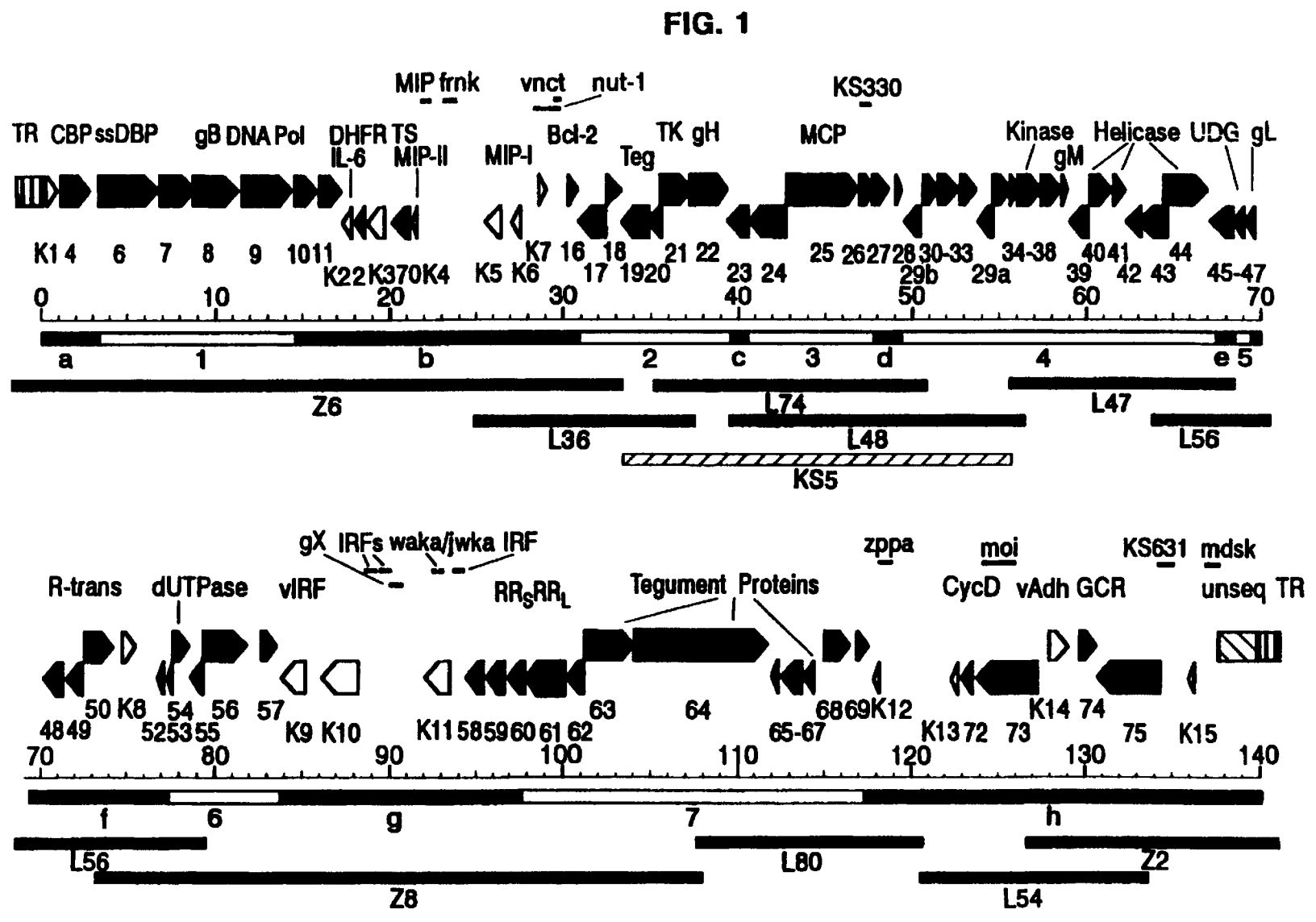

1 CGTGAACACC CCGCGCCCCG CGCCCCCCAC ACCGCGCCGC CCCTCCCCCT CCCCCCGCTC
61 GCCTCCCGGC GCTGCCGCCA GGCCCCGGCC GGAGCCGGCC GCCCGCGGGG GGCAGGGCGC
121 GCCCGGCGGC TCCCTCGCGG GGCGGGGGAC GGGGGAGG*gg ggcgccggg*C CCCCGCGCGC
181 CGCGGCAGCG GAGCGCGAG*c gcccccgccg gccgcca*GCG GCGGCGCAGG CCCCGGGGCC
241 CCGAGCCCCG AGCCCCGCCG GGGTACGGGG CTAG*gccacg cctactttt ttttcgggcg*
301 *gccccccgac cctctctcgg cccccc*GGTC CCCGCGGCCC GCGCGCGCCC CCCCGGGGGG
361 GTAAAACAGG GGGGGGGGA TGCGGCCGCG GCGGCGCCCG CGGCGGCGGC GGCGCTTGC*t*
421 *ttcgttttct cccgcggccc cccgggcgcg agccgcgcgg cggcggcggg cgccccctcc*
481 *cccgggggc tcggcggggg gcc*CCCTGTC CC*cgcgcggg cccgcgaccc cc*GGCGCCGC
541 CGCGCCCCGA TCCCGCGGGC GCCCCGCCCC CCTGCCGGGG ACGCCGCCGG GCCTGCGGCG
601 CCTCCCGCCC GGGCATGGG*g ccgcgcgccg cctcagggcc cggcgcggcc ggcgcctggt*
661 *ccccgccccc gcccgcgggg gaccccgg*GC AGCGAGGGAA GGGGGCGCCC TCTCTCTACT
721 GTGCGAGGAG TCTGGGCTGC TGTGTGTGAG CCTGTTTGGG GGAGCCTCCT CAGTGCTTGC
781 TACGTGGAGC CCTGGACACT A

FIG. 2B

Nde II 1 2 3

```
vMIP-I     MAPVHVLCCV SVLLATFYLT PTESAGSLVS YTPNSCCYGF QQHPPPVQIL  50
vMIP-II    M-DTKGILLV AVLTALLCLQ SGDTLG-ASW HRPDKCCLGY QKRPLPQVLL
huMIP-1α   M-QVSTAAL- AVLLCTMALC NQVLSAPLAA DTPTACCFSY TSRQIPQNFI
huMIP-1β   M-KLCVTVL- SLLMLVAAFC SPALSAPMGS DPPTACCFSY TARKLPRNFV
huRANTES   M-KVSAARL- AVILIATALC APASASPYSS DT-TPCCFAY IARPLPRAHI

vMIP-I     KEWYPTSPAC PKPGVILLTK RGRQICADPS KNWVRQLMQR LPAIA-      100
vMIP-II    SSWYPTSQLC SKPGVIFLTK RGRQVCADKS KDWVKKLMQQ LPVTAR
huMIP-1α   ADYFETSSQC SKPSVIFLTK RGRQVCADPS EEWVQKYVSD LELSA-
huMIP-1β   VDYYETSSLC SQPAVVFQTK RSKQVCADPS ESWVQEYVYD LELN--
huRANTES   KEYFYTSGKC SNPAVVFVTR KNRQVCANPE KKWVREYINS LEMS--
```

FIG. 3B

```
vIL6    MCWFKLWSLL LV----GSLL VSGTRGKLPD AP-EFEKDL- --LIQRLNWM  50
huIL6   MNSFSTSAFG PVAFSLGLLL VLPAAFPAPV PPGEDSKDVA APHRQPLTSS

vIL6    LWV------I DECFRDL--- -CYRTGICKG ILEPAAIFHL KLPAINDTDH 100
huIL6   ERIDKQIRYI LDGISALRKE TCNKSNMCES SKEALAENNL NLPKMAEKDG

vIL6    CGLIGFNETS CLKKLADGFF EFEVLFKFLT TEFGKSVINV DVMELLTKTL 150
huIL6   CFQSGFNEET CLVKIITGLL EFEVYLEYLQ NRFESSEEQA RAVQMSTKVL

vIL6    GWDIQEELNK LTKTHYSPPK FDRGLLGRLQ GLKYWVRHFA SFYVLSAMEK 200
huIL6   IQFLQKKAKN LDAITTPDPT TNASLLTKLQ AQNQWLQDMT THLILRSFKE

vIL6    FAGQAVRVLD SIPDVTPDVH DK
huIL6   FLQSSLRAL- ---------R QM
```

FIG. 3C-1

```
vIRF       MDPGQRPNPF GAPGAIPKKP CLSQGSPGTS GSGAPCDEPS RSESPGEGPS  50
huISGF3γ
huICSBP

vIRF       GTGGSAAAGD ITRQAVVAAI TEWSRTRQLR ISTGASEGKA SIKDWIVCQV 100
huISGF3γ                                    MASGRARCTR KLRNWVVEQV
huICSBP                                      MCDRNGGGR -LRQWLIEQI

vIRF       NSGKFPGVEW EDEERTRFRI PVTPLADPCF EWRRDGELGV VYIRERGNMP 150
huISGF3γ   ESGQFPGVCW DDTAKTMFRI PWKHAGKQDF REDQDAAFFK AWAIFKGKYK
huICSBP    DSSMYPGLIW ENEEKSMFRI PWKHAGKQDY NQEVDASIFK AWAVFKGKPK

vIRF       VDASFKGTRG RRRMLAALRR TRGLQEIG-K GISQDGHHFL VFRVRKPEEE 200
huISGF3γ   EGDTGGPAVW KTRLRCALNK SSEFKEVPER GRMDVAEPYK VYQLLPPGIV
huICSBP    EGDKAEPATW KTRLRCALNK SPDFEEVTDR SQLDISEPYK VYRIVPEEDQ

vIRF       QCVECGVVAG AVHDFNNMA- -RLLQEGFFS -----PGQCL PGEIVTPVPS 250
huISGF3γ   SGQPGTQKVP SKRQHSSVSS ERKEEEDAMQ NCTLSPSVLQ DSLNNEEEGA
huICSBP    KCKLGVATAG CVNEVTEMEC GRSEIDELIK ----EPSVDD YMGMIKRSPS

vIRF       CTTAEGQEAV IDWG------ ---------- ---------- --------RL 300
huISGF3γ   SGGAVHSDIG SSSSSSSPEP QEVTDTTEAP FQGDQRSLEF LLPPEPDYSL
huICSBP    PPDACRSQLL PDWWAHEPST GRRLVTGYTT YDAHHSAFS- --------QM
```

FIG. 3C-2

```
vIRF      FIRMYYNGEQ VHELLTTSQS GCRISSALRR DPAVHYCAVG SPGQVWLP-N 350
huISGF3γ  LLTFIYNGRV VGEAQVQSLD -CRLVAE--- -P--SGS-ES SMEQVLFPKP
huICSBP   VISFYYGGKL VGQATTTCPE GCRLSLSQPG LPGTKLYGPE GLELVRFP-P

vIRF      VFNLACEIAK RELCDTLDAC AKGILLTSSC NGIFCVCYHN GPVHFIGNTV 400
huISGF3γ  GPLEPT--QR -----LLSQL ERGILVASNP RGLFVQRLCP IPISWNAPQA
huICSBP   ADTIPSERQR QVTRKLFGHL ERGVLHSSR- QGVFVKRLCQ GRVFCVVVVV

vIRF      PPDSGPLLLP QGKPTRIFNP NTFLVGLAN- --S--PLPAP SHVTCPLVKL 450
huISGF3γ  PPGPGPHLLP SNECVELFRT AYFCRDLVRY FQGLGPPPKF QVTLNFWEES
huICSBP   VCKGRPNKLE RDEVVQVFDT SQFFRELQQF YNSQGRLPDG RVVLCFGEEF

vIRF      WLGKPVAVGK LEPHAPSP-- RDFAARCSNF SDACVVLEIM PKPLWDAMQ- 500
huISGF3γ  HGSSHTPQNL ITVKMEQAFA RYLLEQTPEQ QAAILSLV-- ----------
huICSBP   PDMAPLRSKL ILVQIEQLYV RQLAEEAGKS CGAGSVMQAP EEPPPDQVFR

vIRF      ---------- ---------- --
huISGF3γ  ---------- ---------- --
huICSBP   MFPDICASHQ RSFFRENQQI TV
```

FIG. 4A
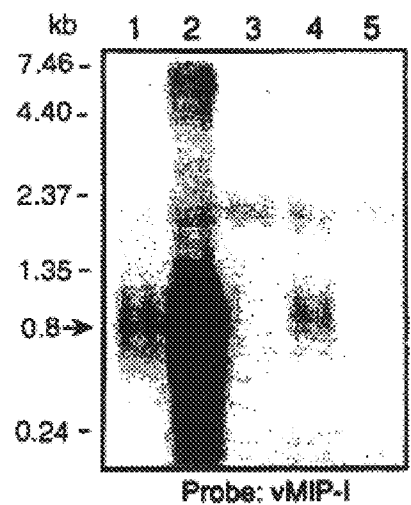
FIG. 4B
1 2 3 4 5
0.8
Probe: vMIP-II
FIG. 4C
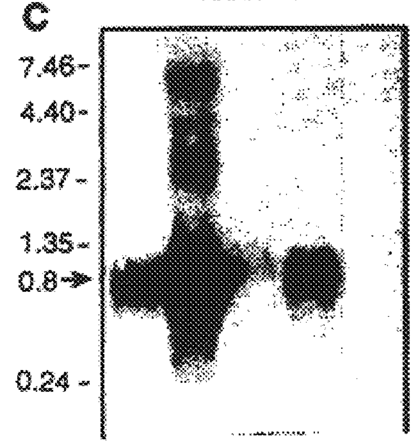
FIG. 4D
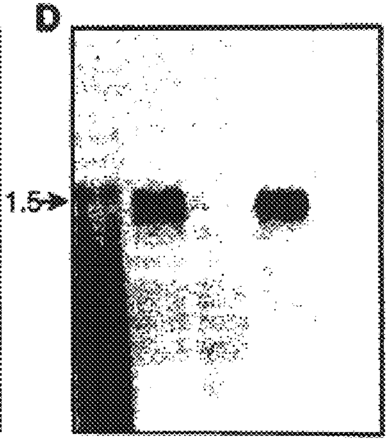
FIG. 4E
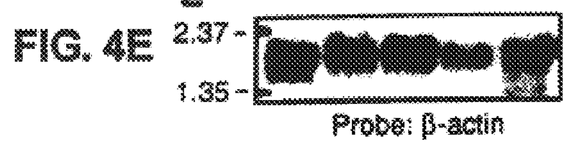
FIG. 4F
F
Probe: β-actin FIG. 7A
A
FIG. 7B
B
FIG. 7C
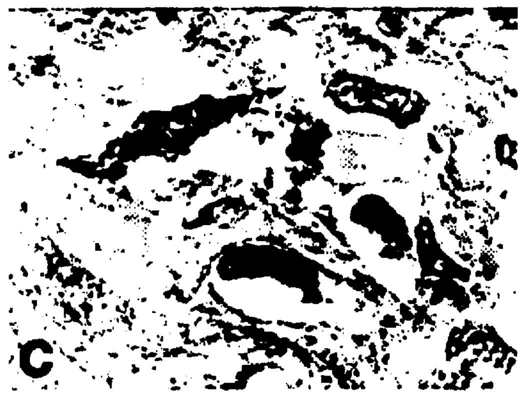
FIG. 7D
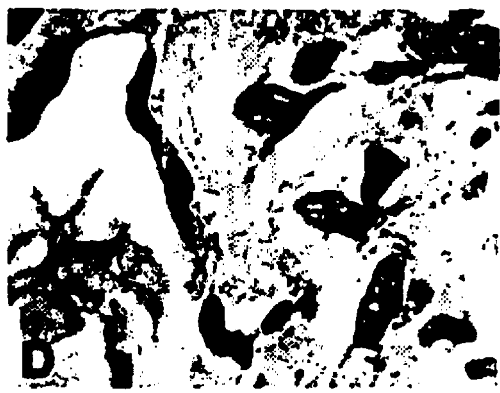
FIG. 7E
E
FIG. 7F

SEQUENCE LISTING

```
<160> NUMBER OF SEQ ID NOS:  30

<210> SEQ ID NO 1
<211> LENGTH: 337
<212> TYPE: PRT
<213> ORGANISM: Kaposi's sarcoma-associated herpesvirus

<400> SEQUENCE: 1

Met Phe Pro Phe Val Pro Leu Ser Leu Tyr Val Ala Lys Lys Leu Phe
  1               5                  10                  15

Arg Ala Arg Gly Phe Arg Phe Cys Gln Lys Pro Gly Val Leu Ala Leu
             20                  25                  30

Ala Pro Glu Val Asp Pro Cys Ser Ile Gln His Glu Val Thr Gly Ala
         35                  40                  45

Glu Thr Pro His Glu Glu Leu Gln Tyr Leu Arg Gln Leu Arg Glu Ile
```

```
     50                  55                  60

Leu Cys Arg Gly Ser Asp Arg Leu Asp Arg Thr Gly Ile Gly Thr Leu
 65                 70                  75                  80

Ser Leu Phe Gly Met Gln Ala Arg Tyr Ser Leu Arg Asp His Phe Pro
                 85                  90                  95

Leu Leu Thr Thr Lys Arg Val Phe Trp Arg Gly Val Val Gln Glu Leu
            100                 105                 110

Leu Trp Phe Leu Lys Gly Ser Thr Asp Ser Arg Glu Leu Ser Arg Thr
        115                 120                 125

Gly Val Lys Ile Trp Asp Lys Asn Gly Ser Arg Glu Phe Leu Ala Gly
    130                 135                 140

Arg Gly Leu Ala His Arg Arg Glu Gly Asp Leu Gly Pro Val Tyr Gly
145                 150                 155                 160

Phe Gln Trp Arg His Phe Gly Ala Ala Tyr Val Asp Ala Asp Ala Asp
                165                 170                 175

Tyr Thr Gly Gln Gly Phe Asp Gln Leu Ser Tyr Ile Val Asp Leu Ile
            180                 185                 190

Lys Asn Asn Pro His Asp Arg Arg Ile Ile Met Cys Ala Trp Asn Pro
        195                 200                 205

Ala Asp Leu Ser Leu Met Ala Leu Pro Pro Cys His Leu Leu Cys Gln
    210                 215                 220

Phe Tyr Val Ala Asp Gly Glu Leu Ser Cys Gln Leu Tyr Gln Arg Ser
225                 230                 235                 240

Gly Asp Met Gly Leu Gly Val Pro Phe Asn Ile Ala Ser Tyr Ser Leu
                245                 250                 255

Leu Thr Tyr Met Leu Ala His Val Thr Gly Leu Arg Pro Gly Glu Phe
            260                 265                 270

Ile His Thr Leu Gly Asp Ala His Ile Tyr Lys Thr His Ile Glu Pro
        275                 280                 285

Leu Arg Leu Gln Leu Thr Arg Thr Pro Arg Pro Phe Pro Arg Leu Glu
    290                 295                 300

Ile Leu Arg Ser Val Ser Ser Met Glu Glu Phe Thr Pro Asp Asp Phe
305                 310                 315                 320

Arg Leu Val Asp Tyr Cys Pro His Pro Thr Ile Arg Met Glu Met Ala
                325                 330                 335

Val


<210> SEQ ID NO 2
<211> LENGTH: 10
<212> TYPE: PRT
<213> ORGANISM: Synthetic Peptide

<400> SEQUENCE: 2

Thr His Tyr Ser Pro Pro Lys Phe Asp Arg
  1               5                  10


<210> SEQ ID NO 3
<211> LENGTH: 10
<212> TYPE: PRT
<213> ORGANISM: Synthetic Peptide

<400> SEQUENCE: 3

Pro Asp Val Thr Pro Asp Val His Asp Arg
  1               5                  10


<210> SEQ ID NO 4
```

<211> LENGTH: 24
<212> TYPE: DNA
<213> ORGANISM: synthetic construct

<400> SEQUENCE: 4
agcatataag gaactcggcg ttac 24

<210> SEQ ID NO 5
<211> LENGTH: 23
<212> TYPE: DNA
<213> ORGANISM: synthetic construct

<400> SEQUENCE: 5
ggtagataaa tcccccccct ttg 23

<210> SEQ ID NO 6
<211> LENGTH: 21
<212> TYPE: DNA
<213> ORGANISM: synthetic construct

<400> SEQUENCE: 6
tgcatcagct tcttcaccca g 21

<210> SEQ ID NO 7
<211> LENGTH: 23
<212> TYPE: DNA
<213> ORGANISM: synthetic construct

<400> SEQUENCE: 7
tgctgtctcg gttaccagaa aag 23

<210> SEQ ID NO 8
<211> LENGTH: 24
<212> TYPE: DNA
<213> ORGANISM: synthetic construct

<400> SEQUENCE: 8
tcacgtcgct ctttacttat cgtg 24

<210> SEQ ID NO 9
<211> LENGTH: 24
<212> TYPE: DNA
<213> ORGANISM: synthetic construct

<400> SEQUENCE: 9
cgcccttcag tgagacttcg taac 24

<210> SEQ ID NO 10
<211> LENGTH: 20
<212> TYPE: DNA
<213> ORGANISM: synthetic construct

<400> SEQUENCE: 10
cttgcgatga accatccagg 20

<210> SEQ ID NO 11
<211> LENGTH: 20
<212> TYPE: DNA
<213> ORGANISM: synthetic construct

<400> SEQUENCE: 11
acaacaccca attccccgtc 20

-continued

<210> SEQ ID NO 12
<211> LENGTH: 24
<212> TYPE: DNA
<213> ORGANISM: synthetic construct

<400> SEQUENCE: 12
tcacgtcgct ctttacttat cgtg 24

<210> SEQ ID NO 13
<211> LENGTH: 24
<212> TYPE: DNA
<213> ORGANISM: synthetic construct

<400> SEQUENCE: 13
cgcccttcag tgagacttcg taac 24

<210> SEQ ID NO 14
<211> LENGTH: 24
<212> TYPE: DNA
<213> ORGANISM: synthetic construct

<400> SEQUENCE: 14
agcatataag gaactcggcg ttac 24

<210> SEQ ID NO 15
<211> LENGTH: 23
<212> TYPE: DNA
<213> ORGANISM: synthetic construct

<400> SEQUENCE: 15
ggtagataaa ctcccccct ttg 23

<210> SEQ ID NO 16
<211> LENGTH: 801
<212> TYPE: DNA
<213> ORGANISM: Kaposi's sarcoma-associated herpesvirus

<400> SEQUENCE: 16
cgtgaacacc ccgcgccccg cgccccccac accgcgccgc ccctccccct ccccccgctc 60
gcctcccggc gctgccgcca ggccccggcc ggagccggcc gcccgcgggg ggcagggcgc 120
gcccggcggc tccctcgcgg ggcgggggac gggggagggg ggcgccgggc ccccgcgcgc 180
cgcggcagcg gagcgcgagg gcccccgccg gccgccagcg gcggcgcagg ccccgggggc 240
ccgagccccg agcggggccg gggtacgggg ctaggccacg aataattttt ttttcgggcg 300
gccccccgaa cctctctcgg ccccccggtc cccgcggccc gcgcgcgccc ccccgggggg 360
gtaaaacagg gggggggga tgcggccgcg gcggcgcccg cggcggcggc ggcgcttgct 420
ttcgttttct cccgcggccc cccgggcgcg agccgcgcgg cggcggcggg cgccccctcc 480 cccgggggc tcggcggggg gccccctgtc cccgcgcggg cccgcgaccc ccggcgccgc 540
cgcgccccga tcccgcgggc gccccgcccc cctgccgggg acgccgccgg gcctgcggcg 600
cctcccgccc gggcatgggg ccgcgcgccg cctcagggcc cggcgcggcc ggcgcctggt 660
ccccgccccc gcccgcgggg gaacccgggc agcgagggaa gggggcgccc tctctctact 720
gtgcgaggag tctgggctgc tgtgtgtgag cctgtttggg ggagcctcct cagtgcttgc 780
tacgtggagc cctggacact a 801

<210> SEQ ID NO 17
<211> LENGTH: 35100

-continued

<212> TYPE: DNA
<213> ORGANISM: Kaposi's sarcoma-associated herpesvirus

<400> SEQUENCE: 17

```
tactaatttt caaaggcggg gttctgccag gcatagtctt tttttctggc ggcccttgtg     60
taaacctgtc tttcagacct tgttggacat cctgtacaat caagatgttc ctgtatgttg    120
tctgcagtct ggcggtttgc tttcgaggac tattaagcct ttctctgcta tcgtctccaa    180
atttgtgccc tggagtgatt tcaacgcctt acacgttgac ctgtctgtct aatgcatcct    240
tgccaatatc ctggtattgc aacaatactc ggcttttgcg actgacggag agaagagtca    300
ttcttgacac cattgcctgc aattttactt gtgtggaaca atctgggcat cgacagagca    360
tttggattac atggcgtgca caacctgtct tacaaacctt gtgtgcacag ccatcaaaca    420
cagtcacttg tggtcagcat gttactttgt attgttctac ctctggaaat aatgttaccg    480
tttggcatct accaaacgga cgaaatgaaa ccgtgtcaca aactaaatac tataatttta    540
cgctgatgag ccaaactgag ggtgttatac cttgttctaa cgggctgtcg tctcgcctgt    600
caaatcgtat atgtttttgg gcgcgttgtg ccaatataac tccagaaact catactgtat    660
ctgtcagcag tactacaggc tttagaacat tgagtactaa tagcttagtg aagataatcc    720
atgcaaccac acgtgatgta gttgtagtga aagaagcaaa atctacacat tttcatattg    780
aagtgcattt tcttgtattt atgacactcg tagctctgat aggaaccatg tgtggtatct    840
taggaactat tatctttgcc cattgtcaaa aacaacgtga ctcaaacaaa acagtgccac    900
aacaattgca ggattattat tccctacacg atttgtgcac ggaagactat acgcaaccag    960
tggattggta ctgacattca ggtaagataa tctaaatatt ctctataaca taattgtaat   1020
gtgttttatg tttatagcta caaatgtttt atgcaaaata cattttatga ggtcggatac   1080
ttattaaaag cattgtctta agtacattaa aaggacattg tataaccgtg ctacttacag   1140
catggccttt ttaagacaaa cactgtggat tttatggaca tttaccatgg ttattggcca   1200
ggacaatgaa aagtgttccc aaaaaacctt aattggatat agacttaaaa tgtctcgtga   1260
cggtgacatt gcagttggag aaacagtgga attacgttgt agatctggat acactactta   1320
tgcccgcaat ataacagcaa catgtttaca aggtgggacg tggtctgaac caacggcaac   1380
atgtaacaaa aagtcctgtc caaacccagg tgaaatacaa aatggaaagg ttatatttca   1440
tggtggacaa gatgccttaa aatatggggc aaacatttca tatgtttgta atgaaggata   1500
ttttttggtt ggtcgagaat acgtgcgata ttgtatgatt ggagcatctg gccaaatggc   1560
gtggtcatct tctcctcctt tttgtgaaaa agaaaagtgt cacagaccga aaatcaaaaa   1620
tggagatttt aagcctgata aagattatta tgagtataat gatgcagttc attttgaatg   1680
taatgaagga tatactctag ttggaccaca ttccattgca tgtgcagtta ataacacgtg   1740
gacatctaac atgccaacct gtgaactcgc aggctgtaaa tttccatcgg tgactcatgg   1800
ttatccaatc caaggttttt ctcttactta taaacataag caaagtgtta cttttgcatg   1860
caatgatgga tttgttctca gaggatcccc cacaattacg tgtaacgtta ctgaatggga   1920
cccaccactt cctaagtgtg ttttggaaga tatagatgat ccaaacaatt caaatcctgg   1980
acgtttgcat ccaacaccca atgaaaaacc aaatggtaat gtctttcaac gctcaaacta   2040
tacagaacct ccaacaaagc ctgaagacac ccatacagca gctacttgtg ataccaactg   2100
tgaacagcca cctaaaatcc tgccaacatc cgaaggtttt aatgagacta ccacatctaa   2160
tacaattaca aaacaattag aggatgagaa aactatatcc cagccaaata cacatattac   2220
```

-continued

```
atctgcctta acatccatga aagcgaaagg taactttacc aacaagacca ataactctac   2280
tgatctacat atagcgtcta cacccacttc ccaagatgat gctacgcctt caatacctag   2340
tgtacagaca cccaattata atactaacgc accgacacgt acactaacgt ctctccatat   2400
tgaagaaggc ccatccaatt ctactacttc agaaaaggcc acttcctcta ctctctcaca   2460
caactcacac aaaaatgaca ccggaggcat atacacaaca ttaaacaaaa caacacagtt   2520
gccatccact aataaaccta caaacagtca agccaagagt tccactaagc cacgcgttga   2580
gacacacaat aaaacaacca gtaatcctgc catttcttta acagattctg cagatgtgcc   2640
tcagagaccg cgagaaccaa cactccctcc cattttcagg ccaccggcgt ctaaaaatcg   2700
ctatctggaa aagcaactag ttattggact actaaccgct gtcgccctaa cgtgtggact   2760
gattacctta tttcactatc tgttctttcg ttagcctaga acttgctcca gtgttagaca   2820
gggctatgat tgcttctcca cgctgtccac cttaacactt cccaataaca aatccggtat   2880
gcagcagcgt gacactacta atgtaaccta aaaaatgtgc atgtggtatg tattgtacta   2940
aagataccga ccaatacaag acaactaata ttaaccatag tgtgcgtttc tttgtataaa   3000
atacgcgtgt gggaaagcga cagaaggggg cggcgtttcc atatgaggcc aagtgcattg   3060
gctattttag gggcggtgac cacgcactat agtgcgcggt gtggcagaaa attcacaccg   3120
tatataaaca aggaaagggg actctgcgcg cttaagcgcc aagccattat acacacgggt   3180
tttttgttgt cttggccaat cgtgtctcca tggcgctaaa gggaccacaa accctcgagg   3240
aaaatattgg gtctgcggcc cccactggtc cctgcgggta cctctatgcc tatctgacac   3300
acaacttccc catagggggaa gcctccctgc tgggcaatgg ctacccggag gcaaaagtat   3360
tttcactacc tcttttgcac gggctcacag tggaatccga tttcccctta aacgtaaagg   3420
cggtgcacaa gaaaatcgat gcaaccacag cttctgtgaa attaacttca taccacaggg   3480
aggccatcgt ctttcataat actcacttat ttcagccaat ctttcaagga aagggactgg   3540
aaaagttatg tcgagagagc cgagagctgt ttggattttc aacgtttgtt gagcaacaac   3600
acaaagggac gctctggagc ccagaggcat gccctcagct accctgcgcg aatgagattt   3660
ttatggcggt catagttaca gagggattca aggagagact gtacggcggc aaactggtgc   3720
ccgtgccctc tcagacaacg cccgtacaca ttggggaaca ccaggcgttc aagataccct   3780
tgtatgacga ggatctgttt ggtccaagtc gcgcccaaga actatgtagg ttttacaacc   3840
ccgatatcag tagataccta catgactcca tattcactgg aatagcacag gctctaaggg   3900
taaaggacgt tagcacggtc atccaagcct cagaaaggca atttgtgcac gaccaataca   3960
agataccaaa gctggtccaa gccaaggact tcccccagtg tgcttccagg ggaaccgacg   4020
ggtctaccct aatggtgata gacagtctgg tggctgaact tggtatgagt tatggtctgt   4080
cctttattga gggaccccag gatagctgcg aggttctaaa ttatgacacg tggcccatct   4140
ttgaaaactg cgagacgcca gatgcccgcc ttcgtgcact agaagtttgg cacgcagagc   4200
aggccttgca tattggcgcc cagctgtttg cggccaactc tgtgctctac ctgaccagag   4260
tggcaaagct gcctcagaag aatcagagag gagacgccaa catgtacaac tcattctacc   4320
tacagcatgg cctgggatac ctctcagagg caacagtaaa ggaaaatgga gcctctgcct   4380
tcaagggcgt gccagtgtct gcactggatg ggtcatctta caccctccag cacctggcct   4440
acgcgtcctc tttctcccca catctcctgg caaggatgtg ttactatctg cagttcttgc   4500
cccaccataa aaacaccaac agtcagtcat acaatgtggt ggactacgtg ggcaccgcgg   4560
cacctagtca aatgtgtgac ctgtgtcagg ggcaatgtcc agctgtatgc atcaacacgc   4620
```

-continued

```
tgttttacag gatgaaggac aggttcccac ctgttctgtc aaacgttaag agagacccat   4680
atgtgatcac gggcacagcg ggaacgtaca atgacctaga gattctcgga aactttgcca   4740
ccttcaggga gagagaggag gaggggaatc ctgtggaaga tgctccaaag tatacatatt   4800
ggcaactatg ccagaatata accgagaagc tagcgtccat gggcatctcg gagggcggcg   4860
atgccctaag aaccctcatt gtggacatcc ccagcttcgt caaagtgttc aaggggatag   4920
acagcacggt agaggcagag ctcctaaagt ttattaactg catgatcaaa aacaattaca   4980
acttcagaga gaacatcaaa tccgtccatc acatccttca gtttgcatgc aacgtatact   5040
ggcaggcgcc gtgcccggtt tttctgaccc tttactacaa gtcactgctg acggtcatac   5100
aggacatatg tctgacgtca tgtatgatgt acgagcagga caacccggcc gtgggaattg   5160
taccatccga gtggcttaaa atgcactttc agacaatgtg gaccaacttc aagggtgcct   5220
gcttcgacaa aggagcaatc acgggcgggg aactaaaaat agtccaccag tccatgttct   5280
gtgacctctt tgacaccgac gctgccatag gagggatgtt tgcacccgct cggatgcagg   5340
tcaggatagc cagagcaatg ctcatggttc caaaaaccat aaaaataaaa aacaggatca   5400
tcttttccaa ctccaccgga gcagagtcga tccaggcagg ttttatgaag ccggccagcc   5460
aaagggattc atacatcgtc ggaggaccct acatgaaatt cctaaacgcc ctgcacaaaa   5520
cactttttcc ttccacaaaa acttctgccc tgtacttgtg gcataagatt ggccagacca   5580
caaaaaatcc catactacca ggtgtctcgg gggaacacct aacggagtta tgtaattatg   5640
taaaggcaag tagccaggct ttcgaagaga taaatgtttt ggaccttgtg ccagacaccc   5700
tgacatcata tgcgaaaata aaactaaaca gttccattct ccgggcttgc ggacagacac   5760
agttttatgc aactactctc tcttgccttt cgccagtgac tcagctggtt ccggccgagg   5820
agtaccccca cgtactgggg ccagtggggt tgtcatctcc agatgaatac agggcaaaag   5880
tcgccggcag gtctgtaacc attgtacagt caacactgaa gcaagctgtt tccaccaacg   5940
gacgactccg gcctatcatt accgtgccac tggtggtcaa caaatataca gggagcaacg   6000
ggaacacaaa cgtctttcac tgtgcaaacc tgggatactt ctcggggaga ggggtggaca   6060
gaaatctcag gccagaaagc gtcccccttta aaaagaataa tgtcagctct atgctaagaa   6120
aacgccacgt gattatgacc cccctggtag acaggctggt aaagagaata gttggcatca   6180
actctgggga attcgaggca gaagcggtta agagaagtgt gcagaatgtc ctggaagaca   6240
gagataaccc aaacctgccg aagacagttg tattagagtt ggttaagcca cctcggtgga   6300
gctcctgtgc aagtctcaca gaggaggacg tgatttacta cctgggccct tatgccgtac   6360
ttggggacga ggtcctgtca ttactgagca cagtgggcca ggcgggggtg ccatggacgg   6420
ccgagggtgt ggcctcggtc atccaggaca taatagatga ttgcgagtta cagtttgtgg   6480
gcccagaaga gccttgcctt atccaaggac agtcggtagt ggaggagctt tttccgtccc   6540
cgggcgtccc aagcctgaca gtgggtaaaa aacgaaaaat cgcatccctg ctctctgacc   6600
tggatttgta gttgtgtacc cgtaacgatg gcaaaggaac tggcggcggt ctatgccgat   6660
gtgtcagccc tagccatgga cctctgtctt cttagttacg cagacccggc aacactggac   6720
actaaaagtc tggccctcac tacagggaag tttcagagcc ttcacggcac actactcccc   6780
ctcctcagac gacaaaacgc acacgaatgc tcaggtctgt cactagaatt ggagcacttt   6840
tggaaaacgt ggctgatgct ctggccacgt tgggagtgtg cactagcaga aaactgtctc   6900
cagaagagca tttttccctc ctgcatttgg acacaacatg caacaagcaa ccggagcgtt   6960
```

-continued

```
aggtttaatt tttacggaaa ttgggccttg gagttaaagc tgtcactaat aaacgacgtt   7020
gaaattttct ttaaacgtct tagtagcgtt ttttattgta taggatcggg cagtgctctg   7080
gagggtttag gggaggtatt gcgtttcgtt gggaagctga ggggtatctc acccgtacct   7140
gggccggacc tatatgtctc aaatctgccc tgcctagaat gccttcagga agtgtgtctg   7200
actcccaacc agggcaccag tctgcaggcc atgctcccag acacggcctg cagtcacata   7260
tgtacccccg catgcggtga gcctgtccgg ggcctctttg agaacgagct aaaacagctc   7320
gggcttcaaa cccctgagtc catacctact acccccctgtc agtcccgggt aaggcaagat   7380
gatgaaatca gacagagctc tctaatggcg gtaggagatc accacatttt cggagaggtg   7440
accagatctg tcctggaaat ctcaaacctg atctattgga gctctggcca ctcggatgcc   7500
acctgcgacg gagacagaga ctgctctcac ctggcctcgc tgtttactca cgaggctgac   7560
atgcataaaa ggcgcgtcga cctggccgga tgcttgggcg aacgcggcac gcccaaacac   7620
ttttttgact gctttcgccc agactcccta gaaacccttt tctgtggtgg tctttttagc   7680
tccgtggagg acaccataga aagtctccaa aaggactgct cttctgcctt ctaccaacag   7740
gtaaactaca ctactgcact gcaaaaacag aacgagtttt acgtccgact cagcaaactg   7800
ctggcagctg gtcagctaaa tttgggcaaa tgttccactg aaagttgcca atccgaggcc   7860
cgtaggcagc tggtaggtgg gggcaaacca gaggaagtgc tgagggatgc aaaacaccgg   7920
caagaactat accttcagaa agtggcacgc gacggtttta aaaaactctc tgattgtata   7980
agacaccagg gccacatcct gtctcagacc ctgggtctaa gactgtgggg gtctgtcatc   8040
tacaacgagg catctgccct acaaaaccac tttttacaca gagcacagtt catatccctc   8100
ccctggcagg acctgacggt cgactgtcca acgcggtttg aaaattctaa atatatcaaa   8160
aattctctgt actgccagcg tctggggcgg gaacacgtag agatcctgac actggagttc   8220
tacaaactta tcacgggccc gctgtcaaag cgacatactt tatttcccag tcctccaaat   8280
gtgacgctgg ctcagtgctt cgaggctgcg ggcatgcttc cccatcaaaa gatgatggta   8340
tcagagatga tctggcccag catagagccg aaggactgga tagagcccaa cttcaaccag   8400
ttctatagct ttgagaatca agacataaac catctgcaaa agagagcttg ggaatatatc   8460
agagagctgg tattatcggt ttctctgtac aacagaactt gggagaggga gctaaaaata   8520
cttctcacgc ctcagggctc accggggttt gaggaaccga aacccgcagg actcacaacg   8580
gggctgtacc taacatttga gacatctgcg cccttggtgt tggtggataa aaaatatggc   8640
tggatattta aagacctgta cgcccttctg taccaccacc tgcaactgag caaccacaat   8700
gactcccagg tctagattgg ccaccctggg gactgtcatc ctgttggtct gcttttgcgc   8760
aggcgcggcg cactcgaggg gtgacacctt tcagacgtcc agttccccca cacccccagg   8820
atcttcctct aaggccccca ccaaacctgg tgaggaagca tctggtccta agagtgtgga   8880
cttttaccag ttcagagtgt gtagtgcatc gatcaccggg gagctttttc ggttcaacct   8940
ggagcagacg tgcccagaca ccaaagacaa gtaccaccaa gaaggaattt tactggtgta   9000
caaaaaaaac atagtgcctc atatctttaa ggtgcggcgc tataggaaaa ttgccacctc   9060
tgtcacggtc tacaggggct tgacagagtc cgccatcacc aacaagtatg aactcccgag   9120
acccgtgcca ctctatgaga taagccacat ggacagcacc tatcagtgct ttagttccat   9180
gaaggtaaat gtcaacgggg tagaaaacac atttactgac agagacgatg ttaacaccac   9240
agtattcctc caaccagtag aggggcttac ggataacatt caaaggtact ttagccagcc   9300
ggtcatctac gcggaacccg gctggtttcc cggcatatac agagttagga ccactgtcaa   9360
```

-continued

```
ttgcgagata gtggacatga tagccaggtc tgctgaacca tacaattact ttgtcacgtc   9420
actgggtgac acggtggaag tctccccttt ttgctataac gaatcctcat gcagcacaac   9480
ccccagcaac aaaaatggcc ttagcgtcca agtagttctc aaccacactg tggtcacgta   9540
ctctgacaga ggaaccagtc ccactcccca aaacaggatc tttgtggaaa cgggagcgta   9600
cacgctttcg tgggcctccg agagcaagac cacggccgtg tgtccgctgg cactgtggaa   9660
aaccttcccg cgctccatcc agactaccca cgaggacagc ttccactttg tggccaacga   9720
gatcacggcc accttcacgg ctcctctaac gccagtggcc aactttaccg acacgtactc   9780
ttgtctgacc tcggatatca acaccacgct aaacgccagc aaggccaaac tggcgagcac   9840
tcacgtccct aacgggacgg tccagtactt ccacacaaca ggcggactct atttggtctg   9900
gcagcccatg tccgcgatta acctgactca cgctcagggc gacagcggga accccacgtc   9960
atcgccgccc ccctccgcat cccccatgac cacctctgcc agccgcagaa agagacggtc  10020
agccagtacc gctgctgccg gcggcggggg gtccacggac aacctgtctt acacgcagct  10080
gcagtttgcc tacgacaaac tgcgggatgg cattaatcag gtgttagaag aactctccag  10140
ggcatggtgt cgcgagcagg tcagggacaa cctaatgtgg tacgagctca gtaaaatcaa  10200
ccccaccagc gttatgacag ccatctacgg tcgacctgta tccgccaagt tcgtaggaga  10260
cgccatttcc gtgaccgagt gcattaacgt ggaccagagc tccgtaaaca tccacaagag  10320
cctcagaacc aatagtaagg acgtgtgtta cgcgcgcccc ctggtgacgt ttaagttttt  10380
gaacagttcc aacctattca ccggccagct gggcgcgcgc aatgagataa tactgaccaa  10440
caaccaggtg gaaacctgca aagacacctg cgaacactac ttcatcaccc gcaacgagac  10500
tctggtgtat aaggactacg cgtacctgcg cactataaac accactgaca tatccaccct  10560
gaacactttt atcgccctga atctatcctt tattcaaaac atagacttca aggccatcga  10620
gctgtacagc agtgcagaga aacgactcgc gagtagcgtg tttgacctgg agacgatgtt  10680
cagggagtac aactactaca cacatcgtct cgcgggtttg cgcgaggatc tggacaacac  10740
catagatatg aacaaggagc gcttcgtaag ggacttgtcg gagatagtgg cggacctggg  10800
tggcatcgga aaaacggtgg tgaacgtggc cagcagcgtg gtcactctat gtggctcatt  10860
ggttaccgga ttcataaatt ttattaaaca cccccctaggt ggcatgctga tgatcattat  10920
cgttatagca atcatcctga tcatttttat gctcagtcgc cgcaccaata ccatagccca  10980
ggcgccggtg aagatgatct accccgacgt agatcgcagg gcacctccta gcggcggagc  11040
cccaacacgg gaggaaatca aaaacatcct gctgggaatg caccagctac aacaagagga  11100
gaggcagaag gcggatgatc tgaaaaaaag tacaccctcg gtgtttcagc gtaccgcaaa  11160
cggccttcgt cagcgtctga gaggatataa acctctgact caatcgctag acatcagtcc  11220
ggaaacgggg gagtgacagt ggattcgagg ttattgtttg atgtaaattt aggaaacacg  11280
gcccgcctct gaagcaccac atacagactg cagttatcaa ccctactcgt tgcacacaga  11340
cacaaattac cgtccgcaga tcatggattt tttcaatcca tttatcgacc caactcgcgg  11400
aggcccgaga aacactgtga ggcaacccac gccgtcacag tcgccaactg tcccctcgga  11460
gacaagagta tgcaggctta taccggcctg tttccaaacc ccggggcgac ccggcgtggt  11520
tgccgtggac accacatttc cacccaccta cttccagggc cccaagcggg gagaagtatt  11580
cgcgggagag actgggtcta tctggaaaac aaggcgcgga caggcacgca atgctcctat  11640
gtcgcacctc atattccacg tatacgacat cgtggagacc acctacacgg ccgaccgctg  11700
```

-continued

```
cgaggacgtg ccatttagct tccagactga tatcattccc agcggcaccg tcctcaagct  11760
gctcggcaga acactagatg gcgccagtgt ctgcgtgaac gttttcaggc agcgctgcta  11820
cttctacaca ctagcacccc aggggtaaa cctgacccac gtcctccagc aggccctcca  11880
ggctggcttc ggtcgcgcat cctgcggctt ctccaccgag ccggtcagaa aaaaaatctt  11940
gcgcgcgtac gacacacaac aatatgctgt gcaaaaaata accctgtcat ccagtccgat  12000
gatgcgaacg cttagcgacc gcctaacaac ctgtgggtgc gaggtgtttg agtccaatgt  12060
ggacgccatt aggcgcttcg tgctggacca cgggttctcg acattcgggt ggtacgagtg  12120
cagcaatccg gccccccgca cccaggccag agactcttgg acggaactgg agtttgactg  12180
cagctgggag gacctaaagt ttatcccgga gaggacggag tggcccccat actcaatcct  12240
atcctttgat atagaatgta tgggcgagaa gggttttccc aacgcgactc aagacgagga  12300
catgattata caaatctcgt gtgttttaca cacagtcggc aacgataaac cgtacacccg  12360
catgctactg ggcctgggga catgcgaccc ccttcctggg gtggaggtct ttgagtttcc  12420
ttcggagtac gacatgctgg ccgccttcct cagcatgctc cgcgattaca atgtggagtt  12480
tataacgggg tacaacatag caaactttga ccttccatac atcatagccc gggcaactca  12540
ggtgtacgac ttcaagctgc aggacttcac caaaataaaa actgggtccg tgtttgaggt  12600
ccaccaaccc agaggcggtt ccgatggggg caacttcatg aggtcccagt caaaggtcaa  12660
aatatcgggg atcgtcccca tagacatgta ccaggtttgc agggaaaagc tgagtctgtc  12720
agactacaag ctggacacag tggctaagca atgcctcggt cgacaaaaag atgacatctc  12780
atacaaggac ataccccgc tttttaaatc tgggcctgat ggtcgcgcaa aggtgggaaa  12840
ctactgtgtt attgactcgg tcctggttat ggatcttctg ctacggtttc agacccatgt  12900
tgagatctcg gaaatagcca agctggccaa gatccccacc cgtagggtac tgacggacgg  12960
ccaacagatc agggtatttt cctgcctctt ggaggctgct gccacggaag gttacattct  13020
ccccgtccca aaaggagacg cggttagcgg gtatcagggg gccactgtaa taagcccctc  13080
tccgggattc tatgacgacc ccgtactcgt ggtggatttt gccagcttgt accccagtat  13140
catccaagcg cacaacttgt gctactccac actgataccc ggcgattcgc tccacctgca  13200
cccacacctc tccccggacg actacgaaac ctttgtcctc agcggaggtc cggtccactt  13260
tgtaaaaaaa cacaaaaggg agtcccttct tgccaagctt ctgacggtat ggctcgcgaa  13320
gagaaaagaa ataagaaaga ccctggcatc atgcacggac cccgcactga aaactattct  13380
agacaaacaa caactggcca tcaaggttac ctgcaacgcc gtttacggct tcacgggcgt  13440
tgcctctggc atactgcctt gcctaaacat agcggagacc gtgacactac aagggcgaaa  13500
gatgctggag agatctcagg cctttgtaga ggccatctcg ccggaacgcc tagcgggtct  13560
cctgcggagg ccaatagacg tctcacccga cgcccgattc aaggtcatat acggcgacac  13620
tgactctctt ttcatatgct gcatgggttt caacatggac agcgtgtcag acttcgcgga  13680
ggagctagcg tcaatcacca ccaacacgct gtttcgtagc cccatcaagc tggaggctga  13740
aaagatcttc aagtgccttc tgctcctgac taaaaagaga tacgtggggg tactcagtga  13800
cgacaaggtt ctgatgaagg gcgtagacct cattaggaaa acagcctgtc gttttgtcca  13860
ggaaaagagc agtcaggtcc tggacctcat actgcgggag ccgagcgtca aggccgcggc  13920
caagcttatt tcggggcagg cgacagactg ggtgtacagg gaagggctcc cagaggggtt  13980
cgtcaagata attcaagtgc tcaacgcgag ccaccgggaa ctgtgcgaac gcagcgtacc  14040
agtagacaaa ctgacgttta ccaccgagct aagccgcccg ctggcggact acaagacgca  14100
```

-continued

```
aaacctcccg cacctgaccg tgtaccaaaa gctacaagct agacaggagg agcttccaca  14160
gatacacgac agaatcccct acgtgttcgt cgacgcccca ggtagcctgc gctccgagct  14220
ggcagagcac cccgagtacg ttaagcagca cggactgcgc gtggcggtgg acctgtactt  14280
cgacaagctg gtacacgcgg tagccaacat catccaatgc ctcttccaga acaacacgtc  14340
ggcaaccgta gctatgttgt ataacttttt agacattccc gtgacttttc ccacgcccta  14400
gtgactcaga cgcggaaaca gcgcctagaa agtttcctct tgcgctatgt gggacaacta  14460
gagtccaacc tggcaagcag tggagcaaga cgccagacag ccgatctcga aaaaaataat  14520
gcagacagag gcaacgttca tcctaggtga ctgggagata acggtgtcta actgccggtt  14580
tacttgcagc agcctaacat gtggcccct ttacagatct agcggcgact acacgcggct  14640
aagaatcccc ttctctctgg atcgactaat acgtgaccat gccatctttg ggctagtgcc  14700
aaatattgag gatctgttaa cccatgggtc atgcgtcgcc gtagtggccg acgcaaacgc  14760
cacaggcggc aacgcgcgac gcatcgtcgc gcctggcgtg ataaacaatt tttcagaacc  14820
catcggcatt tgggtacgcg gccctccgcc gcaaacgcgc aaggaagcta ttaagttctg  14880
catatttttt gtcagtcccc tgcccccgcg ggagatgacc acatatgtgt tcaagggcgg  14940
cgatttgcct cccggagcag aggaacccga aacactacac tccgccgagg cacccctacc  15000
gtcgcgcgag acgctggtaa ctggacagct gcgatccacc tcgccgcgaa cgtatacggg  15060
atactttcac agtcctgtcc cgctctcttt tttggacctc ctgacattcg agtccattgg  15120
gtgtgacaac gtggaaggtg accccgagca attgacaccc aagtacttga cgttcacgca  15180
gacgggagaa agactttgca aagtaaccgt ttacaacacc cattcgacag catgcaagaa  15240
ggcccgtgtt cgtttcgtct acagaccgac gccgtccgcc cgtcagcttg tcatgggtca  15300
ggcttcaccc ctcataacaa cccctctggg agccagggta ttcgcagtct atccagactg  15360
tgagaaaact atcccacctc aggaaaccac caccctgagg attcaattgc tgttcgagca  15420
gcatggtgcc aacgccggag actgcgcctt tgtcatcatg gggctcgccc gtgaaacaaa  15480
gtttgtctca tttcccgcag tactccttcc gggcaagcac gaacacctta ttgtattcaa  15540
cccacagaca catcctctga ccattcaacg ggacacaata gtgggcgtgg caatggcttg  15600
ctatatccac cccggtaagg cagccagcca ggcaccatac agcttctacg actgcaagga  15660
agagagctgg cacgtggggc tcttccagat caaacgcgga ccgggagggg tctgtacacc  15720
accttgccac gtagcgatta gggccgaccg ccacgaggaa cccatgcaat cgtgactgtc  15780
cgagcacata tggcgcagga gtcagagcag tgctcccgtg cgtttgcagt gtgcagtagt  15840
aaacgacagc tcgggcgcgg cgagcccgtg tgggattccg tcattcaccc gagccacatc  15900
gtcatctcta atcgagtacc cctcttacta agagaacagc acatatgtct cccttcgtgc  15960
cccagcgtcg gccagatcct ccacagagcc taccccaact ttacatttga caacacgcac  16020
cgcaagcagc aaacggagac ctacactgca ttctacgctt ttggggacca aaataacaag  16080
gttaggatct tgcccactgt tgtggaaagc tcctcgagcg tgctgatttt tagactgcgt  16140
gcatcggtct ctgcgaacat cgccgtggga gggctcaaaa taataatact tgctctcacc  16200
ctggtgcatg cccaaggagt gtacctgcgt tgcggtaagg acctttctac accacactgc  16260
gcaccggcta ttgttcagcg tgaggtgctg agcagcgggt ttgagccgca gtttaccgta  16320
actggcattc cagtgacatc ctcgaactta aaccaatgct actttctggt aagaaagcca  16380
aaaagccggc tggcaaagcc gtttgcacgc ctgtccgcgg agacgactga ggagtgtcgc  16440
```

-continued

```
gtcaggtcta tccgccttgg gaagacacac ctgcggatat cggtgactgc gcctgcgcag  16500
gaaacgcccg tctgggggct cgtgaccacg agcttcagcc ttacccccac cgcaccgctg  16560
gcctttgatc gtaacccgta caatcacgag acatttgcct gtaatgccaa gcactacatc  16620
ccagtcatct acagcggacc aaaaattacg ctggccccgc gcggccgcca ggtagtctgg  16680
cacaacaaca gctacacgtc ctccctgcca tgcaaagtca cagccatcgt gtcaaaccac  16740
tgctgtaact gtgacatatt tttagaggac tcggaatggc gcccaaacaa gccagcaccc  16800
ctgaaactgg tgaacacgag tgatcatccc gtcatattgg agccggacac acacattgga  16860
aacgccctct tcatcatcgc acccaaggcc cgaggtttac gcagactgac tcgcttaacc  16920
acaaaaacca ttgaacttcc tggcggggta aagatagaca gcaggaaatt acaaacattc  16980
agaaaaatgt atgttgccac cggacgcagt taggtgtccg gttcccaccc acacatttgt  17040
ctttattgct ttcaaataaa acggtgttct gtcaacctcc tccgggctca ctagtattgt  17100
gttcccatac gcgcctgtcg ccccaggatc aacacttcgt cccctatcca ccctaataca  17160
taacacacac aaagacatag tgactgtaga cagttaatct ttattgtcta gacacgcaaa  17220
gtatattagt gttataagaa attttatgtc acgtcgctct ttacttatcg tggacgtcag  17280
gagtcacgtc tgggatagag tccaaaacac gcaccgcttg acctgcaaac ttttccattg  17340
cactcagaac ataaaacgaa gcaaagtgtc tcacccaata cttaagtccc tgaagcctcc  17400
ctaatagacc gcggtcaaat ttgggtggac tgtagtgcgt cttagtcagc ttattgagct  17460
cttcctgtat gtcccatcct aaggtcttcg tcagaagctc catgacgtcc acgtttatca  17520
ctgattttcc aaactccgtc gttaaaaact taaacaacac ctcgaattca aaaaagccat  17580
cggcgagctt tttaaggcag ctagtctcat taaatcctat taacccgcag tgatcagtat  17640
cgttgatggc tggtagtttc agatgaaaaa tagcagcggg ctctagaata cccttgcaga  17700
tgccggtacg gtaacagagg tcgcggaagc attcatcgat cacccatagc atccaattga  17760
gtctctgaat gagaagatcc ttttcaaact cgggggcgtc cggcaacttg ccccgcgttc  17820
cagataccag cagtgaaccg accagcaaga gagaccacaa cttgaaccag cacatggctg  17880
ctaacgcggc atacactagc cggtggtgcc cgagcgggag ttacgaagtc tcactgaagg  17940
gcggggtcgc gggtcggggc cgctccaaat caggcaacgc cgtatccgaa ctctgagtca  18000
cttttatgta ggtctcaaac atgtaaaaga taccacgttc ttgaaaaacc ctctcttgct  18060
cgccaggctt ggggttcacg cgggcatacg cagccaagct atcatgcgag agaaacacgt  18120
cacacgcaaa gtcatgtaaa acccgggtta aaaatagcct aactggccag gggccagtga  18180
gcgcctcccg gtacaagtcc ccacccccga tgacccaaac cttgtcaatt tgctgtgcta  18240
gctctgggct tctcgccaac ccaagcgcgg catcgagcga actcgccaaa aagtgagcac  18300
caggggggcgg ggtttctaac gtgcgactta gaaccacatt gattctaccc gccaatggtc  18360
gacagcccgc gggaatcgaa agccatgtgc gccgccccat aacaaccatg ttttgttttc  18420
caggggcaca gtcggtagtc agctgtcgaa aacgcctcat gtctccccgc aatgcaggcc  18480
acgggagaca tctgtttttt ccgatcccga gtttggtatc aaccgcaact acacagtaaa  18540
gtgtaggatc catgccgcga gggtataggt aaacaccacc aaccacacag tgtgctctta  18600
tatactttta atgaaacata agggcagacg aaacagccga acgtttccta atcacgccca  18660
tggaaccata gccaccccca ggcaaaccct gtggaaggat atcaactaga gaggagggtc  18720
cagccttatt atggcaggag acactataag ccccatcgcc cgactgggca ccaacataac  18780
cgccacagta agtggcccta taccgctcag cgcccaagtt gttacagtca cacccaaccg  18840
```

-continued

```
cggttggctc tacattgtca tcacgtccat cattatgtgt tggttctccc gcttccttgt  18900
accctgcagc ttcatccacg gattcttctg agtcgcgatg cacaggagcg ccatccgcgg  18960
ggccatcttg gtcgcctgga gctgcccccg cggggccatt ttggtcgcct ggagctgccc  19020
ccgcgggccc ctcctcgtcc tggttatccc cacggggaag aatttcctga agctcgatct  19080
cctctactgc acactctggt gatgtcggcc gaggtctata tggaaacact tcaacccgcg  19140
tgtttacagc agcgtatgcc cgccccacgt ggcgcatcat gtggaaaaac gcacccaacc  19200
caaaaacgac aaacaattgg taaaacacga aaaaaacgta gtacgcggct gcagcgacgt  19260
gatctatctc tgggtcatga ccgcccacta tatatagcca aacccacgtc gcagcggcaa  19320
ggccagcggc ccccaatgtc ataatgaaaa taaaaacaat cagttccaga ccctcctggt  19380
aagtcagccg aggcaatagc gtcatttcgc gcaagggtcg ccagaccacg cgcgtgttgt  19440
atacgacgcc acatatctga caggccgtgt ttctagagat agtgagccag gtgcttaaac  19500
aacttctatg gacgttctcg agctctcctg tgcatccaca ggctctaaat ctctcatttc  19560
cgagctcctc gttgcaaatc cagcagacag gaacatcctc atcttccata tcctgagaga  19620
gaacccacaa taaaacatgg cattaacccc tgcaacaagt gaccgtacca gggcacgcgt  19680
ccaggcaacc ggggtccccc tcgttggtct atacaattcc atgactacct actggtaatg  19740
ctacagccac tcactgtaca agccggttaa ctgggaggcg acgctggcgt ggtatcggcc  19800
aactgaaaca caccactcca ctccaaacac ttatgtactt tgtggctcgg ctttattgta  19860
acagccaaga ggggcgtttg tggctcagct ttattgtaac agccaagagg gacgtatgtg  19920
gctatctcac aaaaagtcac cgattcatgt agacaacccg ctcccacgaa ttcggttttt  19980
aaaaagccct cacgtataca gacgggccac taaatacgca catgagcggg catcctgttt  20040
ccgccttgac gcccaccact ctgaccgcac gctaaacatc gccctacctg ctatactgcc  20100
atttccatac gaatggtagg atgcgggcag tagtccacca gtctaaaatc atcaggtgta  20160
aactcttcca tggaagaaac agaccggagt atctccaggc gcggaaaggg acgtggagtg  20220
cgcgtcagct gcagccgtag tggctctata tgcgttttgt agatgtgggc atctcccaac  20280
gtgtgaataa actccccggg tctaagacca gtaacatgag caagcatata agttaagagg  20340
gaatagctgg caatgttaaa aggaactccc aaacccatgt ctcccgacct ctgatacagc  20400
tgacaggaaa gctcaccgtc agctacataa aattgacata acaagtgaca gggcggaagc  20460
gccatcaacg acaagtccgc cgggttccac gcacacataa tgattcttct atcgtgcgga  20520
ttattttttta ttaaatccac aatgtacgac aattggtcaa acccctggcc tgtatagtca  20580
gcatccgcgt ccacgtacgc cgccccaaag tgcctccact ggaaaccgta aacaggtccc  20640
aaatccccct cccttctgtg cgccaggccg cgcccggcca ggaactccct ggagccattt  20700
ttgtcccata tcttgactcc tgttcttgaa agctccctgg agtcagtact ccccttcaga  20760
aaccaaagca gctcttgcac tacgcctcgc caaaacaccc gctttgtggt tagtaaggga  20820
aagtggtccc gcagactata cctggcctgc atgccaaata gagagagggt gcctatgccg  20880
gtgcggtcga gtcgatcgct gccacggcac aaaatttccc tcaactgcct gagatactga  20940
agttcctcgt ggggcgtctc agccccagtt acctcatgct gaatcgaaca agggtcaacc  21000
tcgggggcca aagccaagac gccaggcttt tgacagaagc gaaacccccct ggcacggaat  21060
aactttttgg cgacatacaa gcttaaaggt acaaacggaa acatgataga tcctggaagt  21120
ttgtgaagcc ctgtgcccgg agagacaccc ctcaactcgc agtgctcgga gacctacatg  21180
```

-continued

```
tatactcagg ctcttctata aaccctcccc aaaagtttat aaaacaccgt acgtaataca  21240
cattactcac agttcccacg gtgacgccca aacccatgca cacgggcgtg atcgatacca  21300
gaaaacatca caagaacaaa aagtgtgtgt ctgacattca catttatttt tacaagacaa  21360
ttttgtgcag tagagttgtg ccttccgaca ccccgcgccg ttcgctgttc tcctgtaatt  21420
gggagatccc actccttggc aggcacgttt cacgaaacgc tcttgtctcg ctggccttag  21480
acttgtggac ccaacatggg tatcgttaga gatccgtcgc gtaaatgcgc agctggcaaa  21540
gcattcttca gcgagcagtg actggtaatt gctgcatcag cttcttcacc cagtctttcg  21600
atttgtcggc acacacctgg cgaccacgct ttgtcaaaaa tatcacaccc ggcttgctgc  21660
acagttggga ggtggggtac cagctggaca gaagcacctg tggtaatggt cttttctggt  21720
aaccgagaca gcacttgtcc ggtctatgcc aggacgctcc cagcgtgtcc ccagattgca  21780
aacaaagcaa ggcagtcagc acagcgacga gcaggatgcc cttggtgtcc ataactcccc  21840
tcgtgtgtcc tcgtgtaaat gcgaaacggc gatgttaggt caggcgcggt aaacagctca  21900
actcggttca aaacacgtac gtgatgtagt gctggttcta cgacgcctac ctgtaaactc  21960
caggatcctg ggcttttatt acgaaggcca acaccccaaa aaatccacgc ccccgtgacc  22020
gcaggggcgg ttactaacga cggttacagg tccctcccga gccacgcacc tgccatgtaa  22080
cctgcaaggt aaccagacaa acatctagga agcgtaaata tccccaggta ggagaagtat  22140
tgcatatgtc acagactcaa cacacacggg ccgttacgca acggctaggg gcataaccct  22200
ttaccggcgc gaagcgctac gcgcttcgcg agaggtatct ccgtgtgctt ctccatcaga  22260
agacgcgtgc gccgcttcgc aggcgacccg catactttcc gccccgagtg cgttacaaaa  22320
atgactgcct tctggcgaca atacacggtg gacgtccagt accacccgca tatcagctta  22380
tccggtggca atctggcact ggacagggaa ttctcgcaac aatccgaggc catgatggtg  22440
gcaggaccgc tggccgcaca tagctcaatc acggccaccc agaagagcag ccccaaatgt  22500
gcgcgcaaca cccagcacat gctccacata cagttctggc gccacaacga tgatgcgcaa  22560
aggggtgcat taccctaaat cccagcctag ttataaatta ttgaagccca ggcgaccagg  22620
ggtcgccgcg cttttcctcc ccaaacgcga cgataaagac cagcgttgcc aaatgtaact  22680
tatgtataac ccaaaatatt gcgcatcgat aaggtttgcc aaaacacccg aaagtacaca  22740
cacaaaaaaa cagcaacaag acgctcacta gacattcacc ccttccccca cccccgaaaa  22800
caaaacaact tgacacaggg gaaacaccag gggcggcgga ggttgtcaat agtgtccagt  22860
atttcgttag acgcgggttc ttggacccga tgtcccaggt cattaaagtc tcaaatggga  22920
ttaaaggatc atagttccca ggtttaatac tccaagctat cccagaacag gaccccggca  22980
gaaccccgct taacagcacc aaatccactt gcggtcccag aaaaggtcgc cgaggtggca  23040
aggtgactga aaaggtcata gagaggacac cggtcccatt tcccacggtc caaaaatcca  23100
gcgcgcccca ccggctttcc gagaacttcg gcaaagctaa tttgcatgcg ctaatccttt  23160
tatgtgcata aattatgtag atgaggagtc gcgcatgcgc agaaaaattc agagcgcccg  23220
ggtgcacggg gtcacctcca ggtcacgccg ctaggtggga ccgtgagcga ctcgaaaaat  23280
tataattttt ggccatttca tgggcgccgc catcttgaat ttgctaatcc cccataatcc  23340
tctgccccgc tcccattggt ccgccggccc gtcaatcaaa gttttccgag ccgccattgg  23400
cccatccggc cgaccaatcc cgttcgagct aggcgaccgc gccattccat tggacgcccc  23460
agccgtcaat caaattcgga ggcctcccat tggcccctat ccctagaact cccaagctga  23520
ttggcccaga gcgggaacca atcagcgatt agagttttgt tttgattttt cctatatata  23580
```

-continued

```
tatatataat cctttaatcc tagcgcagct gagtcatcgc agcccctatt ccagtaggta  23640
tacccagctg ggtaatccag taggtatacc caggtgggtg aacccagctg ggtataccca  23700
gctgcaattc tataattaaa caaggtagaa accaacgggg tcctcaggtg gtatttccgg  23760
aagcattacc aaataaggca acctcagctg ggaataccag cggactaccc ccaactgtat  23820
tcaaccctcc tttgttttcc ggaagtatat ccatttatgg aaatcagctg ggtcactcta  23880
ctgggttatt ctttataata gggcccgatg agtcatgggg ttgggatttt tctactaggt  23940
cgtttcggtg gatgggtgcc aggattatag gggccctgtc cacggggttg ttcggtggcg  24000
gggggggggc tagtgagtca cgggcctgga atctcgcctc tgggtggttt cggtagatgg  24060
gggccgggag gatggggccc cgcccaccgc tggcgcgccc cagaacatgg gtggctaacg  24120
cctacatggg cagcttgtcc tacggttacg cccatttgag acgggttaac caactgttac  24180
acccccttcgc cgggaacgct ataaaaacga gggacagcag cccccccctcg cgcactgcgc  24240
gcgcggcggc acgtgggacg gatctcttgg atttacccgt aacgaggagc cccggcagca  24300
ccccaggagc cccggcagca ccccaggagc cccggcagca ccccaggagc cccggcagca  24360
ccccaggagc cccggcagca ccccaggagc cccggcagca ccccaggagc cccggcagca  24420
ccccaggagc cccggcagca ccccaggagc cccggcagca ccccaggagc cccggcagca  24480
ccccaggagc cccggcagca ccccaggagc cccggcagca ccccaggagc cccggcagca  24540
ccccaggagc cccggcagca ccccaggagc cccggcagca ccccaggagc cccggcagca  24600
ccccaggagc cccggcgcgc caccctcccc ggagggggat cccggcgcgc caccctcccc  24660
ggagggggat cccggcgcgc caccctcccc ggagggggat cccggcgcgc caccctcccc  24720
ggagggggat cccggcgcgc caccctcccc ggagggggat cccggcgcgc caccctcccc  24780
ggagggggat cccggcgcgc caccctcccc ggagggggat cccggcgcgc caccctcccc  24840
ggagggggat cccggcgcgc caccctcccc ggagggggat cccggcgcgc caccctcccc  24900
ggcaacaacc tgttgccatg tatggcgatt tgtatcagtc acaagcacac aacccctgct  24960
agtattaatg gtgtttaaaa cgttctacac gtacggcgga ccgcatccgt cgcaagcacg  25020
cgcatataac ccccaaatgc accatgatga gaagcacagc cacgcgtcaa aaaactttaa  25080
aaacatcgtt atccaatatc attaaaaacc acaccgaaat ttacacaggt agcacgtcac  25140
cgtgttagtg tcacccactg tacacaaggc gtgtcgtata tgtagtatag gtatttgatg  25200
aggcggaagc atatcccgct tccagcgaac ggaaataaga atcatccgtt ccagcattta  25260
ttcaaagagg gcacagagga ttcacattgt ttagagagag tttttcttag tcaccattcc  25320
atacttgggc agtattggcc tacgatttgg gcgacgtttc aggctggtct attctccgtc  25380
cacttttccc cggctattct gtcccagcat aggctcttga aataaacaat gtttaccgag  25440
taaaaggttc cactcaccct catttgtcgt tgcacccatc cccccttttgc ttaatcaccc  25500
gaaaactaga ggacacggat ggaaaacata tcgcacgcgg gttgtttgaa agtcaacagc  25560
tacttgtttt taatgaggac agatttgggc acaggccaga gggtaaagcc ctacgtgtgc  25620
gcgggggggg gggtgtatac gctgcgaaaa cctgcacggt gcataacacc cagggcgtca  25680
cgtcacatat ctctgtgcac ccaagtggtt gttcaaccgt tgttttttgg atgatttttc  25740
cgcaccggct tttttgtggg cgcgcatagg tcggtacgcg ctgtccccct aagtcccgca  25800
cggtcgttcg ggcccccgtc cggctcgtct ccggatgaac cgtcacgttc tttgtctcca  25860
gaggcgacgt ctccttcaga tgactcgtcc gtgggctcct cgtccgtccc gcccgcgggt  25920
```

-continued

```
ccgacaagga ccgtcaattc gatgttatct tcgttcgcgg ttggccggcg cggccgtcgg  25980
tatggcagta cggtcacccg ggtgttattt gccgcgtata atgccctcac agtgccactt  26040
acgcggcata tgccgccaaa tgcaaacaca ataaatattt ggtaaaaccc aaagaagcag  26100
agaaaaccga gcacggcccc gggggagaat gttcccgcag gagcagttag gatgaccagg  26160
agcgtccagg tgcacaacgc cacgccgaca agcccagcca ccaccacaga catcagcaga  26220
aacagttcaa aaatttcttg gcgctccatc tccggccaca ggttaaggcg actacgccac  26280
tgcgtgcgcg tgcggtatat aacgcgacac atttgacagg ccgtgtttcg agacactgtt  26340
agccaagtgc ttaaacactg cgggtggacg acatccagct ctccggtaca ggcgcagggg  26400
tgtatgccct cgttccccac ctcttcccta catatccagc agatgggtcc ctctacaccc  26460
tcttctacgt ccttagacgc catctctgca gctggggtgg aagtctgaaa aagggaaagg  26520
ggaggtgagc agagtgccca gttagtctcc gacccgccgt ccgccctact gtcgctatcc  26580
cgccttgaca gatgtctaac gtattcacgg acgccacatg tgtgtctatt ttcctacatc  26640
caggctttcc ctggaaaact gtcacaaccc accctgcttt agctctacat ctgtattttt  26700
gtttacgcac aggatcaacg cttcgtgccc gtccaccccc gcgctctccg cctgtgtttg  26760
gaggttttat gagtggttag ttctaggcag ctccggacaa gttgtccaaa acacggcgcg  26820
ccccgccctt ccttccctcc ggatccgccc acaccggacc tatgaaataa gggacacgcg  26880
tcatcactag ttatgagaga aaaaccacaa cagctttatt ggaaaacacc tgagtggatc  26940
ccccaccccc cgcgtacgac aggcgtttct gtggtgcgct tctgggaaaa acgtttttcc  27000
cccatttctt cctcgacagg tcttctaagg tagataaatc cccccccttt gcgcgtctcc  27060
tagaatggcc taggcgcacg atggcgttgt cgcctcgagc agttgggccg cagtgatatc  27120
ttcaactttc gaccgtctaa gctatggcag gcagccgctg catcagctgc ctaacccagt  27180
ttttggaagg gtctgcgcag atctgacgcc ctcgcttggt cagcaaaata actccgggtt  27240
ttgggcacgc tggggacgtg ggataccact cttttagaat ttggacgggc ggtgggtgct  27300
gctggaaccc gtagcagcag ctattaggcg tgtacgacac gagtgacccc gcgctttctg  27360
tgggcgtcag gtaaaacgtg gcaagcagta cgctaacgca gcataaaacg tggacggggg  27420
ccatctggag gtgccaagtt cgcaacagtc taaagaaaac cgtaaaggct atttggggtt  27480
tctgttctgt cagatgtaac gccgagttcc ttatatgctt acctgattct ggtctcacct  27540
gtttatttat agtggcgtat gctaaccgcc agcttacatg cgggataagt tggcctaact  27600
caccaaaaac gggttgcaga caaaagtgat tgttggggcg cttacttaga aggtgtgagg  27660
gtttctaaga aaccccgcca acgcccggaa accgcatgcg ttccagtcgg tgcggcctgc  27720
gccggcgtcg ctgtggcgcc tttgtgggct ttgagttctg tcattaagcc aggtttccat  27780
tgccacccgg gcgaaaacaa gccgggtagt ttcaggggtc atctggcgat cagtgtacca  27840
tattcccacg acccatcaac accgctgctt gaggcgtgtc tctgtatgtg tcaccggaga  27900
ctgcatgtat cgtgcatatc tgtattgtgc gcttgcgcgg agacaacata ccgacgacca  27960
agtcaggggt cacctccagt gcacgccgct aggtgggacc gtgggcgagc cgaaataatt  28020
atatattttt ttggcacggt tgtgagcaac gccatcgtga gttggttaat accctctaaa  28080
cgcatagtct ttttttattt gtcaaccaac cagtcaatca cctgtcatcg ccgctcagaa  28140
gcacacgtct tcggccaatg ccgtgttggc gggtttgacc acggttactg ataggtagac  28200
gagtccgaca atcacacacg tccgccagcg atttgcagcg cagctaaaat cgcgtggccg  28260
ggttggtaga agcaaattat ccaatggtcg tgtttgggtt tgttttgggg ttatctacat  28320
```

-continued

```
attatattcc ttatcccgac tggttgcgga agtattcgca gcttggctac tctgctcgat  28380
taccccgtga ataactgggc ggggggtgac ccaacatagt gattcggtag atttggggga  28440
ctggatgaac attaatgaaa gtttattaat gttcatccgt attgtgtata tgtaatttgg  28500
tttccatatt tggtaggagt atggagtttt cttatggatt attaagggtc agcttgaagg  28560
atgatgttaa tgacataaag gggcgtggct tccaaaaatg ggtggctaac ctgtccaaaa  28620
tatgggaaca ctggagataa aaggggccag cttgagtcag tttagcactg ggactgccca  28680
gtcaccttgg ctgccgcttc acctatggat tttgtgctcg ctgcttgcct tcttgccgct  28740
tctggttttc attggtgccg ccgattgtgg gttgattgcg tcgcttttgg caatataccc  28800
atcctggctt tcggctaggt tttccgtcct acttttccca cattggcctg agagctgtag  28860
tacaaaaaac accgcgcggt ctggagctct ccataagccc gcagaacaaa agctgcgatt  28920
tgcccaaaaa ccttgccatg gcaactatac agtcacccct tgcgggttat tgcattggat  28980
tcaatctcca ggccagttgt agccccccttt tatgatatgc gaggatactt aacgtgtctg  29040
aatgtggaat ataatgtgaa aggaaagcag cgcccactgg tgtatcagaa cagtggtgca  29100
ctacctatct gctcattcgt tgtttcggtt ctgtgtttgt ctgattctta gatagtgttg  29160
aggtaattct agaaagcgga ttgagtgtaa atcgggccac tttgccctaa atgtgacaat  29220
ctggatgtgt atcttattgg tgcgttgtga agcattttaa aatgcgtttt agattgtatc  29280
aggctagtgc tgtaatggtg tgtttatttt tccagtgtaa gcaagtcgat ttgaatgaca  29340
taggcgacaa agtgaggtgg catttgtcag aagtttcaaa gtcgtgtaag aacattggac  29400
taaagtggtg tgcggcagct gggagcgctc tttcaatgtt aatgttttaa tgtgtatgtt  29460
gtgttggaag ttccaggcta atatttgatg ttttgctagg ttgactaacg atgttttctt  29520
gtaggtgaaa gcgttgtgta acaatgataa cggtgttttg gctgggtttt tccttgttcg  29580
caccggacac ctccagtgac cagacggcaa ggtttttatc ccagtgtata ttggaaaaac  29640
atgttatact tttgacaatt taacgtgcct agagctcaaa ttaaactaat accataacgt  29700
aatgcaactt acaacataaa taaaggtcaa tgtttaatcc atatttcctg acttgtgtct  29760
tgacttgcgt cgattgggat gggggtgtgg gatgggggtg tgggatgggg gtgtgggatg  29820
ggggtgtggg atgggggtgt gggatggggg tgtgggatgg gggtgtggga tgggggtgtg  29880
ggatgggggt gtgggatggg ggtgtgggat gggggtgtgg gatgggggtg tgggatgggg  29940
gtaaatgaca atgggggtaa atgacaatgg ggcgcttggt gacacatttg ccccaccgtc  30000
gcctgcccgg aaccagcttg gtgatgtgct gtctggctct caggtgcact ttatgcaaag  30060
cagttgaggc gcattagata tataaaactt gggtacacac ccttggtgct gtgcgcgtgc  30120
tatgtgccct ggtgaccgtc cacaatggac gaggacgttt tgcctggaga ggtgttggcc  30180
attgaaggga tattcatggc ctgtggatta aacgaacctg agtacctgta ccatcctttg  30240
ctcagcccta ttaagctata catcacaggc ttaatgcgag acaaggagtc tttattcgag  30300
gccatgttgg ctaatgtgag atttcacagc accaccggta taaaccagct tgggttgagc  30360
atgctgcagg ttagcggcga tggaaacatg aactgggggc gagccctggc tatactgacc  30420
tttggcagtt ttgtggccca gaagttatcc aacgaacctc acctgcgaga ctttgctttg  30480
gccgttttac ctgtatatgc gtatgaagca atcggacccc agtggtttcg cgctcgcgga  30540
ggctggcgag gcctgaaggc gtattgtaca caggtgctta ccagaagaag gggacggaga  30600
atgacagcgc tattgggaag cattgcatta ttggccacta tattggcagc ggtcgcgatg  30660
```

-continued

```
agcaggagat aacgcgtaat tcgaggtccc cggaagagta gagggttgca tgttatacaa  30720
acaacataaa cattaaatga acattgttca aaacgtatgt ttattttttt tcaaacaggg  30780
gagtagggta ggaagggtac gtctaatacg taactgttcg ctactgcttg ttcaggagct  30840
cctcgcagaa catcttgcga attttagatt ttggactaga gcgactgctg gcttcaacgc  30900
ggttcgatgt agggttcggc gtaggagcgt ctttctccac cgccgcgcat ggtgtatgcg  30960
tggtctccgg tgcctgttgt tggatgctct gcgtgctgga ggcgggggtg ggttcagcgg  31020
gtggtgcgcc aactaccgcg agtcctgtag agactggcgg gtggctcaca tgtggctgag  31080
caaaaaggat gggcgccgct tgctggaact gaccgtgtgg cgcctgcacg taaatgggtg  31140
ggtgtacgta ggttcctccg tgctccttca ttgtcgggaa ttgacacggg accgctgaat  31200
tggcgtgggg cctgtagtgt ggatctactg cggctgctgc tgcagaggag gacggcggtg  31260
gccctgcgtg ccaaccgttc agtttcatct ctttgagttc agactgtatt tccgctatgt  31320
tctttgacat ggacaagata tccttgtgat acgccggctc ctctcctgga aagaggtgtc  31380
cttcgtcgtc ctctgcgccg cgcttgcgct tccccgtcct atatccaggc agctgtggcg  31440
agtaatacca tggatcgtat gggttcttgt aagcgtagcc gtatggtggc gctgggtttg  31500
aaacatacga aggtaggtga tggtcggtgg ggaacatctg gcccccacac cccattaggc  31560
ctggccctga aagtgtatgt gacatttttg ccgctgtggt cttcattcca tcgatgctgc  31620
tttgtagcat gctcaggaag gcggatttgg ggatggatat gatatcctct tgaccagagc  31680
tgttcatggc tggtctgggt ggtgtgacgg cttggatgcc gaccgggaat tggctggcct  31740
ttaaatacgc cgggctcaat atgctggcca cacctctgtc agttttcaat aggtcgaggc  31800
ggtcccgtat gaagctggca tctatagctt ttgccattaa ggtctccagg ggactgacga  31860
aatttggtgt ggaaaggtcc tccagcctgc agctacttac gtgctggagg atgtgggcgc  31920
gctccgactt agatactgat gagaatctgg aaaccaccca ctcggcgtcg tgtccgtaca  31980
cggccactgt gccgcgtcgg cgccccaggg cgcatagtga tacgtgttga aacacgggac  32040
cgctgggagt ctgggataac tcgcggggat gtatagacga taaagacagc cccgggagcc  32100
acgtgtggag tatctccaac agtggttcct tagggagatt tttcacgggg gctctggcca  32160
cgtgggaggt gtccgccagc ctggatgcca gctctaggaa ggctggcgac gtgatggctc  32220
cggtgcagaa aataccgtgg gacacttgaa atagacccag tgtccagccc acttctgtct  32280
ctggtaggtg ttcgattgtt attggaaggg gttctgtgac tgggagataa tccgtcacct  32340
gatccggatc gagatagagc tcttgctcca gcttggggca ggacacaaca tctacaaacc  32400
ctccgacgta caggccctgt gccatgctcg gaaaatacgt gtgtgagacc gagccgctga  32460
gcccggggct taggaggctc atgtggcgct ttttgcaaaa taagaattta aatacattcc  32520
acgcccaaga gctgcgtttt attcatttgg ttctctgcag gatgtacaat ttcggtctaa  32580
atgtgtacct gttaagggag gctactgcca atgccgggac ctacgacgag gtggtcctgg  32640
gacgcaaggt tcctgcggag gtgtggaagc tcgtgtacga tgggctcgag gagatgggcg  32700
tgtcaagtga gatgctgctg tgtgaggcat accgggacag cctctggatg cacttgaacg  32760
ataaggtggg gctcttgagg ggcctggcga attatctgtt tcaccggcta ggggtcaccc  32820
acgacgttcg catcgccccg gaaaacctgg tggacggaaa ctttttgttt aatctgggaa  32880
gtgtgctccc ctgcaggctg ctccttgcgg cgggctactg cctcgccttt tggggcagcg  32940
atgaacacga acgctgggtg cgcttcttcg cccagaagct tttcatttgc tacctgatag  33000
tctccgggcg tcttatgcca cagaggtctc tgctagtttg ggccagcgaa acgggctatc  33060
```

```
ccggtccggt ggaggcagtc tgtcgcgaca tccgctccat gtacggcata cgaacgtatg  33120
cggtctcggg ttatcttccg gctccgtccg aagcgcagct ggcctacctt ggtgcgttta  33180
acaacaacgc ggtttaaacg accgcgagga ccaccggcag gcagccaaga accataaagt  33240
acgctctatc gtagtcatcg ccgccgccaa actgggactt gataatctcc tggagaaggg  33300
tgggtgggga tgggtgtgaa agcaggacgt ccaggccctc ttctgttgcc aggcggaggg  33360
ctgttctcgc ctggagcagc gccagtggat ctcggaatgt aagctgctgg ttcaggattt  33420
cgaatatctc attaaaccta ctgcctgtca gatttacaaa tggtccgggt tgtttgtggg  33480
acacggtcga tcgcgcctcg agggcggcca gtattatgcc agggaagatg aaggacacgg  33540
gggcgtttgg attagcctgc agtgtgggga ttatgtagtg ctccgatatg aacgaaaata  33600
gctggcccct tttcagcatg ggggcgtttg gatccggtag ggcaccgggc tgaaatttgg  33660
gtcccagcag ggataccagg ttcaagcggc ggtttgggtg ccctcgcgcg acttgcccaa  33720
actccagcaa tccatacgcg aggataaaca cctccagcgc aacaatcccc gctcgcaggt  33780
tccactggta tgcggaaaat ggtggtatat cggacccaaa catggcgctc gtaatggcga  33840
ataccaagtc catggcgggc gctgtccctg gcgcgcccgt acccttgttg tggggaaata  33900
atccagcctt agccatcatt gcgtgaagct tgtggcgctg gaagaaggct gtcggatagc  33960
ggctctcctt attgagaggc gccagcgagg cgcgctcctg gggtttgag tatgtgaagc  34020
tgaagtcccc aggaccgctt tcctgtttta gctgagtgat tagcaggtct agcttttgag  34080
gcaggtctgc taacaggtca tcgggagtag cgggcagttg cctggatgtc ttttgacaaa  34140
agtacgcgtt gacgaggcaa agcgcggcct gggtgtccgt gagatgcctg gcgtcggcga  34200
aaaagtcagc ggtggtcgag gcgaccgtcg tcagggtgtg agagatgagt ttgagcgatg  34260
tggaattctg aaagttaaca gtccccttta gttctttagg gaagacgcgc cgctgcatgg  34320
cgttgtccgt gaggctgatg aaccacggcc caaaggatgg caaccactga ttctggttca  34380
tgtacagggt gggcatgagc tcgccgcgca ggtccctgtc aacggagaag tgagggtccc  34440
cggggacgat cgccacggtg aagttacggt ggctggcctg cggggggggat gtcactaagg  34500
gaggctcatg ggaacggctt tggggcatgt ctatgttgtc agaccatgtc atgttgccta  34560
tcatctgttt caccgcgtcg atatctgcgt taatgacgcg gacgcgtgag tcatggacct  34620
gaacaagccg gtccagctct agggaaagca ggtgtgcctt tgtctttcgt tctcgatttc  34680
gcacgagttg gctgcgcagt ccaagggcga cccttcttgt ttcttccatg gtgggcttgt  34740
gaataaacag cacgttttcc gggtgtgggg cccagaatct tcccgcctct gtccatcttc  34800
ggttttttgg gtaccttaga taggaccttt ctgatgtcag cattttctct agcagtgaga  34860
aaggcgcaca attttccttc ggtggtgtgc accggcgtgg gaaacgcccc gggtgattca  34920
gagtatactg tctttagtgt tttctgattc ttaaatatca gcaggggcgt gatagtccac  34980
gcctcggtac ccggaggggc cgagtgagcg atgtaatgga tcgagtcgga gagttggcac  35040
aggccttgag ctcgctgtga cgttctcacg gtgttggttg ggatcagctg gtgactcaga  35100
```

<210> SEQ ID NO 18
<211> LENGTH: 35100
<212> TYPE: DNA
<213> ORGANISM: Kaposi's sarcoma-associated herpesvirus

<400> SEQUENCE: 18

```
caagtcttga gctctacaac gtaacatacg ggctgatgcc cacccgatac cagaattacg     60
```

-continued

```
cagtcggcaa ttctgtgccc tagagtcacc tcaaagaata atctgtggtg tccaagggga    120
gggttctggg gccggctact tagaaaccgc catagatcgg gcagggtgga gtacttgagg    180
agccggcggt aggtggccag gtgggcccgg ttacctgctc ttttgcgtgc tgctggaagc    240
ctgctcaggg atttcttaac ctcggcctcg gttggacgta ccatggcaga aggcggtttt    300
ggagcggact cggtggggcg cggcggagaa aaggcctctg tgactagggg aggcaggtgg    360
gacttgggga gctcggacga cgaatcaagc acctccacaa ccagcacgga tatggacgac    420
ctccctgagg agaggaaacc actaacggga aagtctgtaa aaacctcgta catatacgac    480
gtgcccaccg tcccgactag caagccgtgg catttaatgc acgacaactc cctctacgca    540
acgcctaggt ttccgcccag acctctcata cggcaccctt ccgaaaaagg cagcattttt    600
gccagtcggt tgtcagcgac tgacgacgac tcgggagact acgcgccaat ggatcgcttc    660
gccttccaga gccccagggt gtgtggtcgc cctcccccttc cgcctccaaa tcacccacct    720
ccggcaacta ggccggcaga cgcgtcaatg gggg acgtgg gctgggcgga tctgcaggga    780
ctcaagagga ccccaaaggg atttttaaaa acatctacca agggggcag tctcaaagcc    840
cgtggacgcg atgtaggtga ccgtctcagg gacggcggct ttgcctttag tcctaggggc    900
gtgaaatctg ccatagggca aaacattaaa tcatggttgg ggatcggaga atcatcggcg    960
actgctgtcc ccgtcaccac gcagcttatg gtaccggtgc acctcattag aacgcctgtg   1020
accgtggact acaggaatgt ttatttgctt tacttagagg gggtaatggg tgtgggcaaa   1080
tcaacgctgg tcaacgccgt gtgcgggatc ttgccccagg agagagtgac aagttttccc   1140
gagcccatgg tgtactggac gagggcattt acagattgtt acaaggaaat ttcccacctg   1200
atgaagtctg gtaaggcggg agacccgctg acgtctgcca aaatatactc atgccaaaac   1260
aagttttcgc tccccttccg gacgaacgcc accgctatcc tgcgaatgat gcagccctgg   1320
aacgttgggg gtgggtctgg gaggggcact cactggtgcg tctttgatag gcatctcctc   1380
tccccagcag tggtgttccc tctcatgcac ctgaagcacg gccgcctatc ttttgatcac   1440
ttctttcaat tactttccat ctttagagcc acagaaggcg acgtggtcgc cattctcacc   1500
ctctccagcg ccgagtcgtt gcggcgggtc agggcgaggg gaagaaagaa cgacgggacg   1560
gtggagcaaa actacatcag agaattggcg tgggcttatc acgccgtgta ctgttcatgg   1620
atcatgttgc agtacatcac tgtggagcag atggtacaac tatgcgtaca aaccacaaat   1680
attccggaaa tctgcttccg cagcgtgcgc ctggcacaca aggaggaaac tttgaaaaac   1740
cttcacgagc agagcatgct acctatgatc accggtgtac tggatcccgt gagacatcat   1800
cccgtcgtga tcgagctttg cttttgtttc ttcacagagc tgagaaaatt acaatttatc   1860
gtagccgacg cggataagtt ccacgacgac gtatgcggcc tgtggaccga aatctacagg   1920
cagatcctgt ccaatccggc tattaaaccc agggccatca actggccagc attagagagc   1980
cagtctaaag cagttaatca cctagaggag acatgcaggg tctagccttc ttggcggccc   2040
ttgcatgctg gcgatgcata tcgttgacat gtggagccac tggcgcgttg ccgacaacgg   2100
cgacgacaat aacccgctcc gccacgcagc tcatcaatgg gagaaccaac ctctccatag   2160
aactggaatt caacggcact agttttttc taaattggca aaatctgttg aatgtgatca    2220
cggagccggc cctgacagag ttgtggacct ccgccgaagt cgccgaggac ctcagggtaa   2280
ctctgaaaaa gaggcaaagt cttttttcc ccaacaagac agttgtgatc tctggagacg    2340
gccatcgcta tacgtgcgag gtgccgacgt cgtcgcaaac ttataacatc accaagggct   2400
```

-continued

```
ttaactatag cgctctgccc gggcaccttg gcggatttgg gatcaacgcg cgtctggtac   2460
tgggtgatat cttcgcatca aaatggtcgc tattcgcgag ggacacccca gagtatcggg   2520
tgttttaccc aatgattgtc atggccgtca agttttccat atccattggc aacaacgagt   2580
ccggcgtagc gctctatgga gtggtgtcgg aagatttcgt ggtcgtcacg ctccacaaca   2640
ggtccaaaga ggctaacgag acggcgtccc atcttctgtt cggtctcccg gattcactgc   2700
catctctgaa gggccatgcc acctatgatg aactcacgtt cgcccgaaac gcaaaatatg   2760
cgctagtggc gatcctgcct aaagattctt accagacact ccttacagag aattacactc   2820
gcatatttct gaacatgacg gagtcgacgc ccctcgagtt cacgcggacg atccagacta   2880
ggatcgtatc aatcgaggcc aggcgcgcct gcgcagctca agaggcggcg ccggacatat   2940
tcttggtgtt gtttcagatg ttggtggcac actttcttgt tgcgcggggc attaccgagc   3000
accgatttgt ggaggtggac tgcgtgtgtc ggcagtatgc ggaactgtat tttctccgcc   3060
gcatctcgcg tctgtgcatg cccacgttca ccactgtcgg gtataaccac accacccttg   3120
gcgctgtggc cgccacacaa atagctcgcg tgtccgccac gaagttggcc agtttgcccc   3180
gctcttccca ggaaacagtg ctggccatgg tccagcttgg cgcccgtgat ggcgccgtcc   3240
cttcctccat tctggagggc attgctatgg tcgtcgaaca tatgtatacc gcctacactt   3300
atgtgtacac actcggcgat actgaaagaa aattaatgtt ggacatacac acggtcctca   3360
ccgacagctg cccgcccaaa gactccggag tatcagaaaa gctactgaga acatatttga   3420
tgttcacatc aatgtgtacc aacatagagc tgggcgaaat gatcgcccgc ttttccaaac   3480
cggacagcct taacatctat agggcattct ccccctgctt tctaggacta aggtacgatt   3540
tgcatccagc caagttgcgc gccgaggcgc cgcagtcgtc cgctctgacg cggactgccg   3600
ttgccagagg aacatcggga ttcgcagaat tgctccacgc gctgcacctc gatagcttaa   3660
atttaattcc ggcgattaac tgttcaaaga ttacagccga caagataata gctacggtac   3720
ccttgcctca cgtcacgtat atcatcagtt ccgaagcact ctcgaacgct gttgtctacg   3780
aggtgtcgga gatcttcctc aagagtgcca tgtttatatc tgctatcaaa cccgattgct   3840
ccggctttaa cttttctcag attgataggc acattcccat agtctacaac atcagcacac   3900
caagaagagg ttgcccccctt tgtgactctg taatcatgag ctacgatgag agcgatggcc   3960
tgcagtctct catgtatgtc actaatgaaa gggtgcagac caacctcttt ttagataagt   4020
cacctttctt tgataataac aacctacaca ttcattattt gtggctgagg gacaacggga   4080
ccgtagtgga gataaggggc atgtatagaa gacgcgcagc cagtgctttg tttctaattc   4140
tctcttttat tgggttctcg gggggttatct actttcttta cagactgttt tccatccttt   4200
attagacggt caataaagcg tagattttta aaaggtttcc tgtgcattct ttttgtatgg   4260
gcatatactt ggcaagaaat ccgagcacct cagaaagtgg attgccgtca catatcagtt   4320
cgaccacccc tgcacctagc catgcggcgc tttgacggtc tttggggcta cacatcataa   4380
agtacttttc catggcttct ataagcacct tggaacaatc tgggggttgg cgaatgggtt   4440
ccctaaacgg gaaatcctct atggtattca ggcagaagac cgcgtcctcc acccgacgtt   4500
tgagtctttc tagcagagcg ccgaagaact cccgctcgtg tgttttcgca ggggcaagtt   4560
ctgcgccgta cagcgatgag aaacacgaca cgatgttttc cagccccatg ctgcgcagca   4620
acacgtgctt caggaacagg tgttgtagcc ggttcagttt tagcttgggt agaaaagtta   4680
tcgagttgtt agcacgctcc atgatggtaa cggtgttgaa gtcacagacc gggctttctc   4740
cgagtctcgg ccgcctgagt ccaatcatgt agaacataga cgcggcctcg ttgtctgtgt   4800
```

-continued

```
taagtgacac gatatcccgt tcgcaaacct gtgcgatgtt gtgtttcagt atagatctgg   4860
tctgaccggc acggggtgtt atggggtgac gcggtaaagg cgactctggg tcaaacacct   4920
ttatgcggtt ggcggcctcg tcgatgacga cacgcttgtt cgcggcgtgt atggggacgc   4980
gacggcatcc cgctggcaga tctataatct taaagttggt ataagactgg tcgctcgtta   5040
tggccagccg gcactccggt agtatctgcg tgtcctcgaa ttcgtggccg cgtacgactg   5100
gcttggagtg caggtaaacg ccaagagatg cggtctcttc gcctacgcac aagtggcttc   5160
ttaacgcgta ggggtgcggt gagagcatga tccgtagcaa cgatagttcc gggtgcctag   5220
ccgcgtagag tggcagggta gacgagtccg gagtcccaaa cttttcgaac aacagtggca   5280
tcgggacttc aggattagag actcccacca tggccgccac cgccggagag gtcaagacgt   5340
gaaacacgcg ctcgcctgtc gacaggcgcg ccgcgccctc tactagacta gccttcacgt   5400
ccggaactcg taacatagct tagaccagcg gacggacgca acgtacgtgg ggatcggctg   5460
gcggtgtctg ctcgttggac gcggccgttc ggtggcgcca gtgcaggcct agtttgcgaa   5520
tggcgtgacg gacaatttgt ggctttagag cggcgaaccg atgacccgtg gtggcgacga   5580
acgaaatgaa gtttgcattg cggcccaact cgtctagcct ggtcttcttg tttcgggcat   5640
agattttcgg gattaggtta cactttttat atcccagtac tgcgcactcg tgtttgcttt   5700
tagtgtgact gattatcttc tttgagaagt caaacaggcc ccgggcggcg gctcgcctaa   5760
tgcaagccac gtcaagcctg agaaacgaac agcattccac cagacactcc aggaaccttt   5820
tgtgtagcgt ctgtatttgg gaacggtttc tgtgctcaag tagggagaat attctatttt   5880
tgtttccgtc gatgcgcgcg tgctggtccg tgagaatggg cgccagctcg tggcgaatct   5940
gttccacaag aggctgcccg tacactttag aaatcgtggc tgtcgcggcc ttaaaccagg   6000
acacgtttag cccatccttg ctggagacca cagatggaaa gtttgtggtc caaaatacgt   6060
tttttcgccc cattctcacc atgtactggt tttccagtcc gtgcaggtcc aacgtggagt   6120
tccaatttgc tatcgataca ggaaatatgt gcctgattgg cagaaagcat ttcagcgtac   6180
ccattgcgaa gagaaagtgc agcatgtccc cactgatgtt gatgtttatt gcggtgcctt   6240
gacacatgtt gtcggaaaaa aacacgctta tggtaaaaga aggttccttt acggagtact   6300
ttcgtataac aaaattgttg gtcaatctgg ggatgtttaa aatagtcttt tgcagggtgt   6360
taggaacgtg gcagcttatc ttagtgttaa tcaccatgtt ggtgttgaat atggtgatct   6420
tgaagttttc caaactgacg tgttttgtgg gttccagcat gtctgacact gtagagctgc   6480
ccagagtccg cgcgtccgtg gccgcgtatc gttggaagca cgcctgcaaa tttcctttca   6540
tggctgctcg ccggtctttc ggcgcgtacc ggattcttga aagcgtcgcc gccaggagac   6600
gcggtgtctc gtgggtgcct aaaaagtttg cgcaggggtg cagtccgctg cacgagtggc   6660
cgatgcagtc tgccactgcc atacacatga cgagtctgta gatggccggt gtgcccggat   6720
acactagata gtaggtacaa tctggggtac tgacgaccac cctgtatggc tttggtccgg   6780
ggtccttgcg ttggattttt acgtgcagac gggacacgag ctggtttaga gccagctgaa   6840
agcccaccag atcccgtccg ttaaccttga cgtcctggtg cttactctgt ttcgacaggt   6900
tcttcagcac ggtgggcagt cgctctacgt tgtgagcgat ggcacggcgc agcgagacca   6960
gctctccgtg ccacccccac gtggccatga agctgctgat gttaaacttt aaaaaatgta   7020
gctgtgcgtc tggggatgcg ggtggcatta ttgaaaacga gagatgcttc aggctctcca   7080
ggagtgcaaa ataattttga tagattgtgg gttgtagact atggggcaac accgccagaa   7140
```

-continued

```
acgcatgaaa acactgttcg aactcccaga actccaggta cctgcacact atcctgaaca   7200
tggctttgta acatatggtg cacgttagta gcgcgggaag atacagcgag cgtagctccc   7260
tgaattcgca gggtttatca caatcatcgg taagttccca tgatcccacc gcaggtaggt   7320
agttgtcggt gtctatctgt ccgcgcgtaa acactccacc accgtcaatt attaaacctt   7380
cgccgctgta ccgtcgaccc acttttccca aaagagtccc ttcttgatgt ataaaagggt   7440
ggaggcgttc cccaggagt agtctgcgta tcgctctgca ggcgaaaaag gtgggctcgg    7500
gctgcatcat cttatcaaga ccttctaagg tcagctctgc ctgcaggtgc gagttggtgg   7560
ccagacagca gaatatttcc agctgtgatt cccaagtcgc ttgataacac gtggtctgcg   7620
gactcgtcgt cagggaggcg ctcggtggca gtagtagggg gccctcgagc gctgccatgg   7680
aggcgacctt ggagcaacga cctttcccgt acctcgccac ggaggccaac ctcctaacgc   7740
agattaagga gtcggctgcc gacggactct tcaagagctt tcagctattg ctcggcaagg   7800
acgccagaga aggcagtgtc cgtttcgaag cgctactggg cgtatatacc aatgtggtgg   7860
agtttgttaa gtttctggag accgccctcg ccgccgcttg cgtcaatacc gagttcaagg   7920
acctgcggag aatgatagat ggaaaaatac agtttaaaat ttcaatgccc actattgccc   7980
acggagacgg gaggaggccc aacaagcaga gacagtatat cgtcatgaag gcttgcaata   8040
agcaccacat cggtgcggag attgagcttg cggccgcaga catcgagctt ctcttcgccg   8100
agaaagagac gcccttggac ttcacagagt acgcgggtgc catcaagacg attacgtcgg   8160
ctttgcagtt tggtatggac gccctagaac gggggttagt ggacacggtt ctcgcagtta   8220
aacttcggca cgctccaccc gtctttattt taaagacgct gggcgatccc gtctactctg   8280
agaggggcct caaaaaggcc gtcaagtctg acatggtatc catgttcaag gcacacctca   8340
tagaacattc attttttcta gataaggccg agctcatgac aagggggaag cagtatgtcc   8400
taaccatgct ctccgacatg ctggccgcgg tgtgcgagga taccgtcttt aagggtgtca   8460
gcacgtacac cacggcctct gggcagcagg tggccggcgt cctggagacg acggacagcg   8520
tcatgagacg gctgatgaac ctgctggggc aagtggaaag tgccatgtcc gggcccgcgg   8580
cctacgccag ctacgttgtc aggggtgcca acctcgtcac cgccgttagc tacggaaggg   8640
cgatgagaaa ctttgaacag tttatggcac gcatagtgga ccatcccaac gctctgccgt   8700
ctgtggaagg tgacaaggcc gctctggcgg acggacacga cgagattcag agaacccgca   8760
tcgccgcctc tctcgtcaag atagggggata agtttgtggc cattgaaagt ttgcagcgca  8820
tgtacaacga gactcagttt ccctgcccac tgaaccggcg catccagtac acctatttct   8880
tccctgttgg ccttcacctt cccgtgcccc gctactcgac atccgtctca gtcaggggcg   8940
tagaatcccc ggccatccag tcgaccgaga cgtgggtggt taataaaaac aacgtgcctc   9000
tttgcttcgg ttaccaaaac gccctcaaaa gcatatgcca ccctcgaatg cacaacccca   9060
cccagtcagc ccaggcacta aaccaagctt ttcccgatcc cgacgggggga catgggtacg  9120
gtctcaggta tgagcagacg ccaaacatga acctattcag aacgttccac cagtattaca   9180
tggggaaaaa cgtggcattt gttcccgatg tggcccaaaa agcgctcgta accacggagg   9240
atctactgca cccaacctct caccgtctcc tcagattgga ggtccacccc ttctttgatt   9300
tttttgtgca cccctgtcct ggagcgagag gatcgtaccg cgccacccac agaacaatgg   9360
ttggaaatat accacaaccg ctcgctccaa gggagtttca ggaaagtaga ggggcgcagt   9420
tcgacgctgt gacgaatatg acacacgtca tagaccagct aactattgac gtcatacagg   9480
agacggcatt tgaccccgcg tatcccctgt tctgctatgt aatcgaagca atgattcacg   9540
```

-continued

```
gacaggaaga aaaattcgtg atgaacatgc cctcattgc cctggtcatt caaacctact   9600
gggtcaactc gggaaaactg gcgtttgtga acagttatca catggttaga ttcatctgta   9660
cgcatatggg gaatggaagc atccctaagg aggcgcacgg ccactaccgg aaaatcttag   9720
gcgagctcat cgcccttgag caggcgcttc tcaagctcgc gggacacgag acggtgggtc   9780
ggacgccgat cacacatctg gtttcggctc tcctcgaccc gcatctgctg cctccctttg   9840
cctaccacga tgtctttacg gatcttatgc agaagtcatc cagacaaccc ataatcaaga   9900
tcggggatca aaactacgac aaccctcaaa atagggcgac attcatcaac ctcaggggtc   9960
gcatggagga cctagtcaat aaccttgtta acatttacca gacaagggtc aatgaggacc  10020
atgacgagag acacgtcctg gacgtggcgc ccctggacga gaatgactac aacccggtcc  10080
tcgagaagct attctactat gttttaatgc cggtgtgcag taacggccac atgtgcggta  10140
tgggggtcga ctatcaaaac gtggccctga cgctgactta caacggcccc gtctttgcgg  10200
acgtcgtgaa cgcacaggat gatattctac tgcacctgga gaacggaacc ttgaaggaca  10260
ttctgcaggc aggcgacata cgcccgacgg tggacatgat cagggtgctg tgcacctcgt  10320
ttctgacgtg ccctttcgtc acccaggccg ctcgcgtgat cacaaagcgg gacccggccc  10380
agagttttgc cacgcacgaa tacgggaagg atgtggcgca gaccgtgctt gttaatggct  10440
ttggtgcgtt cgcggtggcg gaccgctctc gcgaggcggc ggagactatg ttttatccgg  10500
taccctttaa caagctctac gctgacccgt tggtggctgc cacactgcat ccgctcctgg  10560
caaactatgt caccaggctc cccaaccaga gaaacgcggt ggtctttaac gtgccatcca  10620
atctcatggc agaatatgag gaatggcaca agtcgcccgt cgcggcgtat gccgcgtctt  10680
gtcaggccac cccgggcgcc attagcgcca tggtgagcat gcaccaaaaa ctatctgccc  10740
ccagtttcat ttgccaggca aaacaccgca tgcaccctgg ttttgccatg acagtcgtca  10800
ggacggacga ggttctagca gagcacatcc tatactgctc cagggcgtcg acatccatgt  10860
ttgtgggctt gccttcggtg gtacggcgcg aggtacgttc ggacgcggtg acttttgaaa  10920
ttacccacga gatcgcttcc ctgcacaccg cacttggcta ctcatcagtc atcgccccgg  10980
cccacgtggc cgccataact acagacatgg gagtacattg tcaggacctc tttatgattt  11040
tcccagggga cgcgtatcag gaccgccagc tgcatgacta tatcaaaatg aaagcgggcg  11100
tgcaaaccgg ctcaccggga aacagaatgg atcacgtggg atacactgct ggggttcctc  11160
gctgcgagaa cctgcccggt ttgagtcatg gtcagctggc aacctgcgag ataattccca  11220
cgccggtcac atctgacgtt gcctatttcc agacccccag caacccccgg gggcgtgcgg  11280
cgtgcgtggt gtcgtgtgat gcttacagta acgaaagcgc agagcgtttg ctctacgacc  11340
attcaatacc agaccccgcg tacgaatgcc ggtccaccaa caacccgtgg gcttcgcagc  11400
gtggctccct cggcgacgtg ctatacaata tcacctttcg ccagactgcg ctgccgggca  11460
tgtacagtcc ttgtcggcag ttcttccaca aggaagacat tatgcggtac aatagggggt  11520
tgtacacttt ggttaatgag tattctgcca ggcttgctgg ggcccccgcc accagcacta  11580
cagacctcca gtacgtcgtg gtcaacggta cagacgtgtt tttggaccag ccttgccata  11640
tgctgcagga ggcctatccc acgctcgccg ccagccacag agttatgctt gacgagtaca  11700
tgtcaaacaa gcagacacac gccccagtac acatgggcca gtatctcatt gaagaggtgg  11760
cgccgatgaa gagactatta aagctcggaa acaaggtggt gtattagcta acccttctag  11820
cgttggctag tcatggcact cgacaagagt atagtggtta acttcacctc cagactcttc  11880
```

```
gctgatgaac tggccgccct tcagtcaaaa atagggagcg tactgccgct cggagattgc  11940
caccgtttac aaaatataca ggcattgggc ctggggtgcg tatgctcacg tgagacatct  12000
ccggactaca tccaaattat gcagtatcta tccaagtgca cactcgctgt cctggaggag  12060
gttcgcccgg acagcctgcg cctaacgcgg atggatccct ctgacaacct tcagataaaa  12120
aacgtatatg cccccttttt tcagtgggac agcaacaccc agctagcagt gctacccccca  12180
ttttttagcc gaaaggattc caccattgtg ctcgaatcca acggatttga cctcgtgttc  12240
cccatggtcg tgccgcagca actggggcac gctattctgc agcagctgtt ggtgtaccac  12300
atctactcca aaatatcggc cggggccccg gatgatgtaa atatggcgga acttgatcta  12360
tataccacca atgtgtcatt tatggggcgc acatatcgtc tggacgtaga caacacggat  12420
ccacgtactg ccctgcgagt gcttgacgat ctgtccatgt acctttgtat cctatcagcc  12480
ttggttccca gggggtgtct ccgtctgctc acggcgctcg tgcggcacga caggcatcct  12540
ctgacagagg tgtttgaggg ggtggtgcca gatgaggtga ccaggataga tctcgaccag  12600
ttgagcgtcc cagatgacat caccaggatg cgcgtcatgt tctcctatct tcagagtctc  12660
agttctatat ttaatcttgg ccccagactg cacgtgtatg cctactcggc agagactttg  12720
gcggcctcct gttggtattc cccacgctaa cgatttgaag cggggggggg gtatggcgtc  12780
atctgatatt ctgtcggttg caaggacgga tgacggctcc gtctgtgaag tctccctgcg  12840
tggaggtagg aaaaaaacta ccgtctacct gccggacact gaaccctggg tggtagagac  12900
cgacgccatc aaagacgcct tcctcagcga cgggatcgtg gatatggctc gaaagcttca  12960
tcgtggtgcc ctgccctcaa attctcacaa cggcttgagg atggtgcttt tttgttattg  13020
ttacttgcaa aattgtgtgt acctagccct gtttctgtgc cccttaatc cttacttggt  13080
aactccctca agcattgagt ttgccgagcc cgttgtggca cctgaggtgc tcttcccaca  13140
cccggctgag atgtctcgcg gttgcgatga cgcgattttc tgtaaactgc cctataccgt  13200
gcctataatc aacaccacgt ttggacgcat ttacccgaac tctacacgcg agccggacgg  13260
caggcctacg gattactcca tggcccttag aagggctttt gcagttatgg ttaacacgtc  13320
atgtgcagga gtgacattgt gccgcggaga aactcagacc gcatcccgta accacactga  13380
gtgggaaaat ctgctggcta tgttttctgt gattatctat gccttagatc acaactgtca  13440
cccggaagca ctgtctatcg cgagcggcat ctttgacgag cgtgactatg gattattcat  13500
ctctcagccc cggagcgtgc cctcgcctac cccttgcgac gtgtcgtggg aagatatcta  13560
caacgggact tacctagctc ggcctggaaa ctgtgacccc tggcccaatc tatccacccc  13620
tcccttgatt ctaaatttta aataaaggtg tgtcactggt tacaccacga ttaaaaacca  13680
ctcactgaga tgtcttttta accgctaagg gattataccg ggatttaaaa ccgcccactg  13740
attttttac gctaagagtt gggtgcttgg ggggttttgc attgctctgt tgtaaactat  13800
atataagtta aaccaaaatt cgcagggaga caaggtgacg gtggtgagaa ctcagttgag  13860
agtcagagaa tacagtgcta atcagggtag atgagcatga cttccccgtc tccagtcacc  13920
ggaggaatgg tggacggctc cgtcctggtg cgaatggcca ccaagcctcc cgtgattggt  13980
cttataacag tgctcttcct cctagtcata ggcgcctgcg tctactgctg cattcgcgtg  14040
ttcctggcgg ctcgactgtg gcgcgccacc ccactaggca gggccaccgt ggcgtatcag  14100
gtccttcgca ccctgggacc gcaggccggg tcacatgcac cgccgacggt gggcatagct  14160
acccaggagc cctaccgtac aatatacatg ccagattaga acggggtgtg tgctataatg  14220
gatggctatg ggggggctgt agataattga gcgctgtgct tttattgtgg ggatatgggc  14280
```

-continued

```
ttgtacatgt gtctatcatc ggtagccata aaatgggcca tgacaactgc cacaagtaag  14340
tcgtccgaca tgtgcttttg cttggcgctg tatgactgcc ctccatccct aagcgggacg  14400
cacttgatcg cgcggacctg ttctaccagg taggtcaccg ggtcaaatga tattttgatg  14460
gtgttggaca ccaccgtctg gctggcgctc agggtgccgg agttcagagc gtagatgaat  14520
gtctcaaacg cggaggattt ctcgcctccc aacatgtaaa ttggccactg cagggcgctg  14580
ctcttgtcag tatagtgtag aaaatgtatg gggagcgggc atatttcgtt aaggacggtt  14640
gcaatggcca ccccagaatc ttggctgctg ttgccttcga ccgccgcgtt cacgcgctca  14700
attgtggggt ggagcacagc gatcgcctta atcatcgtgc atgcgcagga cgctatctcg  14760
taagcagctg cgccagtgag gtcgcgcagg aagaaatgct ccatgcccaa tatgaggctt  14820
ctggtgggag tctgagtact cgtgacaacg gcgcccacgc cagtaccgga cgcctccgtg  14880
ttgttcgtat acgcggggtc gatgtaaaca aacagctgtt ttccaaggca cttctgaacc  14940
tgctgggcgg tggtgtctac ccgacacatg tcaaactgtg tcagcgctgc gtcacccacc  15000
acgcggtaaa gcgtagcatt tgacgacgct gctccctcgc ccattagttc ggtgtcgaat  15060
gccccctcca taaagaggtt ggtggtggtt ttgatggatt cgtcgatggt gatgtacgtc  15120
ggaatgtgca gtctgtaaca aggacaggac actagtgcgt cttgcaggtg gaaatcttcg  15180
cggtggtccg cacacacgta actgaccaca ttcagcatct tttcctgggc gttcctgagg  15240
ttaagcagga aactcgtgga gcggtctgac gagttcacgg atgatataaa tataagcttg  15300
gcgtctttct gaagcatgaa acccagaata gccggcagtg catccttttt aataaaattc  15360
gcctcgtcta cgtagagcag gttaaaggtc tgtccccgaa tgctctgcag acacggaaag  15420
acacaaaaga ggggctcata agcggctaac agtaaaggag aggaggcgaa cagtgcgtgg  15480
ctcttgttct tgggaataaa agggggcgtg tgtgccgatc gtatgggtga gccagtggat  15540
cctggacatg tggtgaatga gaaagatttt gaggagtgtg aacaattttt cagtcaaccc  15600
cttagggagc aagtggtcgc gggggtcagg gcactcgacg gcctcggtct cgctgactct  15660
ctatgtcaca aaacagaaag actctgcctg ctgatggacc tggtgggcac ggagtgcttt  15720
gcgagggtgt gccgcctaga caccggtgcg aaatgaagag tgtggcgagt cccttatgtc  15780
agttccacgg cgtgttttgc ctgtaccagt gtcgccagtg cctggcatac cacgtgtgtg  15840
atgggggcgc cgaatgcgtt ctcctgcata cgccggagag cgtcatctgc gaactaacgg  15900
gtaactgcat gctcggcaac attcaagagg gccagttttt agggccggta ccgtatcgga  15960
ctttggataa ccaggttgac agggacgcat atcacgggat gctagcgtgt ctgaaacggg  16020
acattgtgcg gtatttgcag acatggccgg acaccaccgt aatcgtgcag gaaatagccc  16080
tgggggacgg cgtcaccgac accatctcgg ccattataga tgaaacattc ggtgagtgtc  16140
ttcccgtact gggggaggcc caaggcgggt acgccatggt ctgtagcatg tatctgcacg  16200
ttatcgtctc catctattcg acaaaaaacgg tgtacaacag tatgctattt aaatgcacaa  16260
agaataaaaa gtacgactgc attgccaagc gggtgcggac aaaatggatg cgcatgctat  16320
caacgaaaga tacgtaggtc ctcgctgcca ccgtttggcc cacgtggtgc tgcctaggac  16380
ctttctgctg catcacgcca taccccctgga gcccgagatc atcttttcca cctacacccg  16440
gttcagccgg tcgccagggt catcccgccg gttggtggtg tgtgggaaac gtgtcctgcc  16500
aggggaggaa aaccaacttg cgtcttcacc ttctggcttg gcgcttagcc tgcctctgtt  16560
ttcccacgat gggaactttc atccatttga catctcggta ctgcgcattt cctgccctgg  16620
```

-continued

```
ttctaatctt agtcttactg tcagatttct ctatctatct ctggtggtgg ctatgggggc  16680
gggacggaat aatgcgcgga gtccgaccgt tgacggggta tcgccgccag agggcgccgt  16740
agcccaccct ttggaggaac tgcagaggct ggcgcgtgct acgccggacc cggcactcac  16800
ccgtggaccg ttgcaggtcc tgaccggcct tctccgcgca gggtcagacg gagaccgcgc  16860
cactcaccac atggcgctcg aggctccggg aaccgtgcgt ggagaaagcc tagacccgcc  16920
tgtttcacag aaggggccag cgcgcacacg ccacaggcca ccccccgtgc gactgagctt  16980
caaccccgtc aatgccgatg tacccgctac ctggcgagac gccactaacg tgtactcggg  17040
tgctccctac tatgtgtgtg tttacgaacg cggtggccgt caggaagacg actggctgcc  17100
gataccactg agcttcccag aagagcccgt gcccccgcca ccgggcttag tgttcatgga  17160
cgacttgttc attaacacga agcagtgcga ctttgtggac acgctagagg ccgcctgtcg  17220
cacgcaaggc tacacgttga gacagcgcgt gcctgtcgcc attcctcgcg acgcggaaat  17280
cgcagacgca gttaaatcgc actttttaga ggcgtgccta gtgttacggg ggctggcttc  17340
ggaggctagt gcctggataa gagctgccac gtccccgccc cttggccgcc acgcctgctg  17400
gatggacgtg ttaggattat gggaaagccg cccccacact ctaggtttgg agttacgcgg  17460
cgtaaactgt ggcggcacgg acggtgactg gttagagatt ttaaaacagc ccgatgtgca  17520
aaagacagtc agcgggagtc ttgtggcatg cgtgatcgtc acacccgcat tggaagcctg  17580
gcttgtgtta cctggggggtt ttgctattaa aggccgctat agggcgtcga aggaggatct  17640
ggtgttcatt cgaggccgct atggctagcc ggaggcgcaa acttcggaat ttcctaaaca  17700
aggaatgcat atggactgtt aacccaatgt caggggacca tatcaaggtc tttaacgcct  17760
gcacctctat ctcgccggtg tatgaccctg agctggtaac cagctacgca ctgagcgtgc  17820
ctgcttacaa tgtgtctgtg gctatcttgc tgcataaagt catgggaccg tgtgtggctg  17880
tgggaattaa cggagaaatg atcatgtacg tcgtaagcca gtgtgtttct gtgcggcccg  17940
tcccggggcg cgatggtatg gcgctcatct actttggaca gtttctggag gaagcatccg  18000
gactgagatt tccctacatt gctccgccgc cgtcgcgcga acacgtacct gacctgacca  18060
gacaagaatt agttcatacc tcccaggtgg tgcgccgcgg cgacctgacc aattgcacta  18120
tgggtctcga attcaggaat gtgaaccctt ttgtttggct cgggggcgga tcggtgtggc  18180
tgctgttctt gggcgtggac tacatggcgt tctgtccggg tgtcgacgga atgccgtcgt  18240
tggcaagagt ggccgccctg cttaccaggt gcgaccaccc agactgtgtc cactgccatg  18300
gactccgtgg acacgttaat gtatttcgtg ggtactgttc tgcgcagtcg ccgggtctat  18360
ctaacatctg tccctgtatc aaatcatgtg ggaccgggaa tggagtgact agggtcactg  18420
gaaacagaaa ttttctgggt cttctgttcg atcccattgt ccagagcagg gtaacagctc  18480
tgaagataac tagccaccca acccccacgc acgtcgagaa tgtgctaaca ggagtgctcg  18540
acgacggcac cttggtgccg tccgtccaag gcaccctggg tcctcttacg aatgtctgac  18600
tacttcagcc gcttgctgat atatgagtgt aaaaaactta aggccctggg cttacgttct  18660
tattgaagca tgttgcgcac atcagcgagc tggaccgtcc tccgggtcgc gtgtagatta  18720
tggttccgtt ctccttcttg atgtttaaat ttttgggggg gaaccaccga caaagcgtct  18780
ttatgatttc cgcgaacacg gagttggcta cgtgcttttg gtgggctacg tacccaatgt  18840
taatgttctc tacggatgcc agtagcatgc tgatgatcgc caccactatc catgtctttc  18900
cgtgtctcct tggtattagg aatacgcttg ccttttgctt aaacgtctgt aaaacactgt  18960
ttggagtttc aaataaaccg aagtactgct taaacaatcc aaacaactgg tgcgtctttt  19020
```

-continued

```
gtggggcctt gattgaaacc aaaaagaaaa aagtgtgcat tactagctgc tgttggaagg  19080
gctccagcca gtgcaccccg ggaacgtaac agccgttcag aaaggacgaa aggttaacca  19140
gaaaagcctg aagttcgcgg tagacagagc aggcgtgcag ggagtcgtgt gtttttctgg  19200
ccgcctggta ctcgaccagt tgatcggccg tggagacgtg cgcgtcctcg cgcacacacc  19260
gcatctgcaa gtatgttgat agggactcca ataggcgcgg ctttgcgggg acgttgtcct  19320
cggacggtct gggggttccc acgtcgggat ttgctgacgt gggcgtggcg ggatggtgcc  19380
gtgtgcagta tgtttccagg accgaactgt atgagtttat tctgtgcacc acgccaataa  19440
aagggtgcgc catccgtgcc gttttgggac agtgtcgcgt gaatgtcggg gcactcagtt  19500
cccacctctc tccggcgtct ttggcggtct cctgcaggtt ggcggcaagg cgctccctgt  19560
gacggctgag cagcatgttt gctttgagct cgctcgtgtc cgagggtgac ccggaggtga  19620
ccagtaggta cgtcaagggc gtacaacttg ccctggacct tagcgagaac acacctggac  19680
aatttaagtt gatagaaact cccctgaaca gcttcctctt ggtttccaac gtgatgcccg  19740
aggtccagcc aatctgcagt ggccggccgg ccttgcggcc agactttagt aatctccact  19800
tgcctagact ggagaagctc cagagagtcc tcgggcaggg tttcggggcg gcgggtgagg  19860
aaatcgcact ggacccgtct cacgtagaaa cacacgaaaa gggccaggtg ttctacaacc  19920
actatgctac cgaggagtgg acgtgggctt tgactctgaa taaggatgcg ctccttcggg  19980
aggctgtaga tggcctgtgt gaccccggaa cttggaaggg tcttcttcct gacgaccccc  20040
ttccgttgct atggctgctg ttcaacggac ccgcctcttt ttgtcgggcc gactgttgcc  20100
tgtacaagca gcactgcggt tacccggcc  cggtgctact tccaggtcac atgtacgctc  20160
ccaaacggga tcttttgtcg ttcgttaatc atgccctgaa gtacaccaag tttctatacg  20220
gagatttttc cgggacatgg gcggcggctt gccgcccgcc attcgctact tctcggatac  20280
aaagggtagt gagtcagatg aaaatcatag atgcttccga cacttacatt tcccacacct  20340
gcctcttgtg tcacatatat cagcaaaata gcataattgc gggtcagggg acccacgtgg  20400
gtggaatcct actgttgagt ggaaaaggga cccagtatat aacaggcaat gttcagaccc  20460
aaaggtgtcc aactacgggc gactatctaa tcatcccatc gtatgacata ccggcgatca  20520
tcaccatgat caaggagaat ggactcaacc aactctaaaa gagagtttat taagtcggct  20580
ctggaggcca acatcaacag gagggcagct gtatcgctat ttgatcgttt tgggggtagc  20640
agcgccgtgt ttgagaagca gtttcaggac gcacagcatg ccgtcagggc ccacggtgca  20700
ctgaagcgcg aagccgagct cgggactctg gtacgcaagg cgggccagag gtttgaggcg  20760
ctgaaaaggg aacggtcaat tttgcgccag ccgcgcgacc tcccacgggt cgccgacatt  20820
gacgccctgg tcgacgccgt cgcggacctc aaagaagagg tggccgtgcg cctagatgcg  20880
ctggaagaga atggagagga gacccccact cactcctctt cggagatcaa ggacacaatc  20940
gtcaggtgga ggcttgacga tttgcccccg gtgtgccctg aaactcccta aggctacccg  21000
gatttcagag agaccctggg cgtccacatg gcagctgaat cagcatatac aggtgtccaa  21060
gactaaaaag gccaccgcgt atcttaaagc gccccgtgaa tgggggcagt gcacgcacca  21120
ggatccagac tggtccaagc gtctgggtcg tggcgccttt ggcataatcg tccctatctc  21180
cgaggatctg tgtgtgaagc agtttgatag ccgccgggag tttttctacg aggcaattgc  21240
caacgacctg atgcaggcca cccgagagag gtaccccatg cattctggtg gatctagact  21300
gctaggattc gtgcagcctt gcataccctg tagatcgatt gtgtatccta gaatgaagtg  21360
```

-continued

```
caacctgctg cagctggact ggagtcaggt caacctgagt gtcatggcgg cggagttcac  21420
cggcctaatg gcggcggtgt cctttctaaa cagatactgt ggcatggtgc actgcgacgt  21480
tagtccagac aatattttgg ccacaggaga cctaacgccc atgaaccccg ggaggctggt  21540
ccttaccgat ttcggttccg ttgcgctaca ctctgggagc aagtggacta accttgtggt  21600
gacctctaac ctggggttta agcaacactg ctacgacttc agggtgccac ccaaactcat  21660
ttgtaagcat ctctataagc cgtcttgcgt cctcttccag tgttacctat ccagtctcgg  21720
taagatgcac gcgcaggtat tggaccaacc gtaccctatc agccctaaca tgggactgac  21780
catcgacatg tcctcgttgg gctacactct gctgacatgc ctggaactct atctcgatct  21840
gccgctaaac aaccctctga agttcttggg ttcagccacc agagacggac gccccgaacc  21900
catgtactac ttgggcttca tgattcccag ggtggtgatg actcagatcc tgtccgctgt  21960
gtggaccatg acgcttgacc tgggactaga ttgcaccggc aaagcccagg cgattcccat  22020
gcgacaggag caccagctgg cgtttcagaa gcagtgctat ttatataaag ccaaccaaaa  22080
ggcagagtcg ttagcgaact gctccgataa gctaaactgc cccatgttaa agtctctcgt  22140
tagaaagcta ctagagcgag actttttcaa ccatggaggc cacccccaca cccgcggact  22200
tgttttctga agactatctg gttgacaccc tggatgggtt aacagtggat gaccaacagg  22260
ctgtcctcgc aagcttgagc ttttcaaagt ttctaaagca cgccaaggtt cgagactggt  22320
gcgcacaggc caagatccaa cccagcatgc ctgcgctgcg catggcttac aactatttcc  22380
ttttttcaaa agtgggcgag tttattggta gtgaggatgt gtgtaacttt ttcgtggacc  22440
gtgtgtttgg tggtgtcagg ttactggacg tggccagcgt gtacgccgcc tgttcgcaaa  22500
tgaacgcaca tcagcggcac cacatctgct gtctagtgga gagggccact agtagtcaga  22560
gtctgaaccc cgtgtgggac gccctgcgag acggaattat atcttcatcc aagtttcact  22620
gggcagttaa acaacagaac acttcaaaaa agatattcag cccatggcct ataacgaaca  22680
accactttgt cgcgggcccg cttgcctttg ggctgcggtg cgaggaggtg gtgaaaacgt  22740
tgctggccac ccttttgcac ccggacgaga caaattgtct cgattatggg tttatgcaga  22800
gtccgcaaaa tggaatattt ggcgtgtcgc tggatttcgc ggcgaacgtc aaaactgaca  22860
ccgagggtcg tctacagttt gaccctaact gtaaagtgta tgaaataaaa tgcaggttca  22920
agtacacctt tgcgaaaatg gagtgtgacc ccatatacgc cgcgtatcag cggctgtacg  22980
aggcacccgg aaagctggca ctgaaggact tcttctatag catttccaag cctgcggttg  23040
agtacgtggg acttggaaaa ctgcccagtg aatctgatta cttggtggct tatgatcagg  23100
aatgggaggc gtgtcctcgc aaaaagagga aattaacgcc ccttcacaat cttattaggg  23160
agtgtatttt gcacaactcg accacggagt ctgacgtcta cgtacttact gatcctcaag  23220
atactcgggg tcaaatcagt attaaagccc gcttcaaagc caacctcttc gtgaacgtcc  23280
gtcacagcta cttttatcag gtattgctgc agagttcgat cgtcgaggag tacattggcc  23340
tagatagcgg cattcctcgc ctcggatcac cgaaatacta catcgccacc ggcttcttca  23400
gaaagcgggg ctatcaggat cctgtcaact gtaccatcgg tggcgatgct ttagacccgc  23460
acgtggagat tcctacgctg ctaatcgtaa cccccgtcta ctttccccga ggcgcaaagc  23520
atcgtctgct tcaccaagct gccaactttt ggtcaagaag tgcgaaggac acctttccat  23580
atatcaaatg ggatttctcc tatctatctg caaacgtccc tcacagcccg tagacgtgga  23640
cggggaaccg ctcgacgtag tcgtggacta tgaccccatt cgcgtttcag aaaagggcat  23700
gttgcttgag caatcgcaat ccccatatcc cgcattaaaa aagaagaaaa aaaataaaga  23760
```

-continued

```
agcaatttat taagcaaaca gtatggtttt ctgtacgtat tttattccgt ggtgggtgaa  23820
aaataacggg ggatggagga agagggatgg gtttataatg ccaatatatc agctaaatga  23880
atatcatttg cgtttcgtcg atttcactgt cactttcatg gtcggactgg tattgggtcc  23940
tcggggcggg cgtcgatatg tccttcactt tggcgcgggc tctggtcttt gctgggaggg  24000
gcggcggttt ctggtgaaca gtcggagttc tatcgaccgt cggcgccgac gtcgccagag  24060
gcatgtatgc cgcactcggc gtacagagtc cccagtcgct ccttataacg cgtataacga  24120
tggctaggat gcacagtata gggatacagg agatattgat agccactatg tagtggagat  24180
tagcctgcac gaacgcgttt tcatacctga tgacaggcag cagtagaatc agataaccca  24240
ccaatactcc cacgtaaaag cctacctgcc gtctcataaa ctttaccagg aaaaattccg  24300
tgtttatgta ccacacgacc gtcaaggcta ggaacatgtt caccgcacca aaaatggcgt  24360
ctgacacgag cacgtaaaag ctgttgccaa cggccatcat ggtgctcaat gaaaacagca  24420
gcatttccaa ggcggttgtt gataggtaca ggttgacgca gaccggtttc caccgagtca  24480
gcagtgactc catcatggta ttatcaggta cgtgctgttc caggagaggt atttcccact  24540
gggcggagtt acatgttatc agtgactgga tgtgggcaaa ggatatgcaa aaatgaatgc  24600
agtagacaaa ggctgccata agtacgtgtt tatatgacag aacatggata aacagttgca  24660
tgctccacat ccttaagatg gcgacataaa gcacgctatg tgatccaagt agcgctatcc  24720
aggattgcat gctcatcatg gtagtggcgt gaacatgctt ggcccgatat acggccaccg  24780
ccgcgagaca gtagtatact atggcaatgc cgtccacgat aaaagtccaa aatatgtaca  24840
ccagcatctc tggtttctct aaaaacaggg tcggggtgag gtgcttcgct gagttgcgca  24900
ccgtgaggtt tagcgcgctg tagtttacca gattgttgaa gtagcagggg aaaccaaggc  24960
cctcgtacgt ggcggccatg ggcacgactg cagagcaaat gtacataatt acagccacaa  25020
acaacagctt gacccaggag gacatgagaa aacggtcgct ctttgaagcg cgcatgtttc  25080
tcggtctttt taactttcgc caggcggcgc tgcggcggga gagccaatct gatgccactg  25140
cctatcgcgg ttgactttta aatacgcgcc ccgggcagaa gccagaggta gtcgactcat  25200
tgactcaatg gcaacgagcg aagaaacggc ggccggttat gtcatcggtg tctactttca  25260
cagcgttcac gtccactgcc gcattattgt ctggcaggtt aattttctac ccctggaccc  25320
aaacgacggg gagactgaat gctactttgt ggtggacacg ctgacgaaag aggcgatgga  25380
gcgcatgccc gaaatccagg aatgcgtccc gtctattact gaacacgccc gtgacctggc  25440
gatctgggag ttggcgctgc gactgcagaa tcagacgatc gtcaaggccg tccggacagc  25500
gtcgcttccg gtggttctaa ttatgactgt gggtcgcata gtgaatgatg tgattccctg  25560
ccccaacgtc agaacaccca gaccactagc ctgtgcttac ctacactgtg aggcgacggt  25620
gacctttgag gtcccactaa ccgggcccgc ggcgtccacc ggaacgtggc acagctctat  25680
ctatagggaa tgtgcgatct cggctatcga gatatgcttg aagaccagtc gaggcatata  25740
ctcctgccag tcgaacgagg cccctgaggc caagagggaa aagcgaggtt tagacatatc  25800
agatgtgttt gtctgtctca cgtatgatat ccctatcgca gggcgggtcc tttctctgct  25860
ggtgccccac gcgcccgctt ttcacgtctt atggatcaat gaggacagca agtggaacgg  25920
ggcagccgtc gaatttttca gagccctaca ccataagctg ttcagtgaac gcaatggtat  25980
accccctctg tggttgtacg tgttcccggg agctgtggaa gagggcacag cctttgcgcc  26040
attacttccc gcattccctt gcataccttt gcggtatggg tcgcctacct ctctggacag  26100
```

-continued

```
ggcgtccgtg cagtgggacc tatttgaacc gcacatcctg acccactttg acgggataaa 26160
gcgaacttct ttggcagata cagtgtttgg gtacgactcc ctggccattt caagggaatg 26220
tgaagatcag tatgtgtggc ccacgcctgt cactgacatt aatattaatt tgtgcacgga 26280
tagtgacact atggccatcg ttagagaacc atccggtctg gtggccgtga atctagaagc 26340
cctgttgcgc accgactccg tattatcgcg ggtctcgtcc attgtctcac tcgatacgct 26400
cttggacctt tccaccccgg agtgccgtag gagcgtggag cttagataca actcactttt 26460
gtcgactgta ttatcatggt ccacctctag ggtcacaaa tgggccgcaa tcgtgaagtg 26520
gaagttattt ttcctcgtcc aagctttgga gcctgaggtg agacctactg tccctgcttg 26580
aagcggagag ggggtggtgc gagttggcag ttgacgggtt tgtgatagct ggagtgctga 26640
ccacggcaca ggacccatta actttcctat gtgtttattt ttagcaatgg tctccagaat 26700
tcaaggatct caaaagggcc tgccagatgg ccgggtttac tctgaagggg gggacttcgg 26760
gggatcttgt attctcatcg catgcgaact tgctcttttc aacctcgatg ggatatttcc 26820
tccatgcagg cagtccaagg tcgacagcgg ggacgggggg tgagcctaac ccacgtcaca 26880
tcaccggacc agacactgag ggaaatgggg aacacagaaa ctcccccaac ctctgcggct 26940
ttgttacctg gctgcaaagc ttaaccacat gcattgaacg agccctaaac atgcctcccg 27000
acacttcctg gctgcagctg atagaggaag tgataccct gtattttcat aggcgaagac 27060
aaacatcatt ctggctcatc cccctatcgc actgtgaagg gatcccagta tgcccccctt 27120
taccatttga ctgcctagca ccaaggctgt ttatagtaac aaagtccgga cccatgtgtt 27180
accgggcagg cttttcgctt cctgtggatg ttaattacct gttctattta gagcagactc 27240
tgaaagctgt ccggcaagtt agcccacagg aacacaaccc ccaagacgca aaggaaatga 27300
ctctacagct agaggcctgg accaggcttt tatctttatt ttgaaaaaag ggaaacaatg 27360
gggggtttga aaagggtgca cattttcaga tattttaaaa cttcattgtt ctccaggtgc 27420
ttggtaaaga tggtatcaca ataaaaaatg tttactgggt ccgcgcaggt ttgtttgtca 27480
tcttcattct ctccactaga ctccagttta aaagactcta gataaatggg tttcattagt 27540
ccccccatgg gggttgaagc gtcgcctatc gccttatgaa gcttaaacat aacgagtggg 27600
gtggccctga aatgatcgtc cacggacagc tcgtaaacaa aggcggccgt ggcagtcaac 27660
gtctctatac cgtgcatgac gaaggccgcg tccatccccg gcgtcctctc atgtgtcttt 27720
ctggcgcgac aaataataga tctcaaaaac gttggtgaca tgtctcgaca gttctcgagc 27780
atcgataaca ggcagcagag ctcggttatg ccgggagatg taggtctaag gaggcacact 27840
cgctcttgga acacgtgagg gtgtaggtct atgtgggtca ccatgtcttc gtgctccacc 27900
aggcacacca ccgtaaatcc cacaaagttg ggcgaggaca ggcgagattt cacgtgctcc 27960
ctgagacacg ctatatctaa gtggcccatc acggacattt tgggggtatt gcttccaacc 28020
agtgcgttgt ttttcctatg cacttccagg acaaggcggg gcaccacagg gtgggggtat 28080
acgggacagg cctcttctga ctcgcgagtc ttcggggcat gagtactcat tggcactcca 28140
gtcagtctcg ccagggccct ttccagggac attctcgaag ggtggtgtaa ctagacagta 28200
tttctgtccc acgtcggtta tatacacaaa gagtctgcta gtctgatata aataggccgc 28260
gatgtcctgc aagctggagg atacgaagga gtgactaatg agctccatct gaagcaggtc 28320
cgcgatcaca tacgtgaatg gaccaagcag gatggatatg gtgtcctgag aataggtgac 28380
gctgagccgc tgcccttggt tgtcaacaac gggagccagc ttgtaggttt gaaacatctc 28440
gctttcccac aggttcgtga gatctttcat gctttctctc actgggggta tgtaagaaga 28500
```

-continued

```
gaaaaagcta tttagcacgg cactgcccga tgggatatgg gaagacgtta gctgcagaga  28560
ggggtcctgt aaacgtccca gagattgaaa tgtgttggcg gtcagcagat tcacactccc  28620
gggacccttt gcgtcaccgg gctgttggtg tgacagctgt gtctcaatac attttagcct  28680
cttcatgcag agctccctct ccttttcaag ttgagttatt gtgtcaaatt gttcgtttat  28740
ctggttggtg agacacttga aaacgctgtt ggacacctgg cgcctgagcc cctgagtggt  28800
cgtctcttgg cctgtgccga atagtttatt cttgtctact atgttttggg acacgtcggt  28860
gacaaagtcc tccacgacgt cggtgacacc gctcactgtc ttgttttctg ccagtttcat  28920
gagcaggttg aggagctctc gcttggggtc tgttctctga gaggcctgct ccaggtgggt  28980
catgatgtct ttgtacacat tgttacaggc gcttccaacg agggccttgg tgggggctgt  29040
gttcaggagc tggcaaagtt ttgcgtgctc tgccgtccgg tgacagctca taatgctggt  29100
atacatcctc tgaatggggc tgtcaaagat cacccgccca gccaagatgg cgggcatagt  29160
aatcacctcc acatgaaccc ttttctgctt atacaatccc acgaaagtgt ttttaacaca  29220
gtcatagtct atgctcacct ctgagtagcc cggaatatag agggcgctta aactagacac  29280
caggttgcta atctcctgag tcacgctggt gagtatccgg cctatggttt tttcaccaga  29340
ggccagacgc tggcaatctt tcatcagctg ttcctggata gagttaacca gcttgtggtc  29400
gggtgtgtgc ttgacgactg gtaccattcc taccgtgacc acccagtcta cgtatctctc  29460
atacgagagc tgtgtcttgg cgtagaggac ccggttgatg gcattgagaa gcaggtggtc  29520
taatgtcatg cgcatagtct gggcccagga gtcgaaggtt gaccttctgt aagaccccca  29580
ctgtgcttcc ttttctggcc acctggtttt tgctgaggac tcgtatgtcc tccagtcgga  29640
caagacgtgg tcgtagctac agttggccaa tgcattcttg tacaggtgga taaatagctg  29700
tctgaaaaaa acacccgggt ttcgcaggct gcagtgtaga gtctgacctc tgacataaga  29760
atacttgcct tgcaggatct caaagaggga gatggacagc tcggaagggt gcactgatat  29820
ggacgagccc agccccgggt tcatcctcaa catgacatcg gatgccaaag tcaggagcgt  29880
agtggaacag attgacaggt tgtcaaatat cactacctcg cccccggaga tgggctggta  29940
tgacctagag ttcgatccac tggaagacga aggccccttt ctgccgtttt cggcatacgt  30000
aataacgggg actgcaggag cggggaaaag caccagcgta tccgccctac atcagaatct  30060
caactgccta attacggggg ctacagtggt agcggcacag aatctttcca gggctttaaa  30120
gtcctactgt cccactatat accacgcctt cggattcaag agcagacaca ttaatatctg  30180
ccagaggaaa gtgcccaagg taactcagtc ctccatcgag caactccaga gatacgagct  30240
ggctaggtac tggccaactg tcaccgatat tattcgagaa tttatgcgca agaaacaaaa  30300
ggggcagtat agctccctct ctcaaagcgc tttcagactc ctttgccgta tgggtggagc  30360
caatttgtgg acgagtaaca ttatcgtgat agacgaagct ggaaccctct cgtcccatat  30420
tttgacggcc gtggtgttct tctattggtt ttacaacagt tggctggaca ccccgctata  30480
cagaaatggt gccgtgcctt gcatagtctg cgtggggtct cccacccaga cggacgcctt  30540
tcagtcggtc ttcaaccaca cgcagcagag aaacgagata tctgcctgtg ataatgtgct  30600
caccttccta ttgggaaaac gtgaggttgc agattatatt aggctggacg agaattgggc  30660
cctatttata aacaataagc gctgtacgga tccccagttt ggtcacttgc tgaagacctt  30720
agaatataat ctagacatat caccagagtt aatggactat atagataggt ttgtggttcc  30780
gaagagtaag attctggacc cgctcgagta tgcagggtgg acaagactct tcatctcaca  30840
```

-continued

```
ccaggaggtg aagtcttttc tggcaacgct gcacacctgc ctgtcgagta ataaggatgc  30900
tgtgtccaca aagcttttca cctgcccagt ggtctgtgag gtgtttacag agccatttga  30960
ggagtacaaa cgggcggtag gcctcacaca catgactccc atagaatggg taacaaaaaa  31020
tcttttcagg ctaagtaact actcgcagtt tgctgatcag gacatggctg tggttgggac  31080
ctatatcaca gacgcgtcca cacagatcac cttcgccact aaatttgtca aaaacagcta  31140
tgctaccctt actggaaaga ccaaaaaatg tatatgcggg tttcacgggt cataccaaag  31200
attcaagtcc atcctagacg gggagctatt tatcgaaagt cattcgcacg ataaccccgc  31260
ttatgtgtac agtttcctta gtaccctgct atataatgcc atgtactcat tttacgcgca  31320
cggggtgaag caggggcatg aagaattcct cagggacctc agggaactgc cggtgtctca  31380
agagctgatc tctgagatga gctccgagga cgttctgggg caggaggggg acacagatgc  31440
cttctacctc accgccagcc tcccaccatc ccccacccac gcggctcttc caacactggt  31500
ggcctattac tccggggcca aggaactatt ctgcaacagg ctggccctgg cacgccgaca  31560
ctttggtgac gagttcctcc actccgattt ttcaacgttt acggtgaaca tcgtggtgcg  31620
agatggcgtg gactttgtgt ccacttcccc cgggctccac ggtctagtgg catacgcatc  31680
cactatagac acctatataa tccagggata tacgttcctc ccagtgagat tcggccgtcc  31740
aggaggacag cgcctcagcg aggacctgcg cagaaagatg ccctccatag ttgtccagga  31800
ctcatcgggg ttcattgcct gcctggaaaa taacgtcacc aagatgacag agaccctcga  31860
aggtggcgac gtgtttaaca tatgttgtgc aggggactac ggtatcagtt ctaatctggc  31920
tatgaccata gtgaaggcac agggggtttc actaagtagg gtggccatat cgttcggcaa  31980
ccaccgcaat atcagagcca gtctagtgta tgtgggtgta tccagggcca tcgacgctcg  32040
ttacctggta atggacagta atccccttaa gctaatggac cgcggtgacg cccagtcccc  32100
atcctcaaag tacatcatca aagccctatg caaccccaag actactctga tctactgacc  32160
cgtacccctc tcttaggaca ctgatgtgtt tgggaataaa gcatgagact tgacacctat  32220
aatggtctgt attgacacca ttcttttatt tatcagtcca gccacggcca gttatatgca  32280
ccgtttccac acaggggtgg cgtggaggcc aggatgcggg ttgggtcgct gcacctggac  32340
cccgcggtag ttgtgcttcc tgatgaaatc gagtgggcgg aagtactggg agattgggtt  32400
gggaggtgac cctttgtgct cgacggagac acgatcacgc tcacggcgga cgagggctcc  32460
tcgtctgtgt cactccccga ggatataatt atcacggacg ccactgcttt gcggcttaag  32520
tttggttgtc tctggcagcg caccacatcc tcgctaccag aggaggcggt agactgcctt  32580
ttgcgcttct ggcccacgtc catgagcccg attctctgac tcaatacttc cccttggtct  32640
tctccgtcct cctcggacga gggtggctgg tgggaaaaat ggcgcgcgtc ggtaaacgcg  32700
gcctcattgt tcacgtccgg agagttggaa ctgtcatcgc tatcagagtc cgatgtcagg  32760
tcgacgatcg cggtgggtgc ggcgcgcagg gggcgccacg agggcccttc atcagggtcg  32820
ctgtatggtg aactttgtgt tccaggtaca ctatttctgg aagcaggtga aagtccgtat  32880
gccccggtcc cagtgtatgc cgccatcggt tccaggatag caaccccctc gtcgtctgaa  32940
ggtgagagcc cagcagggga aaatccgtca tcctgactaa cccatcccat ggacgcctcg  33000
gactccgccg tgtccgttga actgcgcacg cggcccgcta ccactgctac cggtttgggc  33060
gtatgggccc gtctggccag aggcctcggg cgcaagtgag ataaaggttg aaaaaagtct  33120
gcagggtacc cctctggctc gtcttcctcc tgaacatcgt cattttcttc ttcatcttca  33180
tcttcctcat cctcgtcata ttcagattcg ccgctcgact gatccgggga tatctgtaga  33240
```

```
tccagagggg ttgctggcgg cgatggcgtg tcctcggcga agacgtcgtc tggggcagac  33300
atatctatca ccgtgggtcc agcatagccg cgcggcctgc caaatcctgg aagtgatgaa  33360
agaggtggag gtgggaatat gaacttcacg gggggtcgtc tgcgaggcgc tccttcaatt  33420
ggaagcattc tctcttcatc gtgtgtgcta gacgaggtcc tcacaaacat cgccatggcc  33480
ttgtacgggg ttgaccgcta ggggcggaaa tttacaaagc acacgagtta ttgcctttac  33540
tgctccaaca ggccccagtc cacagtctca cgccggtggc gagtcaaata gtcgttggct  33600
aggttaaagt gattacagcc ctggaaccga ggccatcgcg agtgtcggcc accaagagag  33660
gccagcggag atggatgctg ggccgtaagc accaggtgtt tctgtgcgtt tatgagcgga  33720
gttctgtcaa tggccttgcg cccccacagg agaaaaacgc aatgttctaa ctttgaggat  33780
atgctactga tgatgaaact cgtgaaccaa tcccagccaa gtccctcgtg tgagccggcc  33840
ctccccttct ccaccgtcaa aactgtgttt agtagcaaca caccctggcg agcccagctg  33900
tcgaggcacc cgtgggaagg agtactgaaa ttggggacgg aagcctctag ctctctaaag  33960
atgcttctca aactgggtgg aacctgacat tgcggatcca cactaaacgc caggccagta  34020
gcttggccct tgtggtacgg gtcctggcct aagatcacca ctttaatatc ctctggatcg  34080
cagcagtggg accaccacat cagcttgtcc tgtgggggat acactgtggt ggttagccta  34140
agttcccgaa tctgtctgag cagcgagagc agtttctgtt tcagaaatga tgagaggctc  34200
agaaaggaaa tccacttagg tgccagtaac agatcccggt cgtccacccc ctgactgatg  34260
gatagggtgc ccctaaagac cgtctgttgc aaccatgcgt ccatgttgaa cttattttcc  34320
cttttgacct gcgtgcgctc tccggctgct gcttttagcc cgagtctgac ttccgctaac  34380
agaacctgtc cggttcatgg cctttcccac gcttattata attatgttta cgttgtgaat  34440
agagctatct gcagtggtcg cgttaaaacc tacagtatag gccgtcaaac ttcgttgtaa  34500
ataccacaac aacctcaggt tttcctgcga cgcccaggac cccaatcttc gaacgaccgc  34560
gactaaaaat gacctcagat taaacccatt cacgcatgtt tccacggtaa tgtcgcctgt  34620
tttgcttcgc agcttggcta tacagacccc gttgcagtga ttcggatcgg cgaagtggat  34680
agagtggacc gcaaagaaca acggcagggt agaggctgcc gatgcctgaa ttgcgcaaca  34740
tggtaaggcg acgtatgcgt gagatgtgac caatagggtg gtccacagga cggcaaatag  34800
cgcaaagatc cccatggggc aaatccgggt ttcacccttg tgttgcctgg ttcggtgctc  34860
cccagggagc ccccttccgt aatatctgtt ttatatagtg agggttcacg catgcgcgag  34920
tcccgactaa tgaggacaat tactgaaatt gaccttttcg cgacacgggg gtgaggtcta  34980
tttcccacga catacttccg cggaaaaata cccacgctcc ttaatttccg tgggaagacg  35040
atgggggaaa tgtggcatta cctgacacgg tttcaatcat actcatcgtc ggagctgtca  35100
```

<210> SEQ ID NO 19
<211> LENGTH: 35100
<212> TYPE: DNA
<213> ORGANISM: Kaposi's sarcoma-associated herpesvirus

<400> SEQUENCE: 19

```
cacgtctggc tgagattttc taaaaagtca tccaatgaat catcggaatc atcagcacac     60
tctagaacta ctccatatgc cggggtgcgc gggggtcccg agtagtgcac gtcgccatcg    120
ggagacacag atgatgggtt tgaaatgtcc atacgggccg tgtgcacaag ggtcacgtcc    180
ccatccccaa cacaaggacc tttagatacc ctctcccggc atgtgcgcgt atccgggcaa    240
```

-continued

```
gcaagctggt gttctggatt ccaaacgtgc ccagcggtac ccaaaatcgc cagggcgtgt    300
tttattattt ccacaggaac cggtttctct aattgcatca ccagggtatc caaaagccgg    360
gcttccacgt tgatccggct taccgacagt tctttccagg gtttcctggt ggggcgcggc    420
agctgactca aaaaggtcac tgcctctgcc catgggcggg tgggtgacag tccgccatac    480
tcttccagga cactggccat gcatgactcc aaccgtctca cgtccgaggt aatgtgctct    540
atgaagatgt ggtagagcca gcagacgttc aaacacgatg aaatcaagct aagctcccgc    600
cggaactcca catccacaaa ggggtattgc tccggtgtct gtattaggtc tggaatagaa    660
aactcagaaa aagacactga cccaccaagg agaacctggc gtcttgcaaa gttgatgagc    720
cccgcagaaa gaatgtgtct cccgtgggac aaagagcttg ggggggcaga gatggcgcta    780
cagtgggtga tttcttctac cacggtcata cattggtggc acccacaggc ctgttccagt    840
atcagcataa atctatcttt gcagtcatcc cagatcaaag tcatgtcaga tgctgttgcc    900
tggcattttg cccgcatgta catttcctgt cccacatatt ttaacatctg taatactgga    960
agtagattca gtctggtgtt gagccccccc ggggaagcca gcgtatgctt caggaccacc   1020
agggacgcta agaaccccgg gtgtccgcgc tccggaaaca gacctctgag aatacgctcg   1080
gtcttgacga aacccgatgt ggtaccgaat gccacaatct gtgccctcca gctctcacaa   1140
ttttcatctc caatacccgg aattgggata cacacctcca tgttcagtca catgtacgct   1200
agggtctccc cacccaaccc ccataggacc cagctacagc ttatcctcca ctaaatacca   1260
ggcagctacc ggcgactcat taagccccgc ccagaaacca gtagctgggt ggcaatgaca   1320
cgtccccttt aaaaagtcaa ccttactccg caaggggtag tctgttgtga gaatactgtc   1380
caggcagcca caaaaatggc gcaagatgac aaggtaaaga tcgacctttt tattgtatac   1440
tgaacaatgc gtgtttacaa tggtgtaggt gggagcagag ttcgccaagc tctacgtccg   1500
aacagtcggg tgtcagggct cttattaagt gttcggtgta cttgaccaaa gccgcggaac   1560
ctaggttggg tctgtacagg tcgtaccagg caaaaaagga tcgggcggtg cttttcagga   1620
gagttaggga cgtgctgatt atgtggacaa gcttctgctc gtaaatgcac cgctggtaca   1680
tctgaacgac agctgtccaa aaaaaacaaa ggttcagctg cacgttaaaa tctgtatcct   1740
gaaagtcctc gtaaatgaca gtttctacca agaaaaactt ttttaccacg ctggccatcc   1800
actgaaagga gggagcacac gtcccgttgt gcgttgttag gatatcccta acttcggagc   1860
ggagacggcc ggacgctccc acaaaatggg agaggcacca ctctgtgcag tccgcggtct   1920
ggggttctga ttccaggggc gccgtgtggg ggtattggag agtcaaaact ctgggcagtc   1980
ccttaatgag ctctctctca aaacctatgc agccagcgtc cactagtggc agcatgccgt   2040
taataacacc ccttatcttg tcgttgccaa gtttgtacaa ctgctgcagg gaataagcca   2100
aattcgccct agccgcggga accaggtacg gctcgctttg tcggtgctgg accaatatct   2160
gaatggtctt tgcaaggtat agggtcttct caacgtttag agcgggtacg tggcagtctg   2220
gattgagggt ggcgacggac agggtatcta actcctgaag tatctgatcc caggacgggt   2280
aatgatacct aaacagatgg ttgaacaggt gatctttaag ggccttctc gatgtcattg   2340
taaaaactat gacacgccac tctctcctta gggtaagaag cttcggcggt cctgtgtgga   2400
aagcttcgtc ggcctctcgg acgaactgaa ggcccaactc taccagtgtg tgctccttat   2460
aaatgacgca tacgaaacaa tctacgatcc cagtgaccta aatagagtgg tggaagatgt   2520
gtgcattcgg attatgaaag aatgttccaa gcttggtgcg ctatgtggtc tgtttacaga   2580
```

-continued

```
cattaacatg tttaaccttt tctgcttttt tcgtgcctct cgaatgagga ccaaaggcgc   2640
ggccgggtac aacgtgccat gcgcagaggc atcccaaggc attattcgga tcctcacgga   2700
gaggatctta ttctgcacag aaaaggcatt tctgacagcc gcatgcagcg gggtgagcct   2760
gcctccagcc atatgtaagc tactacacga aatatacact gaaatgaagg ccaaatgcct   2820
gggggcctgg aggcgactcg tctgcaatcg gaggcccatt atgatattaa cctcttccct   2880
actgaagctc tacaacacgt acgataccgc cgggctgctc tctgagcagt ccagggccct   2940
ctgccttttg gttttccaac cggtctacct tccgaggatt atggcgccgc tggagatcat   3000
gaccaagggt cagctcgccc ctgaaaactt ttacagcatc accggttctg ctgagaaacg   3060
ccggccaatt accaccggca aggtcactgg actgtcctat ccaggaagcg gtctcatgcc   3120
agaatcttta attttgccaa tcctggagcc aggactgttg ccggcttcca tggtagacct   3180
cagcgatgtg ctggcaaaac ccgccgttat tctgagcgcc cctgccctga gccagtttgt   3240
cattagcaaa ccccatccca acatgccgca caccgtcagc atcatcccct ttaacccatc   3300
gggtacagac ccggcgttta ttagtacgtg gcaggccgcg tcacagaata tggtgtacaa   3360
cacatccacc gcgcccttaa aaccggccac cggtagttca cagacggtgt cagtcaaggc   3420
ggttgctcaa ggggccgtga ttactgcgac aacggtgccg caggcaatgc cagcgcgggg   3480
taccggaggg gagttgcctg taatgtcagc gtccactcct gcaagagatc aggtcgctgc   3540
atgttttgtc gcagagaaca ccggagattc tcccgacaac ccgagctctt tcctgacgtc   3600
atgtcaccct tgcgatccga acacggttat agtggcccag caatttcaac caccgcaatg   3660
cgttacgttg ttgcaggtta cctgtgcccc ctcttcgaca ccaccccccg attcaacagt   3720
ccgggccccg gtggtgcagt tgccaacagt agtccctctg ccggccagcg cgttcctccc   3780
ggcgctcgcc caaccagaag cctcgggcga agagcttccg ggcggtcatg acggagacca   3840
aggtgtgccg tgtagagatt caacggcggc ggctacggcg gcagaggcga caacacccaa   3900
acgaaagcag agaagcaaag agaggagctc aaagaagcgt aaggctttga ccgtgccaga   3960
agccgacacc acgccatcga ccacgacacc tggtacctct ttgggatcaa ttaccacccc   4020
ccaggatgtg cacgccacgg atgtcgccac gtctgaggga ccatcggagg cacaaccccc   4080
gctactgtcg ttacccccgc cactggacgt agatcagagt ctattcgccc tgttagacga   4140
agcgggccct gaaacatggg atgtcgggtc gcctctctcc cccactgacg acgcgctgtt   4200
gtccagtatt ctgcaaggac tgtaccagct ggacacgcca ccgcctctgc ggtcaccctc   4260
ccccgcttcc ttcggcccgg agtctccggc ggatataccg tcaccttctg gtggagagta   4320
tacgcaactg caaccggtca gggcgacctc ggcgacgccc gctaacgagg tacaggagtc   4380
cggcacactg taccagctgc accaatggcg taattacttc cgagactgaa gtgttcgcaa   4440
gggcgtctgt gcctgcgtta acttcccagg cagtttattt ttaacagttt ggtgcaaagt   4500
ggagttaacc tacagattct acttaaaata gctcattttc tcacgaatct ggttgattgt   4560
gactatttgt gaaacaataa tgattaaagg gggtggtatt tcctccgttg tcgactataa   4620
cctggcgtgt aaacgtgtaa ccctgccaaa tgcccagaat gaaggacata cctactaaga   4680
gttccccggg aacggacaat tctgagaaag atgaagctgt cattgaggaa gatctaagcc   4740
tcaacgggca accatttttt acggacaata ctgacggtgg ggaaaacgaa gtctcttgga   4800
caagctcgct gttgtcaacc tacgtaggtt gccagccccc ggccataccg gtctgtgaaa   4860
cggtcattga ccttacagcg ccttcccaaa gtggcgcgcc cggtgacgaa catctgccat   4920
gctcactgaa tgcagaaact aaattccaca tccccgatcc ttcctggacg ctctctcaca   4980
```

-continued

```
caccaccaag aggaccacac atttcgcaac agcttccaac tcgcagatcc aagaggcgac   5040
tacatagaaa gtttgaagag gaacgcttat gcactaaggc caaacagggc gcaggtcgcc   5100
ccgtgcctgc gtctgtagtt aaggtaggga acatcacccc ccattatggg gaagaactga   5160
caaggggtga cgccgtccca gccgccccta taacaccccc ctccccgcgc gttcaacgcc   5220
cagcacagcc cacacatgtc ctgttttctc ctgtttttgt ctctttaaag gccgaagtat   5280
gtgatcagtc acattctccc acgcgaaagc aaggcagata cggccgcgtg tcatcgaaag   5340
catacacaag acagctgcag caggtataga cgggaaacag gtgtctatct tggccggctg   5400
gttactcaaa tgggaacaat ggcgccacct tgctgtcttt gtaggcatta gaagaaaagg   5460
atgcacaact atgtttccta gcggcgagat tggaggcaca taaggaacag attattttcc   5520
ttcgcgacat gctgatgcga atgtgccagc agccagcgtc gccaacggac gcgccactcc   5580
caccatgttg aagcttggtt gtgccgtcgt ccgggagaac catgccagac tttgtgtggt   5640
aagaaggaat tgttatccgg cagcaatatt aaagggaccc aagttaatcc cttaatcctc   5700
tgggattaat aaccatgagt tccacacaga ttcgcacaga aatccctgtg gcgctcctaa   5760
tcctatgcct ttgtctggtg gcgtgccatg ccaattgtcc cacgtatcgt tcgcatttgg   5820
gattctggca agagggttgg agtggacagg tttatcagga ctggctaggc aggatgaact   5880
gttcctacga gaatatgacg gccctagagg ccgtctccct aaacgggacc agactagcag   5940
ctggatctcc gtcgagtgag tatccaaatg tctccgtatc tgttgaagat acgtctgcct   6000
ctgggtctgg agaagatgca atagatgaat cggggtcggg ggaggaagag cgtcccgtga   6060
cctcccacgt gacttttatg acacaaagcg tccaggccac cacagaactg accgatgcct   6120
taatatcagc cttttcaggt gtattacacg tttcaactgt aatccctcgc aattgggtaa   6180
accgtcggtg tgtagggata aagcgtaacc ttacgttctg tctcatctac aggatcatat   6240
tcatctgggg aaccatccag gaccacgcga attcgcgtat caccggtcgc agaaaacggc   6300
agaaatagtg gtgctagtaa ccgtgtgcca ttttctgcca ccactacaac gactagagga   6360
agagacgcgc actacaatgc agaaatacgg acccatcttt acatactatg ggctgtgggt   6420
ttattgctgg gacttgtcct tatactttac ctgtgcgttc cacgatgccg gcgtaagaaa   6480
ccctacatag tgtaacacaa aaccataaaa gtaaataaac gtgtttattg ttcacatgat   6540
aaagagtggt actctttact ggtttggggg ttgggttgtg gcgtggtggc tggtccgcgg   6600
ttcagtcatc aaccccccgcc cgtgttgtcg aggctcctct tcgtcgcctg ttattggcac   6660
caggaggcgg tttagcggtg cccccgtctg acatgcagac gtcgattcta agcgaaagtc   6720
ccttcagggc atcgtccact tgcttttgtg ttacaacctt gctgaatatt gtcctgaccc   6780
tggcttcgat ttcttagcgg gccgccgcac tcagtgcacc cacagtagcg gtaagctgcg   6840
cttccttctc ggtggccgtc agaggccgat ctctcggatc ggcagtggat cccagtgctt   6900
tccgaagctc ccgattctcc acagtcaatt ggcttatctt tgcggttagg tcttccatcg   6960
taaggtcctt tttgggtctg cccctgggcg cggccatgtc aggtacgcgt agatgtacgt   7020
gttggtgatg ctcacaacaa aagcccaaat ccctccttta tacccagctt taaatacttt   7080
attgaaaaac catagctttc gtcagcgctt gtgcgagtaa tcacatgcca gtctatgcat   7140
ggaccacctc gtccacaaac ttgaaaaaac aaagatatac cagatagaaa aatgtggcca   7200
cgacgactag taacgcgtta atcaaggccc agacgctaga aaagctagaa agggaggggc   7260
taaaactatc cgcggaacaa gcaacgtcat agaatcctgg ggtagtgact gatgtgggac   7320
```

-continued

```
cgggcgaagg cctggcgctg agcccagccg tactgggact agaacgctct gtagatgatg   7380
cgacacctgt cgagttggcc gtaacccagc agtgacctag tatcgaggcc acaaataaag   7440
ccagggccac cgtggacgct gtcattatga acaaccgccg aggctccaag ccgtctatcc   7500
aacgttccgc gttcgcctct tatatacact ctgcaatgca gtccgactct gcccctctac   7560
ccagggtgga atatgtgttc gaaacaagca aatttagaat gacgtcgaga gcaaatgaag   7620
ccagactcag actgacaaat gagtgtccga tactggtgag accccacgag ccgttcatca   7680
tgcccaccgg aatacacttc acgcgaaccc ctagctgcgc tttcatcctg accggagaga   7740
ccgacaagga tgtattttgc cacacgggcc taatcgacgg aggctaccgc ggggagatac   7800
aggttatttt actcaacaag aggaagtacc ctgtgacgct gtatcgcggg gagctcaaca   7860
tctgcctgtc tgctttcaat tacgtgctac ctccgttgag ggacgtatca ttcttaaccc   7920
cccctatgta tgcaaacgac gccggatttg acgtgatggt gatgcactct atggttatcc   7980
ctcctactac tgaccaaccg ttcatgatat atctaggagt ggagacccca ggcccccctg   8040
aaccccacgt ggctctagca ttggggcgat ccggtctagc atctaggggt atagttatag   8100
acgttagtga gtggggaccg cgaggattgc agctgaagtt ttataactac tcggggcagc   8160
cgtggctggc gcagcccggt agccgcatat gccagattgt gtttgtggaa cgcagacaca   8220
tcctcaaggg cttcaaaaag tgcttgcgcc ataggaagct agctcctggc gtccgtttcc   8280
gggaggctcg agtgcatttt cgcgaggata caaatagcgt ccgaaaacat acccacgaag   8340
acaaccccgt ccacgaaccc aacgtagcca ccgcttccgc tgacattcgt ggaaccaagg   8400
ggctggggtc gtctgggttt tagagccgcc gccaaatgcg gccagtttat tagggcgatt   8460
cgatcccgca acccacagca tcccccaaat aaaaaaacga gtgtacacag ccaatgtttt   8520
tattattgtt cgattcatta ctggtaccag agaataaagc caacctatgt cgaacctatc   8580
gcgctttctg tcgtctcttc cagggttgac gaaggccggg gagggattga cgaatgcatc   8640
gcggaaacgg acgggtcttc ggtgggtggc ttgggtaaag ttgcctccgg ctggcgcgta   8700
acggcaggcg tgagaggcaa tacagaagtg ggttccgaca aggagtggct gatctcagag   8760
gcccatatta ccgagtcgtc tgacgccata gcagtcgcca gtttttccat ctccatgagc   8820
gaaacgcatt ccccggccct tttgtttaag agggactgga gcgcactgtc gtccacggta   8880
atctcgccga ccgccaaggc cagcattgtg ttccacacga cgttctgaat agactgcagt   8940
tttttcacct gggttttcac ggtctcctgg cagcccgccg gaattttagc cacgtcaaaa   9000
cgcttcaggt agtctgtgat cttgtttgac tgtacagcca gaaggtaggt ctggtgcagc   9060
gccgtcgtgc caaggttcga ctggacaacg tcacccagac acactccggg ggggaggccc   9120
aaatctatct cttgccgcca gcgctctgga cagccttcca gagggtcacc gaggcgcttg   9180
taagcgtggt tgccgcgtcc aaaaaggttt ataccgcaac acgtccaggt gtaccatgga   9240
gacgacatac cgccgcgagg cgctgacagt aagggttatt ttttgtacga gtggcgacag   9300
cgccgagacg atcgccgacg tccttacggg ggccccaacg tcagcgtcct tcttttctgt   9360
actccacgac ctttttttatt cccagatact cgcccccagg gtaaccctaa aattgtgcct   9420
ccccgcacgg cgtcctggca acggcacaag gtgttcgccc gtgttggtcc tacgtactga   9480
cgcatcagtg gcctcggggt tccttggcgg ccggccactg gaggcgtccg acattaaata   9540
tatgctgctc agcgaccaga ccgcggggtt gttcaagccg ctgttggaga taatcggtgg   9600
cgcgcgcgca ccaccaaatc aggacgcgtg cactttccag agccaggtgg cctggctcag   9660
aacgaaattt gttaccgcat tgagaaaact ttacaagatg actccctcac cctactggat   9720
```

```
gctgtctgca tttggcgctc aggaagccca gttcgtcctg accagctcat tctatttttt   9780
tgaacacact gtggtctgta ccacagagac agtttctcac ctgtctagac tgttttcgcc   9840
tcaacaggga cagacgctgg tttccgttac cagccacgag gagctggggc agctatacgg   9900
cacttcccct ttcaggcggc gcgtccccgc gttcgtcgct tatgtaaaag agaaattagc   9960
gagagacagt ctggagacgg aggccatcga ccgcaccata gaccagatca ggggcaaact  10020
catgctgtct aaccaggacc tggtccattt catatatatc tccttttatc agtgcctcaa  10080
caaacgggcg ttcctgcgct actctagaca gacgtcctct tcaagtgctc taagggagct  10140
gggggaagac cctcaattgt gtggcgccct acacggggag tttcgtgacc acgtccagtc  10200
ctactaccac aaaaaaacct acctatccac ttacatagac attcggtacg tgggtggcgt  10260
attaccagac ggctattttg gcgggagtct tgtaggcgag cggtgcgttt attggtgcgg  10320
gcagtcaaag gacacggcca gcctgttggc caccattagc caacaggtgc cgcacctgag  10380
gttgcaaaac gagttcgctg gcatgctaga cgtggccgca ctgcgaggtt ccgatgacgg  10440
tcagtttaaa gagggccttt tctcccacag tcaagcccta cccctgtaca ggtgcgagtt  10500
tctgggcaag cagtttttca caatgcttca ggaagacggc ctagagcgat actgggagca  10560
aagtgtgata tttccaggcg accaggactg ggatatgtta tctgacaaag acctcaccta  10620
ccgaattttt taccatgacc tcagcctatc gctgccaaca ctgaaggaac agctccttgt  10680
ttcaagacac gaatacttca accctcgctt gccagtgtat agatgggtat tagactttga  10740
cctgcccgtc tgccgcgaca ttgacaggac attcgaggag gtgcactctc tctgttgttc  10800
cctgcgtgag gccatactcg acatcattca actccttgga ccagtggatc ctcgaacaca  10860
cccagtatat tttttcaaat cagcctgtcc accggacgag tggcgcggcg aagacgtcgc  10920
cagcaccagc ttctgtcggt gtcatgacaa actgggtatg cgtattatcg tcccgttccc  10980
agaaggagta tgcgtcgttg ggtcggagcc catggtggca ctcactggca ttctaaacag  11040
gacgataaag cttgatccgg agctggtcca cagattcccg tcaatacaaa aaaagggggg  11100
ccctttcgac tgtggcatat acggccgagg acgaagcgtc cggcttcccc actgttacaa  11160
ggtgggctta gtgggggaac tctgccgcct actgaagata ctagtctgtc accccgcccc  11220
caacggcaag gcgcagtacg tgcggcgcgc ctttacgctt cgcgaactgc tccatcactc  11280
cccgggccac agcgccggtc atgtcggccg aatcatctat agcatcatgg atcgcaatga  11340
gaatttttta gaaaacaaga ccattagcta tctgccggcc aaaatacctc acatctttca  11400
gcggatagag accctatccg gtcgttcaat agaggactgg ctacactcgg ccgtttggga  11460
taaagcatac gacactatat gtaaattttt cccagatgaa aaagcacaac agttttctca  11520
cgttgcattt acgcaacaag ggaaaaacat catccagtta agaccccgtc agggaagaca  11580
cttcctctgc atcaaccata atcataaaaa caagtcaaaa acagtccgtg tattccttac  11640
ccttcattcc attagggtga gcgaagtcac ggtaacactt atgagtcagt gttttgccag  11700
caagtgtaac aataatgttc ccacggccca tttttcgttt gtggtaccag tgggactggc  11760
cagttaatcc cactatataa cctggctgcc aggttcccaa aatagcccgc ggcatacggc  11820
tcacttcccc ccacattccc cccgtgcaca atataagaac caaaggacat ggtacaagca  11880
atgatagaca tggacattat gaagggcatc ctagagggta agtcctcgtc tacaacagac  11940
ttttcccatt tctaacgtat cgtgctatct tcgtcgcccg gcggaccatc cccccacccc  12000
tcatttatcg cgtttgatat tacagactct gtgtcctcct ctgagtttga cgaatcgagg  12060
```

-continued

```
gacgacgaga cggacgcacc gacactggaa gacgagcaat tgtccgaacc cgccgagcct  12120
ccggcagacg agcgcatccg tggtacccag tcggcccagg gaatcccacc ccccctgggc  12180
cgcatcccaa aaaaatctca aggtcgttct caactgcgca gtgagatcca gttttgctcc  12240
ccactgtctc gacccaggtc cccctcacca gtaaacaggt acggtaaaaa aatcaagttt  12300
ggaaccgccg gtcaaaacac acgtcctccc cctgaaaagc gtcctcggcg cagaccacgc  12360
gaccgcctac aatacggcag aacaacacgg ggcggacagt gtcgcgctgc accgaagcga  12420
gcgacccgcc gtccgcaggt caattgccag cggcaggatg acgacgtcag acagggtgtg  12480
tctgacgccg taaagaaact cagactccct gcgagcatga taattgacgg tgagagcccc  12540
cgcttcgacg actcgatcat cccccgccac catggcgcat gtttcaatgt cttcattccc  12600
gccccaccat cccacgtccc ggaggtgttt acggacaggg atatcaccgc tctcataaga  12660
gcagggggca aagacgacga actcataaac aaaaaaatca gcgcaaaaaa gattgaccac  12720
ctccacagac agatgctgtc ttttgtgacc agccgccata atcaagcgta ctgggtgagt  12780
tgccgtcgag aaaccgcagc cgccggaggc ctgcaaacgc ttggggcttt cgtggaggaa  12840
caaatgacgt gggcccagac ggttgtgcgc cacggggggt ggtttgatga gaaggacata  12900
gatataattt tggacaccgc aatatttgtc tgcaatgcgt ttgttaccag atttagatta  12960
cttcatcttt cctgcgtttt tgacaagcag agcgagctag cactgatcaa acaggtggca  13020
tatttggtag cgatgggaaa ccgcttagta gaggcatgta accttcttgg cgaggtcaag  13080
cttaacttca ggggagggct gctcttggcc tttgtcctaa ctatcccagg catgcagagt  13140
cgcagaagta tttctgcgcg cggacaggag ctgtttagaa cacttctgga atactacagg  13200
ccaggggatg tgatggggct actaaacgtg atagtaatgg aacatcacag cttgtgcaga  13260
aacagtgaat gtgcagcggc aacccgggcc gcaatggggt cggccaaatt taacaagggt  13320
ttattctttt atccactttc ttaaggattg ccaaacccca tggcagagtg tctcccgtat  13380
tccatgtaac tcacgtagcc tttctctaat aaacaagcta cctgcaaact atacacaaat  13440
gaaatgagtc aggcgtggtc tcttctctac cgtgaatcgc accttaaaca caacaccaga  13500
ccgccaccag gtggcaccca acatccatta tggaaaaacc ccgcgccacc ttccgccacg  13560
tggagccaac aaacaagaca cacccgccaa tgttttggtc tctttattga tatgatatac  13620
tccctcccat aacaatacgg tgtaggcatt ttgtattatt tattgcatgg catcccataa  13680
cggcttcggc attatttcga gtacgacgca ggcgtctgag aaattactgc acctcgccgc  13740
aaagtctcgc ggggacgggg cgtggggctc taacttgcca accgccaccg gtttccccag  13800
ccacagcttc accaaaggac acgtcacgtg agagggtgct ggtaacggtg aatttgccaa  13860
ccccaccaga aatgtattcg ggttaaatat cctcgtcggt tttccctggg gcagcaagag  13920
ggggccggag tcaggcggaa cggtatttcc aataaagtgc acgggcccgt tatgataaca  13980
tacgcaaaat atgccattac aagagctagt cagcagaatg ccttttgcac atgcgtccag  14040
cgtatcgcat agctcccgct tggctatctc gcaggccagg tttggcacat tgggtagcca  14100
tacctggccc ggagacccca ctgcacagta atgaactgcg gggtccctac gcaaggccga  14160
tgagattcga cagcccgact ggcttgtcgt cagtaactca tgaacctgtt cgccattata  14220
atacatcctg ataaacaacc gaccccagtc aatgacggcc tcctgaccct ctgccgtcgt  14280
acaagatggc acgggcgtta caatctcgcc tggcaagcac tgccccgggg aaaaaaatcc  14340
ctcttgcaag agacgtgcca tattgttaaa atcgtggacg gctccggcca cgactccaca  14400
ttccacgcat tgttcttcct ccggtttacg tactctaaag accagaaaat ggtgtccatc  14460
```

-continued

```
ctgagaaatg cctttgccaa tctcttgtaa accccgcgtc ctgcgtagcg cggcaagcat  14520
tcgcctgcgc cccctggtgc ctttaaacga ggcgtccacg ggcatgttac ccctttcgcg  14580
gatatacaca acacccaatt ccccgtctct gcgccattca aaacaggggt ccgcgagggg  14640
cgtaactggt atacggaagc gggtgcgctc ttcgtcttcc cactctactc cgggaaattt  14700
tccactgttg acttgacata ctatccaatc cttgattgac gctttcccct cactggcacc  14760
ggtagatatt cttagttgtc gtgtccggct ccactccgtt atcgcagcca ccacagcctg  14820
ccgtgtaata tcgcctgcgg ctgcagaacc cccggtcccg gagggtcctt ctcccggtga  14880
ctccgacctg gatggttcat cgcaaggagc cccggagcca gatgttcccg gtgacccttg  14940
tgacaaacaa ggttttttgg gtatcgcccc aggcgcccca aaagggttcg gtctttggcc  15000
tgggtccatt gtcccgcaac cagactagct cgcgccgcaa tgtccagtgg taagcacagc  15060
tatgccgggg agccaccggc catcagatat agagaggcga caggctctct atatatcacg  15120
gctaggtggc tgacatatta gtgggcctag ccgcagaatt gcctgggtag tcaaaaacca  15180
gcgtttctca aattaaccga aactacattt ttctatttta agtacgggat acaaagcagg  15240
gtctgaggca atctgccgcc ctccaccccc acccaccata cccaaaaaag atatgtcaga  15300
aagagcactc tacctattaa ctcgtggaga aacatcatac aaaatctgta cattattttt  15360
aatactttaa tttgtgcagg tttcttcacc ccacacctgc tttttgtctg gtacaaaaaa  15420
ccactgcagg gtcccgccta tagccaactc ctaagcgggt tttttgctaa agcacttttt  15480
tagactgtcc cagaaaccac atagcttcct tttcactcat ttgaaaaaca gccccgccca  15540
actgcctgga gaattttcca ccccctctac catttcgcgc ctttaccgct ggtgcgaaat  15600
ctagccatcc tatcaccgcg gatccgctgg accaatatac cacgcccact tttcgtaatc  15660
agcaaccctc tacgcctaca cccctatgac tgaatataac cccaacaag gctatgaaat  15720
catgaatggt aactgtctgg acaccaatct tccgcggggt ggcggcagtg cgacgcaagt  15780
atccacaata aatggtgcaa taattggcga aatgtcgtgt ctggtttatt tggactacaa  15840
gattacatcc ggttttataa ttcacatata tgatcaatgt agactatccc aaatggagcc  15900
tataaaaatt ttaacagtca agggtacatt ttggaaattt tctgtagatg ccggggatgc  15960
gccgaaaaat accgtcccgc acgtcactgg gttgacgctc agcggtgtct gtgggattgc  16020
ggctgtggtt gccaggtatc gcgcggtgtt gaacagctgc tgcggaactc tggggctaaa  16080
gcttcggagg atgcgttcat agcgggaatt tggattacca aaccaccagc cttccacttg  16140
agtggcgttt ctggagtata ttccagacat cgagcaaaat attgggaatc cgtggccaag  16200
gccttcaaaa actcggttca aaatctccat ttgctcgggt gaggggactg taagacgcgg  16260
tatgcgaagc agttctggta cgaaactctg acataggtgc cccaacgtat ccccaacagg  16320
ccagctacat aacattgcct cgcccgcgtc accttcgcgt ctcagagttc cacgaaggtt  16380
cccatacaca aagatttcca caacaaaaga cacccgctga ctatcagggg gatcaaaaaa  16440
catctttgaa ggtggctttt cgggaccgga gtggctaacg ggcgtacgcc gcccgtgcgg  16500
ggacctggac ctcgggcgcc gcctatccgt ggcctgtctg gttgaggagc tcggttcctc  16560
ctgcagctca gacaaaatgt tacccaaccc ttcttcccac gtacatatat cctctccttg  16620
aaggttcgag agcgtaagag ggagacccaa aggcggcggc actaaagatt gttctggtcc  16680
ataacccccc actgcatatc tatctccagc atatgtacta acaagtggaa ctctgggcct  16740
ttcgccacta cccgggcaca cacactcccg ccgctccagc tctgtcggta aatgcgaaac  16800
```

-continued

```
ctcggggttc acagcgggct ccggtgcaga ataaagcacc gtaggttgga aaacgcgcgg  16860
cccactgaca ggtaggggcg tggatgctac agtggtagat ggggtatcgg aatccccagt  16920
gaggtcaata atctccactt cgagggcacc agaactagtt gtcacgcgtc tgtatccagt  16980
cgccatgttg tccccctggc agacgtacgg tattccagac gaggatggct cctgtcgctc  17040
tgccacctct ggggtgggtg gtgcgccggc ggagggcgtg gccgacgcgc caccctgcgt  17100
gtgggaaaga ccctggtttg gagcgcctcc actagaccac ggaatccaaa gcggtgtgcg  17160
aacttccggc accacggcgt gaccaactgg tgggtgccaa acaggcgcgc gtatgggtcg  17220
cgtagctggc ggttctgcca atggactcca attgtaacat gatggtttcg catacccggg  17280
cgcgggggcg ctgggcggtt gaggttcgaa gggatacacc cgctcactcg cagcaccctg  17340
aggagcccgg ccttctgtag atgccccgca agcgccttcg gcaccggttt cccggcgggg  17400
aagccacgcg cgagcacatt ggccgctttg ggggagcaat ccctgtggcg ccagaggtgc  17460
accctggctg aactcaccga caaatgttcc cgcttgggcg tgcggcggaa tccaactggg  17520
ggcagcagga ttcagctggc tgctaggaat ccccgtatat gtccaacggg gggaaagggg  17580
atcaaattgg cccgtggttg gcggatgcac tttctccggg agaccagacg cgccctgagg  17640
ccaccatccc gtgacaggaa gatctcccca tggaaaacac gcaggtatcc acggggacgt  17700
agatggcagc ctagacccat cgcgcatggg aggggctagt tgccccgtat cccccggcgt  17760
ctgtgcgacg ccggagaccc ctgacacagt accggcaagc cgtgtttcgt gctgcggctt  17820
gggcggcgcc gtgcccggta ggcctgcacc agatgagtga gggtctgaag ggccggtcag  17880
cgttgatgga gcaggcggat ctccgggaac ccgccacgta aaggacgagg cctgcgtaac  17940
ttgtcgcgtc ccagaggacc ccatacctga ggtagatgcg ccctcattca ctggtatcca  18000
cacggagcag gcagccttct gttcagtcgt tatatcgcca acattgtaat agcggttcga  18060
tttccgaggg cgacccctca gccccgatgg cgccttaggg ggagcaggtg ctgcagcccc  18120
tgcctcctcg tagctttgtt ctctaagtaa aaggcacgag agttaacgtg gttagggtac  18180
ctaaagtatt tcccgccgac accaacgcat caaacctcac accccccttcc ccgagttaca  18240
tacctagtgt cactgcgtcg cgtagccgtg gtttgcattg ggggggacaa cagacactga  18300
ataaatcgct gcagtttttc aggaccatac gcggccccat agcaatacgt acagttttta  18360
aacggcgttc gcaccaactg ccatactacg tagctaccac caaatgtgtc gctgtaccgt  18420
aaatcgttcc gcacgacggc cctcctggtt ccacgcaaca gtctcccaaa acgtccatac  18480
accgtctgtc ccacgacagg cgatggtccg tagactctat cacactcctc atcaaatgca  18540
tggtacaccg aataccagcc aggcgggata tcgctgccgg caggcagggg cgcgggggct  18600
gcaaaaagaa ggttgttcct atcaaaccag gaaaaatagg gaaacttatt gttttcaagg  18660
gcatcaataa tccataacgt ggcccattct gagccaccgg ctttaggcat ggtccgacac  18720
agaaaccgat cggcgttcgt ctttgaggca cagtcccgac tgagccttat agtgcccccc  18780
ttcttgctat gaaaaaaacc cacgaccgtt acgcaaattt gaggagctac tcacctaaaa  18840
gtagctcctt tgacaaatgt cctggtttta taccaattgt tcacaatgac atattgtgct  18900
ggcggaaaca ggtgtcccga tgtatcctcg gcaagtaagc accattacca tgtgccatca  18960
tattgtgtgg cacaaaaaaa gcaacttttc acgcacgcag cataagaccc gagccagtcg  19020
cgccctccat cgcgcctgcg aattttccca ccacccaata ttgtggcaga tctttcttat  19080
gtatatgtgg ttacaaacac cacgcccctt aagctgtcct ctctcccaag gggactagat  19140
tataacagtg acatacgaaa ccgagacgct ctcaaatgct ttctatttta tttatcgatt  19200
```

```
ccgggttaac ataatcacag gtagctataa aatccccatc ctcttgacct ggtaaccctg  19260
gcttgaggtt tcctctgtta tcaaacaaac ctgaccacaa ctgtacagag aaaagtgggt  19320
gaaatgtagt gtttatttta tcctcacact ttcacttaac cacagcccgt caaaccacag  19380
ggaccctgtt ggctgactat tagtcatcac atgtaactga acgcaatctg agcttgatga  19440
cgagggggac catatcgaac tgttctgccg acgttgggtc acctccgatg aacacagttg  19500
tttttttaat gtgctcatgt ccctgtatgc gatattgtgc cacattaaaa acatccagaa  19560
cagccctaga tgacagtccg cagatcacac caaacttctt tggaggatta tttccatgat  19620
ataatacggt agacttgcac aaattcttaa cataaatgcc agatcggaga gaaactatca  19680
caagacccga agcaaacgag cgcagcacgg ccgccagcag gttaacgtct cctggccctg  19740
tgttattgtc gtcaggtttg ggcaacaaaa ctcttaaccc tttgcgcgaa tgcaagcaag  19800
agtggctaat gtctgccagt gggttctggg aacatagaat aaacaccttt cgttccactt  19860
ccaaagacat tgcagggcgg ccaaaataaa acacttccac accaagccta tcggttatca  19920
ttactggcgg ccgtgccact ctataatatg cggatctaag cttcctgtgg cgaatgcgcc  19980
tcgtggtagg cctctcgtgt ctccgtggcc catcatccca taaaaattcg ccaacaactg  20040
gccggcgtct ggacgccggc ggcagtccag caccatcatc gacttcttcg tcacttatct  20100
ccaacacata ttcccctgct acattctggg cctcgagtgc cccagctaag tacacatcct  20160
ctacacccgc cccgacagcc gaggcggcga ttgagccctc tgttaccacg ccgcttgcat  20220
ccgtgtcgcc tccgggctgt gatgttgcga taacatcctc tgggatgcca agcagatcaa  20280
agaggtcttc atcgcacatc gccctcatta gcatgtccat ctcctgtccc acgtggtaca  20340
tcaatgcaca tgcagattct ttatcaagca gtgtgaggtc atcttcaacg ttgtctgtgt  20400
gcaccgttgt ttcatcggcc ggggggggct gcgagtcgct atgacgcgtc gagggtcctt  20460
cgtctccaga gccaggagag tcggcattgg catcatcaac tggctgaacc ccagacgcac  20520
tatggcgcgt cgatggtccc tcgtctccag agtcctcaga ttccgcgccc gtctgcgtga  20580
ccggcacatc gcaaaaggct gggtgatcct cctcactgga atccgagttt tcacccacaa  20640
atggcctaca gaaaaaaaaa caaatatgtc aaccggacta gggtggccaa accatttgcc  20700
ccacccctcc ccactctttc cccaggggac acatcttacc ttggtcttct ccgatgcttc  20760
tcgagccgta cactgtgttg atacaaaatt tcccatagtg atgacccact gtgtaggtga  20820
gtcctggcat gaacgcacca ccagcattcc tttacctcgg cacacaggag gcgccacctt  20880
ctacaattaa ttccctgtac gacctcgtac tcttcacctg gcaagcgtct aaggcgccgc  20940
gacgtggtac atattttccc aaaagccgta atcggcgagc ccagtaaatc tctgggatgc  21000
aggcccttcg ataggcattc cctcttaaaa tcaatgaaaa actgtaggct atccagagga  21060
attacgtcat tacgggcagc cggagcaaga aatgttccag tagatctatc tagccacttg  21120
accaaaggat atttatcaga gtccaaagca cctacaataa actcagaaat ccaggtaagc  21180
ctgcgtcccg ccatgttgac ctgtcagaat ggtctgcctc cgagcattac cccacctcaa  21240
cagaagtaat ctactacgca aaccacaaca tgcttcctgc agctttaacc ttcagtcacg  21300
ggtcaaaaag cattgcctgt attagacaca tgtgtttctc actatgaatc gtgctctcca  21360
gcgctggcaa gaacatctgg ggtgatgctg ccccggacca gctttgaaac agggtattgc  21420
atgcataatg aagcccacat gtttgtctta ctttactaac ctcattacct tgcattgcag  21480
gggacacccc cttgccttgg cagctgagtg aatcccaacc gcctaggaaa aaaataacca  21540
```

-continued

```
ctcagacttt attttgcagc cacacggtgg cgctaacctt taatgatgtc ccactcagtg  21600
agtttggcca ctcccaagcc cacatgggcc tactataaca ggaaacatag aagttgcgga  21660
tagagcctgg tttctaacgg caatgatatt tatagtgcaa aacggagggc ggtaagacaa  21720
agggaggtac ccggacagag tgacaagaag acttgtcaaa attttagtct ctgtggtaaa  21780
atggggcaag gtaaatgtgc aaaatgactg gatagtgatc cgagtcatat tcaggcgacg  21840
gccggcggcc cagaaacagg gacgcgtacc gggacccttc aggttctcga ttatgtcgct  21900
ccacgtcaaa agcttgttgg atctcgtggc ggtgggacag gggcctacat ttgcctattc  21960
ttcttcgcga tgcatttcca acaaagtatg ctgggtattc caataatccc ttcagaaaaa  22020
tgcccatgtt tgtaccgatg gccacaactc ccatggaaaa cctgtccagc gtctgttcca  22080
aagttcggtt tgcgtccaca ctacagtggg ccgttctggg aagtaagcat ttatacgggg  22140
gtaccgtctg acatatgtgt tcaggggagg cctctgggac ttgggagcaa ataacgatgc  22200
cccccgttaa atcaaagtgg gtcttcacct tttctccgaa ataatacact tccaccacta  22260
ggggcacaag cttgtcaccc actttgtaaa tagcctgttt cttactcagg tatgctgcca  22320
cggattgggt ggcggttaag accttgggcc tcatgtcgct tccataccag taaaatgtct  22380
ggtcagcttt ctcttggtcc tcgacgtccc ggtcatcacg acacaacggt ggaatacaat  22440
caataaaatc atccacattg tcggaagctt ggaaagatga acccatgaca gaggccccag  22500
gtgccgaact ctcaagggga tgcgtggcgg gaagtactga gacactctcc gtggacccct  22560
cctcacctcc ctccgactgc atcgggccct gagggctcgc agtttcacac agaagttcac  22620
tcaggtcgcc taagtcagga agctcctggc ctgaacccat gacagaggcc ccaggtgccg  22680
aactctcaag gggatgcgtg gcgggaagta ctgagacact ctccgtggac cctcctcac   22740
ctccctccga ctgcatcggg ccctgagggc tcgcagtttc acacagaagt tcacccaggt  22800
cgcctaagtc aggaagctcc tggccaacat ctgacaagag atctaacaaa caccccctcaa 22860
tgtgatccac catcggtagg caatcatcca gcccactgac atgactgggg acggggcctt  22920
ctggggaaaa tggggtttgc gactgtccag caggcggcgc taataagcct tgtgtctcat  22980
gtggaaaaat aacaggagaa ggtaaacccc ccgttggcaa acatagatcc gtcggggtgt  23040
gcacgtgtaa tgggccctgc acctggctcg tggagggacg cggggaatcc ggagctaata  23100
agctcgatga ctgaccagat gacccaaacc ccgacggttc tggctcttca aaaaacaaac  23160
tgtgcatatc cctccctaca aaaccctgag cccccaccca aagttcgttt tcgctgtcac  23220
tcgattccgt atcttcgctc tgtgaccgtg atgaaacttc agctgcggag gatgttgtgg  23280
gcgtggcgac tgccgccgcc tgtttcctgg cggcctccct aaacaaaagt taattacaca  23340
aaggtaagtc tgagtgacat ctccaatttc ccgtgatgcc cgctgcacgt acatcccgcc  23400
gcccacacaa cccaccgccc agtacatcaa ccatcctacc tctgggcttt ttttctaagg  23460
ctccttctaa gtgccttttc tctgtgtttg tcatcatggg gatagatccc aaacaatgct  23520
tttagcatgt ttttcatggc tggttcctgc gtcaagtaca caagacatcc ttcacatccc  23580
ttgtatggcc taggtgtcat aatccagcgg ttgagtttca tttttccctt atagatggta  23640
aagggcctct cctgtctggc tcgattggcg gtccttaata gccgtccaaa gcagcccagg  23700
ccagtctcag tctccgggat ttctggcagc ccgtgcctac gtcgctcctc caaaaatgcc  23760
tcatagaagt catcgaagcc ttctggcatt ctctcccgcc ggtttcgacc cggcacggtg  23820
aatattctct tttgttcatc caaccaccct accccccaga agcgtccact gtctaaagca  23880
tctataataa agtccgtgag ccattccgac tccgtgtagc gaggcatctt tttaggcaaa  23940
```

-continued

```
agccacgaca caaaacacct tttccgtggg cgactttctc gccacaacta gctggacccc  24000
aaccccactg gcacgtagac tctgtgccat ctaacaacaa aactcaatat atgcagctca  24060
acaccgcccc ccccagccgg ttgtcgggct gcggaaactt gtggttagaa ctcactacgg  24120
aaaagggaac caatgcagtt gaactactgg cacacaccca taacccggga cagcacccag  24180
gcactgtcca ccctctaata caagcggcct ttggacgcga gggaggggtg tcatggtcaa  24240
caaaccaaga aaaacacatg tattattcaa ttagccaaca actttattta ttaccgacag  24300
gagacatgag atacataaat ttccaaccgt gcatagggcc aataccatct gtggagcgtt  24360
aagtgccctg tggagttttc gcctaattag ctgaatctcg acccccattg cggccagcat  24420
gctcacgagg aataggcagc agaggcagga cctaactagg agcatatccg gacctgatcc  24480
aagtatgtgc accaaggtga gcaacactgc cgccaaaggc aggagaacaa atagcgctcg  24540
tcgggaggcg acggatacgc ccacgcatga cagtaaccca acataaaata gcgtcatata  24600
cttatccagg ccaatcagga ccggagtcag caggccgatc gaggccgtcg atatcagggt  24660
ggccagcagt aaggtcacaa acacgacaac ctcgcgccta cagtaggccc aggcctggaa  24720
cactgaatag gtgatgtact tcccgggcat gatgaatatg gccctcctcc tttgcattcc  24780
ggccctgatg tacacatgct gttccaggtg cctaaatgcc aaaagtcccc cgaccaagaa  24840
gacaatgaag ggcagccaga aaacgccgga cacaaagacc ttcttaaaca acagaaggta  24900
gtacaccata aatgctccgc agaagcccag ctcatagtac ctgtgtacta ttggcggcgc  24960
ctgatacacc gccgttgcgg tggctagcgg ataaggtaac agcagtaaac agttaagtac  25020
gcacagaccc ggtatgaagg gcacacgaga aaatgtaaac ccagaaaagg ccgcgcaaac  25080
tacagcagca aacactgctg acgcgcagat ccattccagc ctccggtcca gctgtttttg  25140
cgccgcaggg cacagacaca tgcatatcag ggccaagtgc gtgactggca gcgaccagaa  25200
aaacacggcc gtgatctctg tggtaaagag tgtgaacgag tacagggcct tgaagataaa  25260
acaccacaga aaggggggtcg ccgccaacgt cccgctcaga taactgaaga gcgacagagc  25320
gcgctcactg tccaggcggc acatggtgtc aaatcagggg gttaaatgtg gttttgggca  25380
ccttcccacg atccctggac tggctcgagt ctgagcgcct cttgtgaggc ctctttgtgc  25440
tgtccttagt tggcgccgct ggggggcagc tggtgacaga ggcagcgtcc tcagaggcgt  25500
cctccagcgg cccaaaggga ccaactggtg tgagaggggg agaatccgga gactccaatt  25560
ccggctgcct cctggagtcc ggtatagaat cgggaacctt ttgcgaagac tcgcctccct  25620
cggcagacac agatcggttt acctctaaaa gtaggacact taactttacg tcacctgatt  25680
ggcagccagt gggcacacct tccacttcta atatttcgtt ggagtgccaa atcagcccgg  25740
gggtaaacca acccgggact ttacacagtc tcagggcggc gattaaggac tccaggctaa  25800
cccggctcag ggcgtcggtg tgcaccacgc ccacatccac cgacttcttc cccttcagac  25860
catcccagcc agaaacgggt ttggtttctg gcttgaaatc aatgatcttg ctcacgccac  25920
caagagaaaa tgtcacgatc gacagcgtct cgctgacaga cacagtcacc gtttggtcct  25980
cttttgtttt ttgctgcctt agccacttaa gtaggaatgc acccgttttg ccacagagga  26040
gaagcctggt ggtcctacca ccggcttcca tccgatcgtg gaaaggtagg ataccctttt  26100
ggtccaccac gcttttgtgc acggtggagg tgaggttgtc cccgtaggaa atggtggtcc  26160
tgacgaactg cggttgggcc cccgtatcgc atgcctcccc ctttcgataa aaggctatgc  26220
cagcgtcgag tacattcgca ccgaatagct cacgcgtgtg cgtgaagccg ctaccgacgg  26280
```

-continued

```
acgtattcct gaagctgaag ctaacgtctc cactgccttc cgtgtgtccc accaggggcg  26340
taagggcatt ctttattctt aaccccagaa cgccagctgt ccccacgctg gacagcacac  26400
tgagggttgg cgtgcaagcc gatccgtgca cttgcactac tccggtttta gtggcactct  26460
taatgtgttc attgaccctc ctgattttag acaggagggt cacgtccacc ctgaccccat  26520
agtgaaaatc cacaggcatg attgcggccg tagacgcaca gagaaatcac aggaaagctg  26580
cgcgcacact gggtgatctg gagacgatag actgccttaa atagaacttt taggggaggt  26640
ggaagtgtgc gacatggaca ggttaacctt cacaaatcgt cagtcacaca cgtggtgtaa  26700
tcagaattgt ctcgctcaaa aaaattcaca gccttgaaac tgccggtgta tgagaggggg  26760
cacgcttctg gcggaggcgt gccaaatatg ggaggaacga aaatatcacg cagaatcctg  26820
tcagcggtgg cttccaggaa cctccggatg tccaccacgt taacaagcgt caccccggcc  26880
gccttggcct ggataaaccg aatctcaata ttcactgcct ccctgaacag cgcctggacc  26940
tctgcgtgac tgggtttttc ctgtatctcc accatagtgt tgtacaacat actggcggcc  27000
ttggtgtgca gcagctcgtc cctggaaatg taatcgttgg caaggcacac cccgggcatg  27060
atgcctcgca ccctgcacaa actgatagag tagaaggagc taataaagta tatcccctcc  27120
acaatcaaaa acatcagaat cttctgagct ttggtggtcg ccttacgcac cctggagtga  27180
agccactcca gcttctcgca aagggcgggg tccaaaatga tcttggcagc atatgctaga  27240
agttcgcctc gactgttgtt gaaaaatatc ttcaagatat tggcatacac gacaccgtgg  27300
atattctcca tggcaacctg ttcggcataa tagtgggcca cgtcgtggct gttaaaattt  27360
gtgacaaggt cctcaatgtt aaagttaact aggcgttcgg ccattcccaa aaacgtaaac  27420
aaaaatctat aaaagtcctt gtcggcatcg ctgagctggt gcacgtggga aacatcaagg  27480
tgcaggggta tctggctagg aaaccatcgg ttctgccaag tctcgcgcgt tagcgccaaa  27540
aatccgtcgt gatcgcttgt atacagaaat cgatcaactg aatccattgg cctcacccgg  27600
cttgcagaga cctacctact gacagaccag gcactcgggg tctgccgcgc aggactcctc  27660
ctccgggttt ttaggtccgg gtaaccacgc cccatcttgt ttcatcccag agtgaggcgg  27720
tgaccctgga tctgccaggc actgaagagc cgtcagacta gattgcttct gaaccctaca  27780
gtagtacatg agggttttta gaccaagcct gtatccatgt agcagcaggt ccctaagata  27840
gctcgcattc ctgactctgt cctccttgag gaagaagctc atggactggc tctggtctac  27900
aaacggcgcc ctggcacgag ccctgtccag tagcttaaat ggacagtaat caaaggctgt  27960
taggaatacc ctatatcttt ccctgtgatg cttggggaac gtggaaacgt ccccaccata  28020
ctgtctaacc acccgaaggt cgtcggggag aaccttctta aaaaaagtca cattgggcct  28080
caacacctct tctttattgg tgaccttgga agatatatta gcaaaaaagg ggtacacaga  28140
ctcggcatag ccagttactt gcgaggtccc agccgtcggc atcaccgcca gaaactgaga  28200
attgaatatg ccatgctcgg caatgctctt tcccaacgcg tcccagcgat ggcgtggtac  28260
aaacgaagca tcctccccct cccatgtttg ccaatgaaac ctgcccttgg cgaagttact  28320
gacctcccag ccatgaaatg ggacaccctg tccctccaaa acaaggttgt gactagtctc  28380
caccgcggtg tagtacatag actggaatat attcttgtct aactcagcgc tctcagcatc  28440
gaggtacccg taccccaatt ccgcaaacac atccgccaac ccctgaacac caatccccat  28500
agacctctcc ttttgacctc gctcgacccc cggtgttgga tgggaaccac ccagaatgca  28560
ggcgttgatg acgaggactg ccacccttac tgcgtcgccc aaggcctcaa aacaaaaaaa  28620
cggcctgttg gcgtccgtgg tgccaaccct cgcgctttca acagttctca gacactttgg  28680
```

-continued aaggcagata tttgccaggt tgcacaccga agtgtttctt cctggcagtt ggactatctc 28740
tgcacacaag tttgagcagt taatggccat gccctgagtg tcggtccagt ggtgttcatt 28800
gagcgcttct tttaaaagca cgtacggtga gcctgtcttt atgatggtgt ggataagagt 28860
gaacatcata gacttcaacg gcatgcaact aacgtacttt ccagcccgca ccaggcgctc 28920
gtattcgtta tcgaacgcag caccgtatag cttaatcaaa ttgggggcgg tggctggatc 28980
gaacaaatac cataacttgg atgggtcctt ttcatacatc ctgaaaaaca atgttgggat 29040
gcacacgccc tgaaagagac tgtgacatct gtcgggattc tccggtagtt tggcgttcaa 29100
aaaatcacag atttgactgt gccagagttc catgtatgcg ctcgcgccaa cgggcctgat 29160
gttattgtca ttgaaataat gaacctgggc atccaccagt ttgaggcaac tggctatgtt 29220
cttttggtgg gagaatgacg taacatccag acccacgcct gacttactgg ccagcaacgg 29280
actcatatcg tggtacaggg cgtccaaagt acccgactca ttcatcatgg agggctgcag 29340
aataaaacag ctggcgagtt gtccgccttc gactccagct gagcgcagta ttggcgtggc 29400
gcagcacacg tgctgcgcag cgaggtagcc aaaaacgtac tccactatag ccatctcaga 29460
tacagactta gcgtcctcaa taaggtcccg cgccaaccaa tacaggcatt catgctctaa 29520
gcactgacag gcaacaaaca cggaaaccct cataaacatt tgcgccacgc tttcatagac 29580
aggctctgtc cccatggtcc ttaggacgta agtatcatac aacctcacgg ccgataggta 29640
gccacagtta agtgtgtcct cgtaagcttt ggaccgtctg taggcgcaca acatatcttc 29700
caaggcatca atgttctttt gaataaacga ttccacccga tgtcccaaca cgcctcgaaa 29760
aatcccaaga tactgcttga gagtcgctgg gcacctagcc tccataattt ggtgccacag 29820
ccgccccgcc atggcattgg cccgcacgtc ccacccgacc ctaaccttta gaaagtctat 29880
gagagattgg gcacacatat caaaatccga caattgtccc gcagacacct gagacccgcg 29940
tcgctctggt gggacagctc ccaagtgaac ctgacaaaat gtccggacag acatgacctt 30000
acagaaacac agtccagggg ccacacgcgg cctcaaagtt cgcaaacacc agtacaggca 30060
aggacgtgcc cttcacgttc agactttggt gcaccggatg agaatcaaag ggaactgtgc 30120
ccagcgtaca aaccgcccca aaaacaagcc gatttatata cagctcgtgc ctcagctgaa 30180
tatacttggt ccggattaca tccgtaaagt gatcctttat catggccaca acctccgcaa 30240
agcccttccc agactggaaa aacgtcagcg ccatagatgg tctctggttc acacggagat 30300
aaaccaacga ggcataaata gtaacgttta ggcctgccgg ttcccggcgc tggaccatgg 30360
gacatgactc atccaaatca actagcatat cacaagggag ggtcaagcct acgtgtgcac 30420
ggggctcgtc ccgggccaac ccaactccct tcatggcgga ggtgaccttg gtcacgaagg 30480
tactgtggac actctggacc attggaccta ctggggtaag gagggtatga aactccccag 30540
tgtccatgag ttcactcaag ttagggatga aatccgccag gccggatcca cttccgtacc 30600
acacaccggc cactttgtga gtctgtggcg cttttgccgc ttccattcca gagagcataa 30660
acagggacgt gggtgttagc agcatatcca tagacgagcc gttgtcctcc tgcttgaatg 30720
aaaataaaaa ggttcccaga ggctcctggg gactaaaggt ctgtgaatac acgaggaaat 30780
ctccataggt cggctgccta aacggcgcct gccgcaaggc ctcatgcagc gagccaaccg 30840
tgggtcgtgt ggacgccgca tatttagaga gtaaatcccg cacccccctg gcaaactccg 30900
gtcctctagt gagggatacc cggtgagttg gtggaggtaa aagacccaac acttgcctac 30960
ccaggcgagc cgcattttca gcctgcacct tcatatccac gccggcaatg gacggcacag 31020

-continued

```
acgctcttga aaagcttacc aaaggcctga gtgggggagg cgggagcctt caccagacaa  31080
agctgttgat ggaatttcaa ctccgaggac tgccggtgcc tgccctctta aacagcagca  31140
caacagagca gtttttaaat actgttgccc aactgccgac ggacctatca aaatttatac  31200
gcgactatcg cgtgttcgca ctggttcgcg cggcgtattt tttagaaccc ccttctagca  31260
tcgacccccct tgaggcagcg cgcgctcttg gacgcctggt tgatatatta tcatcacaac  31320
caccgcagaa caccgcaccg gcgcagccac ccacctccga cgacaccctg aataactgta  31380
cattgctcaa actactagcc cactacgcgg atcagatagc aggtttcaaa acccccgctc  31440
tccctcccgt gccacctgga atcatcggcc tgttcacatg cgtggaacag atgtaccacg  31500
catgttttca gaaatactgg gcagctgcac tacccccaat gtggatactg acatacgacc  31560
ctcccacttc tccgttacag gactggctta tagtcgccta tggtaacaag gaaggactgc  31620
tactcccctc tggcataccc tcggaggagg tgttagccaa aacattagta acagaacacc  31680
acgagttgtt cgtatcgcgg tcgaattcga ccgagaccgc cgtcaccatg cccgtatcca  31740
aagaacgcgc cctcgccatc taccgggtgt tcgccaaggg tgaggtggtg gcggaaaata  31800
ctcccattct tgccttcacc gacgtggaac tatccacact caaaccccac tatctgttca  31860
tctatgattt tatcatagag gcattatgca agagctacac atactcatgc acccaggccc  31920
gcctggaatc ctttttgagc cgaggtatag acttcatgac tgacctaggt cagtacctag  31980
ataccgctac tagcggcaag cagcagctga cgcacagcca aataaaggaa atcaaataca  32040
ggctgctaag ctgcggtctc tcggcttccg cgtgtgatgt tttcagaact gtgatcatga  32100
ccctcccata tcgaccgacc cccaacctcg ctaacctgtc cacgtttatg ggatggttc  32160
accaactgac catgttcgga cactatttct accggtgcct gggcagctac agtcccaccg  32220
gcttggcctt cacagaattg caaaagatac tgacacgcgc cagcgcggag caaacggaac  32280
gtaacccgtg gagacatccg ggtatctcgg acattccact gcgttggaaa atatcgcgtg  32340
ctctagcatt cttcgtccct ccggccccca taaacacttt gcagcgcgtg tacgccgcgc  32400
tgccctcgca actcatgcgg gccatcttcg agatctcggt caagaccaca tggggaggcg  32460
ccgtaccggc aaacctggcg cgcgacattg acacaggacc gaacacacaa catatctcct  32520
ccacaccacc gcccaccctc aaggatgttg agacatactg tcaaggtctg cgggtgggag  32580
acacggagta cgatgaggac attgtgagaa gcccgctctt tgcagacgcg tttaccaaga  32640
gtcacttgtt gcctatactg cgcgaggttc tggaaaaccg cctgcagaaa aacagagctc  32700
tgtttcagat aagatggctg ataatatttg ctgccgaggc ggcaaccggg ctcatccctg  32760
ccaggcgccc gctagccaga gcctacttcc acatcatgga cattctggag gagagacatt  32820
cccaagacgc cctatacaac cttttggact gtatccagga gctcttcacc cacatcaggc  32880
aggctgttcc agacgcacag tgtccgcacg cctttctaca gtccctgttc gtctttcaat  32940
tccgcccttt cgtactcaaa caccagcagg gtgtaacctt gtttctagat ggcttgcaga  33000
catccctccc cccggtgata agtctggcca accttggaga caagctgtgt cgtctcgagt  33060
tcgagtacga cagcgagggc gacttcgtgc gcgtgccagt tgcaccgcca gaacaaccac  33120
cgcacgtaca tctgtcgcat ttcaagaaga caatacagac catcgaacag gccaccaggg  33180
aggccaccgt agccatgaca acaatcgcaa agccaatata ccccgcctac atccggttac  33240
tgcagcggct agaatatctt aacagactca accaccacat tctcaggatt cccttcccac  33300
aggacgccct ttctgaactc caggaaacct acctggcggc gtttgcacgg ttgacaaaat  33360
tggcagcgga cgcagcaaac acttgtagct actccctcac caagtacttt ggagttttat  33420
```

```
tccaacacca gctggtcccc acggccatcg ttaaaaaact gctacatttc gacgaggcta  33480
aagataccac agaagccttt ttacagagcc tggcacaacc cgtagtgcag ggacaacggc  33540
agggggcggc tggcgggtcg ggtgtcctga cgcagaaaga acttgagctc ttgaacaaaa  33600
taaacccaca gtttacagac gctcaggcta acattcctcc atctattaaa cgttcatatt  33660
caaataaata tgacgtccct gaggtctcag tcgactggga aacgtactcc cggtctgcct  33720
tcgaggcacc ggacgacgaa ctccgttttg tcccactgac gctggcaggc ctccggaaac  33780
tgtttgtcga atagaggcca tggcagccca gcctctgtac atggagggaa tggcctccac  33840
ccaccaagct aactgtatat tcggagaaca tgctggatcc cagtgcctca gcaactgcgt  33900
catgtacctg gcgtccagct attataacag cgaaaccccc ctcgtcgaca gagccagcct  33960
ggacgatgta cttgaacagg gcatgaggct ggacctcctc ctacgaaaat ctggcatgct  34020
gggatttaga caatatgccc aacttcatca catccccgga ttcctccgca cagacgactg  34080
ggccaccaag atcttccagt ctccagagtt ttatgggctc atcggacagg acgcggccat  34140
ccgcgagcca ttcatcgagt ccttgaggtc ggttttgagt cgaaactacg cgggcacggt  34200
acagtacctg atcattatct gccagtccaa agccggagca atcgtcgtca aggacaaaac  34260
gtattacatg tttgaccccc actgcatacc aaacatcccc aacagtcctg cacacgtcat  34320
aaagactaac gacgttggcg ttttattacc gtacatagcc acacatgaca ctgaatacac  34380
cgggtgcttc ctttacttta tcccacatga ctacatcagc ccagagcact acatcgcaaa  34440
ccactaccgc accattgtgt tcgaagaact ccacgggccc agaatggata tctcccgcgg  34500
ggtggaatca tgctccatca ccgaaatcac gtccccttct gtatccccccg cgcctagtga  34560
ggcaccattg cgcagggact ccacccaatc acaagacgaa acgcgcccgc gcagacctcg  34620
cgtcgtcatt cctccttacg atccgacaga ccgcccacga ccgcctcacc aagaccgccc  34680
gccagagcag gcagcgggat acggtggaaa caaaggacgc ggcggtaaca aaggacgcgg  34740
cggaaagacg ggacgtggcg gaaatgaagg acgcggtggc caccagccac cagacgagca  34800
ccagccccca cacatcaccg cggaacacat ggaccagtcc gacggacaag gcgccgatgg  34860
agacatggat agtacacccg caaatggtga gacatccgtt acggaaaccc cgggccccga  34920
acccaatccc ccagcacggc ctgacagaga gccaccgccc actcccccgg cgaccccagg  34980
cgccacagcg ctgctctctg acctaactgc cacaagaggg cagaaacgca aattttcctc  35040
gcttaaagaa tcttatccca tcgacagccc accctctgac gacgatgatg tgtcccagcc  35100
```

<210> SEQ ID NO 20
<211> LENGTH: 32207
<212> TYPE: DNA
<213> ORGANISM: Kaposi's sarcoma-associated herpesvirus

<400> SEQUENCE: 20

```
ctcccaacaa acggctccgg atactgaaga tatttggatt gacgacccac tcacaccctt     60
gtacccacta acggatacac catctttcga cataacggcg gacgtcacac ccgacaacac    120
ccaccccgag aaagcagcgg acggggactt taccaacaag accacaagca cggatgcgga    180
caggtatgcc agcgccagtc aggaatcgct gggcaccctg gtctcgccat acgattttac    240
aaacttggat acactgctgg cagagctggg ccggttggga acggcacagc ctatccctgt    300
aatcgtggac agactaacat cgcgaccttt tcgagaagcc agcgctctac aggctatgga    360
taggatacta acacacgtgg tcctagaata cggtctggtt tcgggttaca gcacagctgc    420
```

-continued

```
cccatccaaa tgcacccacg tcctccagtt tttcattttg tggggcgaaa aactcggcat    480
accaacggag gacgcaaaga cgctcctgga aagcgcactg gagatccccg caatgtgcga    540
gatcgtccaa cagggccggt tgaaggagcc cacgttctcc cgccacatta taagcaagct    600
aaacccctgc ttggaatccc tacacgccac tagtcgtcag gacttcaagt ccctgataca    660
ggcattcaac gccgaaggga ttaggatcgc ctcgcgtgag agggagacgt ccatggccga    720
actgatagaa acgataaccg cccgccttaa accaaatttt aacattgtct gtgcccgcca    780
ggacgcacaa accattcaag acggcgtcgg tctcctcagg gccgaggtta acaagagaaa    840
cgcacagata gcccaggagg ctgcgtattt tgagaatata atcacggccc tctccacatt    900
ccaaccacct ccccaatcgc aacagacgtt cgaagtgctg ccggacctca aactgcgcac    960
gctcgtggag cacctgaccc tggttgaggc gcaggtgaca acgcaaacgg tggaaagtct   1020
acaggcatac ctacagagcg ctgccactgc tgagcatcac cttaccaacg tgcccaacgt   1080
ccacagtata ctgtctaaca tatccaacac tctaaaagtt atagattatg taattccaaa   1140
atttataata aacaccgata cactggcccc atataaacag cagttttcat atctgggggg   1200
tgaactggca tctatgttct cccttgactg gcctcacgca cctgcagagg cggtagagcc   1260
actacccgtg ctgacttctc tgcgaggtaa aatcgcagag gcgctgacgc gtcaagaaaa   1320
caaaaacgct gtagatcaaa ttctaaccga cgccgaaggc ctccttaaga acattaccga   1380
tccaaacggc gcacacttcc acgcccaggc cgtatcaatt ccagtgttag aaaactacgt   1440
acataacgcg gggtccttc tcaagggcga aaagagcgag aggttctccc ggctgaagac   1500
cgccatccaa aacctggtat cctccgaatc atttatcacc gtgaccctac acagtacaaa   1560
ccttggaaac ctagttacca acgtaccaaa acttggtgag gcgttcaccg ggggcccgca   1620
cctcctgaca agcccgtccg tgagacagtc cctttccacc ctgtgcacaa ccctgctgcg   1680
agatgccctg gacgccctgg aaaaaaagga tccggccctt cttggtgagg ggaccacgtt   1740
ggcgctggag acactcctag gatacgggtc ggtgcaggac tacaaggaga cggtacagat   1800
aatatccagc cttgtgggca tccaaaaatt agtcagggac cagggcgcgg acaagtgggc   1860
cactgccgtg acaaggctaa ctgacctcaa atcaactctg gccacgaccg ccatcgagac   1920
ggctacgaaa cggaaactat acagattgat ccaaagggac ctcaaagagg ctcaaaaaca   1980
cgagaccaat cgggccatgg aggaatggaa gcagaaagta ctggctcttg acaatgcgtc   2040
tccggaacgt gtcgccaccc tcctgcaaca ggctcccacc gcgaaggcta gagagtttgc   2100
agagaagcac ttcaaaatac tactccccgt acccgcggac gcccccgtcc aagcgtctcc   2160
aacgccgatg gaatacagcg ccagccccct cccggaccca aaggatatag acagagctac   2220
atccatccac ggggaacagg cgtggaagaa gatacagcag gcgttcaagg atttcaactt   2280
cgccgtcctg cggcccgctg actgggatgc cctggcagcg gagtaccaac gccgtggttc   2340
gcccccttccg gcggccgtgg gtccagcgct ctcagggttc ctggagacga tcctagggac   2400
gctgaacgac atctacatgg ataagctccg ctcctttctg cccgacgcgc agccttttca   2460
ggcgccgccc ttcgactggc taacgccgta tcaggaccaa gtcagctttt tcttgcgcac   2520
catagggctg ccgctggtgc gagcgctggc cgacaagatc agcgtgcagg cactgaggct   2580
tagccacgcg ctccagtccg gcgatttgca gcaggccacg gtgggcacgc ccctggagct   2640
ccctgccaca gagtacgcgc gcatcgcctc caacatgaag tccgtgttca acgaccacgg   2700
acttcaggtg cgatcagagg tcgcggatta tgtggaggcc caacgagccg acgcacacac   2760
```

-continued

```
gccacacgtc ccacgtccaa agatacaggc accaaagact ctgattccac atccggacgc   2820
aatcgtcgcg gacggactac ccgcctttct taagacgtcc ctactgcagc aagaggccaa   2880
acttctggcg ctacagcggg cggacttcga gtcgctcgag agcgacatgc gcgccgcaga   2940
ggcccagaga aaagcatcgc gcgaggaaac ccagcgcaaa atggcacacg ccatcactca   3000
gctcttacag caggcaccca gtgcgatctc ggggcgcccg ctatccttac aggacccggt   3060
gggcttcctc gagggcatca tatacgacaa ggtcctggag cgcgaatcct acgagacggg   3120
tctcgaggga ctgtcctggc tcgagcagac catcaagtcc atcaccgtat acgctcccgt   3180
agaggagaag caaagaatgc acgtgctgct ggacgaggtg aaaaagcagc gagcaaacac   3240
tgagaccgct ctcgagctag aggccgcggc tacgcacggc gacgacgcta gactcctgca   3300
gcgagcggtc gatgagctgt caccgttgcg cgttaagggg gggaaggccg cggtggaatc   3360
ctggcggcag aaaatccaaa ccctgaaatc cctggtacag gaagcggagc aggccggcct   3420
cctgttggcc accatagaca cggtggccgg ccaggcccag gagaccatat caccatccac   3480
actccaggga ctgtaccaac agggacagga ggccatggcg gccattaagc ggtttaggga   3540
ctcgccccag ctagctggcc tgcaggaaaa gctggccgag ctacagcagt acgtcaagta   3600
caagaagcag tatctggaac actttgaggc cacccaaagc gtagtgttta cagcctttcc   3660
gctcacacag gaggttacga tcccagccct gcattacgcg ggacctttcg acaacttgga   3720
gcggctctca cgatacctac acatcggcca gacgcagccg gctccgggac agtggctcct   3780
gacacttccc acattcgacc ccacgcgccc ggcctgcgtc ccagccggcg gccacgaacc   3840
cccgttgcac agacaggtgg tgttctccag ctttttggag gcccagatcc gattagcgtt   3900
gtccgtagcg ggccccgtgc ctggacgggg tctgcccgga acaccgcaga tccgaagggg   3960
cgtggaggct gccgcttgtt tcctccacca gtgggacgag atatctcgcc tccttccaga   4020
ggtactggac acctttttcc acaacgcgcc ccttcccgca gagtcttcct ccaatgcttt   4080
cctggccatg tgcgtattga cgcaccttgt ctacctagct gggcgcgccg tcttgggccc   4140
acgggagccg gagcacgccg ccccggacgc gtacccaagg gaggtggcgc tggccccgcg   4200
cgacctgacc taccttctac tggccatgtg gccatcttgg atctcggcaa ttttgaaaca   4260
gccttcgcac gcggaggcgg cgcacgcatg tcttgtcacg ctgccaacaa tgctcaaggc   4320
tgtgccgtac ctcacgctgg aagcctcagc tggaccactg ccggcggaca tgcgccactt   4380
cgccacgcca gaagcgcgtc tgtttttccc cgcgcgatgg caccacgtca acgtgcagga   4440
gaaactgtgg ctgcgtaatg attttatgtc gctgtgtcac cgttccccgg ggcgcgcgcg   4500
catagccgtc ttggtgtggg ccgtcacttg cctagatcct gaggtaataa ggcagctgtg   4560
gtccaccttg cggcccctta ctgcggatga atccgacacg gcttctggac tgctgcgggt   4620
gctagtagaa atggagtttg gtccgccgcc caagacgccg cggcgggagg cggtggcgcc   4680
cggcgcaaca ctgccaccgt accccctacgg ccttgccacc ggcgagcgcc tggtcggcca   4740
ggcgcaggaa cgctctggcg gcgctggcaa gatgccggtg tccgggtttg agatagtttt   4800
aggcgcactg ctgttccgcg ccccccctacg cattttcagc accgcatcaa cccacaggat   4860
ctcagatttc gagggcggtt tccagatact gactcctctc ctggactgtt gcccagatcg   4920
cgagccattc gcctccctgg ccgccgcacc acgaaggacg gtgccactgg gagacccgtg   4980
cgccaacatt cacacccccg aagagataca gatctttgcg cgtcaagccg cctggcttca   5040
atataccttc gcaaattacc agatccccag caccgacaac ccgataccga tcgttgtgct   5100
aaacgctaac aataaccttg aaaacagcta catccctcgc gatcgcaaag cggacccgct   5160
```

-continued

```
acgaccattc tatgtagtcc ctctgaagcc gcagggtaga tggcctgaaa taatgaccac   5220
agcaacaacc ccctgccgcc taccgacatc gccagaagag gcgggatcac agttcgccag   5280
actccttcag agccaggtga gcgccacatg gtctgacatc ttctccaggg ttcccgagcg   5340
cctcgctccc aatgcgcctc agaagagttc ccagacaatg tcagaaatcc acgaggtcgc   5400
cgccacgccg ccactcacaa tcaccccaaa taaaccgacc ggaacccctc acgtctcccc   5460
ggaggctgat ccaataacag aacgcaaacg cggacagcag ccgaagattg tcgcggacaa   5520
catgcctagt cgtattctcc cgtcgctacc gaccccgaaa cccagagagc ctagaatcac   5580
gctaccccac gcactgcccg ttatatcacc cccagcacat cgcccgtcgc ctataccgca   5640
tctgccagca ccgcaggtaa cggagcccaa aggggttctc caaagcaaac gtggaactct   5700
cgtgctgcgg cccgccgcgg tcattgaccc acggaagccc gtctcggcac cgatcacgcg   5760
atatgagagg acggcgctcc agccccccg gactgagggc gaaggccggc gccctcccga    5820
cacgcaaccc gtcactttaa cctttcgtct cccacctacc gcacccactc ccgcaactgc   5880
agccctagaa accaaaacaa ctcccccatc cacgccccca cacgccatag acattagccc   5940
accacagaca cctcccatgt ccacctcacc tcacgcgaga gacacaagcc cccccgcaga   6000
aaagcgggcc gcacccgtca ttcgagtaat ggcgcccacg caaccgtcgg gagaggcaag   6060
agtcaagcga gtggagatcg aacagggcct ttccacacgc aatgaagccc ctccccttga   6120
acgctcgaat cacgccgtgc ccgccgttac cccaaggcgc accgtagccc gcgaaatcag   6180
gatcccgccg gagataaagg cgggttggga cactgcaccg gacattcctc tgccccacag   6240
ctccccggag tcatccccac cgacttcccc ccagcctatc cgcgtggatg ataaatcgcc   6300
tcttcccaac ctcgtagaga gatacgcgcg gggtttcctg gacacgccct ctgtagaggt   6360
gatgtccctg gaaaatcagg acatcgccgt ggaccccgga ctgctaaccc gccggattcc   6420
atccgtggtg cccatgcccc atccaattat gtggtcaccc atagtaccca tcagtttaca   6480
aaacacagac atagacactg caaagataac actgattagt tttattagac gcatcaaaca   6540
aaaagtggcc gccctatcgg cgtccctggc ggagacggtt gacagaataa agaagtggta   6600
cttgtgactc cacggttgtc caatcgttgc ctatttcttt ttgccagagg ggggtttcct   6660
cgcgtcggcc accgcggggg cggccgtttc cgtcgtggat gagagggttg tgagaatgtc   6720
tgacgccggc gacaatgaat ggggaccaga ggacagggtg gttatactgc ttcccgagac   6780
ccccagtgag tcctggcccc cgggcgtggt gccggatgca gggcctggcc tcgaaggcac   6840
ggtgaacgtc cccgcgtcgt aagccgacgc cgcggaaact cggtcagcgc gctcgcgcgg   6900
tttctgatcc ctaagggtct gcagatgatc ccgcctttga attccaccca tcctcctcag   6960
ataggcctca taataatgat gggcaattaa gaacacgaga tagtgtctct tttgcacgag   7020
gtattcggcc tgcgacatat ttccctgatc cagggtattc atgcgagcca ccaggggatg   7080
gtgagcgtag tcatgatcca gtcgctcctg gatcacgggg tctctcacct taaagttgga   7140
catcttccac acaggcgggc gaaatagcct caggaggaac acttcccgca acagaactcc   7200
agcagctgtg aggtgagctg aagcagtccg cgcacgtcac ggtgctttaa tagggcagcc   7260
tcgcagtcgg gcgtcccaag gcaaggcact acaaaactga cagtttgatc taggtctcga   7320
atggcaaggg ccgcgttgtt agctagaaca gccctgatta cgacgcgtgc tagggtcccg   7380
cgtccggtaa tatcgcacag gggatacacc ctcatatgtt cgctgccaca gtaagaacag   7440
tagatcctcc ccgtggtcgc acagatggtg aactgcttct ctttcctgtc cctgctgaaa   7500
```

-continued

```
aacacgttgg tgggaggaaa attgacagta tgaaacttgc cctgccaaa gttaagacag   7560
tgtccacact ccatgcacac aaccgcccga gcgcaacgcg cccgcttggc aagggccgcg   7620
cgggccacgc gagaacagat gacgggtatg gacacgcagg gggagagaac attgtatgcc   7680
agaagcctcc tgccaaggtt ccgcacgaga ccaggtccct cctgctcgca ggcgggcagc   7740
actacgtggc gggacttaat aaggctcaaa aaacacagtg acccaagcat ggcgtcgaac   7800
gggttaccgc agggaaccgt aggggcgacg cgctccaagg cctcccggag gccggtatct   7860
gccgccccta tcccgagccc gttaccgtct tcggtcgcag ccacaccgcg acgggtgtgc   7920
gagggcacct ccaggagggg acgacgcggc aacggcccat gccacttctt ccttagccag   7980
ggtagcgacg gtgggggctt cgaacagcag gtcactaacg gaaagcgaga gcaaagcgcc   8040
aacagcttgc agagttgggc acaggccttg gaaaatggaa gcgacaggta ttttgcccat   8100
acgtggcgcg gtatcgccct agcatggtcg gcggcctggg cacgggacag cgtcaccaca   8160
acccatacgt gggcgccaag cagctgctgc gccgcacaaa tctgcgcctg tttggcgacg   8220
gtgtctgagc cagcgcgcaa cacggcgatc gcctgcgcca gcgacgggcg gtccaacagg   8280
tgcctggccc aggagggcat gtttccctgg aaaccccgct ccccgaatat gacaaaagcc   8340
acatattcct ccactggcac gccattctcg ccctcgaaca cgcggtgggc cgtcagctgg   8400
gcctcatcca aaccaaacca agacacaaga aagcgatccc agcgctgatc cagggccatg   8460
accttctcac cagcgcgacc gcacggccta agctccactg aaaggcgccc agaatccgca   8520
ccgtcctacc cccctggccc gcccaatata ccgctgtgac gtctgatgta caggcccgcg   8580
cgtcgcggcc gttggtggga aaaccggcac caccctgtgc ggccgaatcc gccacggggg   8640
ctgccagaca gtacactgtc tccagcagcg acttcagtct cttgtgactt ttgggcgtca   8700
ccaccaaaaa ttgcaaaacc tgcctgtagt ccgtgaagta ggtacggcat attaccatgg   8760
agttgtacac gcccaggttc tttgagaaca ccaggctcgc cttgaacttt gtaaagtcat   8820
cctgccccag cacgacagac gtatttttgg caaggtatac gtccgactcc acgggaagga   8880
cgtgcccaaa ctgggacacg gcgtcgcttg gtcggcacag aaagcacttc agggttgtgg   8940
aaaggccatt attcgatata acaaagcagg gagagaacgg gtagtgcatc tcctccagga   9000
ggtgcgccca aaacttatac acaaactcta agtggtacac gcaaccgtgc tgcattctaa   9060
ccgtacatat ggcggtagca ccgcccttag cataaactgg ggccccgtcg atgcaccgtt   9120
ccaaatccag ggactgacca gactgtccca agtatgagga taccacccga cacagttcgt   9180
ccactacacg cttaccaacg acactcatgg cgacagcggg gtggggctgg caaggccccc   9240
aaagcgcgac acccgcagtc aatcagggcc gtgcccgcgc ctcggagaat acggcgtccg   9300
tgctcacgat cttgcgcagg acctgcctta ccgtgtccac cttgctctcc aacaccagag   9360
tatgatcgca ggctgcaggc tgtgcccgct ggacgagaaa ggtttttaaa tactgacagt   9420
agttgatggc gttcaatcta caatagatcg tgggaaataa aatttgcatg tcacgaggca   9480
gaagctggtc agacgcgtac tccatgttgg gttccacggg gaggggaaca cacgccccaa   9540
gacacgacgg cgcacatagg gagcggagca aacaattgat tcaaatattt gactccgcag   9600
cgagccggtt tgcagagtgg tcacctgccc tgctccacac ccaccccgc gtctcttcca   9660
actctcaact cacgatccag ggaaaccacc gtccagtggc catgtttgtt ccctggcaac   9720
tcggtacaat tacccgtcac cgagatgagc tccaaaaact actggcagcc tccctgctcc   9780
cggagcaccc ggaggagagc ctcggtaacc ccataatgac acagattcac cagtcgctcc   9840
aaccatcttc cccctgcagg gtctgtcagc tcctattttc tctggtccgc gattcgtcca   9900
```

-continued

```
cccccatggg tttcttcgag gactatgcct gcctctgctt cttctgtcta tacgccccac   9960
actgctggac ctcgaccatg gcggcagcgg cagacctgtg cgagatcatg catctgcact  10020
ttccagaaga ggaggcgaca tacgggctat tcggaccggg tcgccttatg ggtatcgact  10080
tgcagctgca cttctttgtt caaaagtgct ttaagaccac cgccgccgaa aaaatactgg  10140
gaatatccaa cctgcaattt ttaaaatcag aattcatccg ggcatgctc acaggcacca  10200
tcacctgcaa cttctgcttc aaaacgtcct ggcccaggac agacaaggag gaggccaccg  10260
gccccacccc atgctgccag attacagaca ccaccaccgc acccgcgagc ggcataccgg  10320
aactagcccg ggccacattc tgcggcgcaa gtcgccccac aaagcccagc ctacttcccg  10380
cgctaataga tatctggtcc acgagctcag agctccttga cgagccgcgc cctcgactga  10440
tcgcaagcga catgagtgaa ctcaaatccg tggtcgcatc ccacgatccg ttcttctctc  10500
ccccgcttca ggcagacacc tcacagggtc catgtctgat gcacccaacc ctggggctac  10560
gatacaaaaa cgggactgca tccgtctgcc tcctctgcga gtgccttgcg gcacacccag  10620
aggcacccaa ggcgctgcag acccttcagt gcgaggtaat gggccatata gaaaacaacg  10680
taaagctggt agacagaatt gcctttgtgt tggacaaccc attcgccatg ccatatgtat  10740
cagatccgct acttagagag ctgatccggg gctgtacccc acaggaaatt cacaagcacc  10800
tgttctgcga cccgctgtgc gccctcaatg ctaaggtggt gtcagaggac gtactattcc  10860
gcctgcccag ggagcaggag tataaaaagc tcagggcatc cgcggccgcc ggacagctcc  10920
tcgatgccaa caccctgttc gactgcgagg tcgtgcagac tttggtcttt ctctttaagg  10980
gtctccaaaa cgccagggtg gggaaaacca cctcactaga cattattcgg gagctaaccg  11040
cacaactaaa aagacaccgc ctagacctgg cccacccctc acagacgtca cacttgtacg  11100
cttgagctgg tcccgggcct tcgcacccca tccaccgatg ccgaaatcag tgtccagcca  11160
catcagcttg gcgacctcaa ccggtcgcag tggaccgcga gacatcagaa gatgcttgtc  11220
atcccgcctg cggtcggtcc cgcccggggc gcgaagcgcc agcgtcagca gcaagcacag  11280
aaacggcctt cgcaagttta tctcagacaa ggtatttttt agcatcctat cgcacagaca  11340
cgagctagga gtggactttc tccgtgagat ggagaccccg atatgcacct ccaaaacagt  11400
aatgctgccc ctagacctgt ctaccgtcgc acccggccgc tgcgtctccc tctctccgtt  11460
tggacactcc tcaaacatgg ggttccagtg cgctctgtgc ccatccacag aaaatcccac  11520
cgttgcccaa ggctcccggc ctcagacaat ggtgggcgat gcgctcaaaa aaaataacga  11580
gctatgctcg gtagcgctgg ccttttatca ccacgcagac aaagtgatcc aacacaagac  11640
gttttaccta tcactcctca gtcactccat ggatgtggtt cggcagagct tcctgcagcc  11700
tggtctactg tacgctaacc tggtcctaaa aacctttggg cacgatcccc tacccatctt  11760
cactaccaac aacggcatgc taacaatgtg catccttttt aaaacccggg cactacatct  11820
gggagaaact gcgcttaggc tgcttatgga taacctcccc aactacaaga tatcggcgga  11880
ctgctgcaga cagtcctacg tggtcaagtt tgtcccaacg cacccggaca ccgcaagcat  11940
tgcagtgcag gtacacacca tatgcgaagc ggttgcggcg ctagactgca ccgacgagat  12000
gcgggatgac attcaaaagg gaaccgcact tgtcaacgcc ctataacctc acatgtagcc  12060
tgtcacccca gctcctattg caactgacca tgttcaggtg gtaataaagt cattaaacga  12120
caaagtgatt cttttaatct gtttattgtt tttgaacatg tggcacacgc tgcaatgtac  12180
tgccatgaaa ggtggttcta tatccaccac ttggcgtctg ccgaagtcag tgccacaatt  12240
```

-continued

```
tcattaacaa acaaggtcaa tacattgtga gggagtgttt tttgccatgg taccattcgt  12300
gtggtttggg agagcggacg ccatttgcgt gcaaaatgtg ctttgctgga ggccaacttc  12360
cgtcgcgctg gttgatgcgc ggcacattgt gtcaaccagg gcaccctccc ccaccgagtg  12420
ctttaatgcg gagaggaatg gtggcctggt tgacaccgcg tgccggccat ctgaactgtg  12480
actgtgttat gagccacggg tatgccctcg atacgcctgc tcttcagcat tgtatgtgtt  12540
taatgttgtg cttggtgcaa ccgtgattgt gtttttgtat tttattttac tgacactctt  12600
tgggagggca cgctagcttc agtgcgcgcc cgttgcaact cgtgtcctga atgctacggg  12660
gccacgctgg ccactcgggg ggacaacact aatcgccaac agacaaacga gtggtggtat  12720
cgccccaagc ctccagcgcc acccatttag taacacatcc gggacatgaa ctgccacaaa  12780
caccgttaag cctctatcca tgcattggga ttggagtgag gagggaggag ggcaccaggt  12840
tcccggggag gagggcacca ggttcccggg gaggagggca ccaggttccc ggggaggagg  12900
gcaccaggtt cccggggagg agggcaccag gttcccgggg aggagggcac caggttcccg  12960
gggaggaggg caccaggttc ccggggagga gggcaccagg ttcccgggga ggagggcacc  13020
aggttcccgg ggaggagggc accaggttcc cggggaggag ggcaccaggt tcccggggag  13080
gagggcacca ggttcccggg gaggagggca ccaggttccc ggggaggagg ctggggtgcg  13140
ccgcgccggg ttcctggggt gcgccgcgcc gggttcctgg ggtgcgccgc gccgggttcc  13200
tggggtgcgc cgcgccgggt tcctggggtg cgccgcgccg ggttcctggg gtgcgccgcg  13260
ccgggttcct ggggtgcgcc gcgccgggtt cctggggtgc ggggtgcggg ggaccgcgcc  13320
ggggtactgc agggttcgca gggttcgggg gtactacctg gtttcctggg gtgtgccagg  13380
acgggttcct ggggtgccac cgctcctcga tacgtgtaaa tccaagagat ccgtcctccg  13440
tgccgccgcg cgcgtaatgc gcgagggggg tcggtctccc ctcttcttta tagcgtttcc  13500
tgcgaagggg gcgtaaccgt aggacaaact gcttatgtag ggttagcca cccatttccc  13560
ggggccgcgc cagaggtgag cgtggaccta gcatcccgct cccatttacc gaaaccaccc  13620
agaggcgaga ttccagggcc gtgactcact agctcccctc ccatcgaaca accacgcttg  13680
gctaacacgg ctggagtggc ggtgggcggg gcccctataa tcctggcccc catctactga  13740
aacgacccag tagaaaaatc ccaaccccat gactcatcag gccctattat atagaatatc  13800
ccagtagagt gacccagctg gtttccataa atggatatac ttccggaaaa cgaaggaggg  13860
ttgaatacag ttgggggtag tccgctggta ttcccagctg aggttgcctt atttggtaat  13920
gcttccggaa ataccacctg agtaccccat tggtttatac cttgtttaat tgtagaatta  13980
cagctggatt tacccagccg ggtttacgca gctgcgtata cccagctgtg tttacgcagc  14040
ggggtttacg cagctgggta gacccagctg ggtataccta ctggaatagg ggctgcgatg  14100
actcagctgc gctaggatta aaggattata tatatatata taggaaaaat caaaacaaaa  14160
ctctaatcgc tgattggttc ccgctctggg ccaatcagct tgggagttct agggataggg  14220
gccaatggga ggcctccgaa tttgattgac ggctggggcg tccaatggaa tggcgcggtc  14280
gcctagctcg aacgggattg gtcggccgga tgggccaatg gcggctcgga aaactttgat  14340
tgacgggccg gcggaccaat gggagcgggg cagaggatta tgggggatta gcaaattcaa  14400
gatggcggcg cccatgaaat ggccaaaaat tataattttt cgagtcgctc acggtcccac  14460
ctagcggcgt gacctggagg tgaccccgtg cacccgggcg ctctgaattt ttctgcgcat  14520
gcgcgactcc tcatctacat aatttatgca cataaaagga ttagcgcatg caaattagtc  14580
agatagcagg gccatccaca ctttatgttg gccgcgtgcc aggcgccggc gtgggcgccg  14640
```

-continued

```
cgcgcgtgct ctctcagtcg cgcctagctg cttccaacag acaaaagcgg ggcgttagtg  14700
agggagtgcg cgcgctgcgc tgacttggcc gatttccagt gcatgctttg tcaccccagc  14760
gcgagaatgg aattttcatt attgagcaat ttgggcaccc tgggcacgat aaccatacat  14820
ggatacacgg gttccaaata tgcaaagtag acactaaggt accatttggc atatttggac  14880
gtcctgggca ggttagctac ccaccagaat atatgggact ctgggcagga tagccaccca  14940
caattgtttt gcgcccctct ttggccaggg gaccaaggtc gtatggttcg cgctacacta  15000
agcccgaacg ttcagctttg cgtgctttcg acgtccaggc ggctggcaca cgggccgtga  15060
gcgccagcaa catgggatca tggtagtaag atacagcata aatccccgtc cggtggcgct  15120
caacgccaat atgcgcggct gcgtggtatc tcatcggtgg gcacgcgtac ggtggtctca  15180
tgggtattgg acttgtaggc gaggggaggc gcatacgaca aaaattgccg ccgtgaaggt  15240
cgggaacccg cccgcgcttc cgcaaggcac ggggccgcat cggacacagg ctaagcatta  15300
aggatcataa caccgcccta gaaatgttta agctgtgacc aaagcgaacc tcgcatgagg  15360
catacgcgag cgtggaggta ggattcccaa ggctattgag agacggtggg tgaaatgatg  15420
aagaacacac agaacaataa cgggcgacta gataaaaaga ctcgctcaac agcccgaaaa  15480
ccatcagccc gaccgccgat ggattaggtg ctgctggaca agtctttcta aacccgcgca  15540
gggtttgtgt cgatccagac gcttacgaac gcccgcttta aaaacactat tcataattaa  15600
cagaagttga caccagcccg cagttaccca accttctatt tttttggagt gttgacaagt  15660
ttccatcgcc cgtttggcgt ttcccgcatg gtgtcaaatt agtgacgcac cctccccccg  15720
tcactatggg tttaccctga tttagtaagt aaaactgccg cccccgccca ctcatttttt  15780
taccctgtta tttgctgtat ttacatctac ggaccccctt ttggtgagat tgccgtggtt  15840
ctaaataacg ttgtggtttt cggacccttt cagggaccaa atcttttacg tgttgccaag  15900
gtagcatttg ctggacccgc ataggttttt gtggcaccag gttatggtct tatgagcggg  15960
cttgaccggc aagttccagg catcctaagt gcttgatgta gacccttagg gcaccaggga  16020
ctacctaggt caaactcccc cttagtcatg acgccgtgcc cacgaggttt gagaggcgta  16080
gacatccgtg tcgactgctg gacggaggta gtataatcag ctaggcctca gtattctatg  16140
taacaaatga atgccctaga gtactgcggt ttagctagtt atactgcccg gttccaccag  16200
gcggcgttgt ggccacgggc ggttcgtcgc ttggacctgg aggggtgtca cattctgtga  16260
ccgcgacgtt gacgttagac acacgtcgct gccgtcctca gaatgtgata gcccatcaca  16320
ggcattgtag ctgttgcgtt ggttgggagt ttggggacca aatttctata attggtgtca  16380
ccgcggcagc tctagccctg gaagatctgg aagcttgctt caatggctca gatcgacccg  16440
gactacagtt agcgaagtag acccattata atcttaatct taaatctggt tgacggactt  16500
tcgcgccggg aacacgcagg tggcagcgga tgtgttttgc ccaaacacga gggttgcagg  16560
aaacaggtgc tgccggggat tatgtacagc ttacacccag tttcctgtaa tcgcccgcat  16620
ccggccgtcc tgggcagcac cgcaccctgc gtaaacaacc gcgtactttt tcctcctccc  16680
cccaccccca catccttcct cccaccctgc cagtccaacc cgcttcctgt tttattcgcc  16740
ttcaaacaga agcacgcatt ctaatgattc ttacaaaact tgttagtgtt tattaaatca  16800
gatacataca ttctacggac caaaaattag caacagcttg ttatctatgg tgtatggcga  16860
tagtgttggg agtgtgatgg gccggaaagg tgaaggccca ttagggtttg cacttggcgc  16920
tgtaggtcta ctcttgacaa agatctaagc attgacatta gggcatccac gtcagtggga  16980
```

-continued

```
cccagtaggt ctaagttttc catacagtac acccagtgta agatgtctgt ggtgtgctgc  17040
gagaccctat agtgtccttg cttaaaaata tcaaagacct aatatccctc gcacacagct  17100
ccccgtctac gtggagaaca gtgagctgat aagggctgaa ataactcatt gtgcccgcta  17160
ggtggcgctc taaaaaacgc gggtctaagt gaagcaggtc gcgcaagagg tctctgcgac  17220
ctgcacgaaa cagacattcc gctaacaggg gaaacgttaa cctgccctcc tcctttaaag  17280
ctctaagagc tccaattaat tgggccagtg tgggttgagg tatgaacacg tttaggagga  17340
acaataccac ttccctgtca tccgtgccca gtttccgcgc cacctcacag agaacctcgt  17400
aagtggccat ggtgccggct tgtatatgtg aaggcaccga tgtggaaaaa caaaggaaaa  17460
tttatttttc cgccctaaac aaaatcacaa gcttaatagc tgtccagaat gcgcagatca  17520
aagtccgaaa cagatgttag gatctgttcc actgccgcct gtagaacgga aacatcgcat  17580
cccaatatgc ttgccagctg aggaactacc ccacccgagt gggtatcctg cggaatgacg  17640
ttggcaggaa ccaacagcgc acagcctgca gcgctgataa tagaggcggg caatgagcca  17700
gtctttgggt caactaaggc ttttgtaatc agggtgttga cctcgtggtg ccaaaagtcc  17760
aggtgttggg agccccccag caatttaagt aacaagaagg aagtgacgtc cgtcgctaag  17820
actgcctctg ttcgccacgc caacttctca aggagttctt tctcctggtc tataagttct  17880
tggcgggaaa aggagtctgc cgcggcatag caaagtgaac tggtagaaat aggcgtgagg  17940
cttctgagct tactggccac taacaggcag gcgctccctg tcttttgaaa gtgttctttg  18000
gacacctgct ttataagtag gagtctgtcc aaaagattaa gggccaacgc gaccacgtta  18060
ggttctaggt tgtattcctg gcaaactgaa aacatccatg tgcccagtaa cttacgcata  18120
tgcgaagtaa gagattgttg aaaggtccca aatacagagt cagaagttaa aaagcgcggc  18180
tcaatttcaa gaatattgta aaagatccga tcctcacata gcgtgggatc cagaagtccc  18240
gagggcgggt tattggcagt tgccatatag agtggcgagc gtatgtggcc tacctgtaga  18300
gcctggagtt tcagggtgct ctgtcaggtt ctcccatcga cgacgctggg ccgcgagagt  18360
acgctagccg ttgtccgtgt gttcagttga ggtagatggg tcgtgagaac actgcccccc  18420
acacacacca gcacccatgg cgccaaatgc aagtgcggag cggcgacggt ggcttctagg  18480
gaggaaaaag gggagaggt gtggctttta tgtcatttcc tgtggagagt ccccaggacc  18540
ttggttttcc cctggctggg ttaatggcag gggcttttta aacttaacta tggaagattg  18600
taggtttcct gccagggggt gactagcttc ccaggctagg cgggccattt gtactttctt  18660
acttgtgtct ttgttctgac aatacacata tacacaataa gttatgggcg actggtctgg  18720
tccagggtgg ggcaagcagg acacggggcc tgcctttact cctccaaact ggaaggcctg  18780
agataatttt ttaagtccgt atgggtcatt gccccaaaaa atcactgcaa acttccattg  18840
acactttgga tctcgtcttc catcctttcc caaaaagcgt ctataaaaga tgtgttgtgg  18900
cctagctttc gcaggacaat catctatctg tctgtaaggg accggtggtt gttggtatct  18960
tggatgtggc ttttttgggt gggtaactgg aacgcgcctc atacgaactc caggtctgtg  19020
gggtggtgat gttctgagta catagcggta ttcgcgagat gggccaggtt gtgggtcatc  19080
gtctggtgta ttatctcctg gtgggctact ggcaatttgt tcatgtgtgc taacaacagg  19140
gtaatccact tccatttcgt cctcggatga cgacccgtgc aagattatgg gctcttccac  19200
cgtctcctgc tcctgctgtt ccaccccctg ctgctcctgc tcttccacct cctctaactc  19260
ctgctgctcc tgctcttcca cctcctctaa ctcctgctct tcctgctctt ccacctcctc  19320
taactcctgc tcttcctgct cttccacctc ctctaactcc tgctcctcct gctcctcctg  19380
```

-continued ctcctgctct tgctcctcca cctcctctaa ttcctgctct tcctgctcct gctcttgctc 19440
ttccacctcc tgctcttgct cttccacctc ctgctcctct aactcctgct cctgctcctc 19500
taactcctgc tcctgctcct ctaactcctg ctcctgctcc tctaactcct gctcctgctc 19560
ctctaactcc tgctcctgct cctctaactc ctgctcctgc tcctctaact cctgctcctg 19620
ctcctctaac tcctgctcct gctcctctaa ctcctgctcc tgatcctcta actcctgctc 19680
ctgctcctct aactcctgct cctgctcctc ctgctgctcc tgctcctcct gctgctcctg 19740
ttcatcctgc tgctgctgct catcctgctg ctgctgctca tcctgctgct gctgctcatc 19800
ctgctgctgc tgctcatcct gctgctgctg ctcatcctgc tgctgctcat cctgctgctc 19860
ctgctcatcc tgctgctcct gctcatcctg ctgctcctgc tcatcctgct gctgctcatc 19920
ctgctgctgc tcatcctgct gctgctcatc ctgctgctgc tcatcctgct gctgctcatc 19980
ctgctgctgc tcatcctgct gctgctcatc ctgctgctgc tcatcctgct gctgctcatc 20040
ctgctgctgc tcatcctgct gctgctcatc ctgctgctgc tcatcctgct gctgctcatc 20100
ctgctgctgc tcatcctgct gctgctcatc ctgctgctgc tcatcctgct gctgctcatc 20160
ctgctgctgc tcatcctgct gctgctcatc ctgctgctgc tcatcctgct gctgtggctc 20220
ccgctgctgt ggctcccgct gctgtggctc ccgctgctgt ggctcccgct gctgtggctc 20280
ccgctgctgt ggctcccgct gctgtggctc ccgctgctgg ggctcccgct gctgtggctc 20340
ccgctgctgt ggctcctgct gctgtggctc ctgctgctgt ggctcctgct gctgtggctc 20400
ctgctgctgt ggctcctgct gctgtggctc ctgctgctgt ggctcctgct gctgtggctc 20460
ctgctgctgt ggctcctgct gttgtggctc ctgctgttgt ggctcctgca ggggctcctg 20520
ctgctgtggc tcctgctgtt gtggctcctg caggggctcc tgctgctgtg gctcctgctg 20580
ctgtggctcc tgctgttgtg gctcctgcag ggctcctgc tgctgtggct cctgctgctg 20640
tggctcctgc tgttgtggct cctgctgctg ttgtgaactt tggatgctca acgttttgtt 20700
tccatcgccc ccgtcctcct cgtcctcctt cttgtcctcc tcctcgtcat cctcctcgtc 20760
ctcattgtcc tcatcatcgt catcctcctc gtcctcctcc tcctcgtcct cctcctcgtc 20820
ctcctcctcg tcctcctcct cgtcatcctc ctcgtcatcc tcctcgtcat cctcctcgtc 20880
atcctcctcg tcatcctcct cgtcatcctc ctcgtcatcc tcctcgtcat cctcctcgtc 20940
atcctcctcg tcatcctcct cgtcatcctc ctcgtcctcc tcatctgtct cctgctcctc 21000
ctcatcatcc ttattgtcat tgtcatcctt gtcaacctga ctttccttgc taatctcgtt 21060
gtccccatta tcctcgccag cctgattatt ttcggaacat tctttttcat tcttggatgc 21120
ttcttctgca atctccgcaa ggagcaccaa catggctgtg tcatcacccc aggatccctc 21180
agacggggat gatgatccta tggagatggg agatgtaggc ggttggcgtg gcggagtatc 21240
gccatcgctg gatgatccca cgtagatcgg ggactctgtg gcccatgggg ggtacacact 21300
acggttggcg aagtcacatc tagggggaga gactgggggc gactgacata ttgggtttag 21360
tgtagaggga ccttgggggg acgatagcct tctttttctc aggctacgca gggtagacgg 21420
agctaaagag tctggtgacg acttggaggg aggctcgggt ggaggagtcg tgggtgagtg 21480
tggaggtgta gtctgctgcg agggtggcgg acgcataggt gttgaagagt ctggccttcc 21540
tgtaggactt gaaagcggtg gcctttgaga agactctgga gactgcgtgg gtggcaatgc 21600
aggagatgga gaatgagtat ccgtggtccc cggagacaca ggatgggatg gagggattgg 21660
ggaggaagac gtggttacgg ggggtaagag tgccggtgga ggtaaaggtg ttgcgggagc 21720

-continued

```
gggtgaagga atgggagcca ccggtaaagt aggactagac acaaatgctg gcagcccgga  21780
tgtgaacact gtgggacttc caggtatagg caaggtgtgg ggtccacatt cccggccgtc  21840
gatggagtcg gcgacatgct tccttcgcgg ttgtagatgt aggtcatcgc caaggtcaca  21900
tctttccgga gacctgtttc gtttcctaca acttcctctc gttaagggcg cgccggtgct  21960
ccgtcccgac ctcaggcgca ttcccggggg cgccatcctc gggaaatctg gtctgacaac  22020
caaagtaaaa ttatggaggc ggtggcagta tattcacatt atgcaatacc cgtagtgacc  22080
acaaggggga gctctcagac aattaagcgg ttacacacag tagcaggctg cagtaccgcc  22140
catggccaca ggatgtagat cgcagacact gaaacgctga aacacagcat taagctgcaa  22200
taccgccgat ggccaccaga tggcacgcgc cgccagcaaa tttaagtcct ggtggctcac  22260
ctgccaggta aacaaggtta aagtgggttt gctggccttg cgttgccatg gatgctacct  22320
aggcaagtcc agatatataa tccgggcgtg agaaacagaa acggccaata acccatgttt  22380
ttcgaaaacc accacacacc ttaacacaaa tcatgtacac ctggtattac tatttcccac  22440
acatcttata gcatttcaaa gataagggtg ccttacgggc cgcccgaaac aagtgggcgg  22500
gcgctactca ctgtttataa gtcagccgga ccaagctgct gctcttgggg acgtgactgc  22560
ttcgtggcgc agctgcctcc aaatgataca cacatttttt gattgtcccg ggcgccgcgt  22620
agtggagggc ggagttatat caagctactt tctgattggt gccccaggca ggactgccat  22680
aaaaactgaa gaaggcgtgt ctgctttgca gaatttaccc cccactgtgc tcccggttgc  22740
tggcaccggt tcagtggtcc gacctgtcgt ctgtgctccc ccgtggacga cgccgagtgc  22800
ctctcggggg tccatgtcta gcctcttcat ttcattacct tgggtggcgt tcatctggct  22860
agccctcctt ggcgcggttg gggtgcccg cgttcagggg cccatgcggg gctctgctgc  22920
cctcacctgc gccatcacgc cccgtgctga catagttagc gttacctggc aaaaaaggca  22980
gctccccggt cccgtaaacg tcgccacgta cagccattca tatggggtgg tggttcagac  23040
ccagtaccgc cacaaggcaa atataacctg tcctgggctt tggaactcta cccttgttat  23100
ccataacctt gcagtggatg atgagggctg ttacctgtgt atctttaact catttggtgg  23160
ccggcaggtg tcatgcacag cctgcctgga agtgacatct ccccctactg gacacgtgca  23220
ggtaaatagc acagaagacg cagacaccgt cacctgtttg gcaactggtc gcccaccccc  23280
caatgtcacc tgggccgcac cctggaacaa cgcctcttct acccaggagc agttcactga  23340
cagtgatggt cttacagttg cgtggaggac cgtgaggctg ccgcgtgggg ataataccac  23400
cccaagtgag ggaatatgtc tcatcacctg gggaaatgag agcatatcaa tcccggcttc  23460
tattcaaggc cccttggccc atgaccttcc cgcggcccag ggaactcttg ccggggttgc  23520
cattactctg gtgggcctat ttgggatatt cgcattacat cattgccgcc gcaagcaggg  23580
cggtgcatca cctacttcag atgacatgga cccccctatcc acccagtgac tagatggaca  23640
ccccgtgaac cgtcgtgctt acccaccccc ttctgattct gacagacaac actactatgt  23700
cccaaagact gttttttaca gcccgatggc ccttcaggcc tccttgagtg tctagctggt  23760
cccgtggtca ttgtgtggtt tggcagtcac ttccccattt tggtgtcgcg ttttgggttt  23820
tgccctgccc ccagccaacg tggatcatat tctttcccgt caggggagtg acaagctata  23880
ggacagaaag gtcacctggc ccaaacggag gatcctaggt gggtgtgcat ttattagacg  23940
ttggtgtgtt gaaggacgga tcaggcgggg aggagggggt gggggagact tactgcagca  24000
ctaggttagg ttgaaagccg ggtaaaaggg cgtggctaaa caacacctat actacttgtt  24060
attgtaggcc atggcggccg aggatttcct aaccatcttc ttagatgatg atgaatcctg  24120
```

-continued gaatgaaact ctaaatatga gcggatatga ctactctgga aacttcagcc tagaagtgag 24180
cgtgtgtgag atgaccaccg tggtgcctta cacgtggaac gttggaatac tctctctgat 24240
tttcctcata aatgttcttg gaaatggatt ggtcacctac attttttgca agcaccgatc 24300
gcgggcagga gcgatagata tactgctcct gggtatctgc ctaaactcgc tgtgtcttag 24360
catatctcta ttggcagaag tgttgatgtt tttgtttccc aatatcatct ccacaggctt 24420
gtgcagactt gaaatttttt tttactattt atatgtctac ttggatatct tcagtgttgt 24480
gtgcgtcagt ctagtgaggt acctcctggt ggcatattct acgcgttcct ggcccaagaa 24540
gcagtccctc ggatgggtac tgacatccgc tgcactgtta attgcattgg tgctgtcggg 24600
ggatgcctgt cgacacagga gcagggtggt cgacccggtc agcaagcagg ccatgtgtta 24660
tgagaacgcg ggaaacatga ctgcagactg gcgactgcat gtcagaaccg tgtcagttac 24720
tgcaggtttc ctgttacccc tggccctcct tattctgttt tatgctctca cctggtgtgt 24780
ggtgaggagg acaaagctgc aagccaggcg gaaggtaagg ggggtgattg ttgctgtggt 24840
gctgctgttt tttgtgtttt gcttccctta ccacgtacta aatctactgg acactctgct 24900
aaggcgacgc tggatccggg acagctgcta tacgcggggg ttgataaacg tgggtctggc 24960
agtaacctcg ttactgcagg cactgtacag cgccgtggtt cccctgatat actcctgcct 25020
gggatccctc tttaggcaga ggatgtacgg tctcttccaa agcctcaggc agtctttcat 25080
gtccggcgcc accacgtagc ccgcggatgt ctacgtgccc ttccccctta atttaatcta 25140
gcctcccgtt cccatgatgc agagaggcga atttggtttg tacacagatg tgactatgta 25200
tttgttttat tatgcgatta aatgaggggt ctgatcccaa aagcaatgtt tagtggtggt 25260
cgttgatctt cttgacgctc cataggtaga ttgactggaa cgccatggcc cacggggaca 25320
tggacagggg tgttaggtct ggtggaacat gctgccactg ccacggatgg aacatcagag 25380
atgggtctat gatcagggca gcgtgtcgcc cgtcactgga tgtaagtccg gccaccgtgg 25440
agttgcctgt ggggtttctg ggatagtgtc tggctggcag ggtctcatcc gcggcatttc 25500
catggtaggt gagggttatc tcgcctcgct gtctcagtat gtactcgagg gcgtcctgct 25560
cgtaccggac ccccaggtac tctccctggg cccagctggg cagcaccgtc ccccgcaaca 25620
ctcggaggaa aacgctctta gtgttctgag ggatctgtat gtttagccag tggctgtcat 25680
acagcttgga cacgttggtc tccaggttta ccgcccagcg ctggggtggt gtgggtccgt 25740
acgtgtatgg tgaggattcc gaccggccca ctacacccag ggccaccagc agctggaagc 25800
ccacctcgcc acagcagatg gagaatgtgt cgggtctgtt tagaaactct gtcagggtgg 25860
aggcacaggt agggtcgtta cacagcgcca ggacccatcc cctggcgctg gcgtagctgg 25920
cctggcagcc tgttctgaga catgtaatca gaccagagaa ccccgacaag gactgtcctc 25980
gtttaagctc ttccacagtc accgtggcca cctcaaagcc cgtgttctgc aacgcggcca 26040
tgagcgcgta cggggcactg ctcccaggca gcaccaacgc ggccacacgg cgcggggagg 26100
tggggcacga aaacaggcgc agctgactcc caaggcacat ggcccttagg ctgcccaggt 26160
gatgctccag acgacccagg tccttcctgt gcatgtcctc cagtgggtgc aggggaggcg 26220
tcaccaggtt ccacatttcg tcagaaaagg aggtccatga gacttgcaag gaagtcaggg 26280
tctcttgaaa cacaactgtc tcgttctgca aaaccgtgac gttgttgcct tgtccctcgg 26340
ggccaacggt gcccagtggg tgtgccacgc agcggtagtc cctggccgcc cgcagcacct 26400
ctgacaagtg tacctggggc acctcaacca gtgccccagg ggtctctgaa accataagtt 26460

-continued

```
cgagcgggtt agggtgggcg ggtagtgaga gctgcagtcc cctgcagccg gccagggcca  26520
tctcgattgc agatgggaga agccctccgt cccctatgtc gtgcccagat acaatgagcc  26580
tcttggacat caggtactta acaagcatga acaggctggc gaccgtggac gggttcagag  26640
ggggtattgg gtgcctggat gccaggaagt tgtgctcgaa ggtggacccg gctatgagac  26700
agctctgatt cacggccagg tataccaggg cgttgccttc gacctttacg tccggggtga  26760
ccctgtatct ggatcccttg acctcggccc agctggtaaa caccaccgag ttgaagggaa  26820
ggacctccac cgtttcttgc tgttgtgtga tgcgcacatg gcgctccgaa agcgtcggag  26880
agctggcagc cgaggagatg gacagtgcca ctcccagctc ccggcagaat tccttgcagg  26940
cgaagaggca ctcctgtagg aggccggctt ggtggtcctc tggactccac gccacggcgc  27000
cagttagcac tacgtcctgg agcttggaca cgggactgaa catgaggttg gtgagagcct  27060
cggtgatggc ataggtggcc ccggtggata cattagtagc catcttgtag gcctgctccc  27120
ccatggccat tgcctgaccc ctccacgctg gcactggaag cagctcctgg ggcagggcct  27180
tcacccaggt ctcgaagtcc ttgtgtagga ggttggccat ggacggagtg atggcctcca  27240
ccgtgtcggg cactctgggc gccaccctct cggccagcat ggacgagtgc agcaccaggt  27300
ggtagtctga aaccggtatg tccaggggtc ccacgccagc ctgttgggcg atgaggccgt  27360
tggagcatcg gtccatgtgt cgcgtaaaga actccttgct gccaaccgtc gagtggcgaa  27420
gtaactggtg gattgtggag ccggtggcaa aaaggcccca gtcaacatcc tcggggtgcc  27480
ccgagacgcg gacaccatcg gacagcgcca gccaggggga cgggggggtg gacgacggct  27540
ggtctacaga gaagaccctc gtggtctccc cggtcaggtc gtctactatt ctgatgcctg  27600
ggtgctccga ggtcctcccg aggaccgtta cctggcacgc gcacaggcgc gcggcgcgct  27660
gcagtacctc caacggggtc tcgcccagat ccccaggcac cgcgcccgac tctgccacca  27720
ccgcaaacac cagggagcaa tacacgttga gaaagtgctc tgccaccgcc gccttcacgg  27780
catccggacc ggccgcggga tccgcaggca ggtgggtgcg cacctcgtcg ggtagcttgg  27840
agacaaacag ctccaggccg gtccgcggcg ccagcgcctg caggtgcctc accaccgggg  27900
ccgggtcatg cgatctgttt agtccggaga agatagggcc cttggcaagc cgctggacca  27960
gcttcagggt ctccaagatg cgcaccgcat tgtcggagct gtcgcgatag aggttagggt  28020
aggtgtccgg tccatccgtg ggctcaaacc tgcccagaca caccactgtc tgctggggga  28080
tcatccttct cagggagatg cattctttgg aagtagtggt agagatggag cagactgcca  28140
gggcgttgcc aggagtggtg gcgatggtgc gcaccgtttt taagaaaccc cccagggtgg  28200
ggactcccgc tccctgcagc atctcggcct gctgtacgcc cttggcgaat atgcgacgga  28260
atcggctgtg cgcacggggt cccagggccg gttcggtggc atacaggccg gtgagggccc  28320
cctgtgtctg tccgcctgga aacagggtgc tgtgaaacag caggttgcca aggccgcgaa  28380
tacccctctg cacgctgctg tggacgtggg tgtacgctcc gtggatcccg aacgcctgtc  28440
tggcacagtt ccagggccac cgttccatgg tgcatcttcc cggtatcaca aagtacctgg  28500
ccacgttata attgtccccg gttgaagcct gcaccgccag cggtagcagg tctgccccca  28560
gggatatcat aacagcctgc ataatgacat catcttcaat gtgtggccta gccacgggct  28620
ggggaccctc gggcacttcc aacccctcgt acggtaccag gtcggtattt tgtgtaaatg  28680
ccctgataaa ctgaggtggg tgtggttcta gcagggtctg tgtgattttg gacaccaggt  28740
gcctgcccac ttccactcta gcccactcct gcaatcctag ctcttgcagc agaactgcaa  28800
gctctgttga caatgttgtg ggccggtggt gcatgtttgg cccgtagcca aaggatacaa  28860
```

```
cacgctcgct cccccgtggc acagaccgcc tgatgacatg gggatatcca aggagcggtg  28920
acagcacagc gagcaccgtc tgtatttcca catcccgtct ctctcgctcc tccctcgaag  28980
tgggaggtct tcggaaagtt atccatagca gatagtagcc tccggtgcca ccgggtacga  29040
gagtgagtgt gcccgtacgg cttgtataaa agttcacaaa agcttcctca tccgcggtga  29100
gatcactctc caaccacagc ccagtgacgt cgtaggccat gcctagaggg cgcaccgccc  29160
ccggggacac cctctgtagt caggctgccg agaaacccgc gagatctctg gggagtagga  29220
agaaacttag aatccccaaa tatgtcgcag tcacaggttg tcgggcagag tctgtttccg  29280
ctttcatggg atccacagtt acttgtagcc atgtcactaa cctcaaatac tcaaaaaaag  29340
ctatcgatgg aaaaatgctg tggtcctagg ttagtccgtg ggaaacaaaa cttcctcata  29400
cacttcatct gcaggctgaa atggtggcgg atccagactc cttacaccac agttgctcac  29460
attagagata cctgattggt taatacaagc ggacgcacgc gttggtggag gcgtgttgtc  29520
gcccaagata ctagcatagg tgactgtgcg ttcgctatgt agttgctgca tttcaagttg  29580
ggtcgttact tctgtgttgc aaacccttac tggagataat gccatgtctg ttgtggaact  29640
taaaatacgc gagtgtataa catttctaga tggtagaggt ggtaaacggc gagctaaatg  29700
attaacatcg ggacatatcc tgcctgcatg agcatgtggt gtgtcgtgtg gtgtatatat  29760
tggtaatctt gttgttacat tgttgaacga cacaagtctg ctctctcggt agagataacc  29820
caccagtacg gcttggccag tacctaataa gaaaaaataa aatcgttaat ctctgttttt  29880
atgtggcgct ggtgttccaa ttataaataa aaacacaact cacttaatat cacaattaca  29940
caaatcagtc ctgaagtaac acctgtagtc caaccgtcag tgtagagcag gactaactta  30000
acacagcatc cagcacatgt ccatgctaag gaaataaacc aaagttatgt ttcggtttgc  30060
tttatgacca gggagctgct acccaggtac aaaaaatcct tacccaaaaa tagaaacagg  30120
aagccaccag agagtgaagc tttgtgaaag ctttgccagc agaagaaaca atataataaa  30180
aagccacagc ctgctagtaa tgttatactc cctgtaaata aaaaatatgg acagtaataa  30240
tttatgacac ccaataagta tgtggaaaaa atgtaatgta aaccactata ctggtaaaaa  30300
catacttcg ttattggtgt cttgttcgcg ctttataaac agtatcccta ttgttgtggt  30360
tagtgtaacc aacactcctc cttgtaaaag taaaaatgac ataagcccct tagttgatcc  30420
aatccaatgt cgtttcattg ttataaacaa gccggtcata cctgtaataa agttattcat  30480
tacaaaatgt tataatagta ttggtaatgt ttagttaaga taatgtaaac ttcacagtag  30540
tcatatacca atatgtatgc agcttatgca tcctgcgatg attacagaaa ggcatgaatg  30600
ggaaacgcaa aaaaaggccg gtgttgcctt gagtatacct gtagtaaaaa ataaataata  30660
ttgttggttg caatgcttag gtgcaagcag acataattgc atagcagtaa aaaccagact  30720
taccaccaca tattgcaaac acacatgcag cgagcttgag acaaggccca ttatctgttg  30780
caaagatatg tataaaaaaa acaagcaaca atgtccataa tggcaaaaaa aactggcaat  30840
gtgtccagtt gttgtaaatc tgcaatccca ttgagaatat aagtaccaac accataacaa  30900
tgcacagtaa tccgctatca atagtgcatt taacgactct taatgttcca ccaagtgata  30960
gaatggctga aaaacacata caggggaatt acgttttttt aaaaaattgg aaatattaga  31020
tacataattt ttatttaata aaaaaccttt agtaaaactt accagtaatt atagacaata  31080
aacttataat acaaacacaa acagtactca aagtactttg agtagagaaa ctccaactgg  31140
caaaggcaat acatcctaaa acaaaagaca aatacacgag acatttaaac aatgtatact  31200
```

-continued tagaaagaaa taagttaaac atttaaaaaa tgtaacttac caacaattat agatggtcca 31260
atgggagggg aagcttgaaa acgttgtttt tttgactgca catatatgtt gttattgtac 31320
aaaaaagttg gtagtaaaca cttatgttac tgagcaaaaa tatggtgttt tgtaaattta 31380
tagttaaaag acaaaacata atagacaaac acccacaaca tgttataagt gctgcaaacc 31440
aagtacccca caggtatttt ttgtaattca ttgtagacaa aaagcccaag gcccaaaaat 31500
gaagtggaca aaagaaatat gtaattaagt gtagttggac aaggaattat atagctggat 31560
gagttagttt tgcacagaac cagacatcct atttttgttt ggaaacctaa aatccggatg 31620
aagggcttat aaaatggcac agctgcaaaa agctgataat gtaacactgc atcctggtgt 31680
ttttgattgt agcggaaaaa tgtaataaat tttacagaca gttttgccta ctgagaacat 31740
gttgaaaaaa aggcactaag ggcttttttg ccaaaggaaa aatgccccg tggggttagg 31800 ggaaaggggg gatggggtga tgggggaatg gtgggaaagg ggggatgggg tgatggggga 31860
atggtgggaa aggggtgatg gggtgatggg ggaatggggg gaaaggggga atggggggaa 31920
agggggaatg gggggaaagg gggaatgggg ggaaaggggg gatgggggga aagggggaat 31980
ggggggaaag ggggaatggg gggaaagggg ggatgggggg aaaggggggaa tgggggggaaa 32040 ggggggatgg ggggaaacgg gggatggggg gaaagggggg atgggggga aagggggggat 32100 ggggggggaaa gggggggatgg gggggaaagg ggggatgggg gggaaagggg ggatggggaa 32160
gggggggggg agggggaagg gggtgaaggg ggaagggggg aggcgaa 32207

<210> SEQ ID NO 21
<211> LENGTH: 94
<212> TYPE: PRT
<213> ORGANISM: Kaposi's sarcoma-associated herpesvirus

<400> SEQUENCE: 21

Met Ala Pro Val His Val Leu Cys Cys Val Ser Val Leu Leu Ala Thr
1 5 10 15

Phe Tyr Leu Thr Pro Thr Glu Ser Ala Gly Ser Leu Val Ser Tyr Thr
20 25 30

Pro Asn Ser Cys Cys Tyr Gly Phe Gln Gln His Pro Pro Pro Val Gln
35 40 45

Ile Leu Lys Glu Trp Tyr Pro Thr Ser Pro Ala Cys Pro Lys Pro Gly
50 55 60

Val Ile Leu Leu Thr Lys Arg Gly Arg Gln Ile Cys Ala Asp Ser Lys
65 70 75 80

Asn Trp Val Arg Gln Leu Met Gln Arg Leu Pro Ala Ile Ala
85 90

<210> SEQ ID NO 22
<211> LENGTH: 94
<212> TYPE: PRT
<213> ORGANISM: Kaposi's sarcoma-associated herpesvirus

<400> SEQUENCE: 22

Met Asp Thr Lys Gly Ile Leu Leu Val Ala Val Leu Thr Ala Leu Leu
1 5 10 15

Cys Leu Gln Ser Gly Asp Thr Leu Gly Ala Ser Trp His Arg Pro Asp
20 25 30

Lys Cys Cys Leu Gly Tyr Gln Lys Arg Pro Leu Pro Gln Val Leu Leu
35 40 45

Ser Ser Trp Tyr Pro Thr Ser Gln Leu Cys Ser Lys Pro Gly Val Ile

-continued

```
     50                  55                  60

Pro Leu Thr Lys Arg Gly Arg Gln Val Cys Ala Asp Lys Ser Lys Asp
 65                  70                  75                  80

Trp Val Lys Lys Leu Met Gln Gln Leu Pro Val Thr Ala Arg
                 85                  90


<210> SEQ ID NO 23
<211> LENGTH: 93
<212> TYPE: PRT
<213> ORGANISM: Human

<400> SEQUENCE: 23

Met Gln Val Ser Thr Ala Ala Leu Ala Val Leu Leu Cys Thr Met Ala
  1               5                  10                  15

Leu Cys Asn Gln Val Leu Ser Ala Pro Leu Ala Ser Asp Thr Pro Thr
             20                  25                  30

Ala Cys Cys Phe Ser Tyr Thr Ser Arg Gln Ile Pro Gln Asn Phe Ile
         35                  40                  45

Ala Asp Tyr Phe Glu Thr Ser Ser Gln Cys Ser Lys Pro Ser Val Ile
     50                  55                  60

Pro Leu Thr Lys Arg Gly Arg Gln Val Cys Ala Asp Pro Ser Glu Glu
 65                  70                  75                  80

Trp Val Gln Lys Tyr Val Ser Asp Leu Glu Leu Ser Ala
                 85                  90


<210> SEQ ID NO 24
<211> LENGTH: 92
<212> TYPE: PRT
<213> ORGANISM: Human

<400> SEQUENCE: 24

Met Lys Leu Cys Val Thr Val Leu Ser Leu Leu Met Leu Val Ala Ala
  1               5                  10                  15

Phe Cys Ser Pro Ala Leu Ser Ala Pro Met Gly Ser Asp Pro Pro Thr
             20                  25                  30

Ala Cys Cys Phe Ser Tyr Thr Ala Arg Lys Leu Pro Arg Asn Phe Val
         35                  40                  45

Val Asp Tyr Tyr Glu Thr Ser Ser Leu Cys Ser Gln Pro Ala Val Val
     50                  55                  60

Phe Gln Thr Lys Arg Ser Lys Gln Val Cys Ala Asp Pro Ser Glu Ser
 65                  70                  75                  80

Trp Val Gln Glu Tyr Val Tyr Asp Leu Glu Leu Asn
                 85                  90


<210> SEQ ID NO 25
<211> LENGTH: 91
<212> TYPE: PRT
<213> ORGANISM: Human

<400> SEQUENCE: 25

Met Lys Val Ser Ala Ala Arg Leu Ala Val Ile Leu Ile Ala Thr Ala
  1               5                  10                  15

Leu Cys Ala Pro Ala Ser Ala Ser Pro Tyr Ser Ser Asp Thr Thr Pro
             20                  25                  30

Cys Cys Phe Ala Tyr Ile Ala Arg Pro Leu Pro Arg Ala His Ile Lys
         35                  40                  45

Glu Tyr Phe Tyr Thr Ser Gly Lys Cys Ser Asn Pro Ala Val Val Phe
     50                  55                  60
```

```
Val Thr Arg Lys Asn Arg Gln Val Cys Ala Asn Pro Glu Lys Lys Trp
 65                 70                  75                  80

Val Arg Glu Tyr Ile Asn Ser Leu Glu Met Ser
                85                  90


<210> SEQ ID NO 26
<211> LENGTH: 204
<212> TYPE: PRT
<213> ORGANISM: Kaposi's sarcoma-associated herpesvirus

<400> SEQUENCE: 26

Met Cys Trp Phe Lys Leu Trp Ser Leu Leu Leu Val Gly Ser Leu Leu
  1               5                  10                  15

Val Ser Gly Thr Arg Gly Lys Leu Pro Asp Ala Pro Glu Phe Glu Lys
             20                  25                  30

Asp Leu Leu Ile Gln Arg Leu Asn Trp Met Leu Trp Val Ile Asp Glu
         35                  40                  45

Cys Phe Arg Asp Leu Cys Tyr Arg Thr Gly Ile Cys Lys Gly Ile Leu
     50                  55                  60

Glu Pro Ala Ala Ile Phe His Leu Lys Leu Pro Ala Ile Asn Asp Thr
 65                  70                  75                  80

Asp His Cys Gly Leu Ile Gly Phe Asn Glu Thr Ser Cys Leu Lys Lys
                 85                  90                  95

Leu Ala Asp Gly Phe Phe Glu Phe Glu Val Leu Phe Lys Phe Leu Thr
            100                 105                 110

Thr Glu Phe Gly Lys Ser Val Ile Asn Val Asp Val Met Glu Leu Leu
        115                 120                 125

Thr Lys Thr Leu Gly Trp Asp Ile Gln Glu Glu Leu Asn Lys Leu Thr
    130                 135                 140

Lys Thr His Tyr Ser Pro Pro Lys Phe Asp Arg Gly Leu Leu Gly Arg
145                 150                 155                 160

Leu Gln Gly Leu Lys Tyr Trp Val Arg His Phe Ala Ser Phe Tyr Val
                165                 170                 175

Leu Ser Ala Met Glu Lys Phe Ala Gly Gln Ala Val Arg Val Leu Asp
            180                 185                 190

Ser Ile Pro Asp Val Thr Pro Asp Val His Asp Lys
        195                 200


<210> SEQ ID NO 27
<211> LENGTH: 212
<212> TYPE: PRT
<213> ORGANISM: Human

<400> SEQUENCE: 27

Met Asn Ser Phe Ser Thr Ser Ala Phe Gly Pro Val Ala Phe Ser Leu
  1               5                  10                  15

Gly Leu Leu Leu Val Leu Pro Ala Ala Phe Pro Ala Pro Val Pro Pro
             20                  25                  30

Gly Glu Asp Ser Lys Asp Val Ala Ala Pro His Arg Gln Pro Leu Thr
         35                  40                  45

Ser Ser Glu Arg Ile Asp Lys Gln Ile Arg Tyr Ile Leu Asp Gly Ile
     50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95
```

```
Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210


<210> SEQ ID NO 28
<211> LENGTH: 449
<212> TYPE: PRT
<213> ORGANISM: Kaposi's sarcoma-associated herpesvirus

<400> SEQUENCE: 28

Met Asp Pro Gly Gln Arg Pro Asn Pro Phe Gly Ala Pro Gly Ala Ile
  1               5                  10                  15

Pro Lys Lys Pro Cys Leu Ser Gln Gly Ser Pro Gly Thr Ser Gly Ser
             20                  25                  30

Gly Ala Pro Cys Asp Glu Pro Ser Arg Ser Glu Ser Pro Gly Glu Gly
        35                  40                  45

Pro Ser Gly Thr Gly Gly Ser Ala Ala Ala Gly Asp Ile Thr Arg Gln
     50                  55                  60

Ala Val Val Ala Ala Ile Thr Glu Trp Ser Arg Thr Arg Gln Leu Arg
 65                  70                  75                  80

Ile Ser Thr Gly Ala Ser Glu Gly Lys Ala Ser Ile Lys Asp Trp Ile
                85                  90                  95

Val Cys Gln Val Asn Ser Gly Lys Phe Pro Gly Val Glu Trp Glu Asp
            100                 105                 110

Glu Glu Arg Thr Arg Phe Arg Ile Pro Val Thr Pro Leu Ala Asp Pro
        115                 120                 125

Cys Phe Glu Trp Arg Arg Asp Gly Glu Leu Gly Val Val Tyr Ile Arg
    130                 135                 140

Glu Arg Gly Asn Met Pro Val Asp Ala Ser Phe Lys Gly Thr Arg Gly
145                 150                 155                 160

Arg Arg Arg Met Leu Ala Ala Leu Arg Arg Thr Arg Gly Leu Gln Glu
                165                 170                 175

Ile Gly Lys Gly Ile Ser Gln Asp Gly His His Phe Leu Val Phe Arg
            180                 185                 190

Val Arg Lys Pro Glu Glu Glu Gln Cys Val Glu Cys Gly Val Val Ala
        195                 200                 205

Gly Ala Val His Asp Phe Asn Asn Met Ala Arg Leu Leu Gln Glu Gly
    210                 215                 220

Phe Phe Ser Pro Gly Gln Cys Leu Pro Gly Glu Ile Val Thr Pro Val
225                 230                 235                 240

Pro Ser Cys Thr Thr Ala Glu Gly Gln Glu Ala Val Ile Asp Trp Gly
```

-continued

```
                245                 250                 255

Arg Leu Phe Ile Arg Met Tyr Tyr Asn Gly Glu Gln Val His Glu Leu
            260                 265                 270

Leu Thr Thr Ser Gln Ser Gly Cys Arg Ile Ser Ser Ala Leu Arg Arg
        275                 280                 285

Asp Pro Ala Val His Tyr Cys Ala Val Gly Ser Pro Gly Gln Val Trp
    290                 295                 300

Leu Pro Asn Val Pro Asn Leu Ala Cys Glu Ile Ala Lys Arg Glu Leu
305                 310                 315                 320

Cys Asp Thr Leu Asp Ala Cys Ala Lys Gly Ile Leu Leu Thr Ser Ser
                325                 330                 335

Cys Asn Gly Ile Phe Cys Val Cys Tyr His Asn Gly Pro Val His Phe
            340                 345                 350

Ile Gly Asn Thr Val Pro Pro Asp Ser Gly Pro Leu Leu Leu Pro Gln
        355                 360                 365

Gly Lys Pro Thr Arg Ile Phe Asn Pro Asn Thr Phe Leu Val Gly Leu
    370                 375                 380

Ala Asn Ser Pro Leu Pro Ala Pro Ser His Val Thr Cys Pro Leu Val
385                 390                 395                 400

Lys Leu Trp Leu Gly Lys Pro Val Ala Val Gly Lys Leu Glu Pro His
                405                 410                 415

Ala Pro Ser Pro Arg Asp Phe Ala Ala Arg Cys Ser Asn Phe Ser Asp
            420                 425                 430

Ala Cys Val Val Leu Glu Ile Met Pro Lys Pro Leu Trp Asp Ala Met
        435                 440                 445

Gln


<210> SEQ ID NO 29
<211> LENGTH: 393
<212> TYPE: PRT
<213> ORGANISM: Human

<400> SEQUENCE: 29

Met Ala Ser Gly Arg Ala Arg Cys Thr Arg Lys Leu Arg Asn Trp Val
  1               5                  10                  15

Val Glu Gln Val Glu Ser Gly Gln Phe Pro Gly Val Cys Trp Asp Asp
             20                  25                  30

Thr Ala Lys Thr Met Phe Arg Ile Pro Trp Lys His Ala Gly Lys Gln
         35                  40                  45

Asp Phe Arg Glu Asp Gln Asp Ala Ala Phe Phe Lys Ala Trp Ala Ile
     50                  55                  60

Phe Lys Gly Lys Tyr Lys Glu Gly Asp Thr Gly Gly Pro Ala Val Trp
 65                  70                  75                  80

Lys Thr Arg Leu Arg Cys Ala Leu Asn Lys Ser Ser Glu Phe Lys Glu
                 85                  90                  95

Val Pro Glu Arg Gly Arg Met Asp Val Ala Glu Pro Tyr Lys Val Tyr
            100                 105                 110

Gln Leu Leu Pro Pro Gly Ile Val Ser Gly Gln Pro Gly Thr Gln Lys
        115                 120                 125

Val Pro Ser Lys Arg Gln His Ser Ser Val Ser Ser Glu Arg Lys Glu
    130                 135                 140

Glu Glu Asp Ala Met Gln Asn Cys Thr Leu Ser Pro Ser Val Leu Gln
145                 150                 155                 160

Asp Ser Leu Asn Asn Glu Glu Glu Gly Ala Ser Gly Gly Ala Val His
```

```
                165                 170                 175

Ser Asp Ile Gly Ser Ser Ser Ser Ser Ser Ser Pro Glu Pro Gln Glu
            180                 185                 190

Val Thr Asp Thr Thr Glu Ala Pro Phe Gln Gly Asp Gln Arg Ser Leu
        195                 200                 205

Glu Phe Leu Leu Pro Pro Glu Pro Asp Tyr Ser Leu Leu Leu Thr Phe
    210                 215                 220

Ile Tyr Asn Gly Arg Val Val Gly Glu Ala Gln Val Gln Ser Leu Asp
225                 230                 235                 240

Cys Arg Leu Val Ala Glu Pro Ser Gly Ser Glu Ser Ser Met Glu Gln
                245                 250                 255

Val Leu Phe Pro Lys Pro Gly Pro Leu Glu Pro Thr Gln Arg Leu Leu
            260                 265                 270

Ser Gln Leu Glu Arg Gly Ile Leu Val Ala Ser Asn Pro Arg Gly Leu
        275                 280                 285

Phe Val Gln Arg Leu Cys Pro Ile Pro Ile Ser Trp Asn Ala Pro Gln
    290                 295                 300

Ala Pro Pro Gly Pro Gly Pro His Leu Leu Pro Ser Asn Glu Cys Val
305                 310                 315                 320

Glu Leu Phe Arg Thr Ala Tyr Phe Cys Arg Asp Leu Val Arg Tyr Phe
                325                 330                 335

Gln Gly Leu Gly Pro Pro Pro Lys Phe Gln Val Thr Leu Asn Phe Trp
            340                 345                 350

Glu Glu Ser His Gly Ser Ser His Thr Pro Gln Asn Leu Ile Thr Val
        355                 360                 365

Lys Met Glu Gln Ala Phe Ala Arg Tyr Leu Leu Glu Gln Thr Pro Glu
    370                 375                 380

Gln Gln Ala Ala Ile Leu Ser Leu Val
385                 390


<210> SEQ ID NO 30
<211> LENGTH: 425
<212> TYPE: PRT
<213> ORGANISM: Human

<400> SEQUENCE: 30

Met Cys Asp Arg Asn Gly Gly Gly Arg Leu Arg Gln Trp Leu Ile Glu
  1               5                  10                  15

Gln Ile Asp Ser Ser Met Tyr Pro Gly Leu Ile Trp Glu Asn Glu Glu
             20                  25                  30

Lys Ser Met Phe Arg Ile Pro Trp Lys His Ala Gly Lys Gln Asp Tyr
         35                  40                  45

Asn Gln Glu Val Asp Ala Ser Ile Phe Lys Ala Trp Ala Val Phe Lys
     50                  55                  60

Gly Lys Phe Lys Glu Gly Asp Lys Ala Glu Pro Ala Thr Trp Lys Thr
 65                  70                  75                  80

Arg Leu Arg Cys Ala Leu Asn Lys Ser Pro Asp Phe Glu Glu Val Thr
                 85                  90                  95

Asp Arg Ser Gln Leu Asp Ile Ser Glu Pro Tyr Lys Val Tyr Arg Ile
            100                 105                 110

Val Pro Glu Glu Asp Gln Lys Cys Lys Leu Gly Val Ala Thr Ala Gly
        115                 120                 125

Cys Val Asn Glu Val Thr Glu Met Glu Cys Gly Arg Ser Glu Ile Asp
    130                 135                 140
```

-continued

```
Glu Leu Ile Lys Glu Pro Ser Val Asp Asp Tyr Met Gly Met Ile Lys
145                 150                 155                 160

Arg Ser Pro Ser Pro Pro Asp Ala Cys Arg Ser Gln Leu Leu Pro Asp
                165                 170                 175

Trp Trp Ala His Glu Pro Ser Thr Gly Arg Arg Leu Val Thr Gly Tyr
            180                 185                 190

Thr Thr Tyr Asp Ala His His Ser Ala Phe Ser Gln Met Val Ile Ser
        195                 200                 205

Phe Tyr Tyr Gly Gly Lys Leu Val Gly Gln Ala Thr Thr Thr Cys Pro
    210                 215                 220

Glu Gly Cys Arg Leu Ser Leu Ser Gln Pro Gly Leu Pro Gly Thr Lys
225                 230                 235                 240

Leu Tyr Gly Pro Glu Gly Leu Glu Leu Val Arg Phe Pro Pro Ala Asp
                245                 250                 255

Thr Ile Pro Ser Glu Arg Gln Arg Gln Val Thr Arg Lys Leu Phe Gly
            260                 265                 270

His Leu Glu Arg Gly Val Leu His Ser Ser Arg Gln Gly Val Phe Val
        275                 280                 285

Lys Arg Leu Cys Gln Gly Arg Val Phe Cys Val Val Val Val Val Val
    290                 295                 300

Cys Lys Gly Arg Pro Asn Lys Leu Glu Arg Asp Glu Val Val Gln Val
305                 310                 315                 320

Phe Asp Thr Ser Gln Phe Phe Arg Glu Leu Gln Gln Phe Tyr Asn Ser
                325                 330                 335

Gln Gly Arg Leu Pro Asp Gly Arg Val Val Leu Cys Phe Gly Glu Glu
            340                 345                 350

Phe Pro Asp Met Ala Pro Leu Arg Ser Lys Leu Ile Leu Val Gln Ile
        355                 360                 365

Glu Gln Leu Tyr Val Arg Gln Leu Ala Glu Glu Ala Gly Lys Ser Cys
    370                 375                 380

Gly Ala Gly Ser Val Met Gln Ala Pro Glu Glu Pro Pro Pro Asp Gln
385                 390                 395                 400

Val Phe Arg Met Phe Pro Asp Ile Cys Ala Ser His Gln Arg Ser Phe
                405                 410                 415

Phe Arg Glu Asn Gln Gln Ile Thr Val
            420                 425
```

UNIQUE ASSOCIATED KAPOSI'S SARCOMA VIRUS SEQUENCES AND USES THEREOF

This application is a national stage application, filed under 35 U.S.C. §371 of PCT International Application No. PCT/US97/13346, filed Jul. 22, 1997, which is a continuation-in-part and claims priority of U.S. Ser. No. 08/757,669 Nov. 29, 1996, now U.S. Pat. No, 6,183,751, U.S. Ser. No. 08/748,640 Nov. 13, 1996, now U.S. Pat. No. 5,854,398, U.S. Ser. No. 08/747,887 Nov. 13, 1996, now U.S. Pat. No. 5,853,734, U.S. Ser. No. 08/728,323 Oct. 10, 1996, now U.S. Pat. No. 5,948,676, U.S. Ser. No. 08/708,678 Sep. 5, 1996, now U.S. Pat. No. 5,859,225, U.S. Ser. No. 08/729,615 Jul. 25, 1996, now abandoned, U.S. Ser. No. 08/687,253 Jul. 25, 1996, now U.S. Pat. No. 5,854,418, U.S. Ser. No. 08/686,350 Jul. 25, 1996, now U.S. Pat. No. 5,831,064, U.S. Ser. No. 08/686,349 Jul. 25, 1996, now U.S. Pat. No. 5,861,500, and U.S. Ser. No. 08/686,243 Jul. 25, 1996, now U.S. Pat. No. 5,863,787.

The invention disclosed herein was made with Government support under a co-operative agreement CCU210852 from the Centers for Disease Control and Prevention, and under National Institutes of Health, National Cancer Institute award CA67391 of the Department of Health and Human Services. Accordingly, the U.S. Government has certain rights in this invention.

Throughout this application, various publications may be referenced by Arabic numerals in brackets. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

Kaposi's sarcoma-associated herpesvirus (KSHV) is a new human herpesvirus (HHV8) believed to cause Kaposi's sarcoma (KS) [1,2].

Kaposi's sarcoma is the most common neoplasm occurring in persons with acquired immunodeficiency syndrome (AIDS). Approximately 15–20% of AIDS patients develop this neoplasm which rarely occurs in immunocompetent individuals. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS. KS is uncommon among adult AIDS patients infected through heterosexual or parenteral HIV transmission, or among pediatric AIDS patients infected through vertical HIV transmission. Agents previously suspected of causing KS include cytomegalovirus, hepatitis B virus, human papillomavirus, Epstein-Barr virus (EBV), human herpesvirus 6, human immunodeficiency virus (HIV), and Mycoplasma penetrans. Non-infectious environmental agents, such as nitrite inhalants, also have been proposed to play a role in KS tumorigenesis. Extensive investigations, however, have not demonstrated an etiologic association between any of these agents and AIDS-KS.

SUMMARY OF THE INVENTION

This invention provides an isolated nucleic acid molecule which encodes Kaposi's Sarcoma-Associated Herpesvirus (KSHV) polypeptides. This invention provides an isolated polypeptide molecule of KSHV. This invention provides an antibody specific to the polypeptide. Antisense and triplex oligonucleotide molecules are also provided. This invention provides a vaccine for Kaposi's Sarcoma (KS). This invention provides methods of vaccination, prophylaxis, diagnosis and treatment of a subject with KS and of detecting expression of a DNA virus associated with Kaposi's sarcoma in a cell.

BRIEF DESCRIPTION OF THE FIGURES

FIG. 1:

Annotated long unique region (LUR) and terminal repeat (TR) of the KSHV genome. The orientation of identified ORFs in the LUR are denoted by the direction of arrows, with ORFs similar to HVS in dark blue and dis-similar ORFs in light blue. Seven blocks (numbered) of conserved herpesvirus genes with non-conserved interblock regions (lettered) are shown under the kilobase marker; the block numbering scheme differs from the original description by Chee (Chee et al., 1990, *Curr. Topics Microbiol. Immunol.* 154, 125–169) The overlapping cosmid (Z prefix) and lambda (L prefix) clones used to map the KSHV genome are compared to the KS5 lambda phage clone from a KS lesion and shown below. Features and putative coding regions not specifically designated are shown above the ORF map. Repeat regions are shown as white lines (frnk, vnct, waka/jwka, zppa, moi, mdsk). Putative coding regions and other features (see Experimental Details Section I) not designated as ORFs are shown as solid lines.

Figure 2B:
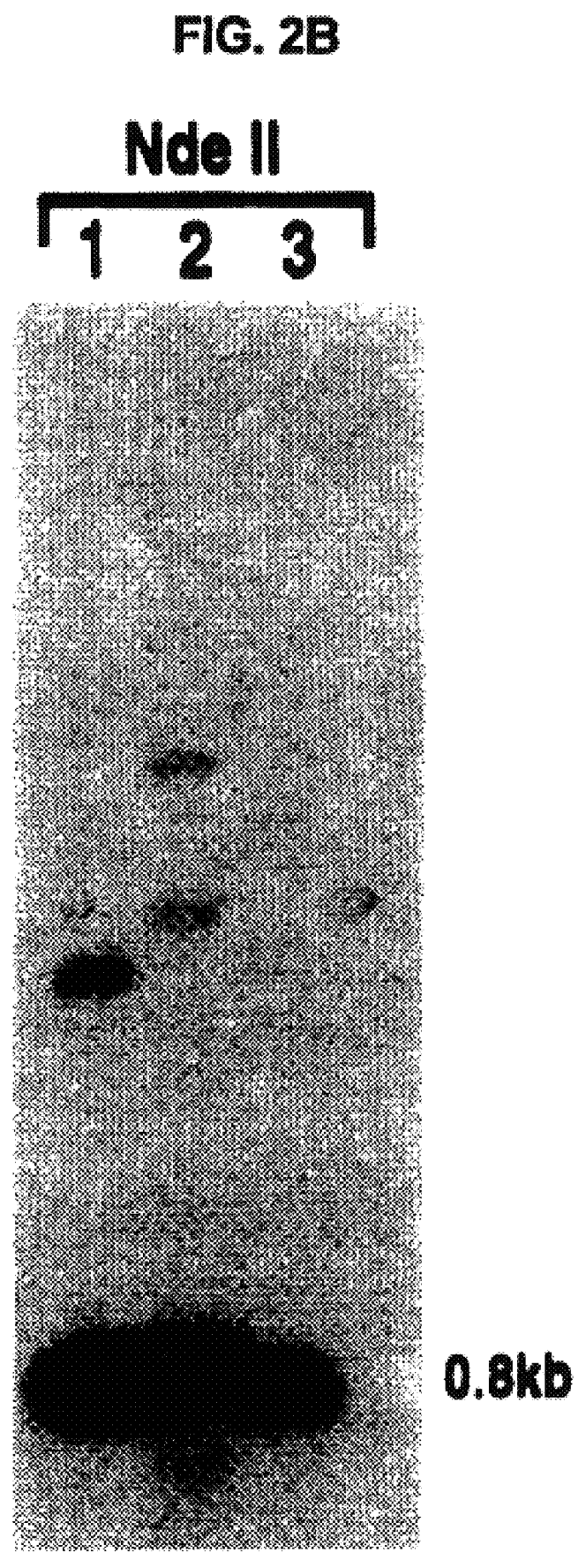
Figure 2C:
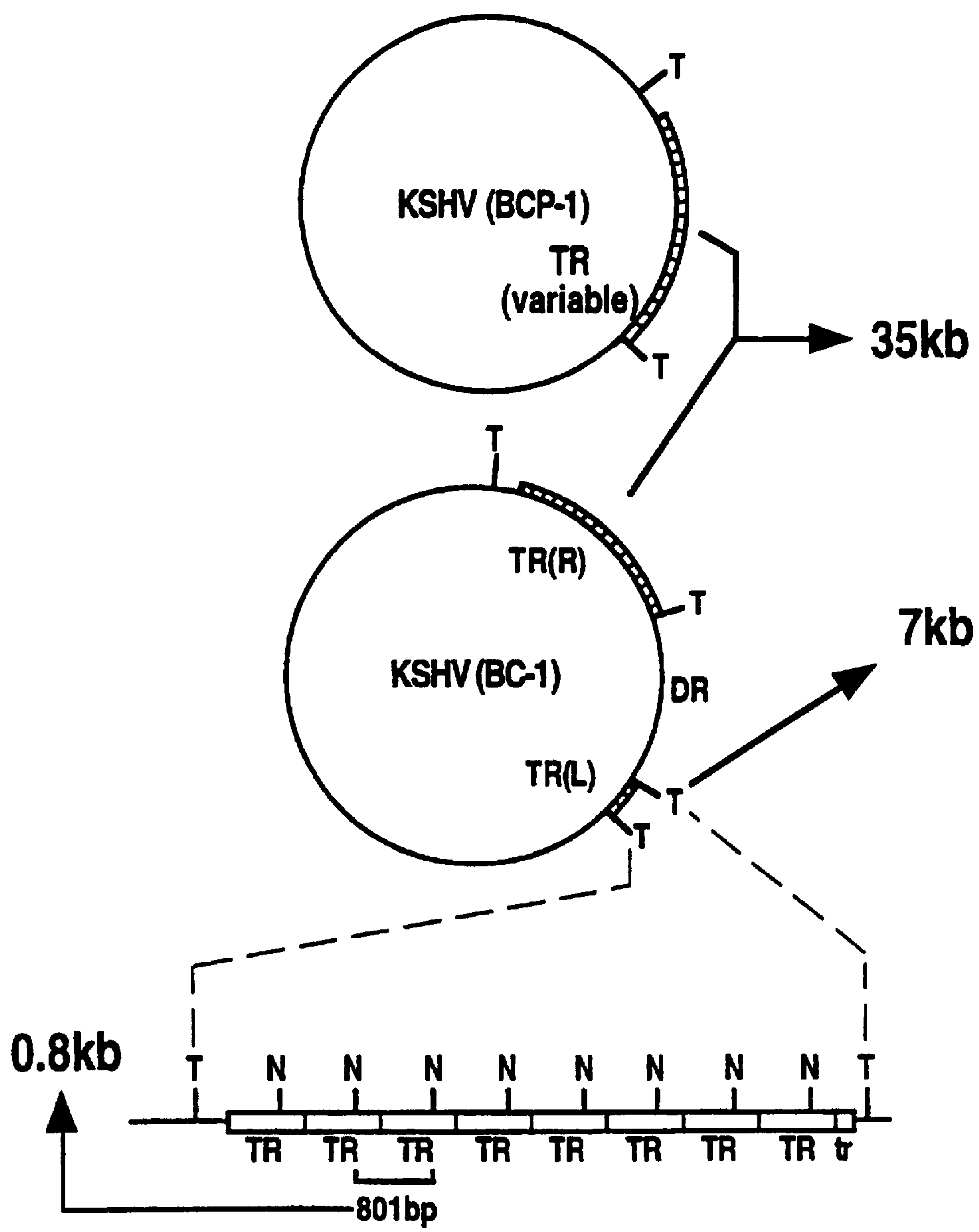
Figure 2D:
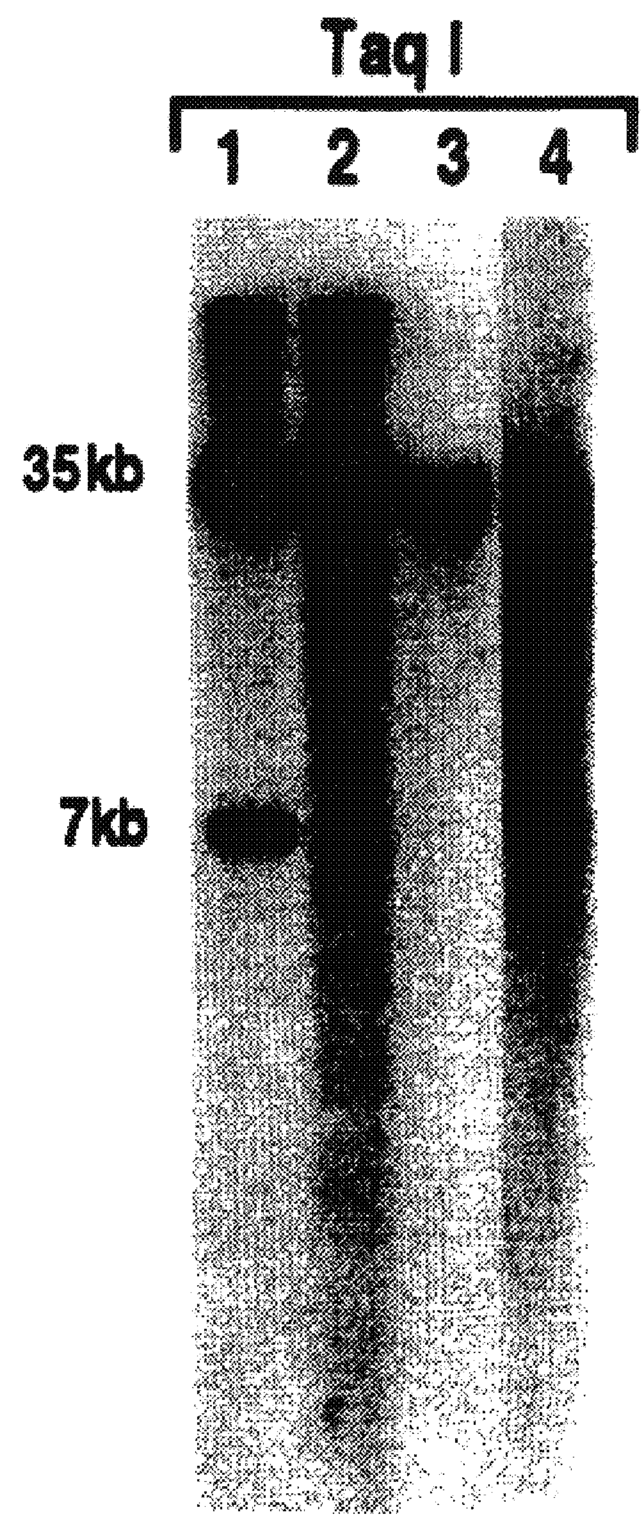

FIGS. 2A–2D:

(FIG. 2A) Sequence of terminal repeat unit (TR) demonstrating its high G+C content (SEQ ID NO:16). Sequences highly similar to conserved herpesvirus pacl sites are underlined with less similar sites to specific pac1 and pac2 sequences italicized. (FIG. 2B) Southern blot of DNA from BC-1 (lane 1), BCP-1 (lane 2) and a KS lesion (lane 3) digested with NdeII which cuts once in the TR sequence and probed with a plasmid containing the TR sequence. The intense hybridization band at 0.8 kb represents multiple copies of the NdeII-digested single unit TR (FIG. 2C). A schematic representation (FIG. 2C) of genome structures of KSHV in BCP-1 and BC-1 cell lines consistent with the data presented in (FIG. 2B) and (FIG. 2D). TaqI (T) sites flank the TR regions and Nde II (N) sites are within the TRs. Lower case tr refers to the deleted truncated TR unit at the left end of the unique region. DR represents the duplicated region of the LUR buried within the TR. (FIG. 2D) Southern blot hybridization with TR probe of DNA from BC-1 (lane 1), BCP-1 (lane 2), a KS lesion (lane 3), and HBL-6 (lane 4) digested with Taq I, which does not cut in the TR. Taq I-digested DNA from both BC-1 (lane 1) and HBL-6 (lane 4) show similar TR hybridization patterns suggesting identical insertion of a unique sequence into the TR region, which sequencing studies demonstrate is a duplicated portion of the LUR (see Experimental Details Section). BCP-1 TR hybridization (lane 2) shows laddering consistent with a virus population having variable TR region lengths within this cell line due to lytic replication. The absence of TR laddering in KS lesion DNA (lane 3) suggests that a clonal virus population is present in the tumor.

FIGS. 3A–3C:

CLUSTAL W alignments of KSHV-encoded polypeptide sequences to corresponding human cell signaling pathway polypeptide sequences. FIG. 3A. Two KSHV MIP-like polypeptides (vMIP-I and vMIP-II) are compared to human MIP-1α, MIP-1β and RANTES (SEQ ID NOS:21–25) (amino acid identity to vMIP-I indicated by black reverse shading, to VMIP-II alone by gray reverse shading, and the C—C dimer motif is italicized). Both KSHV MIP genes encode 19 residue N-terminus hydrophobic secretory leader sequences which are relatively poorly conserved (vMIP-I also has a second C—C dimer in the hydrophobic leader sequence without similarity to the chemokine dicysteine motif). Potential O-linked glycosylation sites for vMIP-I (gapped positions 22 and 27) are not present in VMIP-II, which has only one predicted potential serine glycosylation site (position 51) not found in vMIP-I. FIG. 3B. Alignment of the KSHV vIL-6 to human IL-6 (SEQ ID NOS:26–27). FIG. 3C-1 and 3C-2. Alignment of the KSHV vIRF polypeptide to human ICSBP and ISGF3 with the putative ICS-binding typtophans (W) for ICSBP and ISGF3 in italics (SEQ ID NOS:28–30).

FIGS. 4A–4F:

Northern hybridization of total RNA extracted from BCP-1 and BC-1 cells with or without 48 hour incubation with TPA and control P3HR1 cells after TPA incubation. All four genes (FIG. 4A, vMIP-I; FIG. 4B, vMIP-II; FIG. 4C, vIL-6; FIG. 4D, vIRF) are TPA inducible but constitutive, noninduced expression of vIL-6 (FIG. 4C) and vIRF (FIG. 4D) is also evident for BCP-1 and BC-1 and of vMIP-I for BCP-1 (FIG. 4A). Representative hybridizations to a human β-actin probe (FIGS. 4E–4F) demonstrate comparable loading of RNA for cell preparations.

Figure 5A:
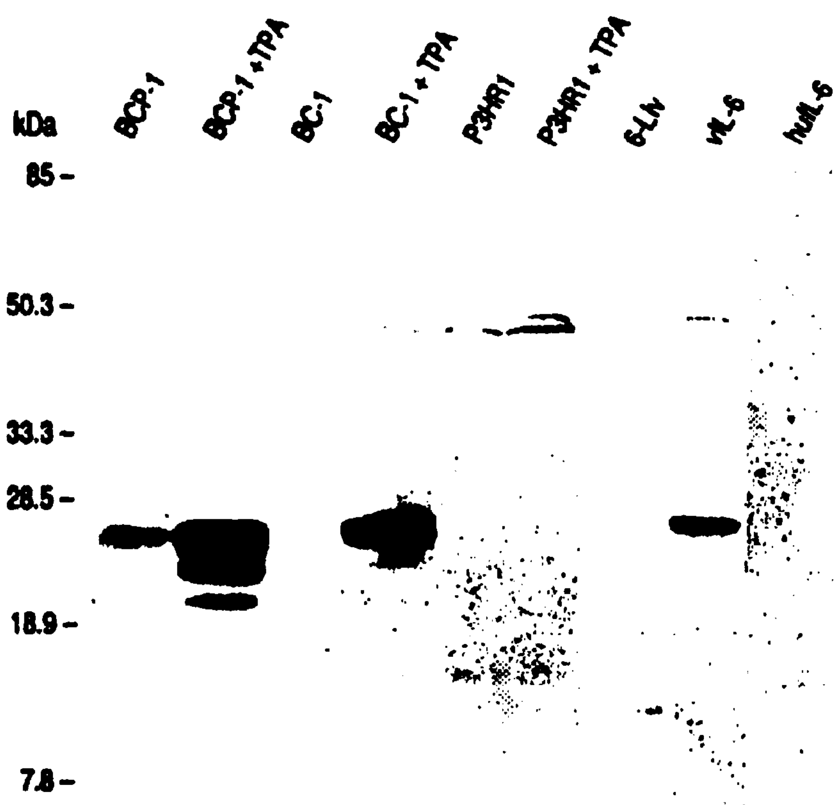
Figure 5B:
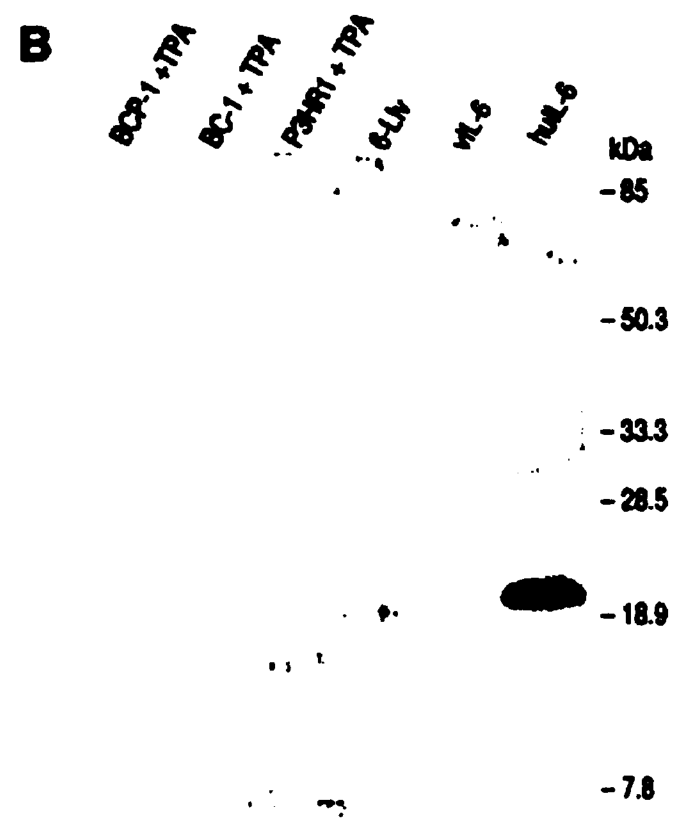

FIGS. 5A–5B:

FIG. 5A. Immunoblot of rabbit antipeptide antibodies generated from amino acid sequences of vIL-6, THYSPPKFDR (SEQ ID NO:2) and PDVTPDVHDR (SEQ ID NO:3), against cell lysates of BCP-1, BC-1, P3HR1 cell lines with and without TPA induction (lanes 1–6), 1 μg human rIL-6 (lane 7), and concentrated COS7 rvIL-6 and 6-LIv supernatants (lanes 8–9). Anti-vIL-6 antibodies specifically recognize the viral IL-6 polypeptide in both recombinant supernatants and cell lines but not human IL-6. The BCP-1 cell line constitutively expresses low levels of vIL-6 whereas polypeptide expression increases on TPA treatment for both BC-i (KSHV and EBV coinfected) and BCP-1 (KSHV infection alone) indicating lytic phase expression. Preimmune sera from immunized rabbits did not react on immunoblotting to any of the preparations. FIG. 5B. Anti-huIL-6 monoclonal antibodies do not cross-react with cell-associated or recombinant vIL-6 preparations.

FIG. 6:

Dose-response curves for $^{3}$H-thymidine uptake in IL-6-dependent B9 mouse plasmacytoma cells with serial dilutions of rhuIL-6 (filled squares) and COS7 supernatants of rvIL-6 (filled circles), r6-LIv (open squares) or control LacZ (open circles) pMET7 transfections. Undiluted rvIL-6 supernatants from this transfection lot show similar B9 proliferation activity to huIL-6>0.02 ng/ml whereas the reverse construct (r6-LIv) and the LacZ control show no increased ability to induce B9 proliferation. Concentrated supernatants at greater than 1:1 dilution may have increased activity due to concentration of COS7 conditioning factors.

FIGS. 7A–7F:

Rabbit anti-vIL-6 peptide antibody reactivity localized using goat-antirabbit immunoglobulin-peroxidase conjugate (brown) with hematoxylin counterstaining (blue) at ×100 magnification demonstrates vIL-6 production in both KSHV-infected cell lines and tissues. The KSHV-infected cell line BCP-1 (FIG. 7A), but not the control EBV-infected cell line P3HR1 (FIG. 7B), shows prominent cytoplasmic vIL-6 localization. (FIG. 7C) Cytoplasmic localization of vIL-6 in spindle-shaped cells from an AIDS-KS lesion. Of eight KS lesions, only one had readily identifiable vIL-6 staining of a subpopulation of cells. In contrast, the majority of pelleted lymphoma cells from a nonAIDS, EBV-negative PEL have intense vIL-6 staining (FIG. 7E). No immunostaining is present in control angiosarcoma (FIG. 7D) or multiple myeloma tissues (FIG. 7F).

Figures 8A, 8B, 8C, 8D:
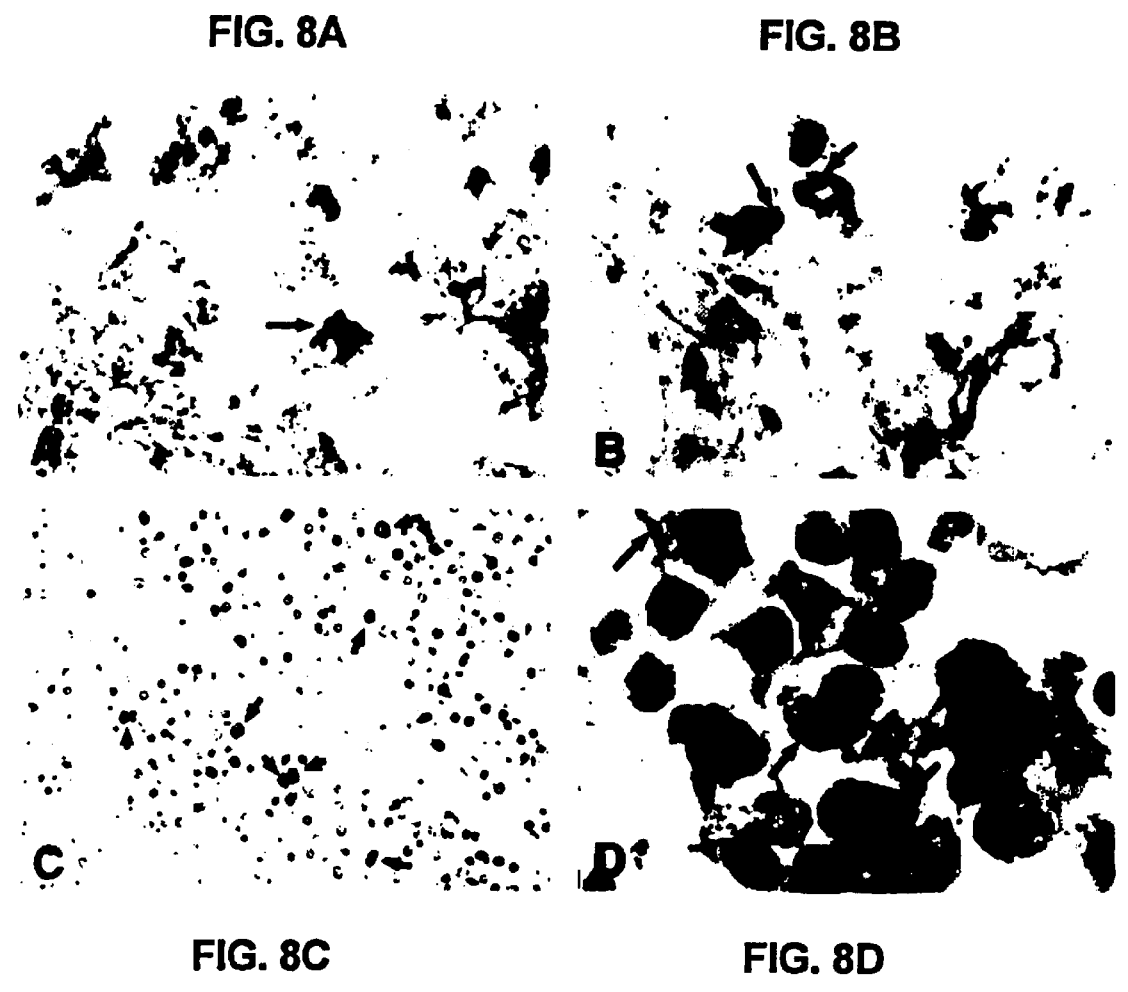

FIGS. 8A–8D:

Double antibody labeling of anti-vIL-6 and cell surface antigens. Examples of both CD34 and CD20 colocalization with vIL-6 were found in a KS lesion. FIG. 8A. CD34 (red) and vIL-6 colocalize (blue) in a KS spindle cell (arrow). Purple coloration is due to overlapping chromagen staining (100×). FIG. 8B. CD45 common leukocyte antigen staining (blue, arrow) on vIL-6 (red) expressing Kaposi's sarcoma cells (100×). FIG. 8C. Low power magnification (20×) demonstrating numerous vIL-6 producing hematopoietic cells (red) in a lymph node from a patient with KS. Arrows only indicate the most prominently staining cells; nuclei counterstained with hematoxylin. FIG. 8D. Colocalization of CD20 (brown, arrows) with vIL-6 (red) in an AIDS-KS patient's lymph node (100×).

FIG. 9:

Quantification of CCC/CD4 cell infection by primary NSI SF162 and M23 HIV-1 strains and HIV-2 strain ROD/B in the presence or absence of vMIP-I. CCC/CD4 cells were transiently cotransfected with CCR5 alone, CCR5 plus empty pMET7 vector, CCR5 plus vMIP-I in pMET7 vector, or CCR5 plus the reverse orientation I-PIMv. The results after 72 hours of incubation with each retrovirus are expressed as a percentage of the foci forming units for cells transfected with CCRS alone. The forward VMIP-I construct inhibited NSI HIV-1 replication but not HIV-2 replication while the reverse I-PIMV construct had no effect on replication of any of the retroviruses.

DETAILED DESCRIPTION OF THE INVENTION

Definitions

The following standard abbreviations are used throughout the specification to indicate specific nucleotides:

| | |
|---|---|
| C = cytosine | A = adenosine |
| T = thymidine | G = guanosine |

The term "nucleic acid", as used herein, refers to either DNA or RNA, including complementary DNA (cDNA), genomic DNA and messenger RNA (mRNA). As used herein, "genomic" means both coding and non-coding regions of the isolated nucleic acid molecule. "Nucleic acid sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

The term "polypeptide", as used herein, refers to either the full length gene product encoded by the nucleic acid, or portions thereof. Thus, "polypeptide" includes not only the full-length protein, but also partial-length fragments, including peptides less than fifty amino acid residues in length.

The term "SSC" refers to a citrate-saline solution of 0.15 M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03 M sodium chloride and 4 mM sodium citrate.

The phrase "selectively hybridizing to" and the phrase "specific hybridization" describe a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization.

"Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al. (1989) *Molecular Cloning: A Laboratory Manual* (2nd ed.), Cold Spring Harbor Laboratory, Vols. 1–3 or Ausubel, F., et al. (1987) *Current Protocols in Molecular Biology,* New York.

The phrase "nucleic acid molecule encoding" refers to a nucleic acid molecule which directs the expression of a specific polypeptide. The nucleic acid sequences include both the DNA strand sequence that is transcribed into RNA, the complementary DNA strand, and the RNA sequence that is translated into protein. The nucleic acid molecule includes both the full length nucleic acid sequence as well as non-full length sequences. It being further understood that the sequence includes the degenerate codons of the native sequence or sequences which may be introduced to provide codon preference in a specific host cell.

A nucleic acid probe is "specific" for a target organism of interest if it includes a nucleotide sequence which when detected is determinative of the presence of the organism in the presence of a heterogeneous population of proteins and other biologics. A specific nucleic acid probe is targeted to that portion of the sequence which is determinative of the organism and will not hybridize to other sequences, especially those of the host, where a pathogen is being detected.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a polypeptide produced using non-native cells. The cells produce the protein because they have been genetically altered by the introduction of the appropriate nucleic acid sequence.

The following terms are used to describe the sequence relationships between two or more nucleic acid molecules: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences in a comparison window may be conducted by the algorithm of Smith and Waterman (1981) *Adv. Appl. Math.* 2:482, by the algorithm of Needleman and Wunsch (1970) *J. Mol. Biol.* 48:443, by the search-for-similarity method of Pearson and Lipman (1988) *Proc. Natl. Acad. Sci.* 85:2444, or by computerized implementations of these algorithms (GAP, BESTFIT, FASTA, and TFASTA in GCG, the Wisconsin Genetics Software Package Release 8.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "195% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties, such as charge or polarity, are not likely to effect the properties of a protein. Examples include glutamine for asparagine or glutamic acid for aspartic acid.

The phrase "substantially purified" or "isolated" when referring to a herpesvirus polypeptide, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a polypeptide, refers to a binding reaction which is determinative of the presence of the KSHV polypeptide of the invention in the presence of a heterogeneous population of polypeptides and other biologics including viruses other than KSHV. Thus, under designated immunoassay conditions, the specified antibodies bind to the KSHV antigen and do not bind in a significant amount to other antigens present in the sample.

"Specific binding" to an antibody under such conditions may require an antibody that is selected for its specificity for a particular antigen. For example, antibodies raised to KSHV antigens described herein can be selected to obtain antibodies specifically immunoreactive with KSHV polypeptides and not with other polypeptides.

"Biological sample" as used herein refers to any sample obtained from a living organism or from an organism that has died. Examples of biological samples include body fluids and tissue specimens.

It will be readily understood by those skilled in the art and it is intended here, that when reference is made to particular sequence listings, such reference includes sequences which substantially correspond to the listing and it's complement, including allowances for minor sequencing errors, single base changes, deletions, substitutions and the like, such that any such sequence variation corresponds to the nucleic acid sequence of the pathogenic organism or disease marker to which the relevant sequence listing relates.

I. Nucleic Acid Molecule from KSHV

This invention provides an isolated nucleic acid molecule which encodes a Kaposi's sarcoma-associated herpesvirus (KSHV) polypeptide.

In one embodiment, the isolated nucleic acid molecule which encodes a KSHV polypeptide has the nucleotide sequence as set forth in GenBank Accession Number U75698 and the start and stop codons set forth in Table 1. In another embodiment, the isolated nucleic acid molecule which encodes a KSHV polypeptide has the amino acid sequence defined by the translation of the nucleotide sequence set forth in GenBank Accession Number U75698 and the start and stop codons set forth in Table 1.

In one embodiment, the isolated nucleic acid molecule for a KSHV polypeptide has the 5' untranslated sequence as set forth in GenBank Accession Number U75698 upstream of the ATG start codon. In another embodiment, the isolated nucleic acid molecule for a KSHV polypeptide has the 3' untranslated sequence as set forth in GenBank Accession Number U75698 downstream of the stop codon.

In one embodiment the isolated nucleic acid molecule is genomic DNA. In another embodiment the isolated nucleic acid molecule is cDNA. In another embodiment RNA is derived from the isolated nucleic acid molecule or is capable of hybridizing with the isolated nucleic acid molecule.

Further, the nucleic acid molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, AIDS related central nervous system lymphoma, post-transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

A. Isolation and Propagation of KSHV

KSHV can be propagated in vitro. For example, techniques for growing herpesviruses have been described by Ablashi et al. in *Virology* 184, 545–552. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 μg/ml polybrene for 2 hours at 37° C. prior to infection. Infected cells are observed by demonstrating morphological changes, as well as being viral antigen positive.

For KSHV isolation, the virus is either harvested directly from cell culture fluid by centrifugation, or the infected cells are harvested, homogenized or lysed and the virus is separated from cellular debris and purified by standard methods of isopycnic sucrose density gradient centrifugation.

One skilled in the art may isolate and propagate KSHV employing the following protocol. Long-term establishment of a B lymphoid cell line infected with KSHV (e.g., RCC-1, HBL-6 or BCBL-1) is accomplished using body-cavity based lymphomas and standard techniques (Glick, 1980, *Fundamentals of Human Lymphoid Culture,* Marcel Dekker, New York; Knowles et al., 1989, *Blood* 73, 792–798; Metcalf, 1984, *Clonal Culture of Hematopoeltic Cells: Techniques and Applications,* Elsevier, New York).

Fresh lymphoma tissue containing viable infected cells is filtered to form a single cell suspension. The cells are separated by Ficoll-Plaque centrifugation and lymphocyte layer is removed. The lymphocytes are then placed at $>1\times10^6$ cells/ml into standard lymphocyte tissue culture medium, such as RPMI 1640 supplemented with 10% fetal calf serum. Immortalized lymphocytes containing KSHV are indefinitely grown in the culture media while non-immortalized cells die during course of prolonged cultivation.

Further, KSHV may be propagated in a new cell line by removing media supernatant containing the virus from a continuously-infected cell line at a concentration of $>1\times10^6$ cells/ml. The media is centrifuged at 2000×g for 10 minutes and filtered through a 0.45 μ filter to remove cells. The media is applied in a 1:1 volume with cells growing at $>1\times10^6$ cells/ml for 48 hours. The cells are washed, pelleted and placed in fresh culture medium, then tested for KSHV after 14 days.

KSHV may be isolated from a cell line in the following manner. An infected cell line is lysed using standard methods, such as hyposmotic shock or Dounce homogenization or using repeated cycles of freezing and thawing in a small volume (<3 ml), and pelleted at 2000×g for 10 minutes. The supernatant is removed and centrifuged again at 10,000×g for 15 minutes to remove nuclei and organelles. The resulting low-speed, cell-free supernatant is filtered through a 0.45μ filter and centrifuged at 100,000×g for 1 hour to pellet the virus. The virus can then be washed and re-pelleted. The DNA is extracted from the viral pellet by standard techniques (e.g., phenol/chloroform) and tested for the presence of KSHV by Southern blotting and/or PCR using the specific probes described above.

For banding whole virion, the low-speed cell-free supernatant is adjusted to contain 7% PEG-8000. The PEG-supernatant is spun at 10,000 ×g for 30 min. The supernatant is poured off and the pellet collected and resuspended in a small volume (1–2 ml) of virus buffer (VB, 0.1 M NaCl, 0.01 M Tris, pH 7.5). The virion are isolated by centrifugation at 25,000 rpm in a 10–50% sucrose gradient made with VB. One ml fractions of the gradient are obtained by standard techniques (e.g., using a fractionator) and each fraction is tested by dot blotting using specific hybridizing probes to determine the gradient fraction containing the purified virus (preparation of the fraction is needed in order to detect the presence of the virus, i.e., standard DNA extraction).

The method for isolating the KSHV genome is based on Pellicer et al.,1978, *Cell* 14, 133–141 and Gibson and Roizmann, 1972, *J. Virol.* 10, 1044–52.

A final method for isolating the KSHV genome is clamped homogeneous electric field (CHEF) gel electrophoresis. Agarose plugs are prepared by resuspending cells infected with KSHV in 1% LMP agarose (Biorad) and 0.9% NaCl at 42° C. to a final concentration of $2.5\times10^7$ cells/ml. Solidified agarose plugs are transferred into lysis buffer (0.5M EDTA pH 8.0, 1% sarcosyl, proteinase K at 1 mg/ml final concentration) and incubated for 24 hours. Approximately $10^7$ cells are loaded in each lane. Gels are run at a gradient of 6.0 V/cm with a run time of 28 h on a CHEF Mapper XA pulsed field gel electrophoresis apparatus (Biorad), Southern blotted and hybridized to KS631Bam, KS330Bam and an EBV terminal repeat sequence.

To make a new cell line infected with KSHV, already-infected cells are co-cultivated with a Raji cell line separated by a 0.45 $\mu$ filter. Approximately, $1–2\times10^6$ already-infected BCBL-1 and $2\times10^6$ Raji cells are co-cultivated for 2–20 days in supplemented RPMI alone or with 20 ng/ml 12-O-tetradecanoyl phorbol-13-acetate (TPA). After 2–20 days co-cultivation, Raji cells are removed, washed and placed in supplemented RPMI 1640 media. A Raji culture co-cultivated with BCBL-1 in 20 ng/ml TPA for 2 days survived and has been kept in continuous suspension culture for >10 weeks. This cell line, designated RCC-1 (Raji Co-Culture, No.1) remains PCR positive for the KSHV sequence after multiple passages. RCC-1 cells periodically undergo rapid cytolysis suggestive of lytic reproduction of KSHV. Thus, RCC-1 is a Raji cell line newly-infected with KSHV.

RCC-1 and RCC-$1_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. HBL-6 was deposited (as BHL-6) on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

B. Hybridization Probes of KSHV

This invention provides a nucleic acid molecule of at least 14 nucleotides capable of specifically hybridizing with the isolated nucleic acid molecule as set forth in GenBank Accession Numbers U75698, U75699, U75700.

In one embodiment the nucleic acid molecule set forth in GenBank Accession Number U75698 comprises the long unique region (LUR) encoding KSHV polypeptides. In another embodiment the nucleic acid molecule set forth in GenBank Accession Number U75699 comprises the prototypical terminal repeat (TR). In another embodiment the nucleic acid molecule set forth in GenBank Accession Number U75700 comprises the incomplete terminal repeat (ITR).

In one embodiment the molecule is 8 to 36 nucleotides. In another embodiment the molecule is 12 to 25 nucleotides. In another embodiment the molecule is 14 nucleotides.

In one embodiment the molecule is DNA. In another embodiment the molecule is RNA.

In one embodiment the TR molecule contains cis-active elements required for DNA replication and packaging. In another embodiment the TR molecule is contained in a gene-cloning vector. In another embodiment the TR molecule is contained in a gene-therapy vector. In another embodiment the gene-therapy vector is expressed in lymphoid cells. In another embodiment, the TR comprises a molecular marker for determining the clonality of a tumor. In another embodiment, the marker provides a defining feature of the natural history of a tumor in a diagnostic assay.

This invention provides a B-lymphotrophic DNA vector comprising a plasmid or other self-replicable DNA molecule containing the 801 bp KSHV TR (SEQ ID NO:16) or a portion thereof.

High stringency hybridization conditions are selected at about 5° C. lower than the thermal melting point (Tm) for the specific sequence at a defined ionic strength and pH. The am is the temperature (under defined ionic strength and pH) at which 50% of the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. For example, high stringency may be attained by overnight hybridization at about 68° C. in a 6×SSC solution, washing at room temperature with 6×SSC solution, followed by washing at about 68° C. in a 0.6×SSC solution.

Hybridization with moderate stringency may be attained for example by: 1) filter pre-hybridizing and hybridizing with a solution of 3×SSC, 50% formamide, 0.1M Tris buffer at pH 7.5, 5×Denhardt's solution; 2.) pre-hybridization at 37° C. for 4 hours; 3) hybridization at 37° C. with amount of labeled probe equal to 3,000,000 cpm total for 16 hours; 4) wash in ×SSC and 0.1% SDS solution; 5) wash 4×for 1 minute each at room temperature in 4×SSC at 60° C. for 30 minutes each; and 6) dry and expose to film.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, 1981, *Tetrahedron Lett.* 22, 1859–1862 or by the triester method according to Matteucci et al., 1981, *Am. Chem. Soc.* 103:3185. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is base pairs (bp) or more in length is also encompassed for use as a probe.

The nucleic acid molecules of the subject invention also include molecules coding for polypeptide analogs, fragments or derivatives of antigenic polypeptides which differ from naturally-occurring forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

C. Polyeitides of KSHV and Antibodies (Ab's) Thereto

This invention provides an isolated KSHV polypeptide, one from the list as set forth in Table 1 and below.

This invention provides the isolated KSHV polypeptide comprising viral macrophage inflammatory protein III (vMIP-III). In one embodiment, vMIP-III comprises an orphan cytokine. In another embodiment, vMIP-III is encoded by nucleotides 22,529–22,185. In another embodiment, vMIP-III comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising dihydrofolate reductase (DHFR) encoded by ORF 2. In one embodiment, DHFR participates in KSHV nucleotide synthesis. In another embodiment. DHFR comprises an enzyme essential for viral replication, inhibition of which prevents virus production. In another embodiment, DHFR comprises a subunit vaccine. In another embodiment, DHFR comprises an antigen for immunologic assays.

In another embodiment, DHFR has the amino acid sequence as set forth in SEQ ID NO:1.

In another embodiment, KSHV DHFR is inhibited by a sulfa drug known to inhibit bacterial DHFR. In a preferred embodiment, KSHV DHFR is inhibited by methotrexate or a derivative thereof known to inhibit mammalian DHFR. In another embodiment, the sulfa drug, methotrexate or a derivative thereof is selective among the human herpesviruses for inhibition of KSHV.

This invention provides the isolated KSHV polypeptide comprising thymidylate synthase (TS) encoded by ORF 70. In one embodiment, TS participates in KSHV nucleotide metabolism. In another embodiment, TS comprises an enzyme essential for viral replication, inhibition of which prevents virus production. In another embodiment, TS comprises a subunit vaccine. In another embodiment, TS comprises an antigen for immunologic assays.

This invention provides the isolated KSHV polypeptide comprising DNA polymerase encoded by ORF 9. In one embodiment, DNA polymerase comprises an enzyme essential for viral replication, inhibition of which prevents virus production. In another embodiment, DNA polymerase comprises a subunit vaccine. In another embodiment, DNA polymerase comprises an antigen for immunologic assays.

This invention provides the isolated KSHV polypeptide comprising alkaline exonuclease encoded by ORF 37. In one embodiment, alkaline exonuclease packages KSHV DNA into the virus particle. In another embodiment, alkaline exonuclease comprises an enzyme essential for viral replication, inhibition of which prevents virus production. In another embodiment, alkaline exonuclease comprises a subunit vaccine. In another embodiment, alkaline exonuclease comprises an antigen for immunologic assays.

This invention provides the isolated KSHV polypeptide comprising helicase-primase, subunits 1, 2 and 3 encoded by ORFs 40, 41 and 44, respectively. In one embodiment, helicase-primase comprises an enzyme activity essential for viral DNA replication. In another embodiment, helicase-primase is inhibited by nucleotide analogs. In another embodiment, helicase-primase is inhibited by known antiviral drugs. In another embodiment, inhibition of helicase-primase prevents KSHV replication.

This invention provides the isolated KSHV polypeptide comprising uracil DNA glycosylase (UDG) encoded by ORF 46. In one embodiment, uracil DNA glycosylase comprises an enzyme essential for KSHV DNA repair during DNA replication. In another embodiment, uracil DNA glycosylase is inhibited by known antiviral drugs. In another embodiment, uracil DNA glycosylase comprises a subunit vaccine. In another embodiment, uracil DNA glycosylase comprises an antigen for immunologic assays.

This invention provides the isolated KSHV polypeptide comprising single-stranded DNA binding protein (SSBP) encoded by ORF 06. In one embodiment, SSBP comprises an enzyme essential for KSHV DNA replication. In another embodiment, SSBP is inhibited by known antiviral drugs. In another embodiment, SSEP increases the processivity of polymerase reactions such as in the conventional PCR method for DNA amplification.

This invention provides the isolated KSHV polypeptide comprising viral protein kinase encoded by ORF 36. In another embodiment, viral protein kinase comprises an antigen for immunologic assays. In another embodiment, viral protein kinase comprises a subunit vaccine.

This invention provides the isolated KSHV polypeptide comprising lytic cycle transactivator protein (LCTP) encoded by ORF 50. In one embodiment, LCTP is required for activation of productive infection from the latent state. In another embodiment, LCTP is inhibited by known antiviral drugs. In another embodiment, prevention of LCTP expression maintains the virus in a latent state unable to replicate.

This invention provides the isolated KSHV polypeptide comprising ribonucleotide reductase, a two-subunit enzyme in which the small and large subunits are encoded by ORF 60 and ORF 61, respectively. In another embodiment, riDonucleotide reductase catalyzes conversion of ribonucleotides into deoxyribonucleotides for DNA replication. In another embodiment, ribonucleotide reductase is inhibited by known antiviral drugs in terminally differentiated cells not expressing cellular ribonucleotide reductase. In another embodiment, ribonucleotide reductase comprises an antigen for immunologic assays.

In another embodiment, ribonucleotide reductase comprises a subunit vaccine. In another embodiment, ribonucleotide reductase comprises a transforming agent for establishment of immortalized cell lines.

This invention provides the isolated KSHV polypeptide comprising the protein encoded by ORF K1.

This invention provides the isolated KSHV polypeptide comprising complement-binding protein (v-CBP; CCP) encoded by ORF 4.

This invention provides the isolated KSHV polypeptide comprising transport protein encoded by ORF 7.

This invention provides the isolated KSHV polypeptide comprising glycoprotein B encoded by ORF 8.

This invention provides the isolated KSHV polypeptide comprising the protein encoded by ORF 10.

This invention provides the isolated KSHV polypeptide comprising the protein encoded by ORF 11.

This invention provides the isolated KSHV polypeptide comprising viral interleukin 6 (vIL-6) encoded by ORF K2. In one embodiment, antibodies selectively recognizing vIL-6 allow differentiation among lymphomas.

This invention provides the isolated KSHV polypeptide comprising BHV4-IE1 I encoded by ORF K3.

This invention provides the isolated KSHV polypeptide comprising vMIP-II encoded by ORF K4. In one embodiment, vMIP-II comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising BHV4-IE1 II encoded by ORF KB.

This invention provides the isolated KSHV polypeptide comprising vMIP-I encoded by ORF K6. In one embodiment, VMIP-I comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising the protein encoded by ORF K7.

This invention provides the isolated KSHV polypeptide comprising Bcl-2 encoded by ORF 16.

This invention provides the isolated KSHV polypeptide comprising capsid protein I encoded by ORF 17.

This invention provides the isolated KSHV polypeptide comprising the protein encoded by ORF 18.

This invention provides the isolated KSHV polypeptide comprising tegument protein I encoded by ORF 19.

This invention provides the isolated KSHV polypeptide comprising the protein encoded by ORF 20.

This invention provides the isolated KSHV polypeptide comprising thymidine kinase encoded by ORF 21.

This invention provides the isolated KSHV polypeptide comprising glycoprotein H encoded by ORF 22.

In one embodiment, the isolated KSHV polypeptide comprises the protein encoded by ORF 23.

This invention provides the isolated KSHV polypeptide comprising the protein encoded by ORF 24.

This invention provides the isolated KSHV polypeptide comprising major capsid protein encoded by ORF 25.

This invention provides the isolated KSHV polypeptide comprising capsid protein II encoded by ORF 26.

This invention provides the isolated KSHV polypeptide comprising the protein encoded by ORF 27.

This invention provides the isolated KSHV polypeptide comprising the protein encoded by ORF 28.

This invention provides the isolated KSHV polypeptide comprising packaging protein II encoded by ORF 29b.

This invention provides the isolated KSHV polypeptide comprising the protein encoded by ORF 30.

This invention provides the isolated KSHV polypeptide comprising the protein encoded by ORF 31.

This invention provides the isolated KSHV polypeptide comprising the protein encoded by ORF 32.

This invention provides the isolated KSHV polypeptide comprising the protein encoded by ORF 33.

This invention provides the isolated KSHV polypeptide comprising packaging protein I encoded by ORF 29a.

This invention provides the isolated KSHV polypeptide comprising the protein encoded by ORF 34.

This invention provides the isolated KSHV polypeptide comprising the protein encoded by ORF 35.

This invention provides the isolated KSHV polypeptide comprising the protein encoded by ORF 38.

This invention provides the isolated KSHV polypeptide comprising glycoprotein M encoded by ORF 39.

This invention provides the isolated KSHV polypeptide comprising the protein encoded by ORF 42.

This invention provides the isolated KSHV polypeptide comprising capsid protein III encoded by ORF 43.

This invention provides the isolated KSHV polypeptide comprising virion assembly protein encoded by ORF 45.

This invention provides the isolated KSHV polypeptide comprising glycoprotein L encoded by ORF 47.

This invention provides the isolated KSHV polypeptide comprising the protein encoded by ORF 48.

This invention provides the isolated KSHV polypeptide comprising the protein encoded by ORF 49.

This invention provides the isolated KSHV polypeptide comprising the protein encoded by ORF K8.

This invention provides the isolated KSHV polypeptide comprising the protein encoded by ORF 52.

This invention provides the isolated KSHV polypeptide comprising the protein encoded by ORF 53.

This invention provides the isolated KSHV polypeptide comprising dUTPase encoded by ORF 54.

This invention provides the isolated KSHV polypeptide comprising the protein encoded by ORF 55.

This invention provides the isolated KSHV polypeptide comprising DNA replication protein I encoded by ORF 56.

This invention provides the isolated KSHV polypeptide comprising immediate early protein II (IEP-II) encoded by ORF 57.

This invention provides the isolated KSHV polypeptide comprising viral interferon regulatory factor 1 (vIRF1; ICSBP) encoded by ORF K9. In one embodiment, vIRF1 is a transforming polypeptide.

This invention provides the isolated KSHV polypeptide comprising the protein encoded by ORF K10.

This invention provides the isolated KSHV polypeptide comprising that protein encoded by ORF K11.

This invention provides the isolated KSHV polypeptide comprising phosphoprotein encoded by ORF 58.

This invention provides the isolated KSHV polypeptide comprising DNA replication protein II encoded by ORF 59.

This invention provides the isolated KSHV polypeptide comprising assembly/DNA maturation protein encoded by ORF 62.

This invention provides the isolated KSHV polypeptide comprising tegument protein II encoded by ORF 63.

This invention provides the isolated KSHV polypeptide comprising tegument protein III encoded by ORF 64.

This invention provides the isolated KSHV polypeptide comprising capsid protein IV encoded by ORF 65.

This invention provides the isolated KSHV polypeptide comprising the protein encoded by ORF 66.

This invention provides the isolated KSHV polypeptide comprising tegument protein IV encoded by ORF 67.

This invention provides the isolated KSHV polypeptide comprising glycoprotein encoded by ORF 68.

This invention provides the isolated KSHV polypeptide comprising the protein encoded by ORF 69.

This invention provides the isolated KSHV polypeptide comprising Kaposin encoded by ORF K12.

This invention provides the isolated KSHV polypeptide comprising the protein encoded by ORF K13.

This invention provides the isolated KSHV polypeptide comprising cyclin D encoded by ORF 72.

This invention provides the isolated KSHV polypeptide comprising immediate-early protein (IEP) encoded by ORF 73.

This invention provides the isolated KSHV polypeptide comprising OX-2 encoded by ORF K14.

This invention provides the isolated KSHV polypeptide comprising G-protein coupled receptor encoded by ORF 74.

This invention provides the isolated KSHV polypeptide comprising tegument protein/FGARAT encoded by ORF 75.

This invention provides the isolated KSHV polypeptide comprising the protein encoded by ORF K15.

This invention provides the isolated KSHV polypeptide comprising viral interferon regulatory factor 2 (vIRF2) encoded by nucleotides 88,910–88,410.

This invention provides the isolated KSHV polypeptide comprising viral interferon regulatory factor 3 (vIRF3) encoded by nucleotides 90,541–89,600.

This invention provides the isolated KSHV polypeptide comprising viral interferon regulatory factor 4 (vIRF4) encoded by nucleotides 94,127–93,636.

This invention provides the isolated KSHV polypeptide comprising a precursor of secreted glycoprotein X (gX) encoded by nucleotides 90,173–90,643.

This invention provides the isolated KSHV polypeptide comprising protein Tl.l (nut-1) encoded by nucleotides 28,661–29,741.

Further, the isolated polypeptide may be linked to a second polypeptide to form a fusion protein by linking the isolated nucleic acid molecule to a second nucleic acid molecule and expression in a suitable host cell.

In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated nucleic acid molecule. In one embodiment the antibody is a monoclonal antibody. In another embodiment the antibody recognizes an epitope of the KSHV polypeptide. In another embodiment the antibody is a polyclonal antibody. In another embodiment the antibody recognizes more than one epitope of the KSHV polypeptide. In another embodiment the antibody is an anti-idiotypic antibody.

An antibody, polypeptide or isolated nucleic acid molecule may be labeled with a detectable marker including, but not limited to: a radioactive label, or a calorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, 57Co, $^{59}Co$, $^{59}Fe$, $^{90}Y$, $^{125}I$, $^{131}I$, and $^{186}Re$. Fluorescent markers include, but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody, polypeptide or nucleic acid molecule may be detected by a second antibody which may be linked to an enzyme, such as alkaline phosphatase or horseradish peroxidase. Other enzymes which may be employed are well known to one of ordinary skill in the art.

This invention provides a method of producing a polypeptide encoded by the isolated nucleic acid molecule, which comprises growing a host-vector system under suitable conditions permitting production of the polypeptide and recovering the polypeptide so produced. Suitable host cells include bacteria, yeast, filamentous fungal, plant, insect and mammalian cells. Host-vector systems for producing and recovering a polypeptide are well known to those skilled in the art and include, but are not limited to, *E. coli* and pMAL (New England Biolabs), the Sf9 insect cell-baculovirus expression system, and mammalian cells (such as HeLa, COS, NIH 3T3 and HEK293) transfected with a mammalian expression vector by Lipofectin (Gibco-BRL) or calcium phosphate precipitation or other methods to achieve vector entry into the cell. Those of skill in the art are knowledgeable in the numerous expression systems available for expression of KSHV polypeptide.

This invention provides a method to select specific regions on the polypeptide encoded by the isolated nucleic acid molecule of the DNA virus to generate antibodies. Amino acid sequences may be analyzed by methods well known to those skilled in the art to determine whether they produce hydrophobic or hydrophilic regions in the polypeptides which they build. In the case of a cell membrane polypeptide, hydrophobic regions are well known to form the part of the polypeptide that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, nucleic acid may be cloned and expressed and the resulting polypeptide recovered and used as an immunogen.

Polyclonal antibodies against the polypeptide may be produced by immunizing animals using a selected KSHV polypeptide. Monoclonal antibodies are prepared using hybridoma technology by fusing antibody producing B cells from immunized animals with myeloma cells and selecting the resulting hybridoma cell line producing the desired antibody, as described further below.

II. Immunoassays

The antibodies raised against KSHV polypeptide antigens may be detectably labeled, utilizing conventional labelling techniques well-known to the art, as described above.

In addition, enzymes may be used as labels. Suitable enzymes include alkaline phosphatase, beta-galactosidase, glucose-6-phosphate dehydrogenase, maleate dehydrogenase and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; activity is thus measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

A description of a radioimmunoassay (RIA) may be found in: *Laboratory Techniques in Biochemistry and Molecular Biology* (1978) North Holland Publishing Company, New York, with particular reference to the chapter entitled "An Introduction to Radioimmune Assay and Related Techniques" by T. Chard. A description of general immunometric assays of various types can be found in the following U.S. Pat. No. 4,376,110 (David et al.) or U.S. Pat. No. 4,098,876 (Piasio).

A. Assays for KSHV Polypeptide Antigens

One can use immunoassays to detect the virus, its components, or antibodies thereto. A general overview of the applicable technology is in Harlow and Lane (1988) *Antibodies, A Laboratory Manual,* Cold Spring Harbor Publication, New York.

In one embodiment, antibodies to KSHV polypeptide antigens can be used. In brief, to produce antibodies, the polypeptide being targeted is expressed and purified. The product is injected into a mammal capable of producing antibodies. Either polyclonal or monoclonal antibodies (including recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane at pages 567–573 and 584–589.

Monoclonal antibodies or recombinant antibodies may be obtained by techniques familiar to those skilled in the art. Briefly, spleen cells or other lymphocytes from an animal immunized with a desired antigen are immortalized, commonly by fusion with a myeloma cell (see, Kohler and Milstein, 1976, *Eur. J. Immunol.* 6, 511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Newer techniques using recombinant phage antibody expression systems can also be used to generate monoclonal antibodies. See, for example: McCafferty et al. (1990) *Nature* 348, 552, Hoogenboom et al. (1991) *Nuc. Acids Res.* 19, 4133; and Marks et al. (1991) *J. Mol Biol.* 222, 581–597.

Methods for characterizing naturally processed peptides bound to MHC (major histocompatibility complex) I molecules can be used. See Falk et al., 1991, *Nature* 351, 290 and PCT publication Nc. WO 92/21033 published Nov. 26, 1992. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey et al., 1991, *Nature* 353, 326), and of the human MHC class I molecule, HLA-A2.1 type by mass spectrometry (Hunt et al., 1991, *Eur. J. Immunol.* 21, 2963–2970). See also, Rötzschke and Falk, 1991, *Immunol. Today* 12, 447, for a general review of the characterization of naturally processed peptides in MHC class I. Further, Marloes et al., 1991, *Eur. J. Immunol.* 21, 2963–2970, describe how class I binding motifs can be applied to the identification of potential viral immunogenic peptides in vitro.

The polypeptides described herein produced by recombinant technology may be purified by standard techniques well known to those of skill in the art. Recombinantly produced viral polypeptides can be directly expressed or expressed as a fusion protein.

The protein is then purified by a combination of cell lysis (e.g., sonication) and affinity chromatography. For fusion products, subsequent digestion of the fusion protein with an appropriate proteolytic enzyme releases the desired peptide.

The polypeptides may be purified to substantial purity by standard techniques well known in the art, including selective precipitation with such substances as ammonium sulfate, column chromatography, immunopurification methods, and others. See, for instance, Scopes, 1982, *Protein Purification: Principles and Practice,* Springer-Verlag, New York.

B. Assays for Antibodies Specifically Binding To KSHV Polypeptides

Antibodies reactive with polypeptide antigens of KSHV can also be measured by a variety of immunoassay methods that are similar to the procedures described above for measurement of antigens. For a review of immunological and immunoassay procedures applicable to the measurement of antibodies by immunoassay techniques, see *Basic and Clinical Immunology,* 7th Edition, Stites and Terr, Eds., and Harlow and Lane, 1988, *Antibodies, A Laboratory Manual,* Cold Spring Harbor, New York.

In brief, immunoassays to measure antibodies reactive with polypeptide antigens of KSHV can be either competitive or noncompetitive binding assays. In competitive binding assays, the sample analyte competes with a labeled analyte for specific binding sites on a capture agent bound to a solid surface. Preferably the capture agent is a purified recombinant human herpesvirus polypeptide produced as described above. Other sources of human herpesvirus polypeptides, including isolated or partially purified naturally occurring polypeptide, may also be used.

Noncompetitive assays are typically sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay formats, separation techniques and labels can also be used similar to those described above for the measurement of KSHV polypeptide antigens.

Hemagglutination Inhibition (HI) and Complement Fixation (CF) are two laboratory tests that can be used to detect infection with human herpesvirus by testing for the presence of antibodies against the virus or antigens of the virus.

Serological methods can also be useful when one wishes to detect antibody to a specific viral variant. For example, one may wish to see how well a vaccine recipient has responded to a new preparation by assay of patient sera.

IIA. Vector, Cell Line and Transgenic Mammal

This invention provides a replicable vector containing the isolated nucleic acid molecule encoding a KSHV polypeptide. The vector includes, but is not limited to: a plasmid, cosmid, λ phage or yeast artificial chromosome (YAC) which contains the isolated nucleic acid molecule.

To obtain the vector, for example, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are available and well-known to those skilled in the art.

This invention provides a host cell containing the vector. Suitable host cells include, but are not limited to, bacteria (such as *E. coli*), yeast, fungi, plant, insect and mammalian cells. Suitable animal cells include, but are not limited to Vero cells, HeLa cells, Cos cells, CV1 cells and various primary mammalian cells.

This invention provides a transgenic nonhuman mammal which comprises the isolated nucleic acid molecule introduced into the mammal at an embryonic stage. Methods of producing a transgenic nonhuman mammal are known to those skilled in the art.

III. Diagnostic Assays for KS

This invention embraces diagnostic test kits for detecting the presence of KSHV in biological samples, such as skin samples or samples of other affected tissue, comprising a container containing a nucleic acid sequence specific for a KSHV polypeptide and instructional material for performing the test. A container containing nucleic acid primers to any one of such sequences is optionally included.

This invention further embraces diagnostic test kits for detecting the presence of KSHV in biological samples, such as serum or solid tissue samples, comprising a container containing antibodies to a KSHV polypeptide, and instructional material for performing the test. Alternatively, inactivated viral particles or polypeptides derived from the human herpesvirus may be used in a diagnostic test kit to detect antibodies specific for a KSHV polypeptide.

A. Nucleic Acid Assays

This invention provides a method of diagnosing Kaposi's sarcoma in a subject which comprises: (a) obtaining a nucleic acid molecule from a tumor lesion or a suitable bodily fluid of the subject; (b) contacting the nucleic acid molecule with a labeled nucleic acid molecule of at least 15 nucleotides capable of specifically hybridizing with the isolated nucleic acid molecule of KSHV under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the nucleic acid molecule from the tumor lesion is amplified before step (b). In another embodiment the polymerase chain reaction (PCR, is employed to amplify the nucleic acid molecule. Methods of amplifying nucleic acid molecules are known to those skilled in the art.

A person of ordinary skill in the art will be able to obtain appropriate nucleic acid sample for diagnosing Kaposi's sarcoma in the subject. The DNA sample obtained by the above described method may be cleaved by restriction enzyme before analysis, a technique well-known in the art.

In the above described methods, a size fractionation may be employed which is effected by a polyacrylamide gel. In one embodiment, the size fractionation is effected by an agarose gel. Further, transferring the nucleic acid fragments into a solid matrix may be employed before a hybridization step. One example of such solid matrix is nitrocellulose paper.

This invention provides a method of detecting expression of a KSHV gene in a cell which comprises obtaining mRNA from the cell, contacting the mRNA with a labeled nucleic acid molecule of KSHV under hybridizing conditions, determining the presence of mRNA hybridized to the molecule, thereby detecting expression of the KSHV gene. In one embodiment cDNA is prepared from the mRNA obtained from the cell and used to detect KSHV expression.

Accepted means for conducting hybridization assays are known and general overviews of the technology can be had from a review of: *Nucleic Acid Hybridization: A Practical Approach* (1985) Hames and Higgins, Eds., IRL Press; *Hybridization of Nucleic Acids Immobilized on Solid Supports,* Meinkoth and Wahl; *Analytical Biochemistry* (1984) 238, 267–284 and Innis et al., *PCR Protocols* (1990) Academic Press, San Diego.

Target-specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of KSHV, nucleic acid probes are about 50 to 1000 nucleotides, most preferably about 200 to 400 nucleotides.

A specific nucleic acid probe can be RNA, DNA, oligonucleotide, or their analogs. The probes may be single or double stranded nucleic acid molecules. The probes of the invention may be synthesized enzymatically, using methods well known in the art (e.g., nick translation, primer extension, reverse transcription, the polymerase chain reaction, and others) or chemically (e.g., by methods described by Beaucage and Carruthers or Matteucci et al., supra).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

For discussions of nucleic acid probe design and annealing conditions see, for example, Ausubel et al., supra; Berger and Kimmel, Eds., Methods in Enzymology Vol. 152, (1987) Academic Press, New York; or *Hybridization with Nucleic Acid Probes,* pp. 495–524, (1993) Elsevier, Amsterdam.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

The following stringent hybridization and washing conditions will be adequate to distinguish a specific probe (e.g., a fluorescently labeled nucleic acid probe) from a probe that is not specific: incubation of the probe with the sample for 12 hours at 37° C. in a solution containing denatured probe, 50% formamide, 2×SSC, and 0.1% (w/v) dextran sulfate, followed by washing in 1×SSC at 70° C. for 5 minutes; 2×SSC at 37° C. for 5 minutes; 0.2×SSC at room temperature for 5 minutes, and $H_2O$ at room temperature for 5 minutes. Those of skill are aware that it will often be advantageous in nucleic acid hybridizations (i.e., in situ, Southern, or Northern) to include detergents (e.g., sodium dodecyl sulfate), chelating agents (e.g., EDTA) or other reagents (e.g., buffers, Denhardt's solution, dextran sulfate) in the hybridization or wash solutions. To evaluate specificity, probes can be tested on host cells containing KSHV and compared with the results from cells containing non-KSHV virus.

It will be apparent to those of ordinary skill in the art that a convenient method for determining whether a probe is specific for a KSHV nucleic acid molecule utilizes a Southern blot (or Dot blot) using DNA prepared from the virus. Briefly, to identify a target-specific probe, DNA is isolated from the virus. Test DNA, either viral or cellular, is transferred to a solid (e.g., charged nylon) matrix. The probes are labeled by conventional methods. Following denaturation and/or prehybridization steps known in the art, the probe is hybridized to the immobilized DNAs under stringent conditions, such as defined above.

It is further appreciated that in determining probe specificity and in utilizing the method of this invention to detect KSHV, a certain amount of background signal is typical and can easily be distinguished by one of skill from a specific signal. Two-fold signal over background is acceptable.

A preferred method for detecting the KSHV polypeptide is the use of PCR and/or dot blot hybridization. Other methods to test for the presence or absence of KSHV for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer or reverse transcriptase PCR may be used for the detection of KSHV messenger RNA in a sample. These procedures are also well known in the art. See Sambrook et al. (1989) *Molecular Cloning: A Laboratory Manual* (2nd ed.), Cold Spring Harbor Laboratory, Vols. 1–3.

An alternative means for determining the presence of the human herpesvirus is in situ hybridization, or more recently, in situ polymerase chain reaction. In situ PCR is described in Neuvo et al. (1993) Intracellular localization of PCR-amplified hepatitis C DNA, in *American Journal of Surgical Pathology* 17(7), 683–690; Bagasra et al. (1992) Detection of HIV-1 provirus in mononuclear cells by in situ PCR, in *New England Journal of Medicine* 326(21),1385–1391; and Heniford et al.(1993) Variation in cellular EGF receptor mRNA expression demonstrated by in situ reverse transcriptase polymerase chain reaction, in *Nucleic Acids Research* 21, 3159–3166. In situ hybridization assays are well known and are generally described in *Methods Enzymol.* Vol. 152, (1987) Berger and Kimmel, Eds., Academic Press, New York. In an in situ hybridization, cells are fixed to a solid support, typically a glass slide. The cells are then contacted with a hybridization solution at a moderate temperature to permit annealing of target-specific probes that are labeled. The probes are preferably labeled with radioisotopes or fluorescent reporters.

The above-described probes are also useful for in situ hybridization or in order to locate tissues which express the gene, or for other hybridization assays for the presence of the gene or its mRNA in various biological tissues. In situ hybridization is a sensitive localization method which is not dependent on expression of polypeptide antigens or native versus denatured conditions.

Synthetic oligonucleotide (oligo) probes and riboprobes made from KSHV phagemids or plasmids are also provided. Successful hybridization conditions in tissue sections is readily transferrable from one probe to another. Commercially-synthesized oligonucleotide probes are prepared using the nucleotide sequence of the identified gene. These probes are chosen for length (45–65 mers), high G–C content (50–70%) and are screened for uniqueness against other viral sequences in GenBank.

Oligos are 3' end-labeled with [$\alpha$-$^{35}$S]dATP to specific activities in the range of $1\times10^{10}$ dpm/$\mu$g using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 $\mu$m intervals and thawed onto 3-aminopropyltriethoxysilane treated slides and allowed to air dry. The slides are then fixed in 4% freshly prepared paraformaldehyde and rinsed in water. Formalin-fixed, paraffin embedded KS tissues cut at 6 $\mu$m and baked onto glass slides can also be used. These sections are then deparaffinized in xylenes and rehydrated through graded alcohols. Prehybridization in 20 mM Tris pH 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (pH 7.4), 3×SSC, 1×Denhardt's solution, 100 $\mu$g/ml salmon sperm DNA, 125 $\mu$g/ml yeast tRNA and the oligo probe ($10^6$ cpm/ml) at 42° C. overnight. The slides are washed twice with 3×SSC and twice with 1×SSC for 15 minutes each at room temperature and visualized by autoradiography. Briefly, sections are dehydrated through graded alcohols containing 0.3M ammonium acetate, and air dried. The slides are dipped in Kodak NTB2 emulsion, exposed for days to weeks, developed, and counterstained with hematoxylin and eosin (H&E).

Alternative immunohistochemical protocols may be employed which are well known to those skilled in the art.

B. Immunologic Assays

This invention provides a method of diagnosing Kaposi's sarcoma in a subject, which comprises (a) obtaining a suitable bodily fluid sample from the subject, (b) contacting the suitable bodily fluid of the subject to a support having already bound thereto an antibody recognizing the KSHV polypeptide, so as to bind the antibody to a specific KSHV polypeptide antigen, (c) removing unbound bodily fluid from the support, and (d) determining the level of the antibody bound by the antigen, thereby diagnosing Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto the KSHV polypeptide antigen, so as to bind the antigen to a specific Kaposi's sarcoma antibody, (c) removing unbound bodily fluid from the support, and (d) determining the level of the antigen bound by the Kaposi's sarcoma antibody, thereby diagnosing Kaposi's sarcoma.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with KSHV may be diagnosed as infected with the above-described methods.

The detection of KSHV and the detection of virus-associated KS are essentially identical processes. The basic principle is to detect the virus using specific ligands that bind to the virus but not to other polypeptides or nucleic acids in a normal human cell or its environs. The ligands can be nucleic acid molecules, polypeptides or antibodies. The ligands can be naturally-occurring or genetically or physically modified, such as nucleic acids with non-natural nucleotide bases or antibody derivatives, i.e., Fab or chimeric antibodies. Serological tests for detection of antibodies to the virus present in subject sera may also be performed by using the KSHV polypeptide as an antigen, as described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS are present.

See Immunoassays above for more details on the immunoreagents of the invention for use in diagnostic assays for KS.

IV. Treatment of Human Herpesvirus-Induced KS

This invention provides a method for treating a subject with Kaposi's sarcoma (KS) comprising administering to the subject having KS a pharmaceutically effective amount of an antiviral agent in a pharmaceutically acceptable carrier, wherein the agent is effective to treat the subject with KSHV.

Further, this invention provides a method of prophylaxis or treatment for Kaposi's sarcoma (KS) by administering to a patient at risk for KS, an antibody that binds to KSHV in a pharmaceutically acceptable carrier.

This invention provides a method of treating a subject with Kaposi's sarcoma comprising administering to the subject an effective amount of an antisense molecule capable of hybridizing to the isolated DNA molecule of KSHV under conditions such that the antisense molecule selectively enters a KS tumor cell of the subject, so as to treat the subject.

A. Nucleic Acid Therapeutics

This invention provides an antisense molecule capable of hybridizing to the isolated nucleic acid molecule of KSHV. In one embodiment the antisense molecule is DNA. In another embodiment the antisense molecule is RNA. In another embodiment, the antisense molecule is a nucleic acid derivative (e.g., DNA or RNA with a protein backbone).

The present invention extends to the preparation of antisense nucleic acids and ribozymes that may be used to interfere with the expression of a polypeptide either by masking the mRNA with an antisense nucleic acid or cleaving it with a ribozyme, respectively.

This invention provides inhibitory nucleic acid therapeutics which can inhibit the activity of herpesviruses in patients with KS by binding to the isolated nucleic acid molecule of KSHV. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene and Toulme (1990) *Biochim. Biophys. Acta.* 1049, 99–125, which is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom et al. (1988) *PNAS* 85, 1028–1032 and Harel-Bellan et al. (1988) *Exp. Med.* 168, 2309–2318. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation, as described in Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

An example of an antiherpes virus inhibitory nucleic acid is ISIS 2922 (ISIS Pharmaceuticals) which has activity against CMV (see *Biotechnology News* 14:5).

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

B. Antiviral Agents

The use of combinations of antiviral drugs and sequential treatments are useful for treatment of herpesvirus infections and will also be useful for the treatment of herpesvirus-induced KS. For example, Snoeck et al. (1992) *Eur. J. Clin. Micro. Infect. Dis.* 11, 1144–1155, found additive or synergistic effects against CMV when combining antiherpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. (1991) *Antimicrob Agents Chemother* 35:2440–3.

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. (1990) *Mol. Pharm.* 37,402–7) describes the use of thymidylate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophylactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach et al., 1992, *Infectious Disease* Ch.35, 289, W. B. Saunders, Philadelphia, Pa.) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

The antiherpesvirus agents that will be useful for treating virus-induced KS can be grouped into broad classes based on their presumed modes of action. These classes include agents that act (1) by inhibition of viral DNA polymerase, (2) by targeting other viral enzymes and proteins, (3) by miscellaneous or incompletely understood mechanisms, or (4) by binding a target nucleic acid (i.e., inhibitory nucleic acid therapeutics, supra). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of DNA Polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al., supra).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al., 1990, *Antiviral Research* 14, 61–74) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq (1993, *Antimicrobial Chemotherapy* 32, Suppl. A, 121–132) and in other references cited supra and infra.

Anti-herpesvirus medications suitable for treating viral induced KS include, but are not limited to, nucleoside analogs including acyclic nucleoside phosphonate analogs (e.g., phosphonyl-methoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1β-D-arabinofuranosyl-cytosine (ara-C); HPMPC [(S)-1-[3-hydroxy-2-(phosphonylmethoxy)propyl]cytosine (e.g., GS 504, Gilead Science)] and its cyclic form (cHPMPC); HPMPA [(S)-9-(3-hydroxy-2-phosphonylmethoxypropyl)adenine] and its cyclic form (cHPMPA); (S)-HPMPDAP [(S)-9-(3-hydroxy-2-phosphonylmethoxypropyl)-2,6-diaminopurine]; PMEDAP [9-(2-phosphonyl-methoxyethyl)-2,6-diaminopurine]; HOE 602 [2-amino-9-(1,3-bis (isopropoxy)-2-propoxymethyl)purine]; PMEA [9-(2-phosphonylmethoxyethyl)adenine]; bromovinyl-deoxyuridine (Burns and Sandford, 1990, *J. Infect. Dis.* 162:634–7); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E) -5-(2-iodovinyl)-2'-deoxyuridine] and its carbocyclic analogue, C-IVDU (Balzarini et al., supra); and 5-mercutithio analogs of 2'-deoxyuridine (Holliday and Williams, 1992, *Antimicrob. Agents Chemother.* 36, 1935); acyclovir [9-([2-hydroxyethoxy]methyl)guanine; e.g., Zovirax (Burroughs Wellcome)]; penciclovir (9-[4-hydroxy-2-(hydroxymethyl) butyl]-guanine); ganciclovir 1(9-[1,3-dihydroxy-2 propoxymethyl]-guanine) e.g., Cymevene, Cytovene (Syntex), DHPG (Stals et al., 1993, *Antimicrobial Agents Chemother.* 37, 218–223; isopropylether derivatives of ganciclovir (see, e.g., Winkelmann et al., 1988, *Drug Res.* 38, 1545–1548); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclo butane ring (e.g., cyclobut-A [(+−)-9-[1β,2α,3β)-2,3-bis (hydroxymethyl)-1-cyclobutyl]adenine], cyclobut-G [(+−)-9-[1β,2α,3β)-2,3-bis(hydroxymethyl)-1-cyclobutyl] guanine], BHCG [(R)-(1α,2β,1α)-9-(2,3-bis (hydroxymethyl)cyclobutyl]guanine], and an active isomer of racemic BHCG, SQ 34,514 (1R-1α,2β,3β)-2-amino-9-[2, 3-bis(hydroxymethyl)cyclobutyl]-6H-purin-6-one (see, Braitman et al., 1991, *Antimicrob. Agents and Chemotherapy* 35, 1464–1468). Certain of these antiherpesviral agents are discussed in Gorach et al., 1992, *Infectious Disease* Ch.35, 289, W. B. Saunders, Philadelphia; Saunders et al., 1990, *J. Acquir. Immune Defic. Syndr.* 3, 571; Yamanaka et al., 1991, *Mol. Pharmacol.* 40, 446; and Greenspan et al., 1990, *J. Acquir. Immune Defic. Syndr.* 3, 571.

Triciribine and triciribine monophosphate are potent inhibitors against herpes viruses. (Ickes et al., 1994, *Antiviral Research* 23, Seventh International Conf. on Antiviral Research, Abstract No. 122, Supp. 1.), HIV-1 and HIV-2 (Kucera et al., 1993, *AIDS Res. Human Retroviruses* 9, 307–314) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella-Zoster, Cytomegalovirus, and Epstein-Barr virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble, 1991, *Clinical Infectious Diseases* 14, 741–6. Treatment protocols for ganciclovir are 5 mg/kg twice a day IV or 2.5 mg/kg. three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK-HSV, VZV or CMV infections in animal models (De Clercq, supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2A-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythro-oxetanosyl)guanine]. Although OXT-G is believed to act by inhibiting viral DNA synthesis its mechanism of action has not yet been elucidated. These and other compounds are described in Andrei et al., 1992, *Eur. J. Clin. microbiol. Infect. Dis.* 11, 143–51. Additional antiviral purine derivatives useful in treating herpesvirus infections are disclosed in U.S. Pat. No. 5,108,994 (assigned to Beecham Group P.L.C.). 6-methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Other Antivirals

Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cycloalkylmethyl]-5-substituted -uracils and -guanines as described in, e.g., U.S. Pat. Nos. 4,863,927 and 4,782,062 (Tolman et al., Merck) as well as other enzymes. It will be apparent to one of ordinary skill in the art that there are additional viral proteins, both characterized and as yet to be discovered, that can serve as target for antiviral agents. Kutapressin is a liver derivative available from Schwarz Parma of Milwaukee, Wis. in an injectable form of 25 mg/ml. The recommended dosage for herpesviruses is from 200 to 25 mg/ml per day for an average adult of 150 pounds.

Poly(I) Poly($C_{12}$U), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/m$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) (see, The Pink Sheet 55(20) May 17, 1993).

Interferon is known inhibit replication of herpes viruses. See Oren and Soble, supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other antiherpesvirus compositions are described in U.S. Pat. Nos. 5,286,649 and 5,098,708 (Konishi et al., Bristol-Meyers Squibb) and U.S. Pat. No. 5,175,165 (Blumenkopf et al.; Burroughs Wellcome). U.S. Pat. No. 4,880,820 (Ashton et al., Merck) describes the antiherpes virus agent (S)-9-(2,3-dihydroxy-1-propoxymethyl)guanine. U.S. Pat. No. 4,708,935 (Suhadolnik et al., Research Corporation) describes a 3'-deoxyadenosine compound effective in inhibiting HSV and EBV. U.S. Pat. No. 4,386,076 (Machida et al., Yamasa Shoyu Kabushiki Kaisha) describes use of (E)-5-(2-halogenovinyl)-arabinofuranosyluracil as an antiherpesvirus agent. U.S. Pat. No. 4,340,599 (Lieb et al., Bayer Aktiengesellschaft) describes phosphonohydroxyacetic acid derivatives useful as antiherpes agents. U.S. Pat. Nos. 4,093,715 and 4,093,716 (Lin et al., Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al., Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

iii) Administration

The subjects to be treated or whose tissue may be used may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy

Having identified a primary causal agent of KS in humans as a novel human herpesvirus, there are immunosuppressive therapies that can modulate the immunologic dysfunction that arises from the presence of viral-infected tissue. In particular, agents that block the immunological attack of the viral-infected cells will ameliorate the symptoms of KS and/or reduce disease progression. Such therapies include antibodies that prevent immune system targeting of viral-infected cells. Such agents include antibodies which bind to cytokines that otherwise upregulate the immune system in response to viral infection.

The antibody may be administered to a patient either singly or in a cocktail containing two or more antibodies, other therapeutic agents, compositions, or the like, including, but not limited to, immunosuppressive agents, potentiators and side-effect relieving agents. Of particular interest are immunosuppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference,* 41st Ed. (1987), Publisher Edward R. Barnhart, New Jersey.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides substances suitable for use as vaccines for the prevention of KS and methods for administering them. The vaccines are directed against KSHV and most preferably comprise antigens obtained from KSHV. In one embodiment, the vaccine contains attenuated KSHV. In another embodiment, the vaccine contains killed KSHV. In another embodiment, the vaccine contains a nucleic acid vector encoding a KSHV polypeptide. In another embodiment, the vaccine is a subunit vaccine containing a KSHV polypeptide.

This invention provides a recombinant KSHV virus with a gene encoding a KSHV polypeptide deleted from the genome. The recombinant virus is useful as an attenuated vaccine to prevent KSHV infection.

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administered to the subject in an effective amount to vaccinate the subject against Kaposi's sarcoma.

This invention provides a method of immunizing a subject against disease caused by KSHV which comprises administering to the subject an effective immunizing dose of an isolated herpesvirus subunit vaccine.

A. Vaccines

The vaccine can be made using synthetic peptide or recombinantly-produced polypeptide described above as antigen. Typically, a vaccine will include from about 1 to 50 micrograms of antigen. More preferably, the amount of polypeptide is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer. of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," *Bioconjugate Chem.* 1, 2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocompromised and normal children (Hardy, I., et al., 1990, *Inf. Dis. Clin. N. Amer.* 4, 159; Hardy, I. et al., 1991, *New Engl. J. Med.* 325, 1545; Levin, M. J. et al., 1992, *J. Inf. Dis.* 166, 253; Gershon, A. A., 1992, *J. Inf. Des.* 166(Suppl), 563. Vaccines against Herpes simplex Types 1 and 2 are also commercially available with some success in protection against primary disease, but have been less successful in preventing the establishment of latent infection in sensory ganglia (Roizman, B., 1991, *Rev. Inf. Disease* 13(Suppl. 11), S892; Skinner, G. R. et al., 1992, *Med. Microbiol. Immunol.* 180, 305).

Vaccines against KSHV can be made from the KSHV envelope glycoproteins. These polypeptides can be purified and used for vaccination (Lasky, L. A., 1990, *J. Med. Virol.* 31, 59). MHC-binding peptides from cells infected with the human herpesvirus can be identified for vaccine candidates per the methodology of Marloes, et al., 1991, *Eur. J. Immunol.* 21, 2963–2970.

The KSHV antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionibacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 $\mu$g to about 100 $\mu$g protein per patient. A preferable range is from about 1 $\mu$g to about 50 $\mu$g per dose. A more preferred range is about 15 $\mu$g to about 45 $\mu$g. A suitable dose size is about 0.5 ml. Accordingly, a dose for intramuscular injection, for example, would comprise 0.5 ml containing 45 $\mu$g of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral polypeptides from the human herpesvirus. For example, it is known in the protein art that certain amino acid residues can be substituted with amino acids of similar size and polarity without an undue effect upon the biological activity of the protein. The human herpesvirus polypeptides have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Monitoring Therapeutic Efficacy

This invention provides a method for monitoring the therapeutic efficacy of treatment for Kaposi's sarcoma which comprises: (a) determining in a first sample from a subject with Kaposi's sarcoma the presence of the isolated nucleic acid molecule; (b) administering to the subject a therapeutic amount of an agent such that the agent is contacted to the cell in a sample; (c) determining after a suitable period of time the amount of the isolated nucleic acid molecule in the second sample from the treated subject; and (d) comparing the amount of isolated nucleic acid molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. Screening Assays for Pharmaceuticals for Alleviating the Symptoms of KS

Since an agent involved in the causation or progression of KS has been identified and described, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus polypeptides or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada et al., 1989, *J. Clin. Microbiol.* 27, 2204; Kikuta et al., 1989, *Lancet* October 7, 861) . Infected cultures and their supernatants can be assayed for the total amount of virus including the presence of the viral genome by quantitative PCR, by dot blot assays or by using immunologic methods. For example, a culture of susceptible cells could be infected with KSHV in the presence of various concentrations of drug, fixed on slides after a period of days, and examined for viral antigen by indirect immunofluorescence with monoclonal antibodies to viral polypeptides (Kikuta et al., supra). Alternatively, chemically adhered MT-4 cell monolayers can be used for an infectious agent assay using indirect immunofluorescent antibody staining to search for focus reduction (Higashi et al., 1989, *J. Clin. Micro.* 27, 2204).

As an alternative to whole cell in vitro assays, purified KSHV enzymes isolated from a host cell or produced by recombinant techniques can be used as targets for rational drug design to determine the effect of the potential drug on enzyme activity. KSHV enzymes amenable to this approach include, but are not limited to, dihydrofolate reductase (DHFR), thymidylate synthase (TS), thymidine kinase or DNA polymerase. A measure of enzyme activity indicates effect on the agent itself.

Drug screens using herpes viral products are known and have been previously described in EP 0514830 (herpes proteases) and WO 94/04920 ($U_L$13 gene product)

This invention provides an assay for screening anti-KS chemotherapeutics. Infected cells can be incubated in the presence of a chemical agent that is a potential chemotherapeutic against KS (e.g., acyclo-guanosine). The level of virus in the cells is then determined after several days by immunofluorescence assay for antigens, Southern blotting for viral genome DNA or Northern blotting for mRNA and compared to control cells. This assay can quickly screen large numbers of chemical compounds that may be useful against KS.

Further, this invention provides an assay system that is employed to identify drugs or other molecules capable of binding to the nucleic acid molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention provides a method of screening for a KSHV-selective antiviral drug in vivo comprising: (a) expression of KSHV DHFR or KSHV TS in a bacterial auxotroph (nutritional mutant); (b) measuring bacterial growth rate in the absence and presence of the drug; and (c) comparing the rates so measured so as to identify the drug that inhibits KSHV DHFR or KSHV TS in vivo.

Methods well known to those skilled in the art allow selection or production of a suitable bacterial auxotroph and measurement of bacterial growth.

The following reviews of antifolate compounds are provided to more fully describe the state of the art, particularly as it pertains to inhibitors of dihydrofolate reductase and thymidylate synthase: (a) Unger, 1996, Current concepts of treatment in medical oncology: new anticancer drugs, *Journal of Cancer Research & Clinical Oncology* 122, 189–198; (b) Jackson, 1995, Toxicity prediction from metabolic pathway modelling, *Toxicology* 102, 197–205; (c) Schultz, 1995, Newer antifolates in cancer therapy, *Progress in Drug Research* 44, 129–157; (d) van der Wilt and Peters, 1994, New targets for pyrimidine antimetabolites in the treatment of solid tumours 1: Thymidylate synthase, *Pharm World Sci* 16, 167; (e) Fleisher, 1993, Antifolate analogs: mechanism of action, analytical methodology, and clinical efficacy, *Therapeutic Drug Monitoring* 15, 521–526; (f) Eggott et al., 1993, Antifolates in rheumatoid arthritis: a hypothetical mechanism of action, *Clinical & Experimental Rheumatology* 11 Suppl 8, S101–S105; (g) Huennekens et al., 1992, Membrane transport of folate compounds, *Journal of Nutritional Science & Vitaminology* Spec No, 52–57; (h) Fleming and Schilsky, 1992, Antifolates: the next generation, *Seminars in Oncology* 19, 707–719; and (i) Bertino et al., 1992, Enzymes of the thymidylate cycle as targets for chemotherapeutic agents: mechanisms of resistance, *Mount Sinai Journal of Medicine* 59, 391–395.

This invention provides a method of determining the health of a subject with AIDS comprising: (a) measuring the plasma concentration of vMIP-I, vMIP-II or vMIP-III; and (b) comparing the measured value to a standard curve relating AIDS clinical course to the measured value so as to determine the health of the subject.

VIII. Treatment of HIV

This invention provides a method of inhibiting HIV replication, comprising administering to the subject or treating cells of a subject with an effective amount of a polypeptide which is encoded by a nucleic acid molecule, so as to inhibit replication of HIV. In one embodiment, the polypeptide is one from the list provided in Table 1.

This invention is further illustrated in the Experimental Details Sections which follow. These sections are set forth to aid in understanding the invention but is not intended to, and should not be construed to, limit in any way the invention as set forth in the claims which follow thereafter.

Experimental Details Section I

Nucleotide Sequenceof the Kaposi's Sarcoma-Associated Herpevirus

The genome of the Kaposi's sarcoma-associated herpesvirus (KSHV or HHVB) was mapped with cosmid and phage genomic libraries from the BC-1 cell line. Its nucleotide sequence was determined except for a 3 kb region at the right end of the genome that was refractory to cloning. The BC-1 KSHV genome consists of a 140.5 kb long unique coding region (LUR) flanked by multiple G+C rich 801 bp terminal repeat sequences. A genomic duplication that apparently arose in the parental tumor is present in this cell culture-derived strain. At least 81 open reading frames (ORFs) including 66 with similarity to herpesvirus saimiri ORFs, and 5 internal repeat regions are present in the LUR. The virus encodes genes similar to complement-binding proteins, three cytokines (two macrophage inflammatory proteins and interleukin-6), dihydrofolate reductase, bcl-2, interferon regulatory factor, IL-8 receptor, NCAM-like adhesin, and a D-type cyclin, as well as viral structural and metabolic proteins. Terminal repeat analysis of virus DNA from a KS lesion suggests a monoclonal expansion of KSHV in the KS tumor. The complete genome sequence is set forth in Genbank Accession Numbers U75698 (LUR), U75699 (TR) and U75700 (ITR).

Kaposi's sarcoma is a vascular tumor of mixed cellular composition (Tappero et al., 1993, *J. Am. Acad. Dermatol.* 28, 371–395). The histology and relatively benign course in persons without severe immunosuppression has led to suggestions that KS tumor cell proliferation is cytokine induced (Ensoli et al., 1992, *Immunol. Rev.* 127, 147–155). Epidemiologic studies indicate the tumor is under strict immunologic control and is likely to be caused by a sexually transmitted infectious agent other than HIV (Petermran et al., 1993, *AIDS* 7, 605–611). KS-associated herpesvirus (KSHV) was discovered in an AIDS-KS lesion by representational difference analysis (RDA) and shown to be present in almost all AIDS-KS lesions (Chang et al., 1994, *Science* 265, 1865–1869). These findings have been confirmed and extended to nearly all KS lesions examined from the various epidemiologic classes of KS (Boshoff et al., 1995, *Lancet* 345, 1043–1044; Dupin et al., 1995, *Lancet* 345, 761–762; Moore and Chang, 1995, *New Eng. J. Med.* 332, 1181–1185; Schalling et al., 1995, *Nature Med.* 1, 707–708; Chang et al., 1996, *Arch. Int. Med.* 156, 202–204). KSHV is the eighth presumed human herpesvirus (HHV8) identified to date.

The virus was initially identifed from two herpesvirus DNA fragments, KS330Bam and KS631Bam (Chang et al., 1994, *Science* 265, 1865–1869). Subsequent sequencing of a 21 kb AIDS-KS genomic library fragment (KSS) hybridizing to KS330Bam demonstrated that KSHV is a gammaherpesvirus related to herpesvirus saimiri (HVS) belonging to the genus Rhadinovirus (Moore et al., 1996, *J. Virol.* 70, 549–558). Colinear similarity (synteny) of genes in this region is maintained between KSHV and HVS, as well as Epstein-Barr virus (EBV) and equine herpesvirus 2 (EHV2). A 12 kb region (L54 and SGL-1) containing the KS631Bam sequence includes cyclin D and IL-8Ra genes unique to rhadinoviruses.

KSHV is not readily transmitted to uninfected cell lines (Moore et al., 1996, *J. Virol.* 70, 549–558), but it is present in a rare B cell primary effusion (body cavity-based) lymphoma (PEL) frequently associated with KS (Cesarman et al., 1995, *New Eng. J. Med.* 332, 1186–1191). BC-1 is a PEL cell line containing a high KSHV genome copy number and is coinfected with EBV (Cesarman et al., 1995, *Blood* 86, 2708–2714). The KSHV genome form in BC-1 and its parental tumor comigrates with 270 kb linear markers on pulsed field gel electrophoresis (PFGE) (Moore et al., 1996, *J. Virol.* 70, 549–558). However, the genome size based on encapsidated DNA from an EBV-negative cell line (Renne et al., 1996, *Nature Med.* 2, 342–346) is estimated to be 165 kb (Moore et al., 1996, *J. Virol.* 70, 549–558). Estimates from KS lesions indicate a genome size larger than that of EBV (172 kb) (Decker et al., 1996, *J. Exp. Med.* 184, 283–288).

To determine the genomic sequence of KSHV and identify novel virus genes, contiguous overlapping virus DNA inserts from BC-1 genomic libraries were mapped. With the exception of a small, unclonable repeat region at its right end, the genome was sequenced to high redundancy allowing definition of the viral genome structure and identification of genes that may play a role in KSHV-related pathogenesis.

Materials and Methods

Library generation and screening. BC-1, HBL-6 and BCP-1 cells were maintained in RPMI 1640 with 20% fetal calf serum (Moore et al., 1996, *J. Virol.* 70, 549–558; Cesarman et al., 1995, *Blood* 86, 2708–2714; Gao et al., 1996, *Nature Med.* 2, 925–928). DNA from BC-1 cells was commercially cloned (Sambrook et al., 1989, *Molecular Cloning: A laboratory manual,* Cold Spring Harbor Press, Salem, Mass.) into either Lambda FIX II or S-Cos1 vectors (Stratagene, La Jolla, Calif.). Phage and cosmid libraries were screened by standard methods (Benton et al., 1977, *Science* 196, 180–182; Hanahan and Meselson, 1983, *Methods Enzymol.* 100, 333–342).

Initial library screening was performed using the KS330Bam and KS631Bam RDA fragments (Chang et al., 1994, *Science* 265, 1865–1869). Overlapping clones were sequentially identified using probes synthesized from the ends of previously identified clones (FIG. 1) (Feinberg and Vogelstein, 1983, *Anal. Biochem.* 132, 6; Melton et al., 1984, *Nucl. Acids Res.* 12, 7035–7056). The map was considered circularly permuted by the presence of multiple, identical TR units in cosmids Z2 and Z6. Each candidate phage or cosmid was confirmed by tertiary screening.

Shotgun Sequencing and Sequence Verification

Lambda and cosmid DNA was purified by standard methods (Sambrook et al., 1989, *Molecular Cloning: A laboratory manual,* Cold Spring Harbor Press, Salem, Mass.). Shotgun sequencing (Deininger, 1983, *Anal. Biochem.* 129, 216–223; Bankier et al., 1987, *Meth. Enzymol.* 155, 51–93) was performed on sonicated DNA. A 1–4 kb fraction was subcloned into M13mp19 (New England Biolabs, Inc., Beverly, Mass.) and propagated in XL1-Blue cells (Stratagene, La Jolla, Calif.) (Sambrook et al., 1989, *Molecular Cloning: A laboratory manual,* Cold Spring Harbor Press, Salem, Mass.) M13 phages were positively screened using insert DNA from the phage or cosmid, and negatively screened with vector arm DNA or adjacent genome inserts.

Automated dideoxy cycle sequencing was performed with M13 (−21) CS+ or FS dye primer kits (Perkin-Elmer, Branchburg N.J.) on ABI 373A or 377 sequenators (ABI, Foster City, Calif.). Approximately 300 M13 sequences were typically required to achieve initial coverage for each 10 kb of insert sequence. Minimum sequence fidelity standards were defined as complete bidirectional coverage with at least 4 overlapping sequences at any given site. For regions with sequence gaps, ambiguities or frameshifts that did not meet these criteria, primer walking was done with custom primers (Perkin-Elmer) and dye terminator chemistry (FS or Ready Reaction kits, Perkin-Elmer). An unsequenced 3 kb region adjacent to the right end TR sequence in the Z2 cosmid insert could not be cloned into M13 or Bluescript despite repeated efforts.

Sequence Assembly and Open Reading Frame Analysis

Sequence data were edited using Factura (ABI, Foster City, Calif.) and assembled into contiguous sequences using electropherograms with AutoAssembler (ABI, Foster City, Calif.) and into larger assemblies with AssemblyLIGN (IBI-Kodak, Rochester N.Y.). Base positions not clearly resolved by multiple sequencing attempts (less than 10 bases in total) were assigned the majority base pair designation. The entire sequence (in 1–5 kb fragments) and all predicted open reading frames (ORFs) were analyzed using BLASTX, BLASTP and BLASTN (Altschul et al., 1990, *J. Mol. Biol.* 215, 403–410). The sequence was further analyzed using MOTIFS (Moore et al., 1996, *J. Virol.* 70, 549–558), REPEAT and BESTFIT (GCG), and MacVector (IBI, New Haven, Conn.).

ORF Assignment and Nomenclature

All ORFs with similarities to HVS were identified. These and other potential ORFs having >100 amino acids were found using MacVector. ORFs not similar to HVS ORFs were included in the map (FIG. 1) based on similarity to other known genes, optimum initiation codon context (Kozak, 1987, *Nucl. Acids Res.* 15, 8125–8148), size and position. Conservative selections were made to minimize spurious assignments; this underestimates the number of true reading frames. KSHV ORF nomenclature is based on HVS similarities; KSHV ORFs not similar to HVS genes are numbered in consecutive order with a K prefix. ORPs with sequence but not positional similarity to HVS ORFs were assigned the HVS ORF number (e.g., ORF 2). As new ORPs are identified, it is suggested that they be designated by decimal notation. The standard map orientation (FIG. 1) of the KSHV genome is the same as for HVS (Albrecht et al., 1992, *J. Virol.* 66, 5047–5058) and EHV2 (Telford et al., 1995, *J. Mol. Biol.* 249, 520–528), and reversed relative to the EBV standard map (Baer et al., 1984, *Nature* 310, 207–211)

Results

Genomic Mapping and Sequence Characteristics

Complete genome mapping was achieved with 7 lambda and 3 cosmid clones (FIG. 1). The structure of the BC-1 KSHV genome is similar to HVS in having a long unique region (LUR) flanked by TR units. The ~140.5 kb LUR sequence has 53.5% G+C content and includes all identified KSHV ORFs. TR regions consist of multiple 801 bp direct repeat units having 84.5% G+C content (FIG. 2A) with potential packaging and cleavage sites. Minor sequence variations are present among repeat units. The first TR unit at the left (Z6) TR junction (205 bp) is deleted and truncated in BC-1 compared to the prototypical TR unit.

The genome sequence abutting the right terminal repeat region is incomplete due to a 3 kb region in the Z2 cosmid insert that could not be cloned into sequencing vectors. Partial sequence information from primer walking indicates that this region contains stretches of 16 bp A+G rich imperfect direct repeats interspersed with at least one stretch of 16 bp C+T rich imperfect direct repeats. These may form a larger inverted repeat that could have contributed to our difficulty in subcloning this region. Greater than 12-fold average sequence redundancy was achieved for the entire LUR with complete bidirectional coverage by at least 4 overlapping reads except in the unclonable region.

The EC-1 TR region was examined by Southern blotting since sequencing of the entire region is not possible due to its repeat structure. BC-1, BCP-1 (an EBV-negative, KSHV infected cell line) and KS lesion DNAs have an intense ~800 bp signal consistent with the unit length repeat sequence when digested with enzymes that cut once in the TR and hybridized to a TR probe (FIGS. 2B and 2C). Digestion with enzymes that do not cut in the TR indicates that the BC-1 strain contains a unique region buried in the TR, flanked by ~7 kb and ~35 kb TR sequences (FIGS. 2C and 2D). An identical pattern occurs in HBL-6, a cell line independently derived from the same tumor as BC-1, suggesting that this duplication was present in the parental tumor (FIGS. 2C and 2D). The restriction pattern with Not I, which also cuts only once within the TR but rarely within the LUR, suggests that the buried region is at least 33 kb. Partial sequencing of this region demonstrates that it is a precise genomic duplication of the region beginning at ORF K8. The LUR is 140 kb including the right end unsequenced gap (<3kb). The estimated KSHV genomic size in BC-1 and HBL-6 (including the duplicated region) is approximately 210 kb.

Based on the EBV replication model used in clonality studies (Raab-Traub and Flynn, 1986, *Cell* 47, 883–889), the polymorphic BCP-1 laddering pattern may reflect lytic virus replication and superinfection (FIG. 2C). The EBV laddering pattern occurs when TR units are deleted or duplicated during lytic replication and is a stochastic process for each infected cell (Raab-Traub and Flynn, 1986, *Cell* 47, 883–889). No laddering is present for SC-1 which is under tight latent KSHV replication control (Moore et al., 1996, *J. Virol.* 70, 549–558). KS lesion DNA also shows a single hybridizing band suggesting that virus in KS tumor cells may be of monoclonal origin.

Features and Coding Regions of the KSHV LUR

The KSHV genome shares the 7 block (B) organization (B1-B7, FIG. 1) of other herpesviruses (Chee et al., 1990, *Curr. Topics Microbiol. Immunol.* 154, 125–169), with subfamily specific or unique ORPs present between blocks (interblock regions (IB) a–h, FIG. 1). ORF analysis indicates that only 79% of the sequenced 137.5 kb LUR encodes 81 identifiable ORPs which is likely to be due to a conservative assignment of ORF positions. The overall LUR CpG dinucleotide observed/expected (O/E) ratio is 0.75 consistent with a moderate loss of methylated cytosines, but there is marked regional variation. The lowest CpG O/E ratios (<0.67) occur in IBa (bp 1–3200), in B5 (68,602–69,405) and IBh (117,352–137,507). The highest O/E ratios (>0.88) extend from B2 to B3 (30,701–47,849), in IBe (67,301–68,600), and in B6 (77,251–83,600). Comparison to the KS5 sequence (Moore et al., 1996, *J. Virol.* 70, 549–558) shows a high sequence conservation between these two strains with only 21 point mutations over the comparable 20.7 kb region (0.1%). A frameshift within BC-1 ORF 28 (position 49,004) compared to KS5 ORF 28 was not resolvable despite repeated sequencing of KS5 and PCR products amplified from BC-1. Two additional frameshifts in noncoding regions (bp 47,862 and 49,338) are also present compared to the KS5 sequence.

Several repeat regions are present in the LUR (FIG. 1). A 143 bp sequence is repeated within ORF K11 at positions 92,678–92,820 and 92,852–92,994 (waka/jwka). Complex repeats are present in other regions of the genome: 20 and 30 bp repeats in the region from 24,285–24,902 (frnk), a 13 bp repeat between bases 29,775 and 29,942 (vnct), two separate 23 bp repeat stretches between bases 118,123 and 118,697 (zppa), and 15 different 11–16 bp repeats throughout the region from 124,527 to 126,276 (moi). A complex A–G rich repeat region (mdsk) begins at 137,099 and extends into the unsequenced gap.

Conserved ORFs with similar genes found in other herpesviruses are listed in Table 1, along with their polarity, map positions, sizes, relatedness to HVS and EBV ORFs, and putative functions. Conserved ORFs coding for viral structural proteins and enzymes include genes involved in viral DNA replication (e.g., DNA polymerase (ORF 9)), nucleotide synthesis (e.g., dihydrofolate reductase (DHFR, ORF 2), thymidylate synthase (TS, ORF 70)), regulators of gene expression (R transactivator (LCTP, ORFSO)) and 5 conserved herpesvirus structural capsid and 5 glycoprotein genes.

Several genes that are similar to HVS ORFs also have unique features. ORF 45 has sequence similarity to nuclear and transcription factors (chick nucleolin and yeast SIR3) and has an extended acidic domain typical for transactivator proteins between amino acids 90 and 115. ORF73 also has an extended acidic domain separated into two regions by a glutamine-rich sequence encoded by the moi repeat. The first region consists almost exclusively of aspartic and glutamic acid residue repeats while the second glutamic acid rich region has a repeated leucine heptad motif suggestive of a leucine zipper structure. ORF 75, a putative tegument protein, has a high level of similarity to the purine biosynthetic enzyme of *E. coli* and *D. melanogaster* N-formylglycinamide ribotide amidotransferase (FGARAT).

ORFs K3 and K5 are not similar to HVS genes but are similar to the major immediate early bovine herpesvirus type 4 (BHV4) gene IEI (12 and 13% identity respectively) (van Santen, 1991, *J. Virol.* 65, 5211–5224). These genes have no significant similarity to the herpes simplex virus I (HSV1) a0 (which is similar to BHV4 IE1), but encode proteins sharing with the HSV1 ICP0 protein a cysteine-rich region which may form a zinc finger motif (van Santen, 1991, *J. Virol.* 65, 5211–5224). The protein encoded by ORF K5 has a region similar to the nuclear localization site present in the late form of the BHV4 protein. ORF K8 has a purine binding motif (GLLVTGKS) in the C-terminus of the protein which is similar to a motif present in the KSHV TK (ORF21) (Moore et al., 1996, *J. Virol.* 70, 549–558).

No KSHV genes with similarity to XVS ORFs 1, 3, 5, 12, 13, 14, 15, 51 and 71 were identified in the KSHV LUR sequence. HVS ORF 1 codes for a transforming protein, responsible for HVS-induced in vitro lymphocyte transformation (Akari et al., 1996, *Virology* 218, 382–388) and has poor sequence conservation among HVS strains (Jung and Desrosiers, 1991, *J. Virol.* 65, 6953–6960; Jung and Desrosiers, 1995, *Molec. Cellular Biol.* 15, 6506–6512). Functional KSHV genes similar to this gene may be present but were not identifiable by sequence comparison. Likewise, no KShV genes similar to EBV latency and transformation-associated proteins (EBNA-1, ESNA-2, EBNA-LP, LMP-1, LMP-2 or gp350/220) were found despite some similarity to repeat sequences present in these genes. KSHV also does not have a gene similar to the BZLF1 EBV transactivator gene.

Several sequences were not given ORF assignments although they have characteristics of expressed genes. The sequence between bp 90,173 and 90,643 is similar to the precursor of secreted glycoprotein X (gX), encoded by a number of alphaherpesviruses (pseudorabies, EHV1), and which does not form part of the virion structure. Like the cognate gene in EHV1, the KSHV form lacks the highly-acidic carboxy terminus of the pseudorabies gene.

Two polyadenylated transcripts expressed at high copy number in BCBL-1 are present at positions 28,661–29,741 (T1.1) in IBb and 118,130–117,436 (T0.7) in IBh. T0.7 encodes a 60 residue polypeptide (ORF K12, also called Kaposin) and T1.1 (also referred to as nut-1) has been speculated to be a U RNA-like transcript.

Cell Cycle Regulation and Cell Signaling Proteins

A number of ORFs which are either unique to KSHV or shared only with other gammaherpesviruses encode genes similar to oncoproteins and cell signaling proteins. ORF 16, similar to EBV BHRF1 and HVS ORF16, encodes a functional Ecl-2-like protein which can inhibit Bax-mediated apoptosis. ORF 72 encodes a functional cyclin D gene, also found in HVS (Nicholas et al., 1992, *Nature* 355, 362–365), that can substitute for human cyclin D in phosphorylating the retinoblastoma tumor suppressor protein.

KSHV encodes a functionally-active IL-6 (ORF K2) and two macrophage inflammatory proteins (MIPs) (ORFs K4 and K6) which are not found in other human herpesviruses. The vIL-6 has 62% amino acid similarity to the human IL-6 and can substitute for human IL-6 in preventing mouse myeloma cell apoptosis. Both MIP-like proteins have conserved C—C dimer signatures characteristic of β-chemokines and near sequence identity to human MIP-1α in their N-terminus regions. vMIP-I (ORF K6) can inhibit CCR-5 dependent HIV-1 replication. An open reading frame spanning nucleotide numbers (bp) 22,529–22,185 (vMIP-III) has low conservation with MIP 1β (BLASTX poisson p=0.0015) but retains the C—C dimer motif. ORF K9 (vIRF1) encodes a 449 residue protein with similarity to the family of interferon regulatory factors (IRF) (David, 1995, *Pharmac. Ther.* 65, 149–161). It has 13.4% amino acid identity to human interferon consensus sequence binding protein and partial conservation of the IRF DNA-binding domain. Three additional open reading frames at bp 88,910–88,410 (vIRF2), bp 90,541–89,600 (vIRF3) and bp 94,127–93,636 (vIRF4) also have low similarity to IRF-like proteins (p >0.35). No conserved interferon consensus sequences were found in this region of the genome.

Other genes encoding signal transduction polypeptides, which are also found in other herpesviruses, include a complement-binding protein (v-CBP, ORF 4), a neural cell adhesion molecule (NCAM)-like protein (v-adh, ORF K14) and an IL8 receptor (ORF 74). Genes similar to ORFs 4 and 74 are present in other rhadinoviruses and ORF 4 is similar to variola B19L and D12L proteins. ORF K14 (v-adh) is similar to the rat and human OX-2 membrane antigens, various NCAMs and the poliovirus receptor-related protein PRRI. OX-2 is in turn similar to ORF U85 of human herpesviruses 6 and 7 but there is no significant similarity between the KSHV and betaherpesvirus OX-2/NCAM ORFs. Like other immunoglobulin family adhesion proteins, v-adh has V-like, C-like, transmembrane and cytoplasmic domains, and an RGD binding site for fibronectin at residues 268–270. The vIL-8R has a seven transmembrane spanning domain structure characteristic of G-protein coupled chemoattractant receptors which includes the EEV-induced EBI1 protein (Birkenbach et al., 1993, *J. Virol.* 67, 2209–2220).

Discussion

The full-length sequence of the KSHV genome in BC-1 cells provides the opportunity to investigate molecular mechanisms of KSHV-associated pathogenesis. The KSHV genome has standard features of rhadinovirus genomes including a single unique coding region flanked by high G+C terminal repeat regions which are the presumed sites for genome circularization. In addition to having 66 conserved herpesvirus genes involved in herpesvirus replication and structure, KSHV is unique in encoding a number of proteins mimicking cell cycle regulatory and signaling proteins.

Our estimated size of the BC-1 derived genome (210 kb including the duplicated portion) is consistent with that found using encapsidated virion DNA (Zhong et al., 1996, *Proc. Natl. Acad. Sci. USA* 93, 6641–6646). Genomic rearrangements are common in cultured herpesviruses (Baer et al., 1984, *Nature* 310, 207–211; Cha et al., 1996, *J. Virol.* 70, 78–83). However, the genomic duplication present in the BC-1 KSHV probably did not arise during tissue culture passage. TR hybridization studies indicate that this insertion of a duplicated LUR fragment into the BC-1 TR is also present in KSHV from the independently derived HBL-6 cell line (Gaidano et al., 1996, Leukemia 10, 1237–40).

Despite this genomic rearrangement, the KSHV genome is well conserved within coding regions. There is less than 0.1% base pair variation between the BC-1 and the 21 kb KS5 fragment isolated from a KS lesion. Higher levels of variation may be present in strains from other geographic regions or other disease conditions. Within the LUR, synteny to HVS is lost at ORFs 2 and 70 but there is concordance in all other regions conserved with HVS. Several conserved genes, such as thymidine kinase (TK) (Cesarman et al., 1995, *Blood* 86, 2708–2714), TS and DHFR (which is present in HVS, see Albrecht et al., 1992, *J. Virol.* 66, 5047–5058, but not human herpesviruses), encode proteins that are appropriate targets for existing drugs.

Molecular mimicry by KSHV of cell cycle regulatory and signaling proteins is a prominent feature of the virus. The KSHV genome has genes similar to cellular complement-binding proteins (ORF 4), cytokines (ORFs K2, K4 and K6), a bcl-2 protein (ORF 16), a cytokine transduction pathway protein (K9), an IL-8R-like protein (ORF74) and a D-type cyclin (ORF72). Additional regions coding for proteins with some similarity to MIP and IRF-like proteins are also present in the KSHV genome. There is a striking parallel between the KSHV genes that are similar to cellular genes and the cellular genes known to be induced by EBV infection. Cellular cyclin D, CD21/CR2, bcl-2, an IL-8R-like protein (EBI1), IL-6 and adhesion molecules are upregulated by EBV infection (Birkenbach et al., 1993, *J. Virol.* 67, 2209–2220; Palmero et al., 1993, *Oncogene* 8, 1049–1054; Finke et al., 1992, *Blood* 80, 459–469; Finke et al., 1994, *Leukemia & Lymphoma* 12, 413–419; Jones et al., 1995, *J. Exper. Med.* 182, 1213–1221). This suggests that KSHV modifies the same signaling and regulation pathways that EBV modifies after infection, but does so by introducing exogenous genes from its own genome.

Cellular defense against virus infection commonly involves cell cycle shutdown, apoptosis (for review, see Shen and Shenk, 1995, *Curr. Opin. Genet. Devel.* 5, 105–111) and elaboration of cell-mediated immunity (CMI). The KSHV-encoded v-bcl-2, v-cyclin and v-IL-6 are active in preventing either apoptosis or cell cycle shutdown (Chang et al., 1996, *Nature* 382, 410). At least one of the 0-chemokine KSHV gene products, v-MIP-I, prevents CCR5-mediated HIV infection of transfected cells. β-chemokines are not known to be required for successful EBV infection of cells although EBV-infected B cells express higher levels of MIP-1α than normal tonsillar lymphocytes (Harris et al., 1993, 151, 5975–5983). The autocrine dependence of EBV-infected B cells on small and uncharacterized protein factors in addition to IL-6 (Tosato et al., 1990, *J. Virol.* 64, 3033–3041) leads to speculation that β-chemokines may also play a role in the EBV life cycle.

KSHV has not formally been shown to be a transforming virus and genes similar to the major transforming genes of HVS and EBV are not present in the BC-1 strain KSHV. Nonetheless, dysregulation of cell proliferation control caused by the identified KSHV-encoded proto-oncogenes and cytokines may contribute to neoplastic expansion of virus-infected cells. Preliminary studies suggest that subgenomic KSHV fragments can transform NIH 3T3 cells. If KSHV replication, like that of EBV, involves recombination of TR units (Raab-Traub and Flynn, 1986, Cell 47, 883–889), a monomorphic TR hybridization pattern present in a KS lesion would indicate a clonal virus population in the tumor. This is consistent with KS being a true neoplastic proliferation arising from single transformed, KS-infected cell rather than KSHV being a "passenger virus". Identification of KSHV genes similar to known oncoproteins and cell proliferation factors in the current study provides evidence that KSHV is likely to be a transforming virus.

Experimental Details Section II

Molecular Mimicry of Human Cytokine and Cytokine Response Pathway Genes by KSHV

Four virus genes encoding proteins similar to two human macrophage inflammatory protein (MIP) chemokines, an IL-6 and an interferon regulatory factor (IRF or ICSBP) polypeptide are present in the genome of Kaposi's sarcoma-associated herpesvirus (KSHV). Expression of these genes is inducible in infected cell lines by phorbol esters. vIL-6 is functionally active in B9 cell proliferation assays. It is primarily expressed in KSHV-infected hematopoietic cells rather than KS lesions. vMIP-I inhibits replication of CCR5-dependent HIV-1 strains in vitro indicating that it is functional and could contribute to interactions between these two viruses. Mimicry of cell signaling proteins by KSHV may abrogate host cell defenses and contribute to KSHV-associated neoplasia.

Kaposi's sarcoma-associated herpesvirus (KSHV) is a gammaherpesvirus related to Epstein-Barr virus (EBV) and herpesvirus saimiri (HVS). It is present in nearly all KS lesions including the various types of HIV-related and HIV-unrelated KS (Chang et al., 1994, *Science* 265, 1865–1869; Boshoff et al., 1995, *Lancet* 345, 1043–1044; Dupin et al., 1995, Lancet 345, 761–762; Schalling et al., 1995, *Nature Med.* 1, 707–708). Viral DNA preferentially localizes to KS tumors (Boshoff et al., 1995, *Nature Med.* 1, 1274–1278) and serologic studies show that KSHV is specifically associated with KS. Related lymphoproliferative disorders frequently occurring in patients with KS, such as primary effusion lymphomas (PEL), a rare B cell lymphoma, and some forms of Castleman's disease are also associated with KSHV infection (Cesarman et al., 1995, *New Eng. J. Med.* 332, 1186–1191; Soulier et al., 1995, *Blood* 86, 1276–1280). Three KSHV-encoded cytokine-like polypeptides and a polypeptide similar to interferon regulatory factor genes have now been identified. Paradoxically, while cytokine dysregulation has been proposed to cause Kaposi's sarcoma (Ensoli et al., 1994, *Nature* 371, 674–680; Miles, 1992, *Cancer Treatment & Research* 63, 129–140), in vitro spindle cell lines used for these studies over the past decade are uniformly uninfected with KSHV (Ambroziak et al., *Science* 268, 582–583; Lebbe et al., 1995, *Lancet* 345, 1180).

To identify unique genes in the KSHV genome, genomic sequencing (see METHODS) was performed using Supercos-1 and Lambda FIX II genomic libraries from BC-1, a nonHodgkin's lymphoma cell line stably infected with both KSHV and EBV (Cesarman et al., 1995, *Blood* 86, 2708–2714). The KSHV DNA fragments KS330Bam and KS631Bam (Chang et al., 1994, *Science* 265, 1865–1869) were used as hybridization starting points for mapping and bi-directional sequencing. Open reading frame (ORF) analysis (see METHODS) of the Z6 cosmid sequence identified two separate coding regions (ORFs K4 and K6) with sequence similarity to β-chemokines and a third coding region (ORF K2) similar to human interleukin-6 (huIL-6); a fourth coding region (ORF K9) is present in the Z8 cosmid insert sequence with sequence similarity to interferon regulatory factor (IRF) polypeptides (FIGS. 3A–3C). None of these KSHV genes are similar to other known viral genes. Parenthetically, a protein with conserved cysteine motifs similar to β-chemokine motif signatures has recently been reported in the molluscum contagiosum virus (MCV) genome. Neither vMIP-I nor vMIP-II has significant similarity to the MCV protein.

The cellular counterparts to these four viral genes encode polypeptides involved in cell responses to infection. For example, the MIP/RANTES (macrophage inflammatory protein/regulated on activation, normal T cell expressed and secreted) family of 8–10 kDa β-chemoattractant cytokines (chemokines) play an important role in virus infection-mediated inflammation (Cook et al., 1995, *Science* 269, 1583–1585). β-chemokines are the natural ligand for CCR5 and can block entry of non-syncytium inducing (NSI), primary lymphocyte and macrophage-tropic HIV-1 strains in vitro by binding to this HIV co-receptor (Cocchi et al., 1995, *Science* 270, 1811–1815). IL-6, initially described by its effect on B cell differentiation (Hirano et al., 1985, *Proc Natl Acad Sci, USA* 85, 5490; Kishimoto et al., 1995, *Blood* 86, 1243–1254), has pleiotropic effects on a wide variety of cells and may play a pathogenic role in multiple myeloma, multicentric Castleman's disease (a KSHV-related disorder), AIDS-KS and EBV-related postransplant lymphoproliferative disease (Klein et al., 1995, *Blood* 85, 863–872; Hilbert et al., 1995, *J Exp Med* 182, 243–248; Brandt et al., 1990, *Curr Topic Microbiol Immunol* 166, 37–41; Leger et al., 1991, *Blood* 78, 2923–2930; Burger et al., 1994, *Annal Hematol* 69, 25–31; Tosato et al., 1993, *J Clin Invest* 91, 2806–2814). IL-6 production is induced by either EBV or CMV infection and is an autocrine factor for EBV-infected lymphoblastoid cells that enhances their tumorigenicity in nude mice (Tosato et al., 1990, *J Virol* 64, 3033–3041; Scala et al., 1990, *J Exp Med* 172, 61–68; Almeida et al., 1994, *Blood* 83, 370–376). Cell lines derived from KS lesions, although not infected with KSHV, also produce and respond to IL-6 (Miles et al., 1990, *Proc Natl Acad Sci USA* 87, 4068–4072; Yang et al., 1994, J Immunol 152, 943–955). While MIP and IL-6 are secreted cytokines, the IRF family of polypeptides regulate interferon-inducible genes in response to γ- or α-/β-interferon cytokines by binding to specific interferon consensus sequences (ICS) within interferon-inducible promoter regions. A broad array of cellular responses to interferons is modulated by the repressor or transactivator functions of IRF polypeptides and several members (IRF-1 and IRF-2) have opposing anti-oncogenic and oncogenic activities (Sharf et al., 1995, *J Biol Chem* 270, 13063–13069; Harada et al., 1993, *Science* 259, 971–974; Weisz et al., 1994, *Internat Immunol* 6, 1125–1131; Weisz et al., 1992, *J Biol Chem* 267, 25589–25596).

The 289 bp ORF K6 (ORF MIPL) gene encodes a 10.5 kDa polypeptide (vMIP-I; MIP1) having 37.9% amino acid identity (71% similarity) to huMIP-1α and slightly lower similarity to other β-chemokines (FIG. 3A). ORF K4 also encodes a predicted 10.5 kDa polypeptide (vMIP-II; vMIPlc-II) with close similarity and amino acid hydrophobicity profile to vMIP-I. The two KSHV-encoded MIP β-chemokines are separated from each other on the KSHV genome by 5.5 kb of intervening sequence containing at least 4 ORFs (see METHODS). Both polypeptides have conserved β-chemokine motifs (FIG. 3A, residues 17–55) which include a characteristic C—C dicysteine dimer (FIG. 3A, residues 36–37), and have near sequence identity to human MIP-1α at residues 56–84. However, the two polypeptides show only 49.0% amino acid identity to each other and are markedly divergent at the nucleotide level indicating that this duplication is not a cloning artifact. The two viral polypeptides are more closely related to each other phylogenetically than to huMIP-1α, huMIP-1β or huRANTES suggesting that they arose by gene duplication rather than independent acquisition from the host genome (see Sequence alignment in METHODS). The reason for this double gene dosage in the viral genome is unknown.

The KSHV ORF K2 (FIG. 3B) encodes a hypothetical 204 residue, 23.4 kDa IL-6-like polypeptide with a hydrophobic 19 amino acid secretory signaling peptide having 24.8!k amino acid identity and 62.2% similarity to the human polypeptide. vIL-6 also has a conserved sequence characteristic for IL-6-like interleukins (amino acids 101–125 of the gapped polypeptide) as well as conserved four cysteines which are present in IL-6 polypeptides (gapped alignment residue positions 72, 78, 101 and 111 in FIG. 3B) IL-6 is a glycosylated cytokine and potential N-linked glycosylation sites in the vIL-6 sequence are present at gapped positions 96 and 107 in FIG. 3C. The 449 residue KSHV vIRF polypeptide encoded by ORF K9 has lower overall amino acid identity (approximately 13%) to its human cellular counterparts than either of the vMIPs or the vIL-6, but has a conserved region derived from the IRF family of polypeptides (FIG. 3C, gapped residues 88–121). This region includes the tryptophan-rich IRF ICS DNA binding domain although only two of four tryptophans thought to be involved in DNA binding are positionally conserved. It is preceded by an 87-residue hydrophilic N-terminus with little apparent IRF similarity. A low degree of amino acid similarity is present at the C-terminus corresponding to the IRF family transactivator/repressor region.

Figure 6:
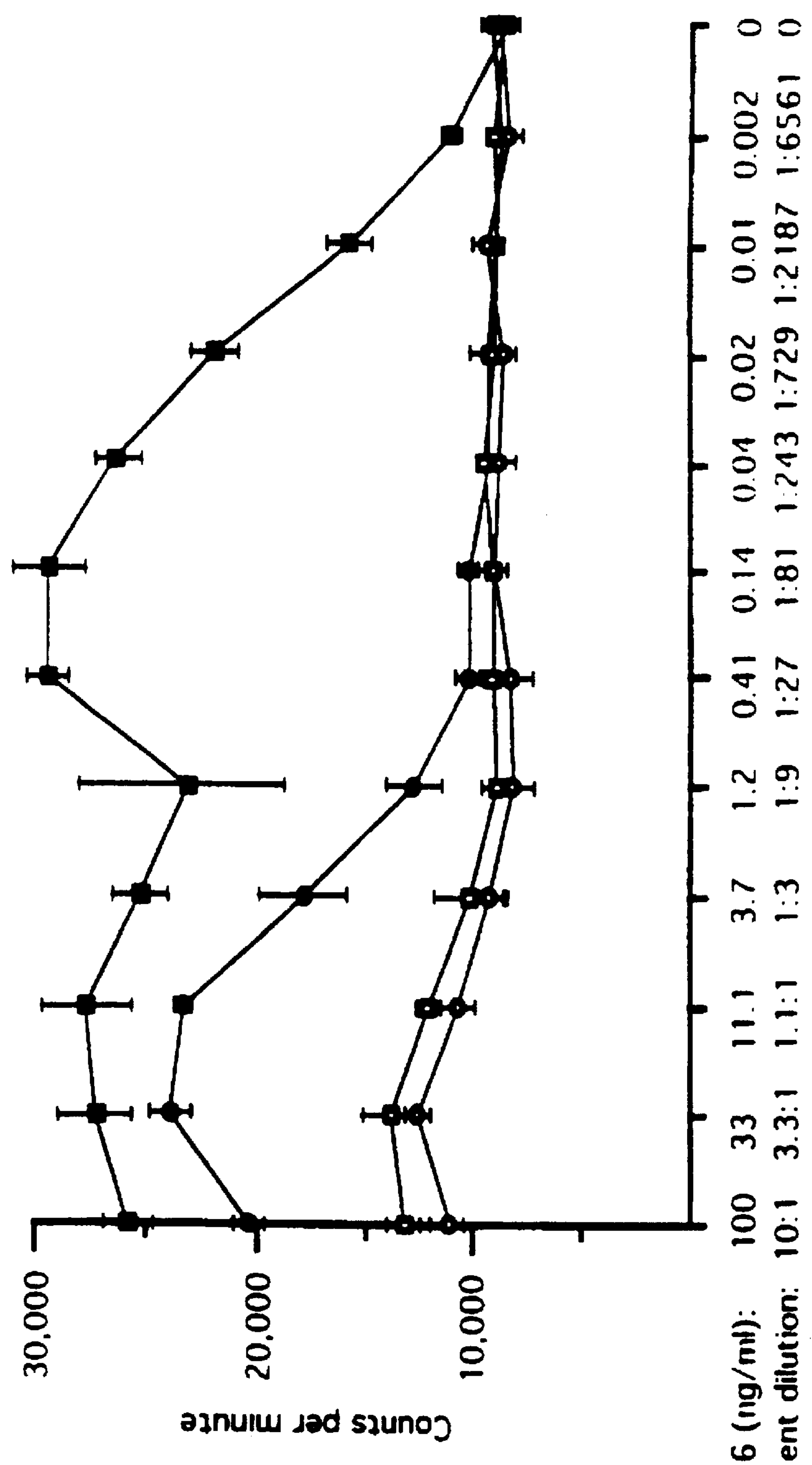

The four KSHV cell signaling pathway genes show similar patterns of expression in virus-infected lymphocyte cell lines by Northern blotting (see METHODS). Whole RNA was extracted from BCP-1 (a cell line infected with KSHV alone) and BC-1 (EBV and KSHV coinfected, see *Cesarman et al.,* 1995, *Blood* 86, 2708–2714) with or without pretreatment with 20 ng/ml 12-O-tetradecanoylphorbol-13-acetate (TPA, Sigma, St. Louis Mo.) for 48 hours. While constitutive expression of these genes was variable between the two cell lines, expression of all four gene transcripts increased in BCP-1 and BC-1 cells after TPA induction (FIGS. 4A–4D). This pattern is consistent with expression occurring primarily during lytic phase virus replication. Examination of viral terminal repeat sequences of BCP-1 and BC-1 demonstrates that low level of virus lytic replication occurs in BCP-1 but not BC-1 without TPA induction (see METHODS), and both cell lines can be induced to express lytic phase genes by TPA treatment despite repression of DNA replication in BC-1. Lower level latent expression is also likely, particularly for vIL-6 (FIG. 4C) and vIRF (FIG. 4D), since these transcripts are detectable without TPA induction in BC-1 cells which are under tight latency control. To determine if in vitro KS spindle cell cultures retain defective or partial virus sequences that include these genes, DNA was extracted from four KS spindle cell lines (KS-2, KS-10, KS-13 and KS-22) and PCR amplified for vMIP-I, vMIP-II, vIL-6 and vIRF sequences (see METHODS). None of the spindle cell DNA samples were positive for any of the four genes.

vIL-6 was examined in more detail using bioassays and antibody localization studies to determine whether it is functionally conserved. Recombinant vIL-6 (rvIL-6) is specifically recognized by antipeptide antibodies which do not cross-react with huIL-6 (FIGS. 5A–5B) (see METHODS). vIL-6 is produced constitutively in BCP-1 cells and increases markedly after 48 hour TPA induction, consistent with Northern hybridization experiments. The BC-1 cell line coinfected with both KSHV and EBV only shows vIL-6 polypeptide expression after TPA induction (FIG. 5A, lanes 3–4) and control EBV-infected P3HR1 cells are negative for vIL-6 expression (FIG. 5A, lanes 5–6). Multiple high molecular weight bands present after TPA induction (21–25 kDa) may represent precursor forms of the polypeptide. Despite regions of sequence dissimilarity between huIL-6 and vIL-6, the virus interleukin 6 has biologic activity in functional bioassays using the IL-6-dependent mouse plasmacytoma cell line B9 (see METHODS). COS7 supernatants from the forward construct (rvIL-6) support B9 cell proliferation measured by $^{3}$H-thymidine uptake indicating that vIL-6 can substitute for cellular IL-6 in preventing B9 apoptosis (FIG. 6). vIL-6 supported B9 proliferation is dose dependent with the unconcentrated supernatant from the experiment shown in FIG. 6 having biologic activity equivalent to approximately 20 pg per ml huIL-6.

Forty-three percent of noninduced BCP-1 cells (FIG. 7A) have intracellular cytoplasmic vIL-6 immunostaining (see METHODS) suggestive of constitutive virus polypeptide expression in cultured infected cells, whereas no specific immunoreactive staining is present in uninfected control P3HR1 cells (FIG. 7B). vIL-6 production was rarely detected in KS tissues and only one of eight KS lesions examined showed clear, specific vIL-6 immunostaining in less than 2% of cells (FIG. 7C) . The specificity of this low positivity rate was confirmed using preimmune sera and neutralization with excess vIL-6 peptides. Rare vIL-6-producing cells in the KS lesion are positive for either CD34, an endothelial cell marker (FIG. 8A), or CD45, a pan-hematopoietic cell marker (FIG. 8B), demonstrating that both endothelial and hematopoietic cells in KS lesions produce vIL6. It is possible that these rare vIL-6 positive cells are entering lytic phase replication which has been shown to occur using the KSHV T1.1 lytic phase RNA probe. In contrast, well over half (65?) of ascitic lymphoma cells pelleted from an HIV-negative PEL are strongly positive for vIL-6 (FIG. 7E) and express the plasma cell marker EMA (Cesarman et al., 1995, *Blood* 86, 2708–2714) indicating that either most PEL cells in vivo are replicating a lytic form of KSHV or that latently infected PEL cells can express high levels of vIL-6. No specific staining occurred with any control tissues examined including normal skin, tonsillar tissue, multiple myeloma or angiosarcoma using either preimmune or post-immune rabbit anti-vIL-6 antibody (FIGS. 7E and 7F).

Virus dissemination to nonKS tissues was found by examining a lymph node from a patient with AIDS-KS who did not develop PEL. Numerous vIL-6-staining hematopoietic cells were present in this lymph node (FIG. 8C) which was free of KS microscopically. vIL-6 positive lymph node cells were present in relatively B-cell rich areas and some express CD20 B cell surface antigen (FIG. 8D), but not EMA surface antigen (unlike PEL cells) (Cesarman et al., 1995, *Blood* 86, 2708–2714). No colocalization of vIL-6 positivity with the T cell surface antigen CD3 or the macrophage antigen CD68 was detected, although phagocytosis of vIL-6 immunopositive cells by macrophages was frequently observed.

To investigate whether the vMIP-I can inhibit NSI HIV-1 virus entry, human CD4+ cat kidney cells (CCC/CD4) were transiently transfected with plasmids expressing human CCR5 and vMIP-I or its reverse construct I-PIMv (see CCR5 and vMIP-I cloning in METHODS). These cells were infected with either M23 or SF162 primary NSI HIV-1 isolates which are known to use CCR5 as a co-receptor (Clapham et al., 1992, *J Virol* 66, 3531–3537) or with the HIV-2 variant ROD/B which can infect CD4+ CCC cells without human CCR5. Virus entry and replication was assayed by immunostaining for retroviral antigen production (FIG. 9). vMIP-I cotransfection reduced NSI HIV-1 foci generation to less than half that of the reverse-construct negative control but had no effect on ROD/B HIV-2 replication.

Molecular piracy of host cell genes is a newly recognized feature of some DNA viruses, particularly herpesviruses and poxviruses (Murphy, 1994, *Infect Agents Dis* 3, 137–154; Albrecht et al., 1992, *J Virol* 66, 5047–5058; Gao and Murphy, 1994, *J Biol Chem* 269, 28539–28542; Chee et al., 1990, *Curr Top Microbiol Immunol* 154, 125–169; Massung et al., 1994, *Virol* 201, 215–240). The degree to which KSHV has incorporated cellular genes into its genome is exceptional. In addition to vMIP-I and vMIP-II, vIL-6 and vIRF, KSHV also encodes polypeptides similar to bcl-2 (ORF 16), cyclin D (ORF 72), complement-binding proteins similiar to CD21/CR2 (ORF 4), an NCAM-like adhesion protein (ORF K14), and an IL-8 receptor (ORF 74). EBV also either encodes (BHRFl/bcl-2) or induces (CR-2;

cyclin D; IL-6; bcl-2; adhesion molecules and an IL-8R-like EBI1 protein) these same cellular polypeptides (Cleary et a7., 1986, *Cell* 47, 19–28;

Tosato et al., 1990, *J Virol* 64, 3033–3041; Palmero et al., 1993, *Oncogene* 8, 1049; Larcher et al., 1995, *Eur J Immunol* 25, 1713–1719; Birkenbach et al., 1993, *J Virol* 67, 2209–2220). Thus, both viruses may modify similar host cell signaling and regulatory pathways. EBV appears to effect these changes through induction of cellular gene expression whereas KSHV introduces the polypeptides exogenously from its own genome.

Identification of these virus-encoded cellular-like polypeptides leads to speculation about their potential roles in protecting against cellular antiviral responses. huIL-6 inhibits γ-interferon-induced, Bax-mediated apoptosis in myeloma cell lines (Lichtenstein et al., 1995, *Cellular Immunology* 162, 248–255) and vIL-6 may play a similar role in infected B cells. KSHV-encoded vIRF, vbcl-2 and v-cyclin may also interfere with host-cell mediated apoptosis induced by virus infection and v-cyclin may prevent G1 cell cycle arrest of infected cells. Interference with interferon-induced MHC antigen presentation and cell-mediated immune reponse (Holzinger et al., 1993, *Immunol Let* 35, 109–117) by vIRF is also possible. The β-chemokine polypeptides vMIP-I and vMIP-II may have agonist or antagonist signal transduction roles. Their sequence conservation and duplicate gene dosage are indicative of a key role in KSHV replication and survival.

Uncontrolled cell growth from cell-signaling pathway dysregulation is an obvious potential by-product of this virus strategy. Given the paucity of vIL-6 expressing cells in KS lesions, it is unlikely that vIL-6 significantly contributes to KS cell neoplasia. KSHV induction of hu-IL6, however, with subsequent induction of vascular endothelial growth factor-mediated angiogenesis (Holzinger et al., 1993, *Immunol Let* 35, 109–117), is a possibility. vIL-6 could also potentially contribute to the pathogenesis of KSHV-related lymphoproliferative disorders such as PEL or the plasma cell variant of Castleman's disease. The oncogenic potential of cellular cyclin and bcl-2 overexpression is well-established and these virus-encoded polypeptides may also contribute to KSHV-related neoplasia.

Figure 9:
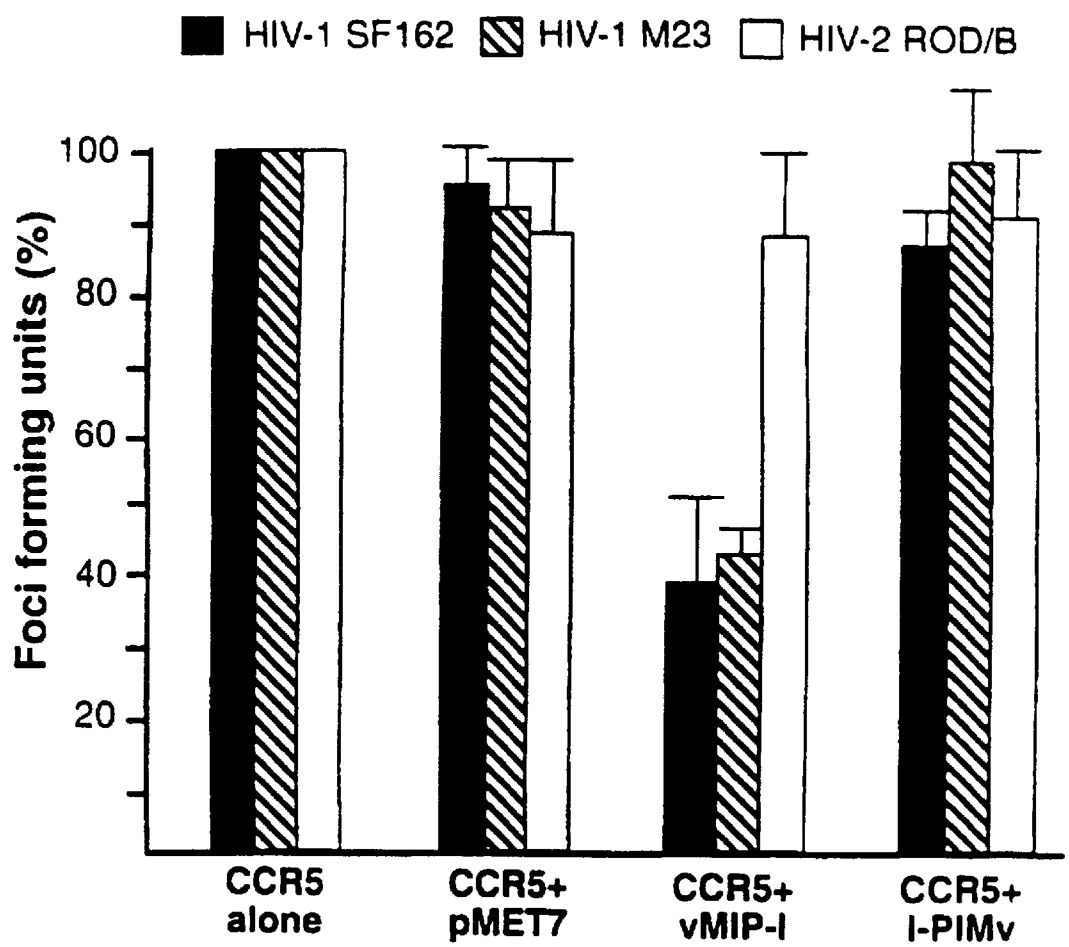

KSHV vMIP-I inhibits NSI HIV-1 replication in vitro (FIG. 9). Studies from early in the AIDS epidemic indicate that survival is longer for AIDS-KS patients than for other AIDS patients, and that 93% of US AIDS patients surviving >3 years had KS compared to only 28% of remaining AIDS patients dying within 3 years of diagnosis (Hardy, 1991, *J AIDS* 4, 386–391; Lemp et al., 1990, *J Am Med Assoc* 263, 402–406; Rothenberg et al., 1987, *New Eng J Med* 317, 1297–1302; Jacobson et al., 1993, *Am J Epidemiol* 138, 953–964; Lundgren et al., l995, *Am J Epidemiol* 141, 652–658). This may be due to KS occuring at relatively high CD4+ counts and high mortality for other AIDS-defining conditions. Recent surveillance data also indicates that the epidemiology of AIDS-KS is changing as the AIDS epidemic progresses (ibid).

Methods

Genomic Sequencing. Genomic inserts were randomly sheared, cloned into M13mp18, and sequenced to an average of 12-fold redundancy with complete bidirectional sequencing. The descriptive nomenclature of KSHV polypeptides is based on the naming system derived for herpesvirus saimiri (Albrecht et al., 1992, *J Virol* 66, 5047–5058).

Open reading frame (ORF) analysis. Assembled sequence contigs were analyzed using Macvector (IBI-Kodak, Rochester N.Y.) for potential open reading frames greater than 25 amino acid residues and analyzed using BLASTX and BEAUTY-BLASTX (Altschul et al., 1990, *J Mol Biol* 215, 403–410; Worley et al., 1995, *Genome Res* 5, 173–184; http://dot.imgen.bcm.tmc.edu:9331/seq-search/nucleic__acid-search.html). Similar proteins aligned to the four KSHV polypeptides (in italics:) included (name (species, sequence bank accession number, smallest sum Poisson distribution probability score)): (1) vMIP-I: LD78 (MIP-1α) (human, gi 127077, p=9.8xe-22), MIP-1α (Rattus, gi 790633, p=3.3xe-20), MIP-1α (Mus, gi 127079, p=1.7xe-19), MIP-1β (Mus, gi 1346534, p=7.8xe-18); (2) vMIP-II: LD78 (MIP-1α) (human, gi 127077, p=7.1xe-23), MIP-1α (Mus, gi 127079, p=8.9xe-21), MIP-1α (Rattus, gi 790633, p=1.2xe-20), MIP-1β (Mus, gi 1346534, p=3.8xe-20); (3) vIL-6: 26 kDa polypeptide (IL-6) (human, gi 23835, p=7.2xe-17), IL-6 (Macaca, gi 514386, p=1.6xe-16); and (4) vIRF: ICSBP (Gallus, gi662355, p1.1xe-11), ICSBP (Mus, sp p23611, p=1.0xe-10), lymphoid specific interferon regulatory factor (Mus, gi 972949, p=2.0xe-10), ISGF3 (Mus, gi 1263310, p=8.lxe-10), IRF4 (human, gi 1272477, p=1.0xe-9), ISGF3 (human, sp Q00978, 3.9xe-9), ICSBP (human, sp Q02556, p=2.3xe-8).

Sequence alignment. Amino acid sequences were aligned using CLUSTAL W (Thompson et al., 1994, *Nuc Acids Res* 22, 4673–4680) and compared using PAUP 3.1.1. Both rooted and unrooted bootstrap comparisons produced phylogenetic trees having all 100 bootstrap replicates with viral polypeptides being less divergent from each other than from the human polypepides.

Northern blotting. Northern blotting was performed using standard conditions with random-labeled probes (Chang et al., 1994, *Science* 265, 1865–1869) derived from PCR products for the following primer sets: VMIP-I: 5'-AGC ATA TAA GGA ACT CGG CGT TAC-3' (SEQ ID NO:4), 5'-GGT AGA TAA ATC CCC CCC CTT TG-3' (SEQ ID NO:5); vMIP-II: 5'-TGC ATC AGC TTC TTC ACC CAG-3' (SEQ ID NO:6), 5'-TGC TGT CTC GGT TAC CAG AAA AG-3' (SEQ ID NO:7); vIL-6: 5'-TCA CGT CGC TCT TTA CTT ATC GTG-3' (SEQ ID NO:8), 5'-CGC CCT TCA GTG AGA CTT CGT AAC-3' (SEQ ID NO:9); vIRF: 5'CTT GCG ATG AAC CAT CCA GG-3' (SEQ ID NO:10), 5'-ACA ACA CCC AAT TCC CCG TC-3' (SEQ ID NO:11) on total cell RNA extracted with RNAzol according to manufacturer's instructions (TelTest Inc, Friendswood Tex.) and 10 $\mu$g of total RNA was loaded in each lane. BCP-1, BC-1 and P3HRl were maintained in culture conditions and induced with TPA as previously described (Gao et al., 1996, *New Eng J Med* 335, 233–241). PCR amplification for these viral genes was performed using the vMIP-I, vMIP-II, vIL-6, and vIRF primer sets with 35 amplification cycles and compared to dilutions of whole BC-1 DNA as a positive control using PCR conditions previously described (Moore and Chang, 1995, *New Eng J Med* 332, 1181–1185). KS spindle cell line DNA used for these experiments was described in Dictor et al., 1996, *Am J Pathol* 148, 2009–2016. Amplifiability of DNA samples was confirmed using human HLA-DQ alpha and pyruvate dehydrogenase primers.

vIL-6 cloning. vIL-6 was cloned from a 695 bp polymerase chain reaction (PCR) product using the following primer set: 5'-TCA CGT CGC TCT TTA CTT ATC GTG-3' (SEQ ID NO:12) and 5'-CGC CCT TCA GTG AGA CTT CGT AAC-3' (SEQ ID NO:13), amplified for 35 cycles using the 0.1 $\mu$g of BC-1 DNA as a template. PCR product was intially cloned into pCR 2.1 (Invitrogen, San Diego Calif.) and an EcoRV insert was then cloned into the pMET7 expression vector (Takebe et al., 1988, *Mol Cell Biol* 8, 466–472) and transfected using DEAE-dextran with chloroquine into COS7 cells (CRL-1651, American Type Culture Collection, Rockville Md.). The sequence was also cloned into the pMET7 vector in the reverse orientation (6-LIv) relative to the SRa promoter as a negative control, with orientation and sequence fidelity of both constructs confirmed by bidirectional sequencing using dye-primer chemistry on an ABI 377 sequenator (Applied Biosystems Inc, Foster City Calif.).

15 ml of serum-free COS7 supernatants were concentrated to 1.5 ml by ultrafiltration with a Centriplus 10 filter (Amicon, Beverly MA) and 100 $\mu$l of supernatant concentrate or 1 $\mu$g of rhuIL-6 (R&D Systems, Minneapolis Minn.) was loaded per each lane in Laemmli buffer. For cell lysate immunoblotting, exponential phase cells with and without 20 ng/ml TPA induction for 48 hours were pelleted and 100 $\mu$g of whole cell protein solubilized in Laemmli buffer was loaded per lane, electrophoresed on a 15% SDS-polyacrylamide gel and immunoblotted and developed using standard conditions (Gao et al., 1996, *New Eng J Med* 335, 233–241) with either rabbit antipeptide antibody (1:100–1:1000 dilution) or anti-huIL-6 (1 $\mu$g per ml, R&D Systems, Minneapolis Minn.).

Cell line B9. B9 mouse plasmacytoma cell line were maintained in Iscove's Modified Dulbeccols Medium (IMDM) (Gibco, Gaithersburg, Md.), 10% fetal calf serum, 1% penicillin/streptomycin, 1% glutamine, 50 $\mu$M β-mercaptoethanol, and 10 ng per ml rhulL-6 (R&D Systems, Minneapolis, Minn.). $^3$H-thymidine uptake was used to measure B9 proliferation in response to huIL-6 or recombinant supernatants according to standard protocols (R&D Systems, Minneapolis, Minn.). Briefly, serial 1:3 dilutions of huIL-6 or Centriplus 10 concentrated recombinant supernatants were incubated with $2\times10^4$ cells per well in a 96 well plate for 24 hours at 37° C. with 10 $\mu$l of thymidine stock solution (50 $\mu$l of 1 mCi/ml $^3$H-thymidine in 1 ml IMDM) added to each well during the final four hours of incubation.

Cells were harvested and incorporated $^3$H-thymidine determined using a liquid scintillation counter. Each data point is the average of six determinations with standard deviations shown.

vIL-6 immunostaining. Immunostaining was performed using avidin-biotin complex (ABC) method after deparaffinization of tissues and quenching for 30 minutes with 0.03% $H_2O_2$ in PBS. The primary antibody was applied at a dilution of 1:1250 after blocking with 10% normal goat serum, 1% BSA, 0.5% Tween 20. The secondary biotinylated goat anti-rabbit antibody (1:200 in PBS) was applied for 30 minutes at room temperature followed by three 5 minute washes in PBS. Peroxidase-linked ABC (1:100 in PBS) was applied for 30 minutes followed by three 5 minute washes in PBS. A diamino-benzidine (DAB) chromogen detection solution (0.25% DAB, 0.01% $H_2O_2$ in PBS) was applied for 5 minutes. Slides are then washed, counterstained with hematoxylin and coverslipped. Amino ethyl carbazole (AEC) or Vector Red staining was also used allowing better discrimination of double-labeled cells with Fast Blue counterstaining for some surface antigens. For CD68, in which staining might be obscured by vIL-6 cytoplasmic staining, double label immunofluorescence was used. Microwaved tissue sections were blocked with 2% human serum, 1% bovine serum albumin (BSA) in PBS for 30 minutes, incubated overnight with primary antibodies and developed with fluorescein-conjugated goat anti-rabbit IgG (1:100, Sigma) for vIL-6 localization and rhodamine-conjugated horse anti-mouse IgG (1:100, Sigma) for CD68 localization for 30 minutes. After washing, secondary antibody incubation was repeated twice with washing for 15 minutes each to amplify staining. For the remaining membrane antigens, slides were developed first for vIL-6 and then then secondly with the cellular antigen, as well as the reverse localization (cellular antigen antibody first, anti-vIL-6 second) to achieve optimal visualization and discrimination of both antigens. In each case, the first antibody was developed using AEC (Sigma) with blocking solution preincubation (1% BSA, 10% normal horse serum, 0.5% Tween 20 for 30 minutes) and development per manufacturer's instructions. The second antibody was developed using the ABC-alkaline phosphatase technique with Fast Blue chromagen. Both microwaving and trypsinization resulted in poorer localization and specificity of vIL-6 immunolocalization. In cases where this was required for optimal localization of membrane antigen, these techniques were applied after vIL-6 AEC localization. Vector-Red (Vector, Burlingame, Calif.) staining was used as an alternative stain to AEC to achieve optimal discrimination and was performed per manufacturer's protocol using the ABC-alkaline phosphatase technique. Cell antigen antibodies examined included CD68 (1:800, from clone Kim 6), epithelial membrane antigen (EMA, 1:500, Dako, Carpinteria, Calif.), CD3 (1:200, Dako), CD20, (1:200, Dako), OPD4 (1:100, Dako), CD34 (1:15, Dako), CD45 (1:400, from clone 9.4), L26 (1:100, Immunotech, Westbrook, Me.) and Leu22 (1:100, Becton-Dickinson, San Jose, Calif.) on tissues prepared according to manufacturer's instructions. Specific vIL-6 colocalization was only found with CD34 and CD45 in KS lesions, EMA in PEL, and CD20 and CD45 in lymph node tissues.

Immunohistochemical vIL-6 localization was performed on exponential phase BCP-1 cells with or without 48 hour TPA incubation after embedding in 1% agar in saline. The percentages of positive cells were determined from cell counts of three random high power microscopic fields per slide. Lower percentages of BCP-1 cells stain positively for vIL-6 after TPA treatment possibly reflecting cell lysis and death from lytic virus replication induction by TPA. Immunostaining of cells and tissues was demonstrated to be specific by neutralization using overnight incubation of antisera with 0.1 μg/ml vIL-6 synthetic peptides at 4° C. and by use of preimmune rabbit antisera run in parallel with the postimmune sera for the tissues or cell preparations. No specific staining was seen after either peptide neutralization or use of preimmune sera.

CCR5 and vMIP-I cloning. CCR5 was cloned into pRc-CMV vector (Invitrogen) and both forward and reverse orientations of the vMIP-I gene were cloned into pMET7 after PCR amplification using the following primer pairs: 5'-AGC ATA TAA GGA ACT CGG CGT TAC-3' (SEQ ID NO:14), 5'-GGT AGA TAA ACT CCC CCC CTT TG-3' (SEQ ID NO:15). CCR5 alone and with the forward construct (vMIP-I), the reverse construct (I-PIMv) and empty pMET7 vector were transfected into CCC/CD4 cells (CCC cat cells stably expressing human CD4, see McKnight et al., 1994, *Virol* 201, 8–18) using Lipofectamine (Gibco). After 48 hours, media was removed from the transfected cells and 1000 $TCID_{50}$ of SF162, M23 or ROD/B virus culture stock was added. Cells were washed four times after 4 hours of virus incubation and grown in DMEM with 5% FCS for 72 hours before immunostaining for HIV-1 p24 or HIV-2 gp105 as previously described. Each condition was replicated 3–4 times (FIG. 9) with medians and error bars representing the standard deviations expressed as percentages of the CCR5 alone foci.

Experimental Details Section III

The following patents are hereby incorporated by reference to more fully describe the invention described herein:

1. Fowlkes CARBOXY TERMINAL IL-6 MUTEINS, U.S. Pat. No. 5,565,336 ISSUED Oct. 15, 1996;
2. Skelly et al., METHOD OF MAKING CYSTEINE DEPLETED IL-6 MUTEINS, U.S. Pat. No. 5,545,537, ISSUED Aug. 13, 1996;
3. Ulrich, COMPOSITION AND METHOD FOR TREATING INFLAMMATION, U.S. Pat. No. 5,376,368, ISSUED Dec. 27, 1994;
4. Skelly et: al., CYSTEINE DEPLETED IL-6 MUTEINS, U.S. Pat. No. 5,359,034, ISSUED Oct. 25, 1994;
5. Williams, ULTRAPURE HUMAN INTERLEUKIN 6, U.S. Pat. No. 5,338,834, ISSUED Aug. 16, 1994;
6. Fowlkes, CARBOXY TERMINAL IL-6 MUTEINS, U.S. Pat. No. 5,338,833, ISSUED Aug. 16, 1994;
7. Ulrich , COMPOSITION AND METHOD FOR TREATING INFLAMMATION, U.S. Pat. No. 5,300,292, ISSUED Apr. 5, 1994;
8. Mikayama et al., MODIFIED HIL-6, U.S. Pat. No. 5,264,209, ISSUED Nov. 23, 1993;
9. Park, HYPERGLYCOSYLATED CYTOKINE CONJUGATES, U.S. Pat. No. 5,217,881, ISSUED Jun. 8, 1993;
10. Goldberg and Faquin, INTERLEUKIN 6 TO STIMULATE ERYTHROPOIETIN PRODUCTION, U.S. Pat. No. 5,188,828, ISSUED Feb. 23, 1993;
11. Miles et al., METHOD TO TREAT KAPOSI'S SARCOMA, U.S. Pat. No. 5,470,824, ISSUED Nov. 28, 1995;
12. Li and Ruben, MACROPHAGE INFLAMMATORY PROTEIN -3 AND -4 [Isolated polynucleotide encoding said polypeptide], U.S. Pat. No. 5,504,003, ISSUED Apr. 2, 1996;
13. Gewirtz, SUPPRESSION OF MEGAKARYOCYTOPOIESIS BY MACROPHAGE INFLAMMATORY PROTEINS [Reducing number of circulating platelets in bloodstream], U.S. Pat. No. 5,306,709, ISSUED Apr. 26, 1994;
14. Fahey et al., METHOD AND AGENTS FOR PROMOTING WOTND HEARING, U.S. Pat. No. 5,145,676, ISSUED Sep. 8, 1992;
15. Rosen et al., POLYNUCLEOTIDE ENCODING MACROPHAGE INFLAMMATORY PROTEIN GAMMA, U.S. Pat. No. 5,556,767, ISSUED Sep. 17, 1996;
16. Chuntharapai et al., ANTIBODIES TO HUMAN IL-8 TYPE A RECEPTOR, U.S. Pat. No. 5,543,503, ISSUED Aug. 6, 1996;
17. Chuntharapai et al., ANTIBODIES TO HUMAN IL-8 TYPE B RECEPTOR [A monoclonal antibody as antiinflammatory agent treating an inflammatory disorder], U.S. Pat. No. 5,440,021, ISSUED Aug. 8, 1995;
18. Kunkel et al., LABELLED MONOCYTE CHEMOATTRACTANT PROTEIN MATERIAL AND MEDICAL USES THEREOF, U.S. Pat. No. 5,413,778, ISSUED May 9, 1995;
19. Lyle and Kunkel, LABELLED INTERLEUKIN-6 AND MEDICAL USES THEREOF [Radionuclide labeled chemokines, imaging agents], U.S. Pat. No. 5,346,686, ISSUED Sep. 13, 1994;
20. Jones et al., ANTI-CANCER QUINAZOLINE DERIVATIVES, U.S. Pat. No. 4,564,616, ISSUED Jan. 14, 1986;
21. DeGraw et al., ANTIINFLAMMATORY AND ANTINEOPLASTIC 5-DEAZAAMINOPTERINS AND 5,10-DIDEAZAAMINOPTERINS, U.S. Pat. No. 5,536,724, ISSUED Jul. 16, 1996;
22. Mahan et al., IN VIVO SELECTION OF MICROBIAL VIRULENCE GENES [Genetic engineering and expression using auxotrophic or antibiotic sensitive microorganism's chromosome], U.S. Pat. No. 5,434,065, ISSUED Jul. 18, 1995;
23. DeGraw et al., 8,10-DIDEAZATETRAHYDROFOLIC ACID DERIVATIVES [Antitumor agents], U.S. Pat. No. 5,167,963, ISSUED Dec. 1, 1992; and
24. Watanabe, 6,7-DIHYDROPYRROL[3,4-C]PYRIDO[2,3-D] PYRIMIDINE DERIVATIVES [STRUCTURALLY SIMILAR TO THYMIDYLIC ACID], U.S. Pat. No. 4,925,939, ISSUED May 15, 1990.

Reference

1. Chang, Yuan, E Cesarman, M S Pessin, F Lee, J Culpepper, D M Knowles and Patrick S Moore (1994) Identification of herpesvirus-like DNA sequences in AIDS-associated Kaposi's sarcoma. *Science* 265, 1865–1869.
2. Moore, Patrick S and Yuan Chang (1995) Detection of herpesvirus-like DNA sequences in Kaposi's sarcoma in patients with and those without HIV infection. *New Eng J Med* 332, 1181–1185.
3. Cesarman, E, Yuan Chang, Patrick S Moore, J W Said and D M Knowles (1995) Kaposi's sarcoma-associated herpesvirus-like DNA sequences are present in AIDS-related body cavity based lymphomas. *New Eng J Med* 332, 1186–1191.
4. Cesarman, E, Patrick S Moore, P H Rao, G Inghirami, D M Knowles and Yuan Chang (1995) In vitro establishment and characterization of two AIDS-related lymphoma cell lines containing Kaposils-sarcoma associated herpesvirus-like (KSHV) DNA sequences. *Blood* 86, 2708–2714.

TABLE 1

KSHV Genome ORFs and their similarity to genes in other herpesviruses.

| Name | Pol | Start | Stop | Size | HVS % Sim | HVS % Id | EBV Name | EBV % Sim | EBV % Id |
|---|---|---|---|---|---|---|---|---|---|
| K1 | + | 105 | 974 | 299 | | | | | |
| ORF4* | + | 1142 | 2794 | 550 | 45.3 | 31.2 | | | |
| ** | | | | | 46.4 | 34.0 | | | |
| ORF6 | + | 3210 | 6611 | 1133 | 74.1 | 55.2 | BALF2 | 65.6 | 42.1 |
| ORF7 | + | 6628 | 8715 | 695 | 65.0 | 44.7 | BALF3 | 59.9 | 41.3 |
| ORF8 | + | 9699 | 11,236 | 845 | 72.5 | 54.9 | BALF4 | 62.1 | 42.6 |
| ORF9 | + | 11,363 | 14,401 | 1012 | 77.6 | 62.1 | BALFS | 70.9 | 55.6 |
| ORF10 | + | 14,519 | 15,775 | 418 | 50.4 | 26.2 | | | |
| ORF11 | + | 15,790 | 17,013 | 407 | 49.4 | 28.9 | Raji LF2 | 44.4 | 27.9 |
| K2 | – | 17,875 | 17,261 | 204 | | | | | |
| ORF02 | – | 18,553 | 17,921 | 210 | 65.8 | 48.4 | | | |
| K3 | – | 19,609 | 18,609 | 333 | | | | | |
| ORF70 | – | 21,104 | 20,091 | 337 | 79.5 | 66.4 | | | |
| K4 | – | 21,932 | 21,548 | 94 | | | | | |
| K5 | – | 26,493 | 25,713 | 257 | | | | | |
| K6 | – | 27,424 | 27,137 | 95 | | | | | |
| K7 | + | 28,622 | 29,002 | 126 | | | | | |
| ORF16 | + | 30,145 | 30,672 | 175 | 50.0 | 26.7 | BHRF1 | 46.3 | 22.9 |
| ORF17 | – | 32,482 | 30,921 | 553 | 60.3 | 42.9 | BVRF2 | 59.8 | 34.3 |
| ORF18 | + | 32,424 | 33,197 | 257 | 70.6 | 48.4 | | | |
| ORF19 | – | 34,843 | 33,194 | 549 | 62.8 | 43.8 | BVRF1 | 62.5 | 42.0 |
| ORF20 | – | 35,573 | 34,611 | 320 | 59.6 | 42.7 | BXRF1 | 54.7 | 34.6 |
| ORF21 | + | 35,383 | 37,125 | 580 | 50.9 | 32.5 | BXLF1 | 50.7 | 28.2 |
| ORF22 | + | 37,113 | 39,305 | 730 | 53.9 | 35.1 | BXLF2 | 48.3 | 26.5 |
| ORF23 | – | 40,516 | 39,302 | 404 | 57.4 | 33.7 | BTRF1 | 51.0 | 31.0 |
| ORF24 | – | 42,776 | 40,520 | 752 | 65.8 | 45.6 | BcRF1 | 56.4 | 37.7 |
| ORF25 | + | 42,777 | 46,907 | 1376 | 80.9 | 65.8 | BcLF1 | 74.9 | 56.8 |
| ORF26 | + | 46,933 | 47,850 | 305 | 76.8 | 58.3 | BDLF1 | 73.4 | 48.8 |
| ORF27 | + | 47,873 | 48,745 | 290 | 49.6 | 29.6 | BDLF2 | 43.3 | 19.6 |
| ORF28 | + | 49,991 | 49,299 | 102 | 42.2 | 21.7 | BDLF3 | | |
| ORF29b | – | 50,417 | 49,362 | 351 | 41.8 | 17.0 | BDRF1 | 43.3 | 16.3 |
| ORF30 | + | 50,623 | 50,856 | 77 | 52.1 | 31.0 | BDLF3.5 | | |
| ORF31 | + | 50,763 | 51,437 | 224 | 63.0 | 43.5 | BDLF4 | 58.9 | 36.4 |
| ORF32 | + | 51,404 | 52,768 | 454 | 51.7 | 30.1 | BGLF1 | 47.0 | 26.6 |
| ORF33 | + | 52,761 | 53,699 | 312 | 58.6 | 36.4 | BGLF2 | 52.8 | 32.2 |
| ORF29a | – | 54,676 | 53,738 | 312 | 41.9 | 15.8 | BGRF1 | 57.1 | 40.6 |
| ORF34 | + | 54,675 | 55,658 | 327 | 58.9 | 42.7 | BGLF3 | 54.8 | 33.0 |
| ORF35 | + | 55,639 | 56,091 | 151 | 60.0 | 31.7 | BGLF3.5 | | |
| ORF36 | + | 55,976 | 57,310 | 444 | 49.4 | 31.1 | BGLF4 | 50.0 | 30.2 |
| ORF37 | + | 57,273 | 58,733 | 486 | 65.9 | 50.4 | BGLF5 | 60.1 | 42.7 |
| ORF38 | + | 58,688 | 58,873 | 61 | 58.6 | 39.7 | BBLF1 | 52.5 | 23.0 |
| ORF39 | – | 60,175 | 58,976 | 399 | 73.2 | 52.1 | BBRF3 | 65.2 | 43.6 |
| ORF40 | + | 60,308 | 61,681 | 457 | 51.9 | 28.1 | BBLF2 | 47.1 | 23.3 |
| ORF41 | + | 61,827 | 62,444 | 205 | 53.4 | 29.2 | BBLF3 | | |
| ORF42 | – | 63,272 | 62,436 | 276 | 55.8 | 39.9 | BBRF2 | 52.9 | 33.0 |
| ORF43 | – | 64,953 | 63,136 | 605 | 74.9 | 60.5 | BBRF1 | 67.6 | 50.1 |
| ORF44 | + | 64,892 | 67,258 | 788 | 75.5 | 61.4 | BBLF4 | 67.8 | 51.1 |
| ORF45 | – | 69,876 | 67,353 | 407 | 50.2 | 30.7 | BKRF4 | 49.9 | 26.2 |
| ORF46 | – | 69,404 | 68,637 | 255 | 73.0 | 59.5 | BKRF3 | 69.2 | 54.8 |
| ORF47 | – | 69,915 | 69,412 | 167 | 53.0 | 29.9 | BKRF4 | 53.8 | 24.2 |
| ORF48 | – | 71,381 | 70,173 | 402 | 47.3 | 24.4 | BRRF2 | 46.1 | 18.8 |
| ORF49 | – | 72,538 | 71,630 | 302 | 45.4 | 21.2 | BRRF1 | 49.8 | 28.0 |
| ORF50 | + | 72,734 | 74,629 | 631 | 46.5 | 24.9 | BRLF1 | 41.4 | 19.0 |
| K8 | + | 74,950 | 75,569 | 239 | | | | | |
| ORF52 | – | 77,197 | 76,802 | 131 | 50.0 | 33.3 | BLRF2 | 54.6 | 36.9 |
| ORF53 | – | 77,665 | 77,333 | 110 | 59.6 | 36.0 | BLRF1 | 58.1 | 40.9 |
| ORP54 | + | 77,667 | 78,623 | 318 | 55.0 | 35.5 | BLLF3 | 53.7 | 32.4 |
| ORF55 | – | 79,448 | 78,765 | 227 | 64.4 | 46.4 | BSRF1 | 61.6 | 44.0 |
| ORF56 | + | 79,436 | 81,967 | 843 | 62.5 | 44.3 | BSLF1 | 56.6 | 35.4 |
| ORF57 | + | 82,717 | 83,544 | 275 | 56.9 | 31.5 | BMLF1 | 45.1 | 22.0 |
| K9 | – | 85,209 | 83,860 | 449 | | | | | |
| K10 | – | 88,164 | 86,074 | 696 | | | | | |
| K11 | – | 93,367 | 91,964 | 467 | | | | | |
| ORF59 | – | 95,544 | 94,471 | 357 | 55.9 | 28.7 | BMRF2 | 50.6 | 25.3 |
| ORF59 | – | 96,739 | 95,549 | 396 | 54.1 | 32.3 | BMRF1 | 50.7 | 26.3 |
| ORF60 | – | 97,787 | 96,870 | 305 | 79.3 | 64.6 | BaRF1 | 74.8 | 57.3 |
| ORF61 | – | 100,194 | 97,816 | 792 | 69.4 | 52.4 | BORF2 | 64.1 | 43.6 |
| ORF62 | – | 101,194 | 100,199 | 331 | 64.6 | 40.2 | BORF1 | 57.7 | 34.7 |
| ORF63 | + | 101,208 | 103,994 | 927 | 53.1 | 32.1 | BOLF1 | 47.0 | 24.5 |
| ORF64 | + | 104,000 | 111,907 | 2635 | 50.1 | 29.7 | BPLF1 | 46.6 | 26.1 |
| ORF65 | – | 112,443 | 111,931 | 170 | 60.4 | 40.3 | BFRF3 | 49.4 | 27.8 |
| ORF66 | – | 113,759 | 112,470 | 429 | 56.7 | 34.7 | BFRF2 | 50.0 | 28.0 |
| ORF67 | – | 114,508 | 113,693 | 271 | 71.9 | 53.0 | BFRF1 | 62.9 | 39.5 |

TABLE 1-continued

KSHV Genome ORFs and their similarity to genes in other herpesviruses.

| Name | Pol | Start | Stop | Size | HVS % Sim | HVS % Id | EBV Name | EBV % Sim | EBV % Id |
|---|---|---|---|---|---|---|---|---|---|
| ORF69 | + | 114,768 | 116,405 | 545 | 64.7 | 45.4 | BFLF1 | 59.3 | 36.2 |
| ORF69 | + | 116,669 | 117,346 | 225 | 71.1 | 53.6 | BFLF2 | 60.7 | 41.7 |
| K12 | − | 118,101 | 117,919 | 60 | | | | | |
| K13 | − | 122,710 | 122,291 | 139 | | | | | |
| ORF72 | − | 123,566 | 122,793 | 257 | 53.0 | 32.5 | | | |
| ORF73 | − | 127,296 | 123,808 | 1162 | 51.2 | 31.8 | | | |
| K14 | + | 127,893 | 128,929 | 346 | | | | | |
| ORF74 | + | 129,371 | 130,399 | 342 | 57.9 | 34.1 | | | |
| ORF75 | − | 134,440 | 130,550 | 1296 | 54.6 | 36.3 | BNRF1 | | |
| K15 | − | 136,279 | 135,977 | 100 | | | | | |

| Name | Function |
|---|---|
| K1 | |
| ORF4* | complement binding protein (v-CBP) |
| ** | |
| ORF6 | ssDNA binding protein (SSBP) |
| ORF7 | Transport protein |
| ORF8 | Glycoprotein B (gB) |
| ORF9 | DNA polymerase (pol) |
| ORF10 | |
| ORF11 | |
| K2 | vIL-6 |
| ORF02 | DHFR |
| K3 | BHV4-IE1 I |
| ORF70 | Thymidylate synthase (TS) |
| K4 | vMIP-II |
| K5 | BHV4-IK1 II |
| K6 | VMIP-I |
| K7 | |
| ORF16 | Bc1-2 |
| ORF17 | Capsid protein I |
| ORF19 | |
| ORF19 | Tegument protein I |
| ORF20 | |
| ORF21 | Thymidine kinase (TK) |
| ORF22 | Glycoprotein H (gH) |
| ORF23 | |
| ORF24 | |
| ORF25 | Major capsid protein (MCP) |
| ORF26 | Capsid protein II |
| ORF27 | |
| ORF29 | |
| ORF29b | Packaging protein II |
| ORF30 | |
| ORF31 | |
| ORF32 | |
| ORF33 | |
| ORF29a | Packaging protein I |
| ORF34 | |
| ORF35 | |
| ORF36 | Viral protein kinase |
| ORF37 | Alkaline exonuclease (AE) |
| ORF38 | |
| ORF39 | Glycoprotein M (gM) |
| ORF40 | Helicase-primase, subunit 1 |
| ORF41 | Helicaee-primase, subunit 2 |
| ORF42 | |
| ORF43 | Capaid protein III |
| ORF44 | Helicase-primase, subunit 3 |
| ORF45 | Virion assembly protein |
| ORF46 | Uracil DNA glycosylase (UDG) |
| ORF47 | Glycoprotein L (gL) |
| ORF48 | |
| ORF49 | |
| ORF50 | Traneactivator (LCTP) |
| KB | |
| ORF52 | |
| ORF53 | |
| ORF54 | dUTPase |
| ORF55 | |
| ORF56 | DNA replication protein I |
| ORF57 | Immediate-early protein II (IEP-II) |
| K9 | vIRF1(ICSBP) |

TABLE 1-continued

KSHV Genome ORFs and their similarity to genes in other herpesviruses.

| Name | Pol | Start | Stop | Size | HVS % Sim | HVS % Id | EBV Name | EBV % Sim | EBV % Id |
|---|---|---|---|---|---|---|---|---|---|
| K10 | | | | | | | | | |
| K11 | | | | | | | | | |
| ORF58 | Phosphoprotein | | | | | | | | |
| ORF59 | DNA replication protein II | | | | | | | | |
| ORF60 | Ribonucleotide reductase, small | | | | | | | | |
| ORF61 | Ribonucleotide reductase, large | | | | | | | | |
| ORF62 | Assembly/DNA maturation | | | | | | | | |
| ORF63 | Tegument protein II | | | | | | | | |
| ORF64 | Tegument protein III | | | | | | | | |
| ORF65 | Capaid protein IV | | | | | | | | |
| ORF66 | | | | | | | | | |
| ORF67 | Tegument protein IV | | | | | | | | |
| ORF68 | Glycoprotein | | | | | | | | |
| ORF69 | | | | | | | | | |
| K12 | Kaposin | | | | | | | | |
| K13 | | | | | | | | | |
| ORF72 | Cyclin D | | | | | | | | |
| ORF73 | Immediate-early protein (IEP) | | | | | | | | |
| K14 | OX-2 (v-adh) | | | | | | | | |
| ORF74 | G-protein coupled receptor | | | | | | | | |
| ORF75 | Tegument protein/FGARAT | | | | | | | | |
| K15 | | | | | | | | | |

Legend to Table 1. Name (e.g. K1 or ORF4) refers to the KSHV ORF designation; Pol signifies polarity of the ORF within the KSHV genome; Start refers to the position of the first LUR nucleotide in the start codon; Stop refers to the position of the last LUR nucleotide in the stop codon; Size indicates the number of amino acid residues encoded by the KSHV ORF;

HVS%Sim indicates the percent similarity of the indicated KSHV ORF to the corresponding ORF of herpesvirus saimiri; HVS%Id indicates the percent identity of the indicated KSHV ORF to the corresponding ORF of herpesvirus saimiri; EBV Name indicates the EBV ORF designation; EBV%Sim indicates the percent similarity of the indicated KSHV ORF to the named Epstein-Barr virus ORF; EBV%Id indicates the percent identity of the indicated KSHV ORF to the named Epstein-Barr virus ORF. The asterisks in the KSHV Name column indicate comparison of KSHV ORF4 to HVS ORF4a (*) and HVS ORF4b (**). The entire unannotated genomic sequence is deposited in GenBank® under the accession numbers: U75698 (LUR), U75699 (terminal repeat), and U75700 (incomplete terminal repeat). The sequence of the LUR (U75698) is also set forth in its entirety in the Sequence Listing below. Specifically, the sequence of the LUR is set forth in 5' to 3' order in SEQ ID Nos:17–20. More specifically, nucleotides 1–35,100 of the LUR are set forth in SEQ ID NO:17 numbered nucleotides 1–35,100, respectively; nucleotides 35,101–70,200 of the LUR are set forth in SEQ ID NO:18 numbered nucleotides 1–35,100, respectively; nucleotides 70,201–105,300 of the LUR are set forth in SEQ ID NO:19 numbered nucleotides 1–35,100, respectively; and nucleotides 105,301–137,507 of the LUR are set forth in SEQ ID NO:20 numbered nucleotides 1–32,207, respectively.

What is claimed is:

1. An isolated nucleic acid which corresponds to a Kaposi's sarcoma-associated herpesvirus terminal repeat and comprises consecutive nucleotides having the nucleic acid sequence set forth in SEQ ID NO:16.

2. The isolated nucleic acid of claim 1, wherein the nucleic acid is DNA.

3. A replicable vector comprising the isolated nucleic acid of claim 1, wherein the isolated nucleic acid is inserted into the replicable vector.

4. The vector of claim 3, wherein the vector is a plasmid.

5. The vector of claim 3, wherein the vector is a cosmid.

6. The vector of claim 3, wherein the vector is a λ page.

7. The vector of claim 3, wherein the vector is a yeast artificial chromosome.

8. A host cell which comprises the vector of claim 3.

9. The host cell of claim 8, wherein the host cell is a eucaryotic cell.

10. An isolated nucleic acid which comprises at least 30 consecutive nucleotides of the isolated nucleic acid of claim 1.

11. An isolated nucleic acid which comprises at least 30 consecutive nucleotides of a nucleic acid which is fully complementary to the isolated nucleic acid of claim 1.

12. The isolated nucleic acid of any one of claims 10–11, wherein the nucleic acid is detectable.

13. The isolated nucleic acid of claim 12, wherein the nucleic acid is labeled with a detectable marker.

14. The isolated nucleic acid of claim 13, wherein the detectable marker is a radioactive label, or a colorimetric marker, a luminescent marker, or a fluorescent marker.

* * * * *